US008883206B2

(12) United States Patent
Dokou et al.

(10) Patent No.: US 8,883,206 B2
(45) Date of Patent: Nov. 11, 2014

(54) PHARMACEUTICAL COMPOSITION AND ADMINISTRATIONS THEREOF

(71) Applicant: Vertex Pharmaceuticals Incorporated, Boston, MA (US)

(72) Inventors: Eleni Dokou, Cambridge, MA (US); Shahla Jamzad, Belmont, MA (US); John P. Caesar, Jr., Lancaster, MA (US); Majed Fawaz, Foxboro, MA (US); Laura Das, Charlestown, MA (US); Chong-Hui Gu, Weban, MA (US); Patricia Nell Hurter, Harvard, MA (US); Meghna Jai Israni, Boston, MA (US); Meghan M. Johnston, Wakefield, MA (US); Dragutin Knezic, Watertown, MA (US); Andrew G. Kuzmission, Shrewsburg, MA (US); HongRen Wang, Lexington, MA (US)

(73) Assignee: Vertex Pharmaceuticals Incorporated, Boston, MA (US)

(*) Notice: Subject to any disclaimer, the term of this patent is extended or adjusted under 35 U.S.C. 154(b) by 0 days.

(21) Appl. No.: 14/286,856

(22) Filed: May 23, 2014

(65) Prior Publication Data

US 2014/0255483 A1 Sep. 11, 2014

Related U.S. Application Data

(63) Continuation of application No. 13/779,654, filed on Feb. 27, 2013.

(60) Provisional application No. 61/603,882, filed on Feb. 27, 2012, provisional application No. 61/710,352, filed on Oct. 5, 2012.

(51) Int. Cl.
| | |
|---|---|
| *A61K 9/48* | (2006.01) |
| *A61K 9/20* | (2006.01) |
| *A61K 38/00* | (2006.01) |
| *A61K 31/47* | (2006.01) |
| *A61K 9/16* | (2006.01) |
| *C07D 215/56* | (2006.01) |

(52) U.S. Cl.
CPC ............ *C07D 215/56* (2013.01); *A61K 9/1623* (2013.01); *A61K 9/2009* (2013.01); *A61K 9/1652* (2013.01); *A61K 9/1617* (2013.01); *A61K 9/2054* (2013.01); *A61K 9/1611* (2013.01); *A61K 9/2013* (2013.01); *A61K 9/2018* (2013.01)
USPC ........... 424/465; 424/451; 424/452; 424/464; 514/1.8; 514/312

(58) Field of Classification Search
None
See application file for complete search history.

(56) References Cited

U.S. PATENT DOCUMENTS

| | | |
|---|---|---|
| 6,039,974 A | 3/2000 | MacLauren et al. |
| 7,407,976 B2 | 8/2008 | Miller et al. |
| 7,495,103 B2 | 2/2009 | Hadida Ruah et al. |
| 7,553,855 B2 | 6/2009 | Young et al. |
| 7,598,412 B2 | 10/2009 | Hadida Ruah et al. |
| 7,645,789 B2 | 1/2010 | Hadida Ruah et al. |
| 7,659,268 B2 | 2/2010 | Hadida Ruah et al. |
| 7,671,221 B2 | 3/2010 | Hadida Ruah et al. |
| 7,691,902 B2 | 4/2010 | Hadida Ruah et al. |
| 7,741,321 B2 | 6/2010 | Hadida Ruah et al. |
| 7,754,739 B2 | 7/2010 | Hadida Ruah et al. |
| 7,776,905 B2 | 8/2010 | Hadida Ruah et al. |
| 7,973,169 B2 | 7/2011 | Hadida Ruah et al. |
| 7,977,322 B2 | 7/2011 | Hadida Ruah et al. |
| 7,999,113 B2 | 8/2011 | Hadida Ruah et al. |
| 8,124,781 B2 | 2/2012 | Siesel |
| 8,163,772 B2 | 4/2012 | Demattei et al. |
| 8,188,283 B2 | 5/2012 | Binch et al. |
| 8,227,615 B2 | 7/2012 | Hadida Ruah et al. |
| 8,242,149 B2 | 8/2012 | Hadida Ruah et al. |
| 8,299,099 B2 | 10/2012 | Hadida Ruah et al. |
| 8,314,239 B2 | 11/2012 | Binch et al. |
| 8,314,256 B2 | 11/2012 | Hadida Ruah et al. |
| 8,344,147 B2 | 1/2013 | Ambhaikar et al. |
| 8,354,427 B2 | 1/2013 | Van Goor |
| 8,367,660 B2 | 2/2013 | Binch et al. |
| 8,389,727 B2 | 3/2013 | Zhang et al. |
| 8,399,479 B2 | 3/2013 | Binch et al. |
| 8,404,865 B2 | 3/2013 | Ambhaikar et al. |

(Continued)

FOREIGN PATENT DOCUMENTS

| | | |
|---|---|---|
| JP | 2006206612 A | 8/2006 |
| WO | 0121159 A2 | 3/2001 |

(Continued)

OTHER PUBLICATIONS

Attached SciFinder search results (Reference_06_28_2014_ 102933_14_286856); dated Jun. 28, 2014 (pdf).*
Aulton, Michael E., "Pharmaceutics: The Science of Dosage Form Design," Churchill Livingstone, Edinburgh, London, Melbourne, and New York, 1988, pp. 304-321.
Iskandarani, B., et al., "Simultaneous optimization of capsule and tablet formulation using response surface methodology," Drug Development and Industrial Pharmacy, 1993, vol. 19, No. 16, pp. 2089-2101.

(Continued)

*Primary Examiner* — Jeffrey T Palenik
(74) *Attorney, Agent, or Firm* — Honigman Miller Schwartz and Cohn LLP; Christopher C. Forbes; Jonathan P. O'Brien

(57) ABSTRACT

The present invention relates to pharmaceutical compositions containing a solid dispersion of N-[2,4-Bis(1,1-dimethylethyl)-5-hydroxyphenyl]-1,4-dihydro-4-oxoquinoline-3-carboxamide including formulations of the solid dispersions into powders, granules and mini-tablets, methods for manufacturing and processing the powders, granules and mini-tablets, and methods for treating cystic fibrosis employing the pharmaceutical composition.

10 Claims, 2 Drawing Sheets

(56) References Cited

U.S. PATENT DOCUMENTS

| | | |
|---|---|---|
| 8,436,014 B2 | 5/2013 | Zhang et al. |
| 8,476,442 B2 | 7/2013 | Demattei et al. |
| 8,507,524 B2 | 8/2013 | Hadida Ruah et al. |
| 8,507,534 B2 | 8/2013 | Keshavarz-Shokri et al. |
| 8,513,282 B2 | 8/2013 | Binch et al. |
| 8,518,441 B2 | 8/2013 | Higuchi et al. |
| 8,552,006 B2 | 10/2013 | Binch et al. |
| 2005/0059687 A1 | 3/2005 | Makings et al. |
| 2005/0113423 A1 | 5/2005 | Van Goor et al. |
| 2005/0147669 A1 | 7/2005 | Lawrence et al. |
| 2006/0003005 A1 | 1/2006 | Cao et al. |
| 2006/0052358 A1 | 3/2006 | Hadida Ruah et al. |
| 2007/0105833 A1 | 5/2007 | Hadida Ruah et al. |
| 2008/0317853 A1 | 12/2008 | Kashid et al. |
| 2009/0105272 A1 | 4/2009 | Grootenhuis et al. |
| 2009/0131492 A1 | 5/2009 | Hadida Ruah et al. |
| 2009/0143381 A1 | 6/2009 | Hadida Ruah et al. |
| 2009/0170905 A1 | 7/2009 | Keshavarz-Shokri et al. |
| 2009/0176839 A1 | 7/2009 | Keshavarz-Shokri et al. |
| 2009/0246820 A1 | 10/2009 | Singh et al. |
| 2009/0253736 A1 | 10/2009 | Hadida Ruah et al. |
| 2009/0285887 A1 | 11/2009 | Abu-Baker et al. |
| 2010/0036130 A1 | 2/2010 | Siesel |
| 2010/0074949 A1 | 3/2010 | Rowe et al. |
| 2010/0087490 A1 | 4/2010 | Young |
| 2010/0113508 A1 | 5/2010 | Binch et al. |
| 2010/0113509 A1 | 5/2010 | Binch et al. |
| 2010/0130547 A1 | 5/2010 | Zhang et al. |
| 2010/0168094 A1 | 7/2010 | Binch et al. |
| 2010/0168158 A1 | 7/2010 | Binch et al. |
| 2010/0184739 A1 | 7/2010 | Van Goor et al. |
| 2010/0249113 A1 | 9/2010 | Hadida Ruah et al. |
| 2010/0249180 A1 | 9/2010 | Gallardo-Godoy |
| 2010/0256184 A1 | 10/2010 | Rowe et al. |
| 2010/0267768 A1 | 10/2010 | Demattei et al. |
| 2011/0064811 A1 | 3/2011 | Hurter et al. |
| 2011/0065928 A1 | 3/2011 | Ambhaikar et al. |
| 2011/0098311 A1 | 4/2011 | Van Goor et al. |
| 2011/0123449 A1 | 5/2011 | Zhang et al. |
| 2011/0177999 A1 | 7/2011 | Singh et al. |
| 2011/0230519 A1 | 9/2011 | Arekar et al. |
| 2011/0251253 A1 | 10/2011 | Keshavarz-Shokri et al. |
| 2011/0256220 A1 | 10/2011 | Verwijs et al. |
| 2011/0257223 A1 | 10/2011 | Van Goor et al. |
| 2011/0263654 A1 | 10/2011 | Keshavarz-Shokri et al. |
| 2011/0288121 A1 | 11/2011 | Sun et al. |
| 2011/0288122 A1 | 11/2011 | Van Goor et al. |
| 2012/0015999 A1 | 1/2012 | Alargova et al. |
| 2012/0046330 A1 | 2/2012 | Alargova et al. |
| 2012/0064157 A1 | 3/2012 | Dokou et al. |
| 2012/0071504 A1 | 3/2012 | Yang et al. |
| 2012/0220625 A1 | 8/2012 | Rowe et al. |
| 2012/0309758 A1 | 12/2012 | Sheth et al. |
| 2013/0018071 A1 | 1/2013 | Arekar et al. |

FOREIGN PATENT DOCUMENTS

| | | | | |
|---|---|---|---|---|
| WO | 0238126 A2 | 5/2002 | | |
| WO | WO 2010/019239 A2 * | 2/2010 | ............. | A61K 47/32 |
| WO | WO 2012/027731 A2 * | 3/2012 | ............... | A61K 9/14 |

OTHER PUBLICATIONS

Hancock, Bruno C., et al., "What is the True Solubility Advantage for Amorphous Pharmaceuticals," Pharmaceutical Research, 2000, vol. 17, No. 4, pp. 397-404.

Pencharz, P.B., et al., "Pathogenesis of malnutrition in cystic fibrosis, and its treatment," Clinical Nutrition, 2000, vol. 19, No. 6, pp. 387-394.

Jivraj, Mira, et al., "An overview of the different excipients useful for the direct compression of tablets," PSTT, 2000, vol. 3, No. 2, pp. 58-63.

Mashkovsky, M.D., "Medicaments," 2001, vol. 1, p. 11.

Tzetis, Maria, et al., "CFTR gene mutations—including three novel nucleotide substitutions—and haplotype background in patients with asthma, disseminated bronchiectasis and chronic obstructive pulmonary disease," Hum. Genet., 2001, vol. 108, pp. 216-221.

[Author unknown], "Guidance for Industry: Food-Effect Bioavailability and Fed Bioequivalence Studies," US Department of Health and Human Services, Food and Drug Administration, Center for Drug Evaluation and Research, 2002, 12 pages.

[Author unknown], "Living Well with COPD: Chronic Bronchitis and Emphysema: Patient Education Guide," American College of Chest Physicians and the Chest Foundation, 2004, 44 pages.

Dif, Fariel, et al., "Severe osteopenia in CFTR-null mice," Bone, 2004, vol. 35, pp. 595-603.

Guo, Dr. Jian-Hwa, "Lactose in Pharmaceutical Applications," Drug Delivery, 2004, vol. 4, No. 5, 7 pages.

International Search Report for PCT/US2013/028097, dated May 10, 2013, 3 pages.

Anonymous, "Vertex Pharmaceuticals initiates Phase I development for VX-770 in Cystic Fibrosis," [online], May 17, 2006 [Retrieved on May 18, 2009]. pp. 1-2, XP002528469.

Shead, Elizabeth F., et al., "Cystic fibrosis transmembrane conductance regulator (CFTR) is expressed in human bone," Thorax, 2007, vol. 62, pp. 650-651.

Vestner, A., et al., Pharmazie Unserer Zeit, vol. 37, No. 5, 2008, pp. 354-355, XP002581329.

Clunes, M.T., et al., "Front-runners for pharmacotherapeutic correction of the airway ion transport defect in cystic fibrosis," Current Opin. In Pharmacology, Jun. 2008 [retrieved on May 28, 2008], pp. 292-299, XP022711870.

Accurso, F.J., et al., "Final results of a 14- and 28-day study of VX-770 in subjects with CF," J. of Cystic Fibrosis, vol. 8, 2009, p. S25, XP026192272.

Jones, Andrew M., et al., "Emerging Treatments in Cystic Fibrosis," Drugs, ADIS International Ltd., NZ, 2009, vol. 69, No. 14, pp. 1903-1910, XP008134754.

Thomson, Sarah A., et al., "Minitablets: New Modality to Deliver Medicines to Preschool-aged Children," Pediatrics, 2009, vol. 123, No. 2, pp. e235-e238.

Van Goor, F., et al., J. of Cystic Fibrosis, vol. 8, Jun. 2009 [retrieved on Jun. 1, 2009], p. S17, XP026192243.

International Search Report for PCT/US2010/024609, dated May 17, 2010, 7 pages.

International Search Report for PCT/US2009/004629, dated Mar. 24, 2011, 3 pages.

Tissen, Corinna, et al., "Development of mini-tablets with 1mm and 2mm diameter," International Journal of Pharmaceutics, 2011, vol. 416, pp. 164-170.

International Search Report for PCT/US2011/033687, dated Aug. 23, 2011, 6 pages.

International Search Report for PCT/US2011/033689, dated Aug. 23, 2011, 6 pages.

International Search Report for PCT/US2011/033693, dated Aug. 23, 2011, 6 pages.

[Author unknown], Patient Information, Kalydeco™ (ivacaftor) Film-Coated Tablets, Reference ID 3079771, Jan. 2012, 13 pages.

International Search Report for PCT/US2011/049467, dated Apr. 2, 2011, 3 pages.

* cited by examiner

PHARMACEUTICAL COMPOSITION AND ADMINISTRATIONS THEREOF

PRIORITY CLAIM

The present application is a continuation of U.S. application Ser. No. 13/779,654, filed Feb. 27, 2013, which claims priority to U.S. Provisional Application Ser. No. 61/603,882, filed on Feb. 27, 2012, and U.S. Provisional Application Ser. No. 61/710,352, filed on Oct. 5, 2012. The entire contents of the aforementioned applications are incorporated by reference herein in their entirety.

FIELD OF THE INVENTION

The present invention relates to pharmaceutical compositions containing a solid dispersion of N-[2,4-Bis(1,1-dimethylethyl)-5-hydroxyphenyl]-1,4-dihydro-4-oxoquinoline-3-carboxamide including formulations of the solid dispersions into powders, granules and mini-tablets, methods for manufacturing and processing the powders, granules, and mini-tablets, and methods for treating cystic fibrosis employing the pharmaceutical composition.

BACKGROUND

Cystic fibrosis (CF) is a recessive genetic disease that affects approximately 30,000 children and adults in the United States and approximately 30,000 children and adults in Europe. Despite progress in the treatment of CF, there is no cure.

CF is caused by mutations in the cystic fibrosis transmembrane conductance regulator gene (CFTR) that encodes cystic fibrosis transmembrane conductance regulator protein (CFTR), an epithelial chloride ion channel responsible for aiding in the regulation of salt and water absorption and secretion in various tissues. Small molecule drugs, known as potentiators that increase the probability of CFTR channel opening represent one potential therapeutic strategy to treat CF.

Specifically, CFTR is a cAMP/ATP-mediated anion channel that is expressed in a variety of cells types, including absorptive and secretory epithelia cells, where it regulates anion flux across the membrane, as well as the activity of other ion channels and proteins. In epithelia cells, normal functioning of CFTR is critical for the maintenance of electrolyte transport throughout the body, including respiratory and digestive tissue. CFTR is composed of approximately 1480 amino acids that encode a protein made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

The gene encoding CFTR has been identified and sequenced (See Gregory, R. J. et al. (1990) Nature 347:382-386; Rich, D. P. et al. (1990) Nature 347:358-362), (Riordan, J. R. et al. (1989) Science 245:1066-1073). A defect or mutation in this gene causes mutations in CFTR resulting in cystic fibrosis ("CF"), the most common fatal genetic disease in humans. Cystic fibrosis affects approximately one in every 2,500 infants in the United States. Within the general United States population, up to 10 million people carry a single copy of the defective gene without apparent ill effects. In contrast, individuals with two copies of the CF associated gene suffer from the debilitating and fatal effects of CF, including chronic lung disease.

In patients with CF, mutations in CFTR endogenously expressed in respiratory epithelia leads to reduced apical anion secretion causing an imbalance in ion and fluid transport. The resulting decrease in anion transport contributes to enhanced mucus accumulation in the lung and the accompanying microbial infections that ultimately cause death in CF patients. In addition to respiratory disease, CF patients typically suffer from gastrointestinal problems and pancreatic insufficiency that, if left untreated, results in death. In addition, the majority of males with cystic fibrosis are infertile and fertility is decreased among females with cystic fibrosis. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). To date, >1000 disease causing mutations in the CF gene have been identified (http://www.genet.sickkids.on.ca/cftr/app). The most prevalent mutation is a deletion of phenylalanine at position 508 of the CFTR amino acid sequence, and is commonly referred to as ΔF508-CFTR. This mutation occurs in approximately 70% of the cases of cystic fibrosis and is associated with a severe disease.

The deletion of residue 508 in ΔF508-CFTR prevents the nascent protein from folding correctly. This results in the inability of the mutant protein to exit the ER, and traffic to the plasma membrane. As a result, the number of channels present in the membrane is far less than observed in cells expressing wild-type CFTR. In addition to impaired trafficking, the mutation results in defective channel gating. Together, the reduced number of channels in the membrane and the defective gating lead to reduced anion transport across epithelia leading to defective ion and fluid transport. (Quinton, P. M. (1990), FASEB J. 4: 2709-2727). Studies have shown, however, that the reduced numbers of ΔF508-CFTR in the membrane are functional, albeit less than wild-type CFTR. (Dalemans et al. (1991), Nature Lond. 354: 526-528; Denning et al., supra; Pasyk and Foskett (1995), J. Cell. Biochem. 270: 12347-50). In addition to ΔF508-CFTR, other disease causing mutations in CFTR that result in defective trafficking, synthesis, and/or channel gating could be up- or down-regulated to alter anion secretion and modify disease progression and/or severity.

Although CFTR transports a variety of molecules in addition to anions, it is clear that this role (the transport of anions) represents one element in an important mechanism of transporting ions and water across the epithelium. The other elements include the epithelial $Na^+$ channel, ENaC, $Na^+/2Cl^-/K^+$ co-transporter, $Na^+-K^+$-ATPase pump and the basolateral membrane $K^+$ channels, that are responsible for the uptake of chloride into the cell.

These elements work together to achieve directional transport across the epithelium via their selective expression and localization within the cell. Chloride absorption takes place by the coordinated activity of ENaC and CFTR present on the apical membrane and the $Na^+$—$K^+$-ATPase pump and $Cl^-$ ion channels expressed on the basolateral surface of the cell. Secondary active transport of chloride from the luminal side leads to the accumulation of intracellular chloride, which can then passively leave the cell via Cr channels, resulting in a vectorial transport. Arrangement of $Na^+/2Cl^-/K^+$ co-transporter, $Na^+$—$K^+$-ATPase pump and the basolateral membrane K⁺ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

As discussed above, it is believed that the deletion of residue 508 in ΔF508-CFTR prevents the nascent protein from folding correctly, resulting in the inability of this mutant protein to exit the ER, and traffic to the plasma membrane. As a result, insufficient amounts of the mature protein are present at the plasma membrane and chloride transport within epithelial tissues is significantly reduced. In fact, this cellular phenomenon of defective ER processing of ABC transporters by the ER machinery has been shown to be the underlying basis not only for CF disease, but for a wide range of other isolated and inherited diseases.

N-[2,4-bis(1,1-dimethylethyl)-5-hydroxyphenyl]-1,4-dihydro-4-oxoquinoline-3-carboxamide is a potent and selective CFTR potentiator of wild-type and mutant (including e.g., ΔF508, R117H, and G551D) forms of human CFTR. N-[2,4-bis(1,1-dimethylethyl)-5-hydroxyphenyl]-1,4-dihydro-4-oxoquinoline-3-carboxamide is useful for treatment of adult patients with cystic fibrosis and at least one G551D-CFTR allele.

Pediatric CF patients may require administration of pharmaceutical compositions in a dosage form that facilitates swallowing or that may be easily mixed with easily digested foods. The use of powders and crushed tablets in the administration of pharmaceutical compositions to children has often presented problems in administration and dosing. Administering crushed tablet formulations to children, can lead to absorption problems, fragments that are either too difficult to swallow or fail to solubilize and remain undigested resulting in therapeutic failure, or dosage inaccuracies. Additionally, the dosing of crushed tablets can lead to dosing inaccuracies because of difficulties associated with the handling of crushed tablets. The use of powder blends may also result in dosage inaccuracies. In other instances, active powder agents may remain adhered to the interior walls of a capsule, pouch, or packet at the time of administration, resulting in less than the required therapeutic dosage. Such dosing inaccuracies are particularly prevalent when the person administering the dose is inexperienced and when the dose is small, as in those used to treat pediatric patients. Dosage errors involving CF pharmaceutical active agents therefore become critical in pediatric populations, particularly considering that pharmaceutical CF active agents are administered in low doses (e.g. less than 100 mg or less than 50 mg per unit dose). These dosing inaccuracies become critical in pediatric patients having a low threshold for dose deviation.

Accordingly, there is a need for stable bioavailable pharmaceutical compositions of N-[2,4-bis(1,1-dimethylethyl)-5-hydroxyphenyl]-1,4-dihydro-4-oxoquinoline-3-carboxamide useful for treating patients, for example, CF patients having problems in swallowing adult tablets, including but not limited to pediatric patients, and methods for manufacturing and administering the same.

There is a need for a stable bioavailable pharmaceutical compositions of N-[2,4-bis(1,1-dimethylethyl)-5-hydroxyphenyl]-1,4-dihydro-4-oxoquinoline-3-carboxamide useful for treating a particular population with an unmet medical need, such as children under 6 years of age, children or infants who cannot swallow adult tablets.

There is a need for a stable bioavailable pharmaceutical compositions of N-[2,4-bis(1,1-dimethylethyl)-5-hydroxyphenyl]-1,4-dihydro-4-oxoquinoline-3-carboxamide which can be administered in combination with some common baby foods for treating infants.

There is a need for a stable bioavailable pharmaceutical compositions of N-[2,4-bis(1,1-dimethylethyl)-5-hydroxyphenyl]-1,4-dihydro-4-oxoquinoline-3-carboxamide which allows for accurate and flexible dosing in pediatric patients, including but not limited to infants, by changing the number of mini-tablets in the unit dose, packet, pouch, or capsule.

Compound 1 (N-[2,4-Bis(1,1-dimethylethyl)-5-hydroxyphenyl]-1,4-dihydro-4-oxoquinoline-3-carboxamide) has been granted a Breakthrough Therapy Designation from the Food and Drug Administration (FDA) for treatment of cystic fibrosis, one of only two such grants at the time of filing of this application. This demonstrates a significant unmet need for the effective treatment of the cause of cystic fibrosis over symptomatic treatments.

SUMMARY OF THE INVENTION

The present invention relates to pharmaceutical compositions comprising a solid dispersion of N-[2,4-Bis(1,1-dimethylethyl)-5-hydroxyphenyl]-1,4-dihydro-4-oxoquinoline-3-carboxamide, and methods of manufacturing and administering pharmaceutical compositions comprising N-[2,4-Bis(1,1-dimethylethyl)-5-hydroxyphenyl]-1,4-dihydro-4-oxoquinoline-3-carboxamide. The pharmaceutical compositions comprising a solid dispersion of N-[2,4-Bis(1,1-dimethylethyl)-5-hydroxyphenyl]-1,4-dihydro-4-oxoquinoline-3-carboxamide (Compound 1 herein after) may also include one or more of the following excipients: one or more fillers, a sweetener, a disintegrant, a wetting agent, a glidant, and a lubricant.

The pharmaceutical compositions of the present invention provide a free-flowing powder composition that can be formulated into tablets, mini-tablets, granules, pellets, troches and other dosage forms. Powder forms of the pharmaceutical composition, such as tablets, mini-tablets, granules, sprinkles, pellets, beads, particles, particulates, troches and other dosage forms containing powder forms of the pharmaceutical composition can be contained in capsules, pouches, packets, sachets, bottles or blister packs. Tablets, mini-tablets, granules, sprinkles, pellets, beads, particulates, or particles can also be compressed into other solid forms. In one embodiment, the pharmaceutical composition can include powder formulations described herein containing: a solid dispersion comprising substantially amorphous or amorphous Compound 1 and an excipient (for example, one or more fillers, a sweetener, a disintegrant, optionally a wetting agent, a glidant and a lubricant) and formulated into a capsule or a packet, the capsule or the packet containing a specified amount of substantially amorphous or amorphous Compound 1 ranging from at least 1 mg to at least 250 mg. Tablets, mini-tablets, granules, sprinkles, pellets, beads, particulates, or particles and other dosage forms may comprise granulated particles or other powder forms of substantially amorphous or amorphous Compound 1.

In one embodiment, the present invention provides a pharmaceutical composition comprising a solid dispersion of amorphous Compound 1, wherein the solid dispersion comprises up to about 1 mg of amorphous Compound 1. In another embodiment, the present invention provides a pharmaceutical composition comprising a solid dispersion of amorphous Compound 1, wherein the solid dispersion comprises up to about 5 mg of amorphous Compound 1. In certain embodiments, the solid dispersion comprises up to about 5 mg of substantially amorphous Compound 1. For instance, the solid dispersion comprises 0.25 mg, 0.5 mg, 0.75 mg, 1 mg, 2 mg, 3 mg, 4 mg, or 5 mg of amorphous or substantially amorphous Compound 1.

In another embodiment, the present invention provides a pharmaceutical composition comprising a solid dispersion of substantially amorphous Compound 1, wherein the solid dispersion comprises up to about 1 mg of substantially amorphous Compound 1. In certain embodiments, the solid dispersion comprises up to about 1 mg of amorphous or substantially amorphous Compound 1. For instance, the solid dispersion comprises 0.25 mg, 0.5 mg, 0.75 mg, or 1 mg of amorphous or substantially amorphous Compound 1.

In one embodiment, the present invention provides a pharmaceutical composition comprising a solid dispersion of amorphous Compound 1, wherein the solid dispersion comprises about 5 mg of amorphous Compound 1. In certain embodiments, the solid dispersion comprises about 5 mg of substantially amorphous Compound 1.

In one embodiment, the present invention provides a pharmaceutical composition comprising a solid dispersion of amorphous Compound 1, wherein the solid dispersion comprises about 10 mg of amorphous Compound 1. In certain embodiments, the solid dispersion comprises about 10 mg of substantially amorphous Compound 1.

In one embodiment, the present invention provides a pharmaceutical composition comprising a solid dispersion of amorphous Compound 1, wherein the solid dispersion comprises about 12.5 mg of amorphous Compound 1. In certain embodiments, the solid dispersion comprises about 12.5 mg of substantially amorphous Compound 1.

In one embodiment, the present invention provides a pharmaceutical composition comprising a solid dispersion of amorphous Compound 1, wherein the solid dispersion comprises about 15 mg of amorphous Compound 1. In certain embodiments, the solid dispersion comprises about 15 mg of substantially amorphous Compound 1.

In one embodiment, the present invention provides a pharmaceutical composition comprising a solid dispersion of amorphous Compound 1, wherein the solid dispersion comprises about 20 mg of amorphous Compound 1. In certain embodiments, the solid dispersion comprises about 20 mg of substantially amorphous Compound 1.

In one embodiment, the present invention provides a pharmaceutical composition comprising a solid dispersion of amorphous Compound 1, wherein the solid dispersion comprises about 25 mg of amorphous Compound 1. In certain embodiments, the solid dispersion comprises about 25 mg of substantially amorphous Compound 1.

In one embodiment, the present invention provides a pharmaceutical composition comprising a solid dispersion of amorphous Compound 1, wherein the solid dispersion comprises about 30 mg of amorphous Compound 1. In certain embodiments, the solid dispersion comprises about 30 mg of substantially amorphous Compound 1.

In one embodiment, the present invention provides a pharmaceutical composition comprising a solid dispersion of amorphous Compound 1, wherein the solid dispersion comprises about 35 mg of amorphous Compound 1. In certain embodiments, the solid dispersion comprises about 35 mg of substantially amorphous Compound 1.

In one embodiment, the present invention provides a pharmaceutical composition comprising a solid dispersion of amorphous Compound 1, wherein the solid dispersion comprises about 37.5 mg of amorphous Compound 1. In certain embodiments, the solid dispersion comprises about 37.5 mg of substantially amorphous Compound 1.

In one embodiment; the present invention provides a pharmaceutical composition comprising a solid dispersion of amorphous Compound 1, wherein the solid dispersion comprises about 40 mg of amorphous Compound 1. In certain embodiments, the solid dispersion comprises about 40 mg of substantially amorphous Compound 1.

In one embodiment, the present invention provides a pharmaceutical composition comprising a solid dispersion of amorphous Compound 1, wherein the solid dispersion comprises about 45 mg of amorphous Compound 1. In certain embodiments, the solid dispersion comprises about 45 mg of substantially amorphous Compound 1.

In one embodiment, the present invention provides a pharmaceutical composition comprising a solid dispersion of amorphous Compound 1, wherein the solid dispersion comprises about 50 mg of amorphous Compound 1. In certain embodiments, the solid dispersion comprises about 50 mg of substantially amorphous Compound 1.

In one embodiment, the present invention provides a pharmaceutical composition comprising a solid dispersion of amorphous Compound 1, wherein the solid dispersion comprises about 62.5 mg of amorphous Compound 1. In certain embodiments, the solid dispersion comprises about 62.5 mg of substantially amorphous Compound 1.

In one embodiment, the present invention provides a pharmaceutical composition comprising a solid dispersion of amorphous Compound 1, wherein the solid dispersion comprises about 75 mg of amorphous Compound 1. In certain embodiments, the solid dispersion comprises about 75 mg of substantially amorphous Compound 1.

In one embodiment, the present invention provides a pharmaceutical composition comprising a solid dispersion of amorphous Compound 1, wherein the solid dispersion comprises about 100 mg of amorphous Compound 1. In certain embodiments, the solid dispersion comprises about 100 mg of substantially amorphous Compound 1.

In one embodiment, the present invention provides a pharmaceutical composition comprising a solid dispersion of amorphous Compound 1, wherein the solid dispersion comprises about 125 mg of amorphous Compound 1. In certain embodiments, the solid dispersion comprises about 125 mg of substantially amorphous Compound 1.

In one embodiment, the present invention provides a pharmaceutical composition comprising a solid dispersion of amorphous Compound 1, wherein the solid dispersion comprises about 150 mg of amorphous Compound 1. In certain embodiments, the solid dispersion comprises about 150 mg of substantially amorphous Compound 1.

In one embodiment, the present invention provides a pharmaceutical composition comprising a solid dispersion of amorphous Compound 1, wherein the solid dispersion comprises about 175 mg of amorphous Compound 1. In certain embodiments, the solid dispersion comprises about 175 mg of substantially amorphous Compound 1.

In one embodiment, the present invention provides a pharmaceutical composition comprising a solid dispersion of amorphous Compound 1, wherein the solid dispersion comprises about 200 mg of amorphous Compound 1. In certain embodiments, the solid dispersion comprises about 200 mg of substantially amorphous Compound 1.

In one embodiment, the present invention provides a pharmaceutical composition comprising a solid dispersion of amorphous Compound 1, wherein the solid dispersion comprises about 225 mg of amorphous Compound 1. In certain embodiments, the solid dispersion comprises about 225 mg of substantially amorphous Compound 1.

In one embodiment, the present invention provides a pharmaceutical composition comprising a solid dispersion of amorphous Compound 1, wherein the solid dispersion comprises about 250 mg of amorphous Compound 1. In certain embodiments, the solid dispersion comprises about 250 mg of substantially amorphous Compound 1.

In one aspect, the solid form of Compound 1 in the pharmaceutical composition is a solid dispersion comprising substantially amorphous or amorphous Compound 1 and a polymer, such as hydroxypropylmethylcellulose (HPMC), hydroxypropylmethylcellulose acetate succinate (HPMCAS), polyvinylpyrrolidone/vinyl acetate copolymer (PVP/VA), polyvinylpyrrolidone (PVP), methacrylic acid/methacrylate copolymers, hydroxypropyl cellulose (HPC), or any combination thereof. Embodiments of this aspect include one or more of the following: The solid dispersion is a powder having mean particle diameter of greater than about 5 μm or the solid dispersion has a bulk density of about 0.10 g/cc or greater.

In some instances, the solid dispersion has a concentration of at least 20 wt % of Compound 1, by weight of the solid dispersion. In other instances, the solid dispersion comprises 80 wt % or less of HPMCAS. Some solid dispersions comprise from about 40 wt % to about 60 wt % of substantially amorphous or amorphous Compound 1 by weight of the solid dispersion and from about 60 wt % to about 40 wt % of polymer by weight of the solid dispersion. Other solid dispersions comprise from about 60 wt % to about 95 wt % of substantially amorphous or amorphous Compound 1 by weight of the solid dispersion and from about 40 wt % to about 5 wt % of polymer by weight of the solid dispersion.

Solid dispersions can also optionally comprise additives such as a wetting agent (e.g., sodium lauryl sulfate (SLS)), which can be present in a concentration of less than 10 wt % of wetting agent by weight of solid dispersion.

Still other solid dispersions comprise from about 45 wt % to about 85 wt % of substantially amorphous or amorphous Compound 1, from about 0.45 wt % to about 0.55 wt % of SLS, and from about 14.45 wt % to about 55.55 wt % of HPMCAS by weight of the solid dispersion.

In still further embodiments, the pharmaceutical compositions also comprise one or more fillers (e.g., mannitol, celluloses, calcium carbonate, starches, sugars (e.g., dextrose, lactose or the like)) in concentrations of at least about 10 wt % by weight of the composition; a sweetener (e.g. sucralose, sorbitol, saccharin, fructose, aspartame, or a combination thereof) in a concentration of about 10% or less by weight of this composition; a disintegrant (e.g., croscarmellose sodium, sodium starch glycolate, or a combination thereof) in concentrations of about 10 wt % or less by weight of the composition; optionally a wetting agent (e.g., sodium lauryl sulfate, SLS) in concentrations of about 10 wt % or less by weight of the composition; a glidant (e.g., colloidal silicon dioxide, talc, or a combination thereof) in concentrations of about 2 wt % or less by weight of the composition; and a lubricant (e.g., magnesium stearate, stearic acid, hydrogenated oil, sodium stearyl fumarate, or any combination thereof) in concentrations of about 5 wt % or less by weight of the composition.

Such pharmaceutical compositions can optionally comprise one or more colorants, fragrances, and/or flavors to enhance its visual appeal, taste, and scent.

In other embodiments, the present invention provides a pharmaceutical composition in the form of a powder composition, as described above, which can also be formulated into solid unit dose forms for the treatment of the various diseases associated with wild-type and mutant (including e.g., ΔF508, R117H, and G551D) forms of human CFTR. The present invention therefore also contemplates novel dosage forms such as granules, pellets, mini-tablets and other solid dose forms which overcome the problems described above with respect to dosing inaccuracies, in particular, for pediatric patients. These stable, solid unit dose forms can have any shape, including oval, spherical, cylindrical, elliptical, cubical, square, or rectangular among others. Tablets or mini-tablets may have flat, shallow, standard, deep convex, or double deep convex faces or combinations thereof.

In one aspect, the pharmaceutical composition can be formulated into a unit dose form, for example, a capsule, a sachet, and the like, containing at least one or more mini-tablets to simplify the administration of the pharmaceutical composition. In some embodiments, the unit dose can include a capsule or a packet containing at least one mini-tablet, or a plurality of mini-tablets as provided above and in the descriptions below. In another embodiment, the unit dose can include a pouch, a packet or sachet containing a specific dose of substantially amorphous or amorphous Compound 1 in powder form.

Such pharmaceutical compositions as described herein can be in the form of a mini-tablet, and/or a plurality of mini-tablets made up of any number of mini-tablets (e.g., at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, or any number greater than 60). The pharmaceutical compositions as described herein can also be in the form of a mini-tablet, and/or a plurality of mini-tablets (e.g. at least 2, at least 4, at least 6, at least 8, at least 10, at least 12, at least 14, at least 16, at least 18, at least 20, at least 22, at least 24, at least 26, at least 28, at least 29, at least 30, at least 32, at least 34, at least 36, at least 38, at least 39 or at least 60 mini-tablets, inclusive of all of the ranges in between). In one embodiment, the pharmaceutical composition is in the form of 10, 19, 29 or 58 mini-tablets. In another embodiment, the pharmaceutical composition is in the form of 13, 26, 39 or 77 mini-tablets. In yet another embodiment, the pharmaceutical composition is in the form of 30, 60, 90 or 179 mini-tablets. In another embodiment, the pharmaceutical composition is in the form of 1, 2, 3, 4 or 5 mini-tablets. In another embodiment, the pharmaceutical composition is in the form of 13, 21, 26, 39, 52, 65, 78, 91, 104, 117, 130, or 336 mini-tablets. In still a further embodiment, the pharmaceutical composition is in the form of 5 mini-tablets. In another embodiment, the pharmaceutical composition is in the form of 10 mini-tablets. In one embodiment, the pharmaceutical composition is in the form of 13 mini-tablets. In still a further embodiment, the pharmaceutical composition is in the form of 15 mini-tablets. In another embodiment, the pharmaceutical composition is in the form of 21 mini-tablets. In one embodiment, the pharmaceutical composition is in the form of 26 mini-tablets. In another embodiment, the pharmaceutical composition is in the form of 39 mini-tablets. In one embodiment, the pharmaceutical composition is in the form of 52 mini-tablets. Another aspect of the present invention provides a pharmaceutical composition consisting of at least one mini-tablet, the mini-tablet comprising a solid dispersion, one or more fillers, a sweetener, a disintegrant, optionally a wetting agent, a glidant, and a lubricant, wherein the mini-tablet has a dissolution of at least about 50% in about 30 minutes, and the solid dispersion comprises amorphous Compound 1. As noted below, dissolution can be measured with a standard USP Type II apparatus containing a dissolution media of 0.5 or 0.7% sodium lauryl sulfate dissolved in 900 mL of 50 mM sodium phosphate buffer at a pH of 6.8 at a temperature of about 37° C. The dissolution of mini-tablets is determined by recording the dissolution of a plurality of mini-tablets containing, in the aggregate, 75 mg (using 0.5% sodium lauryl sulfate) or 150 mg (using 0.7% sodium lauryl sulfate) of Compound 1 in the dissolution media. Individual mini-tablets can exhibit dissolution that is lower, equivalent to or higher than the dissolution of the plurality, with the mean dissolution of each individual mini-tablet being similar to the mean dissolution of the plurality.

Another aspect of the present invention provides a pharmaceutical composition consisting of a mini-tablet or a plurality of mini-tablets wherein each mini-tablet comprises a solid dispersion comprising amorphous or substantially amorphous Compound 1 and HPMCAS; and, one or more fillers, a sweetener, a disintegrant, optionally a wetting agent, a glidant, and a lubricant, wherein the mini-tablet has an average tensile strength of between about 0.5 MPa and about 4 MPa. In some embodiments, the mini-tablet has an average tensile strength of at least 0.5 MPa, at least 1.0 MPa, at least 1.5 MPa, at least 2.0 MPa, or at least 2.5 MPa. In yet another aspect, the mini-tablets described herein are optionally coated.

In another aspect, the coated mini-tablets described herein are colored, such as by incorporating a colorant in the mini-tablet formulation or by coloring the surface of the mini-tablet.

In another aspect, the present invention provides novel manufacturing techniques which enable the formulation of miniaturized versions of adult dosage forms and other solid unit dose forms described above, that range in size from about 1 mm to about 5 mm (e.g. 2 mm or 4 mm) in any one or more dimensions. These miniaturized solid unit dose forms can be further formulated to be encapsulated into capsules, bottles or sachets. In other embodiments, the pharmaceutical composition comprising a mini-tablet or plurality of mini-tablets can be in pouches, sachets, packets, bottles or blister packs, or optionally further compressed into different solid unit dose forms that can be easily administered to patients that have difficulty in swallowing adult sized tablet formulations. As such, these novel powder pharmaceutical compositions and unit dose forms containing said pharmaceutical compositions are organoleptically acceptable to said patients, are sprinkled into liquids or soft food and disintegrated or dispersed in those various liquids and soft foods or food compositions such as milk (including breast milk), baby formula or infant formula, apple sauce, water, plain yogurt, ice cream, baby food, ensuring that the entire prescribed dose has been disintegrated or dispersed and are capable of administration to patients having difficulty swallowing adult tablets. Baby food includes, but is not limited to, carrots or carrot puree. The pharmaceutical composition can also be administered in strawberry preserves, rice pudding, chocolate pudding and the like. In one embodiment, the unit dose form is sprinkled into soft food and administered. In another embodiment, the unit dose form is sprinkled into liquid and administered. In one embodiment, the unit dose form is sprinkled into soft food, mixed, and administered. In another embodiment, the unit dose form is sprinkled into liquid, mixed, and administered. Liquids may include, but are not limited to, baby formula, infant formula, milk or breast milk. In some instances, for smaller sized mini-tablets or granules, the contents of packets, pouches, capsules, bottles or sachets may be administered directly to the mouth followed by breast milk or formula. Methods of administration of the present invention can optionally also include, for smaller sized mini-tablets or granules, administering the contents of packets, pouches, capsules, bottles or sachets directly to the mouth followed by a liquid or beverage. In some embodiments, any methods of administration of the present invention can optionally include orally administering with fat-containing food such as a standard CF high-calorie, high-fat meal or snack. In other embodiments, any methods of administration of the present invention can optionally include orally administering concurrently with, before, or after fat-containing food such as a standard CF high-calorie, high-fat meal or snack. In one embodiment, the pharmaceutical compositions of the present invention and solid unit dose forms thereof find particular utility in the treatment of CFTR mediated disease in the pediatric patient population.

Another aspect of the present invention provides a method of producing a pharmaceutical composition comprising the steps of providing an admixture of a solid dispersion of amorphous Compound 1, a sweetener, one or more fillers, a disintegrant, optionally a wetting agent, a glidant, and a lubricant, and compressing the admixture into a solid dose form, for example a granule, a pellet or mini-tablets, the solid dose form having a dissolution of at least about 50% in about 30 minutes. In one example, the admixture is compressed to a solid dose form, for example, a mini-tablet having an average tensile strength of between about 0.5 MPa and about 4 MPa. Another aspect of the present invention provides a method of producing a pharmaceutical composition comprising the steps of providing an admixture of a solid dispersion of amorphous Compound 1, one or more fillers, a sweetener, a disintegrant, optionally a wetting agent, a glidant, and a lubricant, and compressing the admixture into a solid dose form, for example, one or more mini-tablets, wherein the solid dose form is capable of dissolution of at least about 70% in about 30 minutes.

Another aspect of the present invention provides a method of administering a pharmaceutical composition by orally administering to a patient, for example, a human pediatric patient, at least once per day, a unit dose (via capsule, sachet, blister pack, pouch, packet, bottle, or other container) comprising powder form of the pharmaceutical composition and/or a mini-tablet or plurality of mini-tablets, wherein the unit dose comprises a solid dispersion of substantially amorphous or amorphous Compound 1, one or more fillers, a sweetener, a disintegrant, optionally a wetting agent, a glidant, and a lubricant, in which the unit dose comprises at least about 10 mg of substantially amorphous or amorphous Compound 1. In some embodiments, the unit dose is orally administered to the patient once per day. In some other embodiments, the unit dose is orally administered to the patient twice per day or every 12 hours.

Another aspect of the present invention provides a method of administering a pharmaceutical composition by orally administering to a patient, for example, a human pediatric patient, at least once per day, a unit dose (via capsule, sachet, blister pack, pouch, packet, bottle, or other container) comprising powder form of the pharmaceutical composition and/or a mini-tablet or plurality of mini-tablets, wherein the unit dose comprises a solid dispersion of substantially amorphous or amorphous Compound 1, one or more fillers, a sweetener, a disintegrant, optionally a wetting agent, a glidant, and a lubricant, in which the unit dose comprises at least about 12.5 mg of substantially amorphous or amorphous Compound 1. In some embodiments, the unit dose is orally administered to the patient once per day. In some other embodiments, the unit dose is orally administered to the patient twice per day, or every 12 hours.

Another aspect of the present invention provides a method of administering a pharmaceutical composition by orally administering to a patient, for example, a human pediatric patient, at least once per day, a unit dose (via capsule, sachet, blister pack, pouch, packet, bottle, or other container) comprising powder form of the pharmaceutical composition and/or a mini-tablet or plurality of mini-tablets, wherein the unit dose comprises a solid dispersion of substantially amorphous or amorphous Compound 1, one or more fillers, a sweetener, a disintegrant, optionally a wetting agent, a glidant, and a lubricant, in which the unit dose comprises at least about 15 mg of substantially amorphous or amorphous Compound 1. In some embodiments, the unit dose is orally administered to the patient once per day. In some other embodiments, the unit dose is orally administered to the patient twice per day, or every 12 hours.

Another aspect of the present invention provides a method of administering a pharmaceutical composition by orally administering to a patient, for example, a human pediatric patient, at least once per day, a unit dose (via capsule, sachet, blister pack, pouch, packet, bottle, or other container) comprising powder form of the pharmaceutical composition and/or a mini-tablet or plurality of mini-tablets, wherein the unit dose comprises a solid dispersion of substantially amorphous or amorphous Compound 1, one or more fillers, a sweetener, a disintegrant, optionally a wetting agent, a glidant, and a lubricant, in which the unit dose comprises at least about 20 mg of substantially amorphous or amorphous Compound 1. In some embodiments, the unit dose is orally administered to the patient once per day. In some other embodiments, the unit dose is orally administered to the patient twice per day, or every 12 hours.

Another aspect of the present invention provides a method of administering a pharmaceutical composition by orally administering to a patient, for example, a human pediatric patient, at least once per day, a unit dose (via capsule, sachet, blister pack, pouch, packet, bottle, or other container) comprising powder form of the pharmaceutical composition and/or a mini-tablet or plurality of mini-tablets, wherein the unit dose comprises a solid dispersion of substantially amorphous or amorphous Compound 1, one or more fillers, a sweetener, a disintegrant, optionally a wetting agent, a glidant, and a lubricant, in which the unit dose comprises at least about 25 mg of substantially amorphous or amorphous Compound 1. In some embodiments, the unit dose is orally administered to the patient once per day. In some other embodiments, the unit dose is orally administered to the patient twice per day, or every 12 hours.

Another aspect of the present invention provides a method of administering a pharmaceutical composition by orally administering to a patient, for example, a human pediatric patient, at least once per day, a unit dose (via capsule, sachet, blister pack, pouch, packet, bottle, or other container) comprising powder form of the pharmaceutical composition and/or a mini-tablet or plurality of mini-tablets, wherein the unit dose comprises a solid dispersion of substantially amorphous or amorphous Compound 1, one or more fillers, a sweetener, a disintegrant, optionally a wetting agent, a glidant, and a lubricant, in which the unit dose comprises at least about 30 mg of substantially amorphous or amorphous Compound 1. In some embodiments, the unit dose is orally administered to the patient once per day. In some other embodiments, the unit dose is orally administered to the patient twice per day, or every 12 hours.

Another aspect of the present invention provides a method of administering a pharmaceutical composition by orally administering to a patient, for example, a human pediatric patient, at least once per day, a unit dose (via capsule, sachet, blister pack, pouch, packet, bottle, or other container) comprising powder form of the pharmaceutical composition and/or a mini-tablet or plurality of mini-tablets, wherein the unit dose comprises a solid dispersion of substantially amorphous or amorphous Compound 1, one or more fillers, a sweetener, a disintegrant, optionally a wetting agent, a glidant, and a lubricant, in which the unit dose comprises at least about 37.5 mg of substantially amorphous or amorphous Compound 1. In some embodiments, the unit dose is orally administered to the patient once per day. In some other embodiments, the unit dose is orally administered to the patient twice per day, or every 12 hours.

Another aspect of the present invention provides a method of administering a pharmaceutical composition by orally administering to a patient, for example, a human pediatric patient, at least once per day, a unit dose (via capsule, sachet, blister pack, pouch, packet, bottle, or other container) comprising powder form of the pharmaceutical composition and/or a mini-tablet or plurality of mini-tablets, wherein the unit dose comprises a solid dispersion of substantially amorphous or amorphous Compound 1, one or more fillers, a sweetener, a disintegrant, optionally a wetting agent, a glidant, and a lubricant, in which the unit dose comprises at least about 40 mg of substantially amorphous or amorphous Compound 1. In some embodiments, the unit dose is orally administered to the patient once per day. In some other embodiments, the unit dose is orally administered to the patient twice per day, or every 12 hours.

Another aspect of the present invention provides a method of administering a pharmaceutical composition by orally administering to a patient, for example, a human pediatric patient, at least once per day, a unit dose (via capsule, sachet, blister pack, pouch, packet, bottle, or other container) comprising powder form of the pharmaceutical composition and/or a mini-tablet or plurality of mini-tablets, wherein the unit dose comprises a solid dispersion of substantially amorphous or amorphous Compound 1, one or more fillers, a sweetener, a disintegrant, optionally a wetting agent, a glidant, and a lubricant, in which the unit dose comprises at least about 50 mg of substantially amorphous or amorphous Compound 1. In some embodiments, the unit dose is orally administered to the patient once per day. In some other embodiments, the unit dose is orally administered to the patient twice per day, or every 12 hours.

Another aspect of the present invention provides a method of administering a pharmaceutical composition by orally administering to a patient, for example, a human pediatric patient, at least once per day, a unit dose (via capsule, sachet, blister pack, pouch, packet, bottle, or other container) comprising powder form of the pharmaceutical composition and/or a mini-tablet or plurality of mini-tablets, wherein the unit dose comprises a solid dispersion of substantially amorphous or amorphous Compound 1, one or more fillers, a sweetener, a disintegrant, optionally a wetting agent, a glidant, and a lubricant, in which the unit dose comprises at least about 62.5 mg of substantially amorphous or amorphous Compound 1. In some embodiments, the unit dose is orally administered to the patient once per day. In some other embodiments, the unit dose is orally administered to the patient twice per day, or every 12 hours.

Another aspect of the present invention provides a method of administering a pharmaceutical composition by orally administering to a patient, for example, a human pediatric patient, at least once per day, a unit dose (via capsule, sachet, blister pack, pouch, packet, bottle, or other container) comprising powder form of the pharmaceutical composition and/or a mini-tablet or plurality of mini-tablets, wherein the unit dose comprises a solid dispersion of substantially amorphous or amorphous Compound 1, one or more fillers, a sweetener, a disintegrant, optionally a wetting agent, a glidant, and a lubricant, in which the unit dose comprises at least about 75 mg of substantially amorphous or amorphous Compound 1. In some embodiments, the unit dose is orally administered to the patient once per day. In some other embodiments, the unit dose is orally administered to the patient twice per day, or every 12 hours.

Another aspect of the present invention provides a method of administering a pharmaceutical composition by orally administering to a patient, for example, a human pediatric patient, at least once per day, a unit dose (via capsule, sachet, blister pack, pouch, packet, bottle, or other container) comprising powder form of the pharmaceutical composition and/or a mini-tablet or plurality of mini-tablets, wherein the unit dose comprises a solid dispersion of substantially amorphous or amorphous Compound 1, one or more fillers, a sweetener, a disintegrant, optionally a wetting agent, a glidant, and a lubricant, in which the unit dose comprises at least about 100 mg of substantially amorphous or amorphous Compound 1. In some embodiments, the unit dose is orally administered to the patient once per day. In some other embodiments, the unit dose is orally administered to the patient twice per day.

Another aspect of the present invention provides a method of administering a pharmaceutical composition by orally administering to a patient, for example, a human pediatric patient, at least once per day, a unit dose (via capsule, sachet, blister pack, pouch, packet, bottle, or other container) comprising powder form of the pharmaceutical composition and/or a mini-tablet or plurality of mini-tablets, wherein the unit dose comprises a solid dispersion of substantially amorphous or amorphous Compound 1, one or more fillers, a sweetener, a disintegrant, optionally a wetting agent, a glidant, and a lubricant, in which the unit dose comprises at least about 125 mg of substantially amorphous or amorphous Compound 1. In some embodiments, the unit dose is orally administered to the patient once per day. In some other embodiments, the unit dose is orally administered to the patient twice per day.

Another aspect of the present invention provides a method of administering a pharmaceutical composition by orally administering to a patient, for example, a human pediatric patient, at least once per day, a unit dose (via capsule, sachet, blister pack, pouch, packet, bottle, or other container) comprising powder form of the pharmaceutical composition and/or a mini-tablet or plurality of mini-tablets, wherein the unit dose comprises a solid dispersion of substantially amorphous or amorphous Compound 1, one or more fillers, a sweetener, a disintegrant, optionally a wetting agent, a glidant, and a lubricant, in which the unit dose comprises at least about 150 mg of substantially amorphous or amorphous Compound 1. In some embodiments, the unit dose is orally administered to the patient once per day. In some other embodiments, the unit dose is orally administered to the patient twice per day.

Another aspect of the present invention provides a method of administering a pharmaceutical composition by orally administering to a patient, for example, a human pediatric patient, at least once per day, a unit dose (via capsule, sachet, blister pack, pouch, packet, bottle, or other container) comprising powder form of the pharmaceutical composition and/or a mini-tablet or plurality of mini-tablets, wherein the unit dose comprises a solid dispersion of substantially amorphous or amorphous Compound 1, one or more fillers, a sweetener, a disintegrant, optionally a wetting agent, a glidant, and a lubricant, in which the unit dose comprises at least about 175 mg of substantially amorphous or amorphous Compound 1. In some embodiments, the unit dose is orally administered to the patient once per day. In some other embodiments, the unit dose is orally administered to the patient twice per day.

Another aspect of the present invention provides a method of administering a pharmaceutical composition by orally administering to a patient, for example, a human pediatric patient, at least once per day, a unit dose (via capsule, sachet, blister pack, pouch, packet, bottle, or other container) comprising powder form of the pharmaceutical composition and/or a mini-tablet or plurality of mini-tablets, wherein the unit dose comprises a solid dispersion of substantially amorphous or amorphous Compound 1, one or more fillers, a sweetener, a disintegrant, optionally a wetting agent, a glidant, and a lubricant, in which the unit dose comprises at least about 200 mg of substantially amorphous or amorphous Compound 1. In some embodiments, the unit dose is orally administered to the patient once per day. In some other embodiments, the unit dose is orally administered to the patient twice per day.

Another aspect of the present invention provides a method of administering a pharmaceutical composition by orally administering to a patient, for example, a human pediatric patient, at least once per day, a unit dose (via capsule, sachet, blister pack, pouch, packet, bottle, or other container) comprising powder form of the pharmaceutical composition and/or a mini-tablet or plurality of mini-tablets, wherein the unit dose comprises a solid dispersion of substantially amorphous or amorphous Compound 1, one or more fillers, a sweetener, a disintegrant, optionally a wetting agent, a glidant, and a lubricant, in which the unit dose comprises at least about 225 mg of substantially amorphous or amorphous Compound 1. In some embodiments, the unit dose is orally administered to the patient once per day. In some other embodiments, the unit dose is orally administered to the patient twice per day.

Another aspect of the present invention provides a method of administering a pharmaceutical composition by orally administering to a patient, for example, a human pediatric patient, at least once per day, a unit dose (via capsule, sachet, blister pack, pouch, packet, bottle, or other container) comprising powder form of the pharmaceutical composition and/or a mini-tablet or plurality of mini-tablets, wherein the unit dose comprises a solid dispersion of substantially amorphous or amorphous Compound 1, one or more fillers, a sweetener, a disintegrant, optionally a wetting agent, a glidant, and a lubricant, in which the unit dose comprises at least about 250 mg of substantially amorphous or amorphous Compound 1. In some embodiments, the unit dose is orally administered to the patient once per day. In some other embodiments, the unit dose is orally administered to the patient twice per day.

Unit dose forms useful in this method comprise a solid dispersion containing at least about 5 mg of substantially amorphous or amorphous Compound 1, at least about 10 mg of substantially amorphous or amorphous Compound 1, at least 12.5 mg of substantially amorphous or amorphous Compound 1, at least 15 mg of substantially amorphous or amorphous Compound 1, at least about 20 mg of substantially amorphous or amorphous Compound 1, at least 25 mg of substantially amorphous or amorphous Compound 1, at least about 30 mg of substantially amorphous or amorphous Compound 1, at least 37.5 mg of substantially amorphous or amorphous Compound 1, at least about 40 mg of substantially amorphous or amorphous Compound 1, at least 50 mg of substantially amorphous or amorphous Compound 1, at least 62.5 mg of substantially amorphous or amorphous Compound 1, at least 75 mg of substantially amorphous or amorphous Compound 1, at least 100 mg of substantially amorphous or amorphous Compound 1, at least 125 mg of substantially amorphous or amorphous Compound 1, at least 150 mg of substantially amorphous or amorphous Compound 1, at least 175 mg of substantially amorphous or amorphous Compound 1, at least 200 mg of substantially amorphous or amorphous Compound 1, at least 225 mg of substantially amorphous or amorphous Compound 1, or at least 250 mg of substantially amorphous or amorphous Compound 1. Some unit dosage forms useful in this method comprise a solid dispersion containing at least about 1 mg to about 250 mg of substantially amorphous or amorphous Compound 1 (including all of the values and ranges contained therein) in admixture with one or more excipients.

In another aspect, the present invention provides a method for manufacturing a unit dose form comprising a mini-tablet or plurality of mini-tablets comprising the pharmaceutical composition described herein. The method includes the steps of a) mixing a solid dispersion of substantially amorphous Compound 1 or amorphous Compound 1 and a polymer, the polymer comprising HPMCAS, with a glidant, a sweetener and optionally a wetting agent to form a first mixture;

b) screening the first mixture;

c) blending the screened first mixture to 20% of a screened lubricant to form a first blended mixture;

d) blending screened filler and screened disintegrant to the first blended mixture forming a second blended mixture;

e) de-lumping the second blended mixture forming a homogeneous mixture;

f) mixing 80% of the screened lubricant with the homogeneous mixture forming a compression mixture; and g) compressing the compression mixture to form mini-tablets. In other embodiments, the mini-tablets of the present invention can be made according to the following steps:

i) mixing a solid dispersion of substantially amorphous Compound 1 or amorphous Compound 1 and a polymer, the polymer comprising HPMCAS, PVP/VA or combinations thereof with a glidant, and a sweetener to form a first mixture;

ii) screening the first mixture;

iii) blending the screened first mixture;

iv) blending screened filler and screened disintegrant with the first blended mixture forming a second blended mixture;

v) de-lumping the second blended mixture forming a homogeneous mixture;

vi) mixing the screened lubricant with the homogeneous mixture forming a compression mixture; and vii) compressing the compression mixture to form mini-tablets.

The administration comprises orally administering to a patient at least once per day at least one unit dosage form comprising a solid dispersion of substantially amorphous or amorphous Compound 1, one or more fillers, a sweetener, a disintegrant, optionally a wetting agent, a glidant, and a lubricant, in which at least one dosage form contains at least about 75 mg of substantially amorphous or amorphous Compound 1. In some embodiments, at least one dosage form contains at least about 75 mg of substantially amorphous or amorphous Compound 1.

In various embodiments, the pharmaceutical composition is powder and is further formulated into a capsule or a packet. In other embodiments, the pharmaceutical composition is formulated into a solid dose form, such as one or more mini-tablets or granules or pellets, and optionally encapsulated into capsules, sachet, blister packs, pouches, packets, bottles, or other container. The solid dose form of the pharmaceutical composition or the contents of the capsules or packets may then be administered orally to the patient once per day. For instance, the powder pharmaceutical composition or mini-tablets are removed from a capsule or a packet, added to food and then fed to the patient. Alternatively, the powder pharmaceutical composition or mini-tablets are removed from a capsule or a packet, added to food, mixed, and then fed to the patient. Further, the powder pharmaceutical composition or mini-tablets are removed from a capsule or a packet and then fed to the patient if the patient is able to directly ingest the powder pharmaceutical composition or mini-tablets.

In one aspect, the invention includes a pharmaceutical composition comprising a solid dispersion of amorphous or substantially amorphous Compound 1, one or more fillers, a sweetener, a disintegrant, a glidant and a lubricant, and optionally a wetting agent.

In one embodiment of this aspect, the pharmaceutical composition comprises from about 30 to about 50 percent of a solid dispersion, by weight of the composition.

In one embodiment, the pharmaceutical composition comprises about 35 percent of a solid dispersion, by weight of the composition.

In another embodiment, the pharmaceutical composition comprises about 47 percent of a solid dispersion, by weight of the composition.

In one embodiment, the pharmaceutical composition comprises about 46.9 percent of a solid dispersion, by weight of the composition.

In one embodiment, the filler comprises:

mannitol, lactose, sucrose, dextrose, maltodextrin, sorbitol, xylitol, powdered cellulose, polyhydric alcohols, microcrystalline cellulose, silicified microcrystalline cellulose, cellulose acetate, methylcellulose, ethylcellulose, hydroxyethylcellulose, methylhydroxyethylcellulose, talc, starch, pregelatinized starch, dibasic calcium phosphate, calcium sulfate, calcium carbonate or combinations thereof.

In another embodiment, the filler comprises mannitol which is present in an amount from about 30 to about 80 percent by weight of the composition.

In a further embodiment, the filler comprises mannitol which is present in an amount from about 42 to about 57.5 percent by weight of the composition.

In one embodiment, the sweetener comprises:

glucose, sucrose, maltose, mannose, dextrose, fructose, lactose, trehalose, maltitol, lactitol, xylitol, sorbitol, mannitol, tagatose, glycerin, erythritol, isomalt, maltose, sucralose, aspartame, neotame, alitame, neohesperidin dihydrochalcone, cyclamate, thaumatin, acesulfame potassium, saccharin, saccharin sodium or combinations thereof.

In another embodiment, the sweetener comprises sucralose which is present in an amount from about 0.1 to about 5 percent by weight of the composition.

In one embodiment, wherein the disintegrant comprises: croscarmellose sodium, sodium alginate, calcium alginate, alginic acid, starch, pregelatinized starch, sodium starch glycolate, polyvinylpyrrolidone, copolymers of polyvinylpyrrolidone, crospovidone, carboxymethylcellulose calcium, cellulose and its derivatives, carboxymethylcellulose sodium, soy polysaccharide, clays, gums, an ion exchange resin, an effervescent system based on food acids and an alkaline carbonate component, sodium bicarbonate or combinations thereof.

In a further embodiment, the disintegrant comprises croscarmellose sodium which is present in an amount from about 1.5 to about 8 percent by weight of the composition.

In one embodiment, wherein the wetting agent comprises: sodium lauryl sulfate, cetostearyl alcohol, cetomacrogol emulsifying wax, gelatin, casein, docusate sodium, benzalkonium chloride, calcium stearate, polyethylene glycols, phosphates, polyoxyethylene sorbitan fatty acid esters, gum acacia, cholesterol, tragacanth, polyoxyethylene 20 stearyl ethers, polyoxyethylene alkyl ethers, polyoxyethylene castor oil derivatives, pegylated hydrogenated castor oils, sorbitan esters of fatty acids, Vitamin E or tocopherol derivatives, vitamin E TPGS, tocopheryl esters, lecithin, phospholipids and their derivatives, poloxamers, stearic acid, oleic acid, oleic alcohol, cetyl alcohol, mono and diglycerides, propylene glycol esters of fatty acids, glycerol esters of fatty acids, ethylene glycol palmitostearate, polyoxylglycerides, propylene glycol monocaprylate, propylene glycol monolaurate, alkyl aryl polyether alcohols and polyglyceryl oleate or combinations thereof.

In another embodiment, the wetting agent comprises sodium lauryl sulfate which is present in an amount of about 2 or less percent by weight of the composition.

In one embodiment, the glidant comprises: talc, colloidal silica, precipitated silica, magnesium oxide, magnesium silicate, leucine and starch.

In a further embodiment, the glidant comprises colloidal silica which is present in an amount from about 0.1 to about 5 percent by weight of the composition.

In one embodiment, the lubricant comprises: talc, fatty acid, stearic acid, magnesium stearate, calcium stearate, sodium stearate, stearic acid, glyceryl monostearate, sodium lauryl sulfate, sodium stearyl fumarate, hydrogenated oils, polyethylene glycol, fatty alcohol, fatty acid ester, glyceryl behenate, mineral oil, vegetable oil, leucine, sodium benzoate, or a combination thereof.

In a further embodiment, the lubricant comprises magnesium stearate which is present in an amount from about 0.1 to about 7 percent by weight of the composition.

In one embodiment, the solid dispersion comprises about 80 percent of amorphous Compound 1 by weight of the solid dispersion, and about 19.5 percent of HPMCAS by weight of the solid dispersion, and about 0.5 percent SLS by weight of the dispersion.

In another aspect, the invention includes a pharmaceutical composition comprising:
a solid dispersion of amorphous or substantially amorphous Compound 1 in an amount of about 15 to about 47 percent by weight of the pharmaceutical composition;
sucralose in an amount of about 2 percent by weight of the pharmaceutical composition;
croscarmellose sodium in an amount from about 3 to about 6 percent of by weight of the pharmaceutical composition;
SLS in an amount of about 0 to about 0.5 percent by weight of the pharmaceutical composition;
colloidal silicon dioxide in an amount of about 1 percent by weight of the pharmaceutical composition;
magnesium stearate in an amount of about 1.5 percent by weight of the pharmaceutical composition; and
mannitol in an amount of about 42 to about 77.5 percent of by weight of the pharmaceutical composition.

In another aspect, the invention includes a pharmaceutical composition comprising:
a solid dispersion of amorphous or substantially amorphous Compound 1 in an amount of about 35 to about 47 percent by weight of the pharmaceutical composition;
sucralose in an amount of about 2 percent by weight of the pharmaceutical composition;
croscarmellose sodium in an amount from about 3 to about 6 percent of by weight of the pharmaceutical composition;
SLS in an amount of about 0 to about 0.5 percent by weight of the pharmaceutical composition;
colloidal silicon dioxide in an amount of about 1 percent by weight of the pharmaceutical composition;
magnesium stearate in an amount of about 1.5 percent by weight of the pharmaceutical composition; and
mannitol in an amount of about 42 to about 57.5 percent of by weight of the pharmaceutical composition.

In one embodiment of this aspect, the croscarmellose sodium is present in an amount of about 5 percent of by weight of the pharmaceutical composition.

In another embodiment, the SLS is present in an amount of about 0.5 percent by weight of the pharmaceutical composition.

In one embodiment, the solid dispersion is present in an amount of about 35 percent by weight of the pharmaceutical composition.

In another embodiment, the solid dispersion is present in an amount of about 47 percent by weight of the pharmaceutical composition.

In another aspect, the invention includes a pharmaceutical composition comprising:
a solid dispersion of amorphous or substantially amorphous Compound 1 in an amount of about 35 percent by weight of the pharmaceutical composition;
sucralose in an amount of about 2 percent by weight of the pharmaceutical composition;
croscarmellose sodium in an amount of about 6 percent of by weight of the pharmaceutical composition;
colloidal silicon dioxide in an amount of about 1 percent by weight of the pharmaceutical composition;
magnesium stearate in an amount of about 1.5 percent by weight of the pharmaceutical composition;
mannitol in an amount of about 13.5 percent of by weight of the pharmaceutical composition; and
lactose in an amount of about 41 percent of by weight of the pharmaceutical composition.

In one embodiment, the pharmaceutical composition is a unit dose form comprising one or a plurality of granules, pellets, particles or mini-tablets, and wherein the unit dose form comprises from about 1 mg to about 250 mg of substantially amorphous or amorphous Compound 1.

In a further embodiment, the unit dose form comprises from about 50 mg of substantially amorphous or amorphous Compound 1.

In another embodiment, the unit dose form comprises from about 75 mg of substantially amorphous or amorphous Compound 1.

In a further embodiment, the unit dose form comprises from about 25 to about 40 mini-tablets.

In a further embodiment, the unit dose form comprises from about 1, 2, 3, 4, or 5 mini-tablets.

In a further embodiment, the solid dispersion is present in an amount of about 35 percent by weight of the pharmaceutical composition and the unit dose form comprises 1, 2, 3, 4, or 5 mini-tablets.

In a further embodiment, the solid dispersion is present in an amount of about 35 percent by weight of the pharmaceutical composition and the unit dose form comprises 1 mini-tablet.

In a further embodiment, the unit dose form comprises from about 21 to about 52 mini-tablets.

In a further embodiment, the solid dispersion is present in an amount of about 35 percent by weight of the pharmaceutical composition and the unit dose form comprises 5 mini-tablets.

In a further embodiment, the solid dispersion is present in an amount of about 35 percent by weight of the pharmaceutical composition and the unit dose form comprises 13 mini-tablets.

In a further embodiment, the solid dispersion is present in an amount of about 35 percent by weight of the pharmaceutical composition and the unit dose form comprises about 21 mini-tablets.

In one embodiment, the solid dispersion is present in an amount of about 35 percent by weight of the pharmaceutical composition and the unit dose form comprises about 26 mini-tablets.

In a further embodiment, the solid dispersion is present in an amount of about 35 percent by weight of the pharmaceutical composition and the unit dose form comprises about 39 mini-tablets.

In a further embodiment, the solid dispersion is present in an amount of about 35 percent by weight of the pharmaceutical composition and the unit dose form comprises about 52 mini-tablets.

In one embodiment, the pharmaceutical composition is a unit dose form comprising a granule, pellet, particle or mini-tablet, and wherein the unit dose form comprises about 10 mg of substantially amorphous or amorphous Compound 1.

In a further embodiment, the solid dispersion is present in an amount of about 47 percent by weight of the pharmaceutical composition and the unit dose form is a mini-tablet having a shape that is cylinder-like, oval-like, cone-like, sphere-like, ellipsis-like, polygon-like or combinations thereof, wherein the mini-tablet has as its longest dimension or diameter a length of about 4 mm.

In another embodiment, the solid dispersion is present in an amount of about 35 percent by weight of the pharmaceutical composition and the unit dose form is a mini-tablet having a shape that is cylinder-like, oval-like, cone-like, sphere-like, ellipsis-like, polygon-like or combinations thereof, wherein the mini-tablet has as its longest dimension or diameter a length of about 4 mm.

In a further embodiment, the solid dispersion is present in an amount of about 35 percent by weight of the pharmaceutical composition and the unit dose form is a mini-tablet having a shape that is cylinder-like, oval-like, cone-like, sphere-like, ellipsis-like, polygon-like or combinations thereof, wherein the mini-tablet has as its longest dimension or diameter a length of about 2 mm.

Another aspect of the present invention provides a method of administering a pharmaceutical composition by orally administering to a patient at least once per day at least one unit dosage form comprising powder pharmaceutical composition and/or a solid dose form of the pharmaceutical composition (for example, a mini-tablet or plurality of mini-tablets), comprising a solid dispersion of substantially amorphous or amorphous Compound 1, one or more fillers, a sweetener, a disintegrant, optionally a wetting agent, a glidant, and a lubricant, in which the powder pharmaceutical composition and/or a solid dose form of the pharmaceutical composition comprises up to about 5 mg of substantially amorphous or amorphous Compound 1. For instance the solid dispersion comprises 0.25 mg, 0.5 mg, 0.75 mg, 1 mg, 2 mg, 3 mg, 4 mg, or 5 mg of substantially amorphous or amorphous Compound 1. In some embodiments, the powder pharmaceutical composition and/or a solid dose form of the pharmaceutical composition is orally administered to the patient once per day. For instance, the powder pharmaceutical composition or mini-tablets are removed from a capsule or a packet, added to food, mixed and then fed to the patient.

In still another aspect, the present invention provides a method of administering a pharmaceutical composition by orally administering to a patient at least once per day at least one unit dosage form comprising powder pharmaceutical composition and/or a solid dose form of the pharmaceutical composition (for example, a mini-tablet or plurality of mini-tablets), comprising a solid dispersion of substantially amorphous or amorphous Compound 1, one or more fillers, a sweetener, a disintegrant, optionally a wetting agent, a glidant, and a lubricant, in which the powder pharmaceutical composition and/or a solid dose form of the pharmaceutical composition comprises up to about 1 mg of substantially amorphous or amorphous Compound 1. In another embodiment, the solid dispersion comprises from about 0.1 mg to about 1 mg of substantially amorphous or amorphous Compound 1. In another embodiment, the solid dispersion comprises from about 0.1 mg to about 5 mg (inclusive of all of the values and ranges therein). In a particular embodiment, the solid dispersion comprises 0.25 mg, 0.5 mg, 0.75 mg, or 1 mg of substantially amorphous or amorphous Compound 1. In some embodiments, the present invention provides for a method of orally administering the pharmaceutical compositions described herein at least once a day. In other embodiments, the present invention provides for a method of orally administering the pharmaceutical composition described herein once a day. In some embodiments, the present invention provides for a method of orally administering the pharmaceutical compositions described herein at least once a day. In some embodiments, the present invention provides for a method of orally administering the pharmaceutical composition described herein twice a day or more times a day.

In one aspect, the invention also provides a method of treating or lessening the severity of a disease in a patient comprising administering to said patient one of the compositions as defined herein, and said disease is selected from cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), liver disease, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulinemia, Diabetes mellitus, Laron dwarfism, myeloperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurohypophyseal DI, nephrogenic DI, Charcot-Marie Tooth syndrome, Pelizaeus-Merzbacher disease, neurodegenerative diseases such as Alzheimer's disease, Parkinson's disease, amyotrophic lateral sclerosis, progressive supranuclear palsy, Pick's disease, several polyglutamine neurological disorders such as Huntington's, spinocerebellar ataxia type I, spinal and bulbar muscular atrophy, dentatorubral pallidoluysian atrophy, and myotonic dystrophy, as well as spongiform encephalopathies, such as hereditary Creutzfeldt-Jakob disease (due to prion protein processing defect), Fabry disease, Gerstmann-Strä ussler-Scheinker syndrome, COPD, dry-eye disease, Sjogren's disease, Osteoporosis, Osteopenia, Gorham's Syndrome, chloride channelopathies such as myotonia congenita (Thomson and Becker forms), Bartter's syndrome type III, Dent's disease, epilepsy, hyperekplexia, lysosomal storage disease, Angelman syndrome, and Primary Ciliary Dyskinesia (PCD), a term for inherited disorders of the structure and/or function of cilia, including PCD with situs inversus (also known as Kartagener syndrome), PCD without situs inversus and ciliary aplasia.

Figure 1:
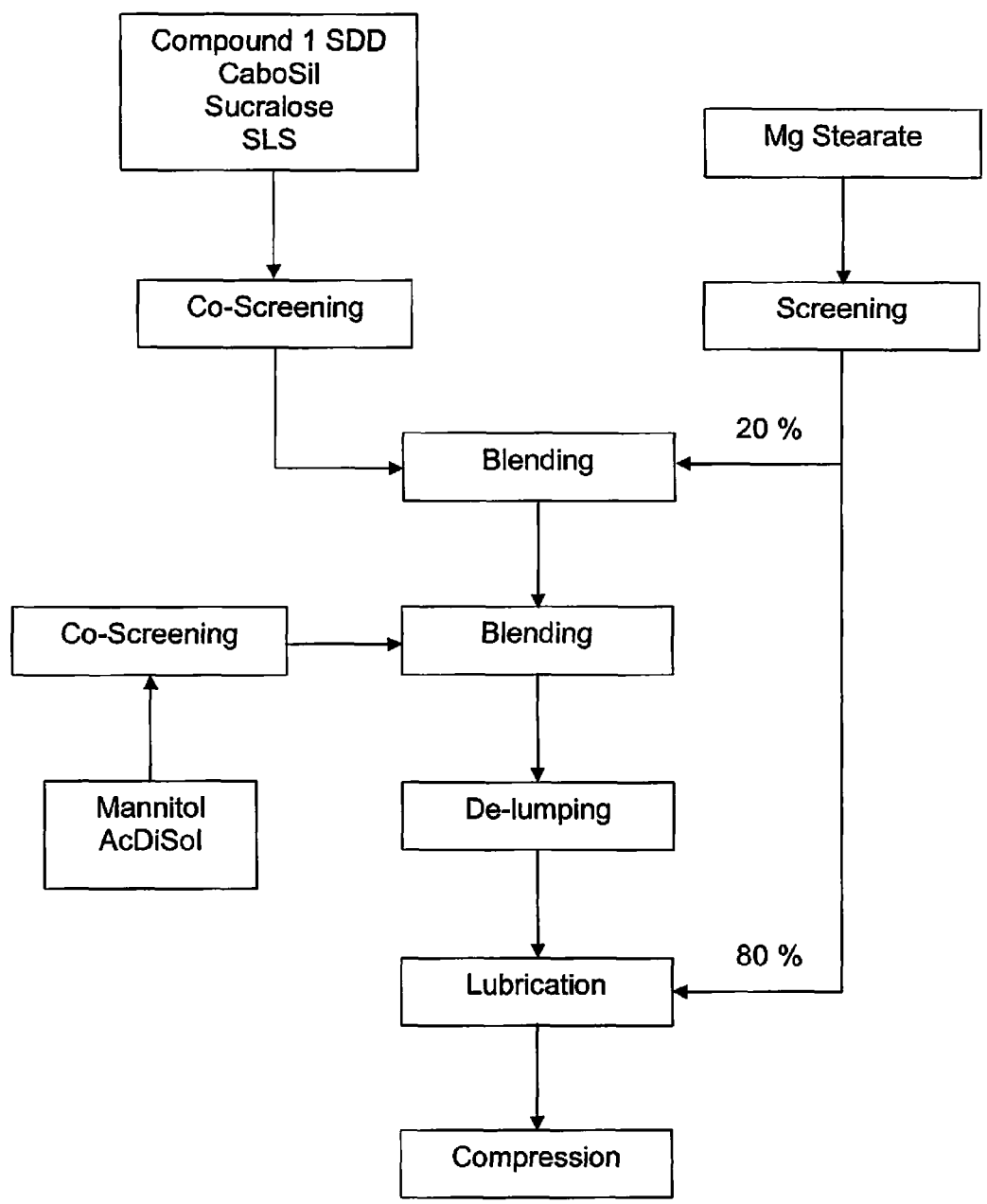
FIG. 1 presents a schematic representation of the manufacturing and process steps used to make some exemplary mini-tablets in accordance with various embodiments of the present invention.
Figure 2:
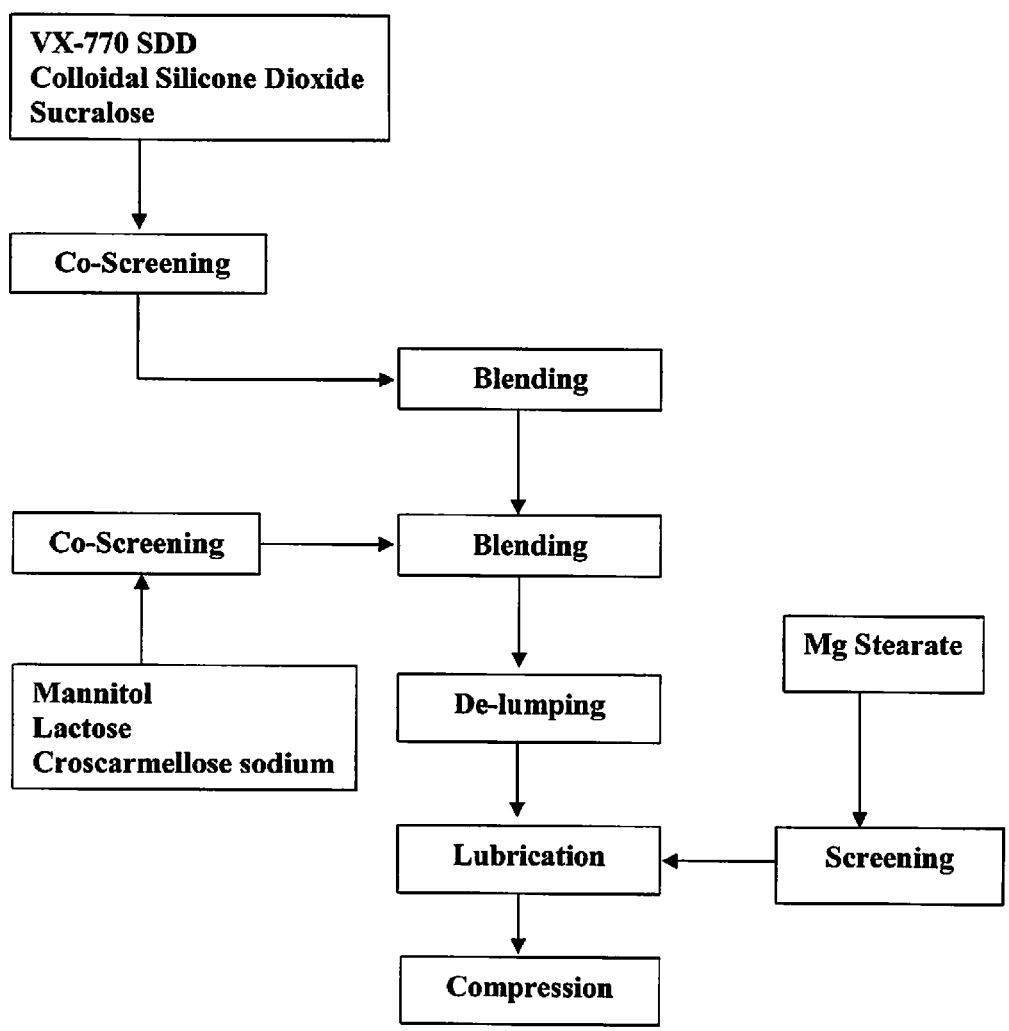
FIG. 2 presents a schematic representation of the manufacturing and process steps used to make other exemplary mini-tablets in accordance with various embodiments of the present invention.

The figures are presented by way of example and are not intended to be limiting.

DETAILED DESCRIPTION

The present invention provides a pharmaceutical composition comprising a solid dispersion of N-[2,4-bis(1,1-dimethylethyl)-5-hydroxyphenyl]-1,4-dihydro-4-oxoquinoline-3-carboxamide, a method of manufacturing a pharmaceutical composition comprising N-[2,4-bis(1,1-dimethylethyl)-5-hydroxyphenyl]-1,4-dihydro-4-oxoquinoline-3-carboxamide, and a method of administering a pharmaceutical composition comprising a solid form of N-[2,4-bis(1,1-dimethylethyl)-5-hydroxyphenyl]-1,4-dihydro-4-oxoquinoline-3-carboxamide.

I. DEFINITIONS

As used herein, the term "active pharmaceutical ingredient" or "API" refers to a biologically active compound. Exemplary APIs include a CF potentiator (e.g., N-[2,4-bis(1,1-dimethylethyl)-5-hydroxyphenyl]-1,4-dihydro-4-oxoquinoline-3-carboxamide).

As used herein, the term "Compound 1" is used interchangeably with "N-[2,4-bis(1,1-dimethylethyl)-5-hydroxyphenyl]-1,4-dihydro-4-oxoquinoline-3-carboxamide", which has the following structure:

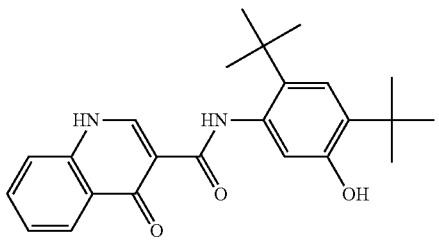 [SMILES: CC(C)(C)c1cc(C(C)(C)C)c(NC(=O)c2c[nH]c3ccccc3c2=O)cc1O]

"Compound 1" also means tautomeric forms such as:

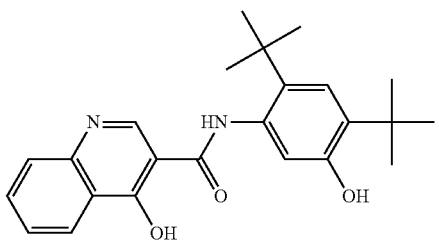 [SMILES: CC(C)(C)c1cc(C(C)(C)C)c(NC(=O)c2cnc3ccccc3c2O)cc1O]

As used herein, the term "amorphous" refers to a solid material having no long range order in the position of its molecules. Amorphous solids are generally supercooled liquids in which the molecules are arranged in a random manner so that there is no well-defined arrangement, e.g., molecular packing, and no long range order. Amorphous solids are generally isotropic, i.e. exhibit similar properties in all directions and do not have definite melting points. For example, an amorphous material is a solid material having no sharp characteristic crystalline peak(s) in its X-ray power diffraction (XRPD) pattern (i.e., is not crystalline as determined by XRPD). Instead, one or several broad peaks (e.g., halos) appear in its XRPD pattern. Broad peaks are characteristic of an amorphous solid. See, US 2004/0006237 for a comparison of XRPDs of an amorphous material and crystalline material.

As used herein, the term "substantially amorphous" refers to a solid material having little or no long range order in the position of its molecules. For example, substantially amorphous materials have less than about 15% crystallinity (e.g., less than about 10% crystallinity or less than about 5% crystallinity). It is also noted that the term 'substantially amorphous' includes the descriptor, 'amorphous', which refers to materials having no (0%) crystallinity.

As used herein, the term "dispersion" refers to a disperse system in which one substance, the dispersed phase, is distributed, in discrete units, throughout a second substance (the continuous phase or vehicle). The size of the dispersed phase can vary considerably (e.g. single molecules, colloidal particles of nanometer dimension, to multiple microns in size). In general, the dispersed phases can be solids, liquids, or gases. In the case of a solid dispersion, the dispersed and continuous phases are both solids. In pharmaceutical applications, a solid dispersion can include: an amorphous drug in an amorphous polymer; an amorphous drug in crystalline polymer; a crystalline drug in an amorphous polymer; or a crystalline drug in crystalline polymer. In this invention, a solid dispersion can include an amorphous drug in an amorphous polymer or an amorphous drug in crystalline polymer. In some embodiments, a solid dispersion includes the polymer constituting the dispersed phase, and the drug constitutes the continuous phase. Or, a solid dispersion includes the drug constituting the dispersed phase, and the polymer constitutes the continuous phase.

As used herein, the term "solid dispersion" generally refers to a solid dispersion of two or more components, usually one or more drugs (e.g., one drug (e.g., Compound 1)) and polymer, but possibly containing other components such as surfactants or other pharmaceutical excipients, where the drug(s) (e.g., Compound 1) is substantially amorphous (e.g., having about 15% or less (e.g., about 10% or less, or about 5% or less)) of crystalline drug (e.g., N-[2,4-bis(1,1-dimethylethyl)-5-hydroxyphenyl]-1,4-dihydro-4-oxoquinoline-3-carboxamide) or amorphous (i.e., having no crystalline drug), and the physical stability and/or dissolution and/or solubility of the substantially amorphous or amorphous drug is enhanced by the other components. Solid dispersions typically include a compound dispersed in an appropriate carrier medium, such as a solid state carrier. For example, a carrier comprises a polymer (e.g., a water-soluble polymer or a partially water-soluble polymer) and can include optional excipients such as functional excipients (e.g., one or more surfactants) or nonfunctional excipients (e.g., one or more fillers). Another exemplary solid dispersion is a co-precipitate or a co-melt of N-[2,4-bis(1,1-dimethylethyl)-5-hydroxyphenyl]-1,4-dihydro-4-oxoquinoline-3-carboxamide with at least one polymer.

A "Co-precipitate" is a product after dissolving a drug and a polymer in a solvent or solvent mixture followed by the removal of the solvent or solvent mixture. Sometimes the polymer can be suspended in the solvent or solvent mixture. The solvent or solvent mixture includes organic solvents and supercritical fluids. A "co-melt" is a product after heating a drug and a polymer to melt, optionally in the presence of a solvent or solvent mixture, followed by mixing, removal of at least a portion of the solvent if applicable, and cooling to room temperature at a selected rate.

As used herein, "crystallinity" refers to the degree of structural order in a solid. For example, Compound 1, which is substantially amorphous, has less than about 15% crystallinity, or its solid state structure is less than about 15% crystalline. In another example, Compound 1, which is amorphous, has zero (0%) crystallinity.

As used herein, a "CF potentiator" refers to a compound that exhibits biological activity characterized by increasing gating functionality of the mutant CFTR protein present in the cell surface to approximately wild type levels (i.e., a compound that augments or induces the channel activity of CFTR protein located at the cell surface, resulting in increased functional activity).

As used herein, the term "CFTR corrector" refers to a compound that augments or induces the amount of functional CFTR protein to the cell surface, resulting in increased functional activity.

As used herein, a "solid dose form" includes capsules, packets, sachets, and pouches containing the pharmaceutical composition either in powder form or in a compressed form, such as granules, pellets, particles, mini-tablets and the like, the solid dose form containing a specified amount of Compound 1.

As used herein, an "excipient" is an inactive ingredient in a pharmaceutical composition. Examples of excipients include a filler, a sweetener, a disintegrant, a glidant, a lubricant, and the like.

As used herein, a "disintegrant" is an excipient that hydrates a pharmaceutical composition and aids in tablet dispersion. Examples of disintegrants include sodium croscarmellose and/or sodium starch glycolate.

As used herein, a "diluent" or "filler" is an excipient that adds bulkiness to a pharmaceutical composition. Examples of fillers include mannitol, celluloses, ethyl cellulose, cellulose acetate, calcium carbonate, potato starch, sorbitol, polyhydric alcohols, dextrose, or combinations thereof.

As used herein, a "wetting agent" is an excipient that imparts pharmaceutical compositions with enhanced solubility and/or wetability. Examples of wetting agents include sodium lauryl sulfate (SLS), sodium stearyl fumarate (SSF), polyoxyethylene 20 sorbitan mono-oleate (e.g., Tween™), or any combination thereof.

As used herein, a "sweetener" is an excipient that imparts a pharmaceutical composition with a sweet taste and/or masks other unpleasant tastes. Examples of sweeteners include sucralose, sorbitol, xylitol, and combinations thereof.

As used herein, a "glidant" is an excipient that imparts a pharmaceutical compositions with enhanced flow properties. Examples of glidants include colloidal silica, precipitated silica and/or talc.

As used herein, a "colorant" is an excipient that imparts a pharmaceutical composition with a desired color. Examples of colorants include commercially available pigments such as FD&C Blue #1 Aluminum Lake, FD&C Blue #2, other FD&C Blue colors, titanium dioxide, iron oxide, and/or combinations thereof.

As used herein, a "lubricant" is an excipient that is added to pharmaceutical compositions to minimize adherence to surfaces, especially for pharmaceutical compositions that are pressed into tablets. The lubricant aids in ejection of a tablet of a pharmaceutical composition from a compression die. Examples of lubricants include magnesium stearate, stearic acid (stearin), hydrogenated oil, sodium stearyl fumarate, or any combination thereof.

As used herein, "mean particle diameter" is the average particle diameter as measured using techniques such as laser light scattering, image analysis, or sieve analysis.

As used herein, "bulk density" is the mass of particles of material divided by the total volume the particles occupy. The total volume includes particle volume, inter-particle void volume and internal pore volume. Bulk density is not an intrinsic property of a material; it can change depending on how the material is processed.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof.

As used herein, the term "mini-tablet" is equivalent to the term "granule".

As used herein, "CFTR" or "CFTR protein" stands for cystic fibrosis transmembrane conductance regulator protein.

As used herein, "CFTR" or "CFTR gene" stands for cystic fibrosis transmembrane conductance regulator gene.

As used herein, "mutations" can refer to mutations in the CFTR gene or the CFTR protein. A "CFTR mutation" refers to a mutation in the CFTR gene, and a "CFTR mutation" refers to a mutation in the CFTR protein. A genetic defect or mutation, or a change in the nucleotides in a gene in general results in a mutation in the CFTR protein translated from that gene. For example, a G551D CFTR mutation is a mutation or change in the nucleotides of the CFTR gene that results in a G551D CFTR mutation in the translated CFTR protein, wherein amino acid in position 551 of the CFTR protein changes from glycine (G) to aspartic acid (D) due to the mutation or change in the nucleotides of the CFTR gene. Similarly, ΔF508 or F508del is a specific mutation within the CFTR protein. A ΔF508 or F508del CFTR mutation is a deletion of the three nucleotides in the CFTR gene that comprise the codon for amino acid phenylalanine at position 508 of the CFTR protein, resulting in a ΔF508 or F508del CFTR mutation or CFTR protein that lacks this particular phenylalanine.

The term "CFTR gating mutation" as used herein means a CFTR mutation that results in the production of a CFTR protein for which the predominant defect is a low channel open probability compared to normal CFTR (Van Goor, F., Hadida S. and Grootenhuis P., "Pharmacological Rescue of Mutant CFTR function for the Treatment of Cystic Fibrosis", Top. Med. Chem. 3: 91-120 (2008)). Gating mutations include, but are not limited to, G551D, G178R, S549N, S549R, G551S, G970R, G1244E, S1251N, S1255P, and G1349D.

The term "residual function phenotype" as used herein refers to having CFTR with residual function. In other words, an individual who demonstrates a residual function phenotype has CFTR residual function. Individuals who have CFTR residual function, such as the R117H mutation (due either to defects in gating, conductance or amounts of functional CFTR protein) tend to have later onset of clinical symptoms and milder disease. Many of these individuals have evidence of either pancreatic sufficiency or late-onset partial pancreatic insufficiency. Such individuals also tend to have slower progression of sinopulmonary diseases, later diagnosis, and a sweat chloride value that is intermediate between normal and severe mutations (McKone E. F., et al., "CFTR Genotype as a Predictor as a Predictor of Prognosis in Cystic Fibrosis", Chest., 130: 1441-7 (2006); Kristidis, P., et al, "Genetic Determination of Exocrine Pancreatic Function in Cystic Fibrosis", Am. J. Hum. Genet., 50: 1178-84 (1992);

Kerem, E. and Kerem B, "Genotype-Phenotype Correlations in Cystic Fibrosis", Pediatr. Pulmonol., 22:387-95 (1996); Green, D. M., et al., "Mutations that Permit Residual CFTR Function Delay Acquisition of Multiple Respiratory Pathogens in CF Patients", Respir. Res., 11:140-(2010)).

Pharmaceutically acceptable salts are well known in the art. For example, S. M. Berge, et al. describes pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange.

Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, edisylate (ethanedisulfonate), ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N+(C1-4alkyl)4 salts. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

II. PHARMACEUTICAL COMPOSITION

In one aspect, the present invention provides a pharmaceutical composition comprising a powder admixture comprising a CF potentiator API (e.g., a solid dispersion of Compound 1). As exemplified herein, the pharmaceutical composition of the present invention can be a powder admixture of a CF potentiator API (e.g., a solid dispersion of Compound 1) and one or more excipients described herein. Alternatively, the pharmaceutical composition can be formulated into a unit dose form containing the powder admixture or a unit dose form formulated to contain a compressed solid dose form of the powder admixture in addition to one or more additional functional excipients, for example, optionally a wetting agent and/or lubricant to enable the compression of the powder admixture into granules, pellets, particles, or one or more mini-tablets, the pharmaceutical composition and/or the unit dose form comprising the specified ingredients in the specified amounts. The pharmaceutical composition is capable of being formulated into a unit dose form, for example, a tablet, capsule, sachet, troches, blister pack and the like containing the powder and/or compressed form of the pharmaceutical composition of the present invention.

In one embodiment, the present invention provides a pharmaceutical composition comprising a solid dispersion of substantially amorphous Compound 1, wherein the pharmaceutical composition comprises up to about 1 mg of substantially amorphous Compound 1. For instance, the solid dispersion comprises about 0.25 mg, about 0.5 mg, about 0.75 mg, or about 1 mg of substantially amorphous Compound 1.

In one embodiment, the present invention provides a pharmaceutical composition comprising a solid dispersion of substantially amorphous Compound 1, wherein the pharmaceutical composition comprises up to about 5 mg of substantially amorphous Compound 1. For instance, the pharmaceutical composition comprises about 0.25 mg, 0.5 mg, about 0.75 mg, about 1 mg, about 2 mg, about 3 mg, about 4 mg, or about 5 mg of substantially amorphous Compound 1.

In one embodiment, the present invention provides a pharmaceutical composition comprising a solid dispersion of substantially amorphous Compound 1, wherein the pharmaceutical composition comprises about 10 mg of substantially amorphous Compound 1.

In one embodiment, the present invention provides a pharmaceutical composition comprising a solid dispersion of substantially amorphous Compound 1, wherein the pharmaceutical composition comprises about 12.5 mg of substantially amorphous Compound 1.

In one embodiment, the present invention provides a pharmaceutical composition comprising a solid dispersion of substantially amorphous Compound 1, wherein the solid dispersion comprises about 15 mg of substantially amorphous Compound 1.

In one embodiment, the present invention provides a pharmaceutical composition comprising a solid dispersion of substantially amorphous Compound 1, wherein the solid dispersion comprises about 20 mg of substantially amorphous Compound 1.

In one embodiment, the present invention provides a pharmaceutical composition comprising a solid dispersion of substantially amorphous Compound 1, wherein the solid dispersion comprises about 25 mg of substantially amorphous Compound 1.

In one embodiment, the present invention provides a pharmaceutical composition comprising a solid dispersion of substantially amorphous Compound 1, wherein the solid dispersion comprises about 30 mg of substantially amorphous Compound 1.

In one embodiment, the present invention provides a pharmaceutical composition comprising a solid dispersion of substantially amorphous Compound 1, wherein the solid dispersion comprises about 37.5 mg of substantially amorphous Compound 1.

In one embodiment, the present invention provides a pharmaceutical composition comprising a solid dispersion of substantially amorphous Compound 1, wherein the solid dispersion comprises about 40 mg of substantially amorphous Compound 1.

In one embodiment, the present invention provides a pharmaceutical composition comprising a solid dispersion of substantially amorphous Compound 1, wherein the solid dispersion comprises about 50 mg of substantially amorphous Compound 1.

In one embodiment, the present invention provides a pharmaceutical composition comprising a solid dispersion of substantially amorphous Compound 1, wherein the solid dispersion comprises about 62.5 mg of substantially amorphous Compound 1.

In one embodiment, the present invention provides a pharmaceutical composition comprising a solid dispersion of substantially amorphous Compound 1, wherein the solid dispersion comprises about 75 mg of substantially amorphous Compound 1.

In one embodiment, the present invention provides a pharmaceutical composition comprising a solid dispersion of substantially amorphous Compound 1, wherein the pharmaceutical composition comprises about 100 mg of substantially amorphous Compound 1.

In one embodiment, the present invention provides a pharmaceutical composition comprising a solid dispersion of substantially amorphous Compound 1, wherein the solid dispersion comprises about 125 mg of substantially amorphous Compound 1.

In one embodiment, the present invention provides a pharmaceutical composition comprising a solid dispersion of substantially amorphous Compound 1, wherein the solid dispersion about 150 mg of substantially amorphous Compound 1.

In one embodiment, the present invention provides a pharmaceutical composition comprising a solid dispersion of substantially amorphous Compound 1, wherein the solid dispersion comprises about 175 mg of substantially amorphous Compound 1.

In one embodiment, the present invention provides a pharmaceutical composition comprising a solid dispersion of substantially amorphous Compound 1, wherein the solid dispersion comprises about 200 mg of substantially amorphous Compound 1.

In one embodiment, the present invention provides a pharmaceutical composition comprising a solid dispersion of substantially amorphous Compound 1, wherein the solid dispersion comprises about 225 mg of substantially amorphous Compound 1.

In one embodiment, the present invention provides a pharmaceutical composition comprising a solid dispersion of substantially amorphous Compound 1, wherein the solid dispersion comprises about 250 mg of substantially amorphous Compound 1.

In one embodiment, the present invention provides a pharmaceutical composition comprising a solid dispersion of amorphous Compound 1, wherein the solid dispersion comprises up to about 1 mg of amorphous Compound 1. For instance, the solid dispersion comprises about 0.25 mg, about 0.5 mg, about 0.75 mg, or about 1 mg of amorphous Compound 1.

In one embodiment, the present invention provides a pharmaceutical composition comprising a solid dispersion of substantially amorphous Compound 1, wherein the solid dispersion comprises up to about 5 mg of amorphous Compound 1. For instance, the solid dispersion comprises about 0.5 mg, about 0.75 mg, about 1 mg, about 2 mg, about 3 mg, about 4 mg, or about 5 mg of amorphous Compound 1.

In one embodiment, the present invention provides a pharmaceutical composition comprising a solid dispersion of amorphous Compound 1, wherein the solid dispersion comprises about 10 mg of amorphous Compound 1.

In one embodiment, the present invention provides a pharmaceutical composition comprising a solid dispersion of amorphous Compound 1, wherein the solid dispersion comprises about 12.5 mg of amorphous Compound 1.

In one embodiment, the present invention provides a pharmaceutical composition comprising a solid dispersion of amorphous Compound 1, wherein the solid dispersion comprises about 15 mg of amorphous Compound 1.

In one embodiment, the present invention provides a pharmaceutical composition comprising a solid dispersion of amorphous Compound 1, wherein the solid dispersion comprises about 20 mg of amorphous Compound 1.

In one embodiment, the present invention provides a pharmaceutical composition comprising a solid dispersion of amorphous Compound 1, wherein the solid dispersion comprises about 25 mg of amorphous Compound 1.

In one embodiment, the present invention provides a pharmaceutical composition comprising a solid dispersion of amorphous Compound 1, wherein the solid dispersion comprises about 30 mg of amorphous Compound 1.

In one embodiment, the present invention provides a pharmaceutical composition comprising a solid dispersion of amorphous Compound 1, wherein the solid dispersion comprises about 37.5 mg of amorphous Compound 1.

In one embodiment, the present invention provides a pharmaceutical composition comprising a solid dispersion of amorphous Compound 1, wherein the solid dispersion comprises about 40 mg of amorphous Compound 1.

In one embodiment, the present invention provides a pharmaceutical composition comprising a solid dispersion of amorphous Compound 1, wherein the solid dispersion comprises about 50 mg of amorphous Compound 1.

In one embodiment, the present invention provides a pharmaceutical composition comprising a solid dispersion of amorphous Compound 1, wherein the solid dispersion comprises about 62.5 mg of amorphous Compound 1.

In one embodiment, the present invention provides a pharmaceutical composition comprising a solid dispersion of amorphous Compound 1, wherein the solid dispersion comprises about 75 mg of amorphous Compound 1.

In one embodiment, the present invention provides a pharmaceutical composition comprising a solid dispersion of amorphous Compound 1, wherein the solid dispersion comprises about 100 mg of amorphous Compound 1.

In one embodiment, the present invention provides a pharmaceutical composition comprising a solid dispersion of amorphous Compound 1, wherein the solid dispersion comprises about 125 mg of amorphous Compound 1.

In one embodiment, the present invention provides a pharmaceutical composition comprising a solid dispersion of amorphous Compound 1, wherein the solid dispersion comprises about 150 mg of amorphous Compound 1.

In one embodiment, the present invention provides a pharmaceutical composition comprising a solid dispersion of amorphous Compound 1, wherein the solid dispersion comprises about 175 mg of amorphous Compound 1.

In one embodiment, the present invention provides a pharmaceutical composition comprising a solid dispersion of amorphous Compound 1, wherein the solid dispersion comprises about 200 mg of amorphous Compound 1.

In one embodiment, the present invention provides a pharmaceutical composition comprising a solid dispersion of amorphous Compound 1, wherein the solid dispersion comprises about 225 mg of amorphous Compound 1.

In one embodiment, the present invention provides a pharmaceutical composition comprising a solid dispersion of amorphous Compound 1, wherein the solid dispersion comprises about 250 mg of amorphous Compound 1.

In one embodiment, the present invention provides a pharmaceutical composition comprising a solid dispersion of substantially amorphous Compound 1 and HPMCAS, wherein the pharmaceutical composition comprises up to about 1 mg of substantially amorphous Compound 1. For instance, the solid dispersion comprises about 0.5 mg, about 0.75 mg, or about 1 mg of substantially amorphous Compound 1.

In one embodiment, the present invention provides a pharmaceutical composition comprising a solid dispersion of substantially amorphous Compound 1 and HPMCAS, wherein the solid dispersion comprises from about 0.1 mg to about 5 mg of substantially amorphous Compound 1. For instance, the solid dispersion comprises about 0.25 mg, about 0.5 mg, about 0.75 mg, about 1 mg, about 2 mg, about 3 mg, about 4 mg, or about 5 mg of substantially amorphous Compound 1.

In one embodiment, the present invention provides a pharmaceutical composition comprising a solid dispersion of substantially amorphous Compound 1 and HPMCAS, wherein the pharmaceutical composition comprises about 10 mg of substantially amorphous Compound 1.

In one embodiment, the present invention provides a pharmaceutical composition comprising a solid dispersion of substantially amorphous Compound 1 and HPMCAS, wherein the pharmaceutical composition comprises about 12.5 mg of substantially amorphous Compound 1.

In one embodiment, the present invention provides a pharmaceutical composition comprising a solid dispersion of substantially amorphous Compound 1 and HPMCAS, wherein the pharmaceutical composition comprises about 15 mg of substantially amorphous Compound 1.

In one embodiment, the present invention provides a pharmaceutical composition comprising a solid dispersion of substantially amorphous Compound 1 and HPMCAS, wherein the pharmaceutical composition comprises about 20 mg of substantially amorphous Compound 1.

In one embodiment, the present invention provides a pharmaceutical composition comprising a solid dispersion of substantially amorphous Compound 1 and HPMCAS, wherein the pharmaceutical composition comprises about 25 mg of substantially amorphous Compound 1.

In one embodiment, the present invention provides a pharmaceutical composition comprising a solid dispersion of substantially amorphous Compound 1 and HPMCAS, wherein the pharmaceutical composition comprises about 30 mg of substantially amorphous Compound 1.

In one embodiment, the present invention provides a pharmaceutical composition comprising a solid dispersion of substantially amorphous Compound 1 and HPMCAS, wherein the pharmaceutical composition comprises about 35 mg of substantially amorphous Compound 1.

In one embodiment, the present invention provides a pharmaceutical composition comprising a solid dispersion of substantially amorphous Compound 1 and HPMCAS, wherein the pharmaceutical composition comprises about 37.5 mg of substantially amorphous Compound 1.

In one embodiment, the present invention provides a pharmaceutical composition comprising a solid dispersion of substantially amorphous Compound 1 and HPMCAS, wherein the pharmaceutical composition comprises about 40 mg of substantially amorphous Compound 1.

In one embodiment, the present invention provides a pharmaceutical composition comprising a solid dispersion of substantially amorphous Compound 1 and HPMCAS, wherein the pharmaceutical composition comprises about 45 mg of substantially amorphous Compound In one embodiment, the present invention provides a pharmaceutical composition comprising a solid dispersion of substantially amorphous Compound 1 and HPMCAS, wherein the pharmaceutical composition comprises about 50 mg of substantially amorphous Compound In one embodiment, the present invention provides a pharmaceutical composition comprising a solid dispersion of substantially amorphous Compound 1 and HPMCAS, wherein the pharmaceutical composition comprises about 62.5 mg of substantially amorphous Compound 1.

In one embodiment, the present invention provides a pharmaceutical composition comprising a solid dispersion of substantially amorphous Compound 1 and HPMCAS, wherein the pharmaceutical composition comprises about 75 mg of substantially amorphous Compound 1.

In one embodiment, the present invention provides a pharmaceutical composition comprising a solid dispersion of substantially amorphous Compound 1 and HPMCAS, wherein the pharmaceutical composition comprises about 100 mg of substantially amorphous Compound 1.

In one embodiment, the present invention provides a pharmaceutical composition comprising a solid dispersion of substantially amorphous Compound 1 and HPMCAS, wherein the pharmaceutical composition comprises about 125 mg of substantially amorphous Compound 1.

In one embodiment, the present invention provides a pharmaceutical composition comprising a solid dispersion of substantially amorphous Compound 1 and HPMCAS, wherein the pharmaceutical composition comprises about 150 mg of substantially amorphous Compound 1.

In one embodiment, the present invention provides a pharmaceutical composition comprising a solid dispersion of substantially amorphous Compound 1 and HPMCAS, wherein the pharmaceutical composition comprises about 175 mg of substantially amorphous Compound 1.

In one embodiment, the present invention provides a pharmaceutical composition comprising a solid dispersion of substantially amorphous Compound 1 and HPMCAS, wherein the pharmaceutical composition comprises about 200 mg of substantially amorphous Compound 1.

In one embodiment, the present invention provides a pharmaceutical composition comprising a solid dispersion of substantially amorphous Compound 1 and HPMCAS, wherein the pharmaceutical composition comprises about 225 mg of substantially amorphous Compound 1.

In one embodiment, the present invention provides a pharmaceutical composition comprising a solid dispersion of substantially amorphous Compound 1 and HPMCAS, wherein the pharmaceutical composition comprises about 250 mg of substantially amorphous Compound In one embodiment, the present invention provides a pharmaceutical composition comprising a solid dispersion of amorphous Compound 1 and HPMCAS, wherein the solid dispersion comprises up to about 5 mg of amorphous Compound 1. For instance, the solid dispersion comprises about 0.25 mg, about 0.5 mg, about 0.75 mg, about 1 mg, about 2 mg, about 3 mg, about 4 mg, or about 5 mg of amorphous Compound 1.

In one embodiment, the present invention provides a pharmaceutical composition comprising a solid dispersion of amorphous Compound 1 and HPMCAS, wherein the pharmaceutical composition comprises about 10 mg of amorphous Compound 1.

In one embodiment, the present invention provides a pharmaceutical composition comprising a solid dispersion of amorphous Compound 1 and HPMCAS, wherein the pharmaceutical composition comprises about 12.5 mg of amorphous Compound 1.

In one embodiment, the present invention provides a pharmaceutical composition comprising a solid dispersion of amorphous Compound 1 and HPMCAS, wherein the pharmaceutical composition comprises about 15 mg of amorphous Compound 1.

In one embodiment, the present invention provides a pharmaceutical composition comprising a solid dispersion of amorphous Compound 1 and HPMCAS, wherein the pharmaceutical composition comprises about 20 mg of amorphous Compound 1.

In one embodiment, the present invention provides a pharmaceutical composition comprising a solid dispersion of amorphous Compound 1 and HPMCAS, wherein the pharmaceutical composition comprises about 25 mg of amorphous Compound 1.

In one embodiment, the present invention provides a pharmaceutical composition comprising a solid dispersion of amorphous Compound 1 and HPMCAS, wherein the pharmaceutical composition comprises about 30 mg of amorphous Compound 1.

In one embodiment, the present invention provides a pharmaceutical composition comprising a solid dispersion of amorphous Compound 1 and HPMCAS, wherein the pharmaceutical composition comprises about 35 mg of amorphous Compound 1.

In one embodiment, the present invention provides a pharmaceutical composition comprising a solid dispersion of amorphous Compound 1 and HPMCAS, wherein the pharmaceutical composition comprises about 37.5 mg of amorphous Compound 1.

In one embodiment, the present invention provides a pharmaceutical composition comprising a solid dispersion of amorphous Compound 1 and HPMCAS, wherein the pharmaceutical composition comprises about 40 mg of amorphous Compound 1.

In one embodiment, the present invention provides a pharmaceutical composition comprising a solid dispersion of amorphous Compound 1 and HPMCAS, wherein the pharmaceutical composition comprises about 45 mg of amorphous Compound 1.

In one embodiment, the present invention provides a pharmaceutical composition comprising a solid dispersion of amorphous Compound 1 and HPMCAS, wherein the pharmaceutical composition comprises about 50 mg of amorphous Compound 1.

In one embodiment, the present invention provides a pharmaceutical composition comprising a solid dispersion of amorphous Compound 1 and HPMCAS, wherein the pharmaceutical composition comprises about 62.5 mg of amorphous Compound 1.

In one embodiment, the present invention provides a pharmaceutical composition comprising a solid dispersion of amorphous Compound 1 and HPMCAS, wherein the pharmaceutical composition comprises about 75 mg of amorphous Compound 1.

In one embodiment, the present invention provides a pharmaceutical composition comprising a solid dispersion of amorphous Compound 1 and HPMCAS, wherein the pharmaceutical composition comprises about 100 mg of amorphous Compound 1.

In one embodiment, the present invention provides a pharmaceutical composition comprising a solid dispersion of amorphous Compound 1 and HPMCAS, wherein the pharmaceutical composition comprises about 125 mg of amorphous Compound 1.

In one embodiment, the present invention provides a pharmaceutical composition comprising a solid dispersion of amorphous Compound 1 and HPMCAS, wherein the pharmaceutical composition comprises about 150 mg of amorphous Compound 1.

In one embodiment, the present invention provides a pharmaceutical composition comprising a solid dispersion of amorphous Compound 1 and HPMCAS, wherein the pharmaceutical composition comprises about 175 mg of amorphous Compound 1.

In one embodiment, the present invention provides a pharmaceutical composition comprising a solid dispersion of amorphous Compound 1 and HPMCAS, wherein the pharmaceutical composition comprises about 200 mg of amorphous Compound 1.

In one embodiment, the present invention provides a pharmaceutical composition comprising a solid dispersion of amorphous Compound 1 and HPMCAS, wherein the pharmaceutical composition comprises about 225 mg of amorphous Compound 1.

In one embodiment, the present invention provides a pharmaceutical composition comprising a solid dispersion of amorphous Compound 1 and HPMCAS, wherein the pharmaceutical composition comprises about 250 mg of amorphous Compound 1.

In one embodiment, the present invention provides a pharmaceutical composition comprising a solid dispersion of amorphous Compound 1 and HPMCAS, wherein the pharmaceutical composition comprises from about 5 mg to about 250 mg of Compound 1.

In one embodiment, the present invention provides a pharmaceutical composition comprising:
a. a solid dispersion of substantially amorphous Compound 1 and a polymer;
b. one or more fillers;
c. a sweetener;
d. a glidant; and
e. a lubricant,
wherein the solid dispersion comprises up to about 1 mg of substantially amorphous Compound 1.

In one embodiment, the present invention provides a pharmaceutical composition comprising:
a. a solid dispersion of substantially amorphous Compound 1 and a polymer;
b. one or more fillers;
c. a sweetener;
d. a glidant; and
e. a lubricant,
wherein the solid dispersion comprises up to about 5 mg of substantially amorphous Compound 1.

In one embodiment, the present invention provides a pharmaceutical composition comprising:
a. a solid dispersion of substantially amorphous Compound 1 and a polymer;
b. one or more fillers;
c. a sweetener;
d. a glidant; and
e. a lubricant,
wherein the pharmaceutical composition comprises about 5 mg of substantially amorphous Compound 1.

In one embodiment, the present invention provides a pharmaceutical composition comprising:
a. a solid dispersion of substantially amorphous Compound 1 and a polymer;
b. one or more fillers;
c. a sweetener;
d. a glidant; and
e. a lubricant,
wherein the pharmaceutical composition comprises about 10 mg of substantially amorphous Compound 1.

In one embodiment, the present invention provides a pharmaceutical composition comprising:
a. a solid dispersion of substantially amorphous Compound 1 and a polymer;

b. one or more fillers;
c. a sweetener;
d. a glidant; and
e. a lubricant,
wherein the pharmaceutical composition comprises about 12.5 mg of substantially amorphous Compound 1.

In one embodiment, the present invention provides a pharmaceutical composition comprising:
a. a solid dispersion of substantially amorphous Compound 1 and a polymer;
b. one or more fillers;
c. a sweetener;
d. a glidant; and
e. a lubricant,
wherein the pharmaceutical composition comprises about 15 mg of substantially amorphous Compound 1.

In one embodiment, the present invention provides a pharmaceutical composition comprising:
a. a solid dispersion of substantially amorphous Compound 1 and a polymer;
b. one or more fillers;
c. a sweetener;
d. a glidant; and
e. a lubricant,
wherein the pharmaceutical composition comprises about 20 mg of substantially amorphous Compound 1.

In one embodiment, the present invention provides a pharmaceutical composition comprising:
a. a solid dispersion of substantially amorphous Compound 1 and a polymer;
b. one or more fillers;
c. a sweetener;
d. a glidant; and
e. a lubricant,
wherein the pharmaceutical composition comprises about 25 mg of substantially amorphous Compound 1.

In one embodiment, the present invention provides a pharmaceutical composition comprising:
a. a solid dispersion of substantially amorphous Compound 1 and a polymer;
b. one or more fillers;
c. a sweetener;
d. a glidant; and
e. a lubricant,
wherein the pharmaceutical composition comprises about 30 mg of substantially amorphous Compound 1.

In one embodiment, the present invention provides a pharmaceutical composition comprising:
a. a solid dispersion of substantially amorphous Compound 1 and a polymer;
b. one or more fillers;
c. a sweetener;
d. a glidant; and
e. a lubricant,
wherein the pharmaceutical composition comprises about 35 mg of substantially amorphous Compound 1.

In one embodiment, the present invention provides a pharmaceutical composition comprising:
a. a solid dispersion of substantially amorphous Compound 1 and a polymer;
b. one or more fillers;
c. a sweetener;
d. a glidant; and
e. a lubricant,
wherein the pharmaceutical composition comprises about 37.5 mg of substantially amorphous Compound 1.

In one embodiment, the present invention provides a pharmaceutical composition comprising:
a. a solid dispersion of substantially amorphous Compound 1 and a polymer;
b. one or more fillers;
c. a sweetener;
d. a glidant; and
e. a lubricant,
wherein the pharmaceutical composition comprises about 40 mg of substantially amorphous Compound 1.

In one embodiment, the present invention provides a pharmaceutical composition comprising:
a. a solid dispersion of substantially amorphous Compound 1 and a polymer;
b. one or more fillers;
c. a sweetener;
d. a glidant; and
e. a lubricant,
wherein the pharmaceutical composition comprises about 45 mg of substantially amorphous Compound 1.

In one embodiment, the present invention provides a pharmaceutical composition comprising:
a. a solid dispersion of substantially amorphous Compound 1 and a polymer;
b. one or more fillers;
c. a sweetener;
d. a glidant; and
e. a lubricant,
wherein the pharmaceutical composition comprises about 50 mg of substantially amorphous Compound 1.

In one embodiment, the present invention provides a pharmaceutical composition comprising:
a. a solid dispersion of substantially amorphous Compound 1 and a polymer;
b. one or more fillers;
c. a sweetener;
d. a glidant; and
e. a lubricant,
wherein the pharmaceutical composition comprises about 62.5 mg of substantially amorphous Compound 1.

In another embodiment, the present invention provides a pharmaceutical composition comprising:
a. a solid dispersion of substantially amorphous Compound 1 and a polymer;
b. one or more fillers;
c. a sweetener;
d. a glidant; and
e. a lubricant,
wherein the pharmaceutical composition comprises about 75 mg of substantially amorphous Compound 1.

In one embodiment, the present invention provides a pharmaceutical composition comprising:
a. a solid dispersion of substantially amorphous Compound 1 and a polymer;
b. one or more fillers;
c. a sweetener;
d. a glidant; and
e. a lubricant,
wherein the pharmaceutical composition comprises about 100 mg of substantially amorphous Compound 1.

In one embodiment, the present invention provides a pharmaceutical composition comprising:
a. a solid dispersion of substantially amorphous Compound 1 and a polymer;
b. one or more fillers;
c. a sweetener;
d. a glidant; and
e. a lubricant, wherein the pharmaceutical composition comprises about 125 mg of substantially amorphous Compound 1.

In one embodiment, the present invention provides a pharmaceutical composition comprising:
a. a solid dispersion of substantially amorphous Compound 1 and a polymer;
b. one or more fillers;
c. a sweetener;
d. a glidant; and
e. a lubricant,
wherein the pharmaceutical composition comprises about 150 mg of substantially amorphous Compound 1.

In one embodiment, the present invention provides a pharmaceutical composition comprising:
a. a solid dispersion of substantially amorphous Compound 1 and a polymer;
b. one or more fillers;
c. a sweetener;
d. a glidant; and
e. a lubricant,
wherein the pharmaceutical composition comprises about 175 mg of substantially amorphous Compound 1.

In one embodiment, the present invention provides a pharmaceutical composition comprising:
a. a solid dispersion of substantially amorphous Compound 1 and a polymer;
b. one or more fillers;
c. a sweetener;
d. a glidant; and
e. a lubricant,
wherein the pharmaceutical composition comprises about 200 mg of substantially amorphous Compound 1.

In one embodiment, the present invention provides a pharmaceutical composition comprising:
a. a solid dispersion of substantially amorphous Compound 1 and a polymer;
b. one or more fillers;
c. a sweetener;
d. a glidant; and
e. a lubricant,
wherein the pharmaceutical composition comprises about 225 mg of substantially amorphous Compound 1.

In one embodiment, the present invention provides a pharmaceutical composition comprising:
a. a solid dispersion of substantially amorphous Compound 1 and a polymer;
b. one or more fillers;
c. a sweetener;
d. a glidant; and
e. a lubricant,
wherein the pharmaceutical composition comprises about 250 mg of substantially amorphous Compound 1.

In a further embodiment, the one or more fillers is a binary filler comprising a mixture of 2 fillers. In another further embodiment, the binary filler is a mixture of mannitol and another filler. In another further embodiment, the binary filler is a mixture of lactose and another filler. In another further embodiment, the binary filler is a mixture of mannitol and lactose.

In another further embodiment, the pharmaceutical composition comprises a binary filler, wherein the binary filler comprises mannitol in an amount up to about 100 wt % of the binary filler, In still another further embodiment, the pharmaceutical composition comprises a binary filler, wherein the binary filler comprises lactose in an amount up to about 100 wt % of the binary filler, In still another further embodiment, the pharmaceutical composition comprises a binary filler, wherein the binary filler comprises mannitol in an amount up to about 100 wt % of the binary filler and lactose in an amount such that the sum of the amount of mannitol and lactose is equal to 100 wt %.

In some embodiments, the pharmaceutical composition comprises a binary filler, wherein the binary filler comprises mannitol and another filler in a ratio of about 3:1 mannitol to other filler, a ratio of about 1:1 mannitol to other filler, or a ratio of about 1:3 mannitol to other filler. In some embodiments, the pharmaceutical composition comprises a binary filler, wherein the binary filler comprises lactose and another filler in a ratio of about 3:1 lactose to other filler, a ratio of about 1:1 lactose to other filler, or a ratio of about 1:3 lactose to other filler. In some embodiments, the pharmaceutical composition comprises a binary filler, wherein the binary filler comprises mannitol and lactose in a ratio of about 3:1 mannitol to lactose, a ratio of about 1:1 mannitol to lactose, or a ratio of about 1:3 mannitol to lactose.

In one embodiment, the present invention provides a pharmaceutical composition comprising:
a. a solid dispersion of amorphous Compound 1 and a polymer;
b. one or more fillers;
c. a sweetener;
d. a glidant; and
e. a lubricant,
wherein the solid dispersion comprises up to about 1 mg of amorphous Compound 1.

In one embodiment, the present invention provides a pharmaceutical composition comprising:
a. a solid dispersion of amorphous Compound 1 and a polymer;
b. one or more fillers;
c. a sweetener;
d. a glidant; and
e. a lubricant,
wherein the solid dispersion comprises up to about 5 mg of amorphous Compound 1.

In one embodiment, the present invention provides a pharmaceutical composition comprising:
a. a solid dispersion of amorphous Compound 1 and a polymer;
b. one or more fillers;
c. a sweetener;
d. a glidant; and
e. a lubricant,
wherein the pharmaceutical composition comprises about 10 mg of amorphous Compound 1.

In one embodiment, the present invention provides a pharmaceutical composition comprising:
a. a solid dispersion of amorphous Compound 1 and a polymer;
b. one or more fillers;
c. a sweetener;
d. a glidant; and
e. a lubricant,
wherein the pharmaceutical composition comprises about 12.5 mg of amorphous Compound 1.

In one embodiment, the present invention provides a pharmaceutical composition comprising:
a. a solid dispersion of amorphous Compound 1 and a polymer;
b. one or more fillers;
c. a sweetener;
d. a glidant; and
e. a lubricant, wherein the pharmaceutical composition comprises about 15 mg of amorphous Compound 1.

In one embodiment, the present invention provides a pharmaceutical composition comprising:
a. a solid dispersion of amorphous Compound 1 and a polymer;
b. one or more fillers;
c. a sweetener;
d. a glidant; and
e. a lubricant,
wherein the pharmaceutical composition comprises about 20 mg of amorphous Compound 1.

In one embodiment, the present invention provides a pharmaceutical composition comprising:
a. a solid dispersion of amorphous Compound 1 and a polymer;
b. one or more fillers;
c. a sweetener;
d. a glidant; and
e. a lubricant,
wherein the pharmaceutical composition comprises about 25 mg of amorphous Compound 1.

In one embodiment, the present invention provides a pharmaceutical composition comprising:
a. a solid dispersion of amorphous Compound 1 and a polymer;
b. one or more fillers;
c. a sweetener;
d. a glidant; and
e. a lubricant,
wherein the pharmaceutical composition comprises about 30 mg of amorphous Compound 1.

In one embodiment, the present invention provides a pharmaceutical composition comprising:
a. a solid dispersion of amorphous Compound 1 and a polymer;
b. one or more fillers;
c. a sweetener;
d. a glidant; and
e. a lubricant,
wherein the pharmaceutical composition comprises about 35 mg of amorphous Compound 1.

In one embodiment, the present invention provides a pharmaceutical composition comprising:
a. a solid dispersion of amorphous Compound 1 and a polymer;
b. one or more fillers;
c. a sweetener;
d. a glidant; and
e. a lubricant,
wherein the pharmaceutical composition comprises about 37.5 mg of amorphous Compound 1.

In one embodiment, the present invention provides a pharmaceutical composition comprising:
a. a solid dispersion of amorphous Compound 1 and a polymer;
b. one or more fillers;
c. a sweetener;
d. a glidant; and
e. a lubricant,
wherein the pharmaceutical composition comprises about 40 mg of amorphous Compound 1.

In one embodiment, the present invention provides a pharmaceutical composition comprising:
a. a solid dispersion of amorphous Compound 1 and a polymer;
b. one or more fillers;
c. a sweetener;
d. a glidant; and
e. a lubricant,
wherein the pharmaceutical composition comprises about 45 mg of amorphous Compound 1.

In one embodiment, the present invention provides a pharmaceutical composition comprising:
a. a solid dispersion of amorphous Compound 1 and a polymer;
b. one or more fillers;
c. a sweetener;
d. a glidant; and
e. a lubricant,
wherein the pharmaceutical composition comprises about 50 mg of amorphous Compound 1.

In one embodiment, the present invention provides a pharmaceutical composition comprising:
a. a solid dispersion of amorphous Compound 1 and a polymer;
b. one or more fillers;
c. a sweetener;
d. a glidant; and
e. a lubricant,
wherein the pharmaceutical composition comprises about 62.5 mg of amorphous Compound 1.

In another embodiment, the present invention provides a pharmaceutical composition comprising:
a. a solid dispersion of amorphous Compound 1 and a polymer;
b. one or more fillers;
c. a sweetener;
d. a glidant; and
e. a lubricant,
wherein the pharmaceutical composition comprises about 75 mg of amorphous Compound 1.

In one embodiment, the present invention provides a pharmaceutical composition comprising:
a. a solid dispersion of amorphous Compound 1 and a polymer;
b. one or more fillers;
c. a sweetener;
d. a glidant; and
e. a lubricant,
wherein pharmaceutical composition comprises about 100 mg of amorphous Compound 1.

In one embodiment, the present invention provides a pharmaceutical composition comprising:
a. a solid dispersion of amorphous Compound 1 and a polymer;
b. one or more fillers;
c. a sweetener;
d. a glidant; and
e. a lubricant,
wherein the pharmaceutical composition comprises about 125 mg of amorphous Compound 1.

In one embodiment, the present invention provides a pharmaceutical composition comprising:
a. a solid dispersion of amorphous Compound 1 and a polymer;
b. one or more fillers;
c. a sweetener;
d. a glidant; and
e. a lubricant,
wherein the pharmaceutical composition comprises about 150 mg of amorphous Compound 1.

In one embodiment, the present invention provides a pharmaceutical composition comprising:
  a. a solid dispersion of amorphous Compound 1 and a polymer;
  b. one or more fillers;
  c. a sweetener;
  d. a glidant; and
  e. a lubricant,
wherein the pharmaceutical composition comprises about 175 mg of amorphous Compound 1.

In one embodiment, the present invention provides a pharmaceutical composition comprising:
  a. a solid dispersion of amorphous Compound 1 and a polymer;
  b. one or more fillers;
  c. a sweetener;
  d. a glidant; and
  e. a lubricant,
wherein the pharmaceutical composition comprises about 200 mg of amorphous Compound 1.

In one embodiment, the present invention provides a pharmaceutical composition comprising:
  a. a solid dispersion of amorphous Compound 1 and a polymer;
  b. one or more fillers;
  c. a sweetener;
  d. a glidant; and
  e. a lubricant,
wherein the pharmaceutical composition comprises about 225 mg of amorphous Compound 1.

In one embodiment, the present invention provides a pharmaceutical composition comprising:
  a. a solid dispersion of amorphous Compound 1 and a polymer;
  b. one or more fillers;
  c. a sweetener;
  d. a glidant; and
  e. a lubricant,
wherein the pharmaceutical composition comprises about 250 mg of amorphous Compound 1.

In a further embodiment, the one or more fillers is a binary filler comprising a mixture of 2 fillers. In another further embodiment, the binary filler is a mixture of mannitol and another filler. In another further embodiment, the binary filler is a mixture of lactose and another filler. In another further embodiment, the binary filler is a mixture of mannitol and lactose.

In another further embodiment, the pharmaceutical composition comprises a binary filler, wherein the binary filler comprises mannitol in an amount up to about 100 wt % of the binary filler, In still another further embodiment, the pharmaceutical composition comprises a binary filler, wherein the binary filler comprises lactose in an amount up to about 100 wt % of the binary filler, In still another further embodiment, the pharmaceutical composition comprises a binary filler, wherein the binary filler comprises mannitol in an amount up to about 100 wt % of the binary filler and lactose in an amount such that the sum of the amount of mannitol and lactose is equal to 100 wt %.

In some embodiments, the pharmaceutical composition comprises a binary filler, wherein the binary filler comprises mannitol and another filler in a ratio of about 3:1 mannitol to other filler, a ratio of about 1:1 mannitol to other filler, or a ratio of about 1:3 mannitol to other filler. In some embodiments, the pharmaceutical composition comprises a binary filler, wherein the binary filler comprises lactose and another filler in a ratio of about 3:1 lactose to other filler, a ratio of about 1:1 lactose to other filler, or a ratio of about 1:3 lactose to other filler. In some embodiments, the pharmaceutical composition comprises a binary filler, wherein the binary filler comprises mannitol and lactose in a ratio of about 3:1 mannitol to lactose, a ratio of about 1:1 mannitol to lactose, or a ratio of about 1:3 mannitol to lactose.

In one embodiment, the present invention provides a pharmaceutical composition comprising:
  a. a solid dispersion of substantially amorphous Compound 1 and HPMCAS;
  b. one or more fillers;
  c. a sweetener;
  d. a glidant; and
  e. a lubricant,
wherein the solid dispersion comprises up to about 1 mg of substantially amorphous Compound 1.

In one embodiment, the present invention provides a pharmaceutical composition comprising:
  a. a solid dispersion of substantially amorphous Compound 1 and HPMCAS;
  b. one or more fillers;
  c. a sweetener;
  d. a glidant; and
  e. a lubricant,
wherein the solid dispersion comprises up to about 5 mg of substantially amorphous Compound 1.

In one embodiment, the present invention provides a pharmaceutical composition comprising:
  a. a solid dispersion of substantially amorphous Compound 1 and HPMCAS;
  b. one or more fillers;
  c. a sweetener;
  d. a glidant; and
  e. a lubricant,
wherein the pharmaceutical composition comprises about 5 mg of substantially amorphous Compound 1.

In one embodiment, the present invention provides a pharmaceutical composition comprising:
  a. a solid dispersion of substantially amorphous Compound 1 and HPMCAS;
  b. one or more fillers;
  c. a sweetener;
  d. a glidant; and
  e. a lubricant,
wherein the pharmaceutical composition comprises about 10 mg of substantially amorphous Compound 1.

In one embodiment, the present invention provides a pharmaceutical composition comprising:
  a. a solid dispersion of substantially amorphous Compound 1 and HPMCAS;
  b. one or more fillers;
  c. a sweetener;
  d. a glidant; and
  e. a lubricant,
wherein the pharmaceutical composition comprises about 12.5 mg of substantially amorphous Compound 1.

In one embodiment, the present invention provides a pharmaceutical composition comprising:
  a. a solid dispersion of substantially amorphous Compound 1 and HPMCAS;
  b. one or more fillers;
  c. a sweetener;
  d. a glidant; and
  e. a lubricant,
wherein the pharmaceutical composition comprises about 15 mg of substantially amorphous Compound 1.

In one embodiment, the present invention provides a pharmaceutical composition comprising:
a. a solid dispersion of substantially amorphous Compound 1 and HPMCAS;
b. one or more fillers;
c. a sweetener;
d. a glidant; and
e. a lubricant,
wherein the pharmaceutical composition comprises about 20 mg of substantially amorphous Compound 1.

In one embodiment, the present invention provides a pharmaceutical composition comprising:
a. a solid dispersion of substantially amorphous Compound 1 and HPMCAS;
b. one or more fillers;
c. a sweetener;
d. a glidant; and
e. a lubricant,
wherein the pharmaceutical composition comprises about 25 mg of substantially amorphous Compound 1.

In one embodiment, the present invention provides a pharmaceutical composition comprising:
a. a solid dispersion of substantially amorphous Compound 1 and HPMCAS;
b. one or more fillers;
c. a sweetener;
d. a glidant; and
e. a lubricant,
wherein the pharmaceutical composition comprises about 30 mg of substantially amorphous Compound 1.

In one embodiment, the present invention provides a pharmaceutical composition comprising:
a. a solid dispersion of substantially amorphous Compound 1 and HPMCAS;
b. one or more fillers;
c. a sweetener;
d. a glidant; and
e. a lubricant,
wherein the pharmaceutical composition comprises about 35 mg of substantially amorphous Compound 1.

In one embodiment, the present invention provides a pharmaceutical composition comprising:
a. a solid dispersion of substantially amorphous Compound 1 and HPMCAS;
b. one or more fillers;
c. a sweetener;
d. a glidant; and
e. a lubricant,
wherein the pharmaceutical composition comprises about 37.5 mg of substantially amorphous Compound 1.

In one embodiment, the present invention provides a pharmaceutical composition comprising:
a. a solid dispersion of substantially amorphous Compound 1 and HPMCAS;
b. one or more fillers;
c. a sweetener;
d. a glidant; and
e. a lubricant,
wherein the pharmaceutical composition comprises about 40 mg of substantially amorphous Compound 1.

In one embodiment, the present invention provides a pharmaceutical composition comprising:
a. a solid dispersion of substantially amorphous Compound 1 and HPMCAS;
b. one or more fillers;
c. a sweetener;
d. a glidant; and
e. a lubricant,
wherein the pharmaceutical composition comprises about 45 mg of substantially amorphous Compound 1.

In one embodiment, the present invention provides a pharmaceutical composition comprising:
a. a solid dispersion of substantially amorphous Compound 1 and HPMCAS;
b. one or more fillers;
c. a sweetener;
d. a glidant; and
e. a lubricant,
wherein the pharmaceutical composition comprises about 50 mg of substantially amorphous Compound 1.

In one embodiment, the present invention provides a pharmaceutical composition comprising:
a. a solid dispersion of substantially amorphous Compound 1 and HPMCAS;
b. one or more fillers;
c. a sweetener;
d. a glidant; and
e. a lubricant,
wherein the pharmaceutical composition comprises about 62.5 mg of substantially amorphous Compound 1.

In another embodiment, the present invention provides a pharmaceutical composition comprising:
a. a solid dispersion of substantially amorphous Compound 1 and HPMCAS;
b. one or more fillers;
c. a sweetener;
d. a glidant; and
e. a lubricant,
wherein the pharmaceutical composition comprises about 75 mg of substantially amorphous Compound 1.

In one embodiment, the present invention provides a pharmaceutical composition comprising:
a. a solid dispersion of substantially amorphous Compound 1 and HPMCAS;
b. one or more fillers;
c. a sweetener;
d. a glidant; and
e. a lubricant,
wherein the pharmaceutical composition comprises about 100 mg of substantially amorphous Compound 1.

In one embodiment, the present invention provides a pharmaceutical composition comprising:
a. a solid dispersion of substantially amorphous Compound 1 and HPMCAS;
b. one or more fillers;
c. a sweetener;
d. a glidant; and
e. a lubricant,
wherein the pharmaceutical composition comprises about 125 mg of substantially amorphous Compound 1.

In one embodiment, the present invention provides a pharmaceutical composition comprising:
a. a solid dispersion of substantially amorphous Compound 1 and HPMCAS;
b. one or more fillers;
c. a sweetener;
d. a glidant; and
e. a lubricant,
wherein the pharmaceutical composition comprises about 150 mg of substantially amorphous Compound 1.

In one embodiment, the present invention provides a pharmaceutical composition comprising:
a. a solid dispersion of substantially amorphous Compound 1 and HPMCAS;

b. one or more fillers;
c. a sweetener;
d. a glidant; and
e. a lubricant,
wherein the pharmaceutical composition comprises about 175 mg of substantially amorphous Compound 1.

In one embodiment, the present invention provides a pharmaceutical composition comprising:
a. a solid dispersion of substantially amorphous Compound 1 and HPMCAS;
b. one or more fillers;
c. a sweetener;
d. a glidant; and
e. a lubricant,
wherein the pharmaceutical composition comprises about 200 mg of substantially amorphous Compound 1.

In one embodiment, the present invention provides a pharmaceutical composition comprising:
a. a solid dispersion of substantially amorphous Compound 1 and HPMCAS;
b. one or more fillers;
c. a sweetener;
d. a glidant; and
e. a lubricant,
wherein the pharmaceutical composition comprises about 225 mg of substantially amorphous Compound 1.

In one embodiment, the present invention provides a pharmaceutical composition comprising:
a. a solid dispersion of substantially amorphous Compound 1 and HPMCAS;
b. one or more fillers;
c. a sweetener;
d. a glidant; and
e. a lubricant,
wherein the pharmaceutical composition comprises about 250 mg of substantially amorphous Compound 1.

In a further embodiment, the one or more fillers is a binary filler comprising a mixture of 2 fillers. In another further embodiment, the binary filler is a mixture of mannitol and another filler. In another further embodiment, the binary filler is a mixture of lactose and another filler. In another further embodiment, the binary filler is a mixture of mannitol and lactose.

In another further embodiment, the pharmaceutical composition comprises a binary filler, wherein the binary filler comprises mannitol in an amount up to about 100 wt % of the binary filler, In still another further embodiment, the pharmaceutical composition comprises a binary filler, wherein the binary filler comprises lactose in an amount up to about 100 wt % of the binary filler, In still another further embodiment, the pharmaceutical composition comprises a binary filler, wherein the binary filler comprises mannitol in an amount up to about 100 wt % of the binary filler and lactose in an amount such that the sum of the amount of mannitol and lactose is equal to 100 wt %.

In some embodiments, the pharmaceutical composition comprises a binary filler, wherein the binary filler comprises mannitol and another filler in a ratio of about 3:1 mannitol to other filler, a ratio of about 1:1 mannitol to other filler, or a ratio of about 1:3 mannitol to other filler. In some embodiments, the pharmaceutical composition comprises a binary filler, wherein the binary filler comprises lactose and another filler in a ratio of about 3:1 lactose to other filler, a ratio of about 1:1 lactose to other filler, or a ratio of about 1:3 lactose to other filler. In some embodiments, the pharmaceutical composition comprises a binary filler, wherein the binary filler comprises mannitol and lactose in a ratio of about 3:1 mannitol to lactose, a ratio of about 1:1 mannitol to lactose, or a ratio of about 1:3 mannitol to lactose.

In one embodiment, the present invention provides a pharmaceutical composition comprising:
a. a solid dispersion of amorphous Compound 1 and HPMCAS;
b. one or more fillers;
c. a sweetener;
d. a glidant; and
e. a lubricant,
wherein the solid dispersion comprises up to about 1 mg of amorphous Compound 1.

In one embodiment, the present invention provides a pharmaceutical composition comprising:
a. a solid dispersion of amorphous Compound 1 and HPMCAS;
b. one or more fillers;
c. a sweetener;
d. a glidant; and
e. a lubricant,
wherein the solid dispersion comprises up to about 5 mg of amorphous Compound 1.

In one embodiment, the present invention provides a pharmaceutical composition comprising:
a. a solid dispersion of amorphous Compound 1 and HPMCAS;
b. one or more fillers;
c. a sweetener;
d. a glidant; and
e. a lubricant,
wherein the pharmaceutical composition comprises about 5 mg of amorphous Compound 1.

In one embodiment, the present invention provides a pharmaceutical composition comprising:
a. a solid dispersion of amorphous Compound 1 and HPMCAS;
b. one or more fillers;
c. a sweetener;
d. a glidant; and
e. a lubricant,
wherein the pharmaceutical composition comprises about 10 mg of amorphous Compound 1.

In one embodiment, the present invention provides a pharmaceutical composition comprising:
a. a solid dispersion of amorphous Compound 1 and HPMCAS;
b. one or more fillers;
c. a sweetener;
d. a glidant; and
e. a lubricant,
wherein the pharmaceutical composition comprises about 12.5 mg of amorphous Compound 1.

In one embodiment, the present invention provides a pharmaceutical composition comprising:
a. a solid dispersion of amorphous Compound 1 and HPMCAS;
b. one or more fillers;
c. a sweetener;
d. a glidant; and
e. a lubricant,
wherein the pharmaceutical composition comprises about 15 mg of amorphous Compound 1.

In one embodiment, the present invention provides a pharmaceutical composition comprising:
a. a solid dispersion of amorphous Compound 1 and HPMCAS;
b. one or more fillers;

c. a sweetener;
d. a glidant; and
e. a lubricant,
wherein the pharmaceutical composition comprises about 20 mg of amorphous Compound 1.

In one embodiment, the present invention provides a pharmaceutical composition comprising:
a. a solid dispersion of amorphous Compound 1 and HPMCAS;
b. one or more fillers;
c. a sweetener;
d. a glidant; and
e. a lubricant,
wherein the pharmaceutical composition comprises about 25 mg of amorphous Compound 1.

In one embodiment, the present invention provides a pharmaceutical composition comprising:
a. a solid dispersion of amorphous Compound 1 and HPMCAS;
b. one or more fillers;
c. a sweetener;
d. a glidant; and
e. a lubricant,
wherein the pharmaceutical composition comprises about 30 mg of amorphous Compound 1.

In one embodiment, the present invention provides a pharmaceutical composition comprising:
a. a solid dispersion of amorphous Compound 1 and HPMCAS;
b. one or more fillers;
c. a sweetener;
d. a glidant; and
e. a lubricant,
wherein the pharmaceutical composition comprises about 35 mg of amorphous Compound 1.

In one embodiment, the present invention provides a pharmaceutical composition comprising:
a. a solid dispersion of amorphous Compound 1 and HPMCAS;
b. one or more fillers;
c. a sweetener;
d. a glidant; and
e. a lubricant,
wherein the pharmaceutical composition comprises about 37.5 mg of amorphous Compound 1

In one embodiment, the present invention provides a pharmaceutical composition comprising:
a. a solid dispersion of amorphous Compound 1 and HPMCAS;
b. one or more fillers;
c. a sweetener;
d. a glidant; and
e. a lubricant,
wherein the pharmaceutical composition comprises about 40 mg of amorphous Compound 1.

In one embodiment, the present invention provides a pharmaceutical composition comprising:
a. a solid dispersion of amorphous Compound 1 and HPMCAS;
b. one or more fillers;
c. a sweetener;
d. a glidant; and
e. a lubricant,
wherein the pharmaceutical composition comprises about 45 mg of amorphous Compound 1.

In one embodiment, the present invention provides a pharmaceutical composition comprising:
a. a solid dispersion of amorphous Compound 1 and HPMCAS;
b. one or more fillers;
c. a sweetener;
d. a glidant; and
e. a lubricant,
wherein the pharmaceutical composition comprises about 50 mg of amorphous Compound 1.

In one embodiment, the present invention provides a pharmaceutical composition comprising:
a. a solid dispersion of amorphous Compound 1 and HPMCAS;
b. one or more fillers;
c. a sweetener;
d. a glidant; and
e. a lubricant,
wherein the pharmaceutical composition comprises about 62.5 mg of amorphous Compound 1.

In another embodiment, the present invention provides a pharmaceutical composition comprising:
a. a solid dispersion of amorphous Compound 1 and HPMCAS;
b. one or more fillers;
c. a sweetener;
d. a glidant; and
e. a lubricant,
wherein the pharmaceutical composition comprises about 75 mg of amorphous Compound 1.

In one embodiment, the present invention provides a pharmaceutical composition comprising:
a. a solid dispersion of amorphous Compound 1 and HPMCAS;
b. one or more fillers;
c. a sweetener;
d. a glidant; and
e. a lubricant,
wherein the pharmaceutical composition comprises about 100 mg of amorphous Compound 1.

In one embodiment, the present invention provides a pharmaceutical composition comprising:
a. a solid dispersion of amorphous Compound 1 and HPMCAS;
b. one or more fillers;
c. a sweetener;
d. a glidant; and
e. a lubricant,
wherein the pharmaceutical composition comprises about 125 mg of amorphous Compound 1.

In one embodiment, the present invention provides a pharmaceutical composition comprising:
a. a solid dispersion of amorphous Compound 1 and HPMCAS;
b. one or more fillers;
c. a sweetener;
d. a glidant; and
e. a lubricant,
wherein the pharmaceutical composition comprises about 150 mg of amorphous Compound 1.

In one embodiment, the present invention provides a pharmaceutical composition comprising:
a. a solid dispersion of amorphous Compound 1 and HPMCAS;
b. one or more fillers;
c. a sweetener;
d. a glidant; and
e. a lubricant, wherein the pharmaceutical composition comprises about 175 mg of amorphous Compound 1.

In one embodiment, the present invention provides a pharmaceutical composition comprising:
 a. a solid dispersion of amorphous Compound 1 and HPMCAS;
 b. one or more fillers;
 c. a sweetener;
 d. a glidant; and
 e. a lubricant,
wherein the pharmaceutical composition comprises about 200 mg of amorphous Compound 1.

In one embodiment, the present invention provides a pharmaceutical composition comprising:
 a. a solid dispersion of amorphous Compound 1 and HPMCAS;
 b. one or more fillers;
 c. a sweetener;
 d. a glidant; and
 e. a lubricant,
wherein the pharmaceutical composition comprises about 225 mg of amorphous Compound 1.

In one embodiment, the present invention provides a pharmaceutical composition comprising:
 a. a solid dispersion of amorphous Compound 1 and HPMCAS;
 b. one or more fillers;
 c. a sweetener;
 d. a glidant; and
 e. a lubricant,
wherein the pharmaceutical composition comprises about 250 mg of amorphous Compound 1.

In a further embodiment, the one or more fillers is a binary filler comprising a mixture of 2 fillers. In another further embodiment, the binary filler is a mixture of mannitol and another filler. In another further embodiment, the binary filler is a mixture of lactose and another filler. In another further embodiment, the binary filler is a mixture of mannitol and lactose.

In another further embodiment, the pharmaceutical composition comprises a binary filler, wherein the binary filler comprises mannitol in an amount up to about 100 wt % of the binary filler, In still another further embodiment, the pharmaceutical composition comprises a binary filler, wherein the binary filler comprises lactose in an amount up to about 100 wt % of the binary filler, In still another further embodiment, the pharmaceutical composition comprises a binary filler, wherein the binary filler comprises mannitol in an amount up to about 100 wt % of the binary filler and lactose in an amount such that the sum of the amount of mannitol and lactose is equal to 100 wt %.

In some embodiments, the pharmaceutical composition comprises a binary filler, wherein the binary filler comprises mannitol and another filler in a ratio of about 3:1 mannitol to other filler, a ratio of about 1:1 mannitol to other filler, or a ratio of about 1:3 mannitol to other filler. In some embodiments, the pharmaceutical composition comprises a binary filler, wherein the binary filler comprises lactose and another filler in a ratio of about 3:1 lactose to other filler, a ratio of about 1:1 lactose to other filler, or a ratio of about 1:3 lactose to other filler. In some embodiments, the pharmaceutical composition comprises a binary filler, wherein the binary filler comprises mannitol and lactose in a ratio of about 3:1 mannitol to lactose, a ratio of about 1:1 mannitol to lactose, or a ratio of about 1:3 mannitol to lactose.

Suitable solid dispersions of Compound 1, i.e., N-[2,4-bis(1,1-dimethylethyl)-5-hydroxyphenyl]-1,4-dihydro-4-oxoquinoline-3-carboxamide, include, without limitation, those dispersions described in PCT publication no. WO 2007/079139, WO 2010/019239, WO 2011/019413, US 2010/0074949, US 2010/0256184, and US 2011/0064811, which are hereby incorporated by reference in their entirety.

In one embodiment, the pharmaceutical composition of the present invention comprises a solid dispersion of Compound 1. For example, the solid dispersion comprises substantially amorphous Compound 1, where Compound 1 is less than about 15% (e.g., less than about 10% or less than about 5%) crystalline, and at least one polymer. In another example, the solid dispersion comprises amorphous Compound 1, i.e., Compound 1 has about 0% crystallinity. The concentration of Compound 1 in the solid dispersion depends on several factors such as the amount of pharmaceutical composition needed to provide a desired amount of Compound 1 and the desired dissolution profile of the pharmaceutical composition.

Polymers useful in these solid dispersions are inert, pharmaceutically acceptable polymers that are at least partially soluble in water or biological fluids. Polymers can include homopolymers (e.g., polysaccharides) or copolymers (e.g., block copolymers). In one example, the solid dispersion comprises substantially amorphous or amorphous N-[2,4-bis(1,1-dimethylethyl)-5-hydroxyphenyl]-1,4-dihydro-4-oxo-quinoline-3-carboxamide and at least one polymer independently selected from hydroxypropylmethylcellulose (HPMC), hydroxypropylmethylcellulose acetate succinate (HPMCAS), polyvinylpyrrolidone/vinyl acetate copolymer (PVP/VA), polyvinylpyrrolidone (PVP), methacrylic acid/methacrylate copolymers, hydroxypropyl cellulose (HPC), or any combination thereof. In another example, the solid dispersion comprises substantially amorphous or amorphous N-[2,4-bis(1,1-dimethylethyl)-5-hydroxyphenyl]-1,4-dihydro-4-oxoquinoline-3-carboxamide and HPMCAS or PVP/VA.

In another embodiment, the pharmaceutical composition comprises a solid dispersion that contains substantially amorphous Compound 1 and HPMCAS, in which the solid dispersion has a mean particle diameter, measured by light scattering (e.g., using a Malvern Mastersizer available from Malvern Instruments in England) of greater than about 5 μm (e.g., greater than about 6 μm, greater than about 7 μm, greater than about 8 μm, or greater than about 10 μm). For example, the pharmaceutical composition comprises a solid dispersion that contains amorphous Compound 1 and HPMCAS, in which the solid dispersion has a mean particle diameter, measured by light scattering, of greater than about 5 μm (e.g., greater than about 6 μm, greater than about 7 μm, greater than about 8 μm, or greater than about 10 μm). In another example, the pharmaceutical composition comprises a solid dispersion comprising substantially amorphous Compound 1 and HPMCAS, in which the solid dispersion has a mean particle diameter, measured by light scattering, of from about 7 μm to about 25 μm. For instance, the pharmaceutical composition comprises a solid dispersion comprising amorphous Compound 1 and HPMCAS, in which the solid dispersion has a mean particle diameter, measured by light scattering, of from about 7 μm to about 25 μm. In yet another example, the pharmaceutical composition comprises a solid dispersion comprising substantially amorphous Compound 1 and HPMCAS, in which the solid dispersion has a mean particle diameter, measured by light scattering, of from about 10 μm to about 35 μm. For instance, the pharmaceutical composition comprises a solid dispersion comprising amorphous Compound 1 and HPMCAS, in which the solid dispersion has a mean particle diameter, measured by light scattering, of from about 10 µm to about 35 µm.

For instance, the pharmaceutical composition comprises a solid dispersion comprising amorphous Compound 1 and HPMCAS, in which the solid dispersion has a mean particle diameter, measured by light scattering, of from about 10 µm to about 100 µm.

For instance, the pharmaceutical composition comprises a solid dispersion comprising amorphous Compound 1 and HPMCAS, in which the solid dispersion has a mean particle diameter, measured by light scattering, of from about 50 µm to about 150 µm.

For instance, the pharmaceutical composition comprises a solid dispersion comprising amorphous Compound 1 and HPMCAS, in which the solid dispersion has a mean particle diameter, measured by light scattering, of from about 100 µm to about 200 µm.

For instance, the pharmaceutical composition comprises a solid dispersion comprising amorphous Compound 1 and HPMCAS, in which the solid dispersion has a mean particle diameter, measured by light scattering, of from about 150 µm to about 300 µm.

In another example, the pharmaceutical composition comprises a solid dispersion comprising substantially amorphous Compound 1 and HPMCAS, in which the solid dispersion has a bulk density of about 0.10 g/cc or greater (e.g., 0.15 g/cc or greater, 0.17 g/cc or greater). For instance, the pharmaceutical composition comprising a solid dispersion comprising amorphous Compound 1 and HPMCAS, in which the solid dispersion has a bulk density of about 0.10 g/cc or greater (e.g., 0.15 g/cc or greater, 0.17 g/cc or greater). In another instance, the pharmaceutical composition comprises a solid dispersion that comprises substantially amorphous Compound 1 and HPMCAS, in which the solid dispersion has a bulk density of from about 0.10 g/cc to about 0.45 g/cc (e.g., from about 0.15 g/cc to about 0.42 g/cc, or from about 0.17 g/cc to about 0.40 g/cc). In still another instance, the pharmaceutical composition comprises a solid dispersion that includes amorphous Compound 1 and HPMCAS, in which the solid dispersion has a bulk density of from about 0.10 g/cc to about 0.45 g/cc (e.g., from about 0.15 g/cc to about 0.42 g/cc, or from about 0.17 g/cc to about 0.40 g/cc). In another example, the pharmaceutical composition comprises a solid dispersion that comprises substantially amorphous Compound 1 and HPMCAS, in which the solid dispersion has a bulk density of from about 0.10 g/cc to about 0.45 g/cc (e.g., from about 0.15 g/cc to about 0.42 g/cc, or from about 0.17 g/cc to about 0.40 g/cc). For instance, the pharmaceutical composition includes a solid dispersion that comprises amorphous Compound 1 and HPMCAS, in which the solid dispersion has a bulk density of from about 0.10 g/cc to about 0.45 g/cc (e.g., from about 0.15 g/cc to about 0.42 g/cc, or from about 0.17 g/cc to about 0.40 g/cc).

Alternative solid dispersions comprise substantially amorphous or amorphous Compound 1 and HPMCAS, wherein substantially amorphous Compound 1 or amorphous Compound 1 is present in an amount of at least 20 wt % (e.g., at least 40 wt %, at least 45 wt %, at least 49 wt %, or at least 50 wt %) by weight of the solid dispersion. In some embodiments, the solid dispersion comprises HPMCAS and from about 20 wt % to about 99 wt %, including all of the values and ranges contained therein, (e.g., from about 40 wt % to about 90 wt %, from about 42 wt % to about 88 wt %, from about 45 wt % to about 85 wt %, or from about 50 wt % to about 80 wt %) of substantially amorphous or amorphous Compound 1 by weight of the solid dispersion. For example, the solid dispersion comprises HPMCAS and from about 40 wt % to about 60 wt %, including all of the values and ranges contained therein, (e.g., from about 42 wt % to about 57 wt %, from about 45 wt % to about 55 wt %, or from about 47 wt % to about 53 wt %) of substantially amorphous or amorphous Compound 1 by weight of the solid dispersion. In another example, the solid dispersion comprises HPMCAS and from about 65 wt % to about 95 wt %, including all of the values and ranges contained therein, (e.g., from about 67 wt % to about 92 wt %, from about 70 wt % to about 90 wt %, or from about 72 wt % to about 88 wt %) of substantially amorphous Compound 1 or amorphous Compound 1 by weight of the solid dispersion.

In other embodiments, the solid dispersion comprises 80 wt % or less (e.g., 60 wt % or less, 55 wt % or less, or 50 wt % or less) of polymer (e.g., HPMCAS) by weight of solid dispersion. In some instances, the solid dispersion comprises from about 1 wt % to about 80 wt %, including all of the values and ranges contained therein, (e.g., from about 10 wt % to about 60 wt %) of polymer (e.g., HPMCAS).

Some solid dispersions comprise from about 40 wt % to about 60 wt %, including all of the values and ranges contained therein, (e.g., from about 42 wt % to about 57 wt %, from about 45 wt % to about 55 wt %, or from about 47 wt % to about 53 wt %) of substantially amorphous Compound 1 by weight of the solid dispersion and from about 60 wt % to about 40 wt % of polymer (e.g., HPMCAS). Alternative solid dispersions comprise from about 40 wt % to about 60 wt %, including all of the values and ranges contained therein, (e.g., from about 42 wt % to about 57 wt %, from about 45 wt % to about 55 wt %, or from about 47 wt % to about 53 wt %) of amorphous Compound 1 by weight of the solid dispersion and from about 60 wt % to about 40 wt % of polymer (e.g., HPMCAS).

Other solid dispersions comprise from about 65 wt % to about 95 wt %, including all of the values and ranges contained therein (e.g., from about 67 wt % to about 92 wt %, from about 70 wt % to about 90 wt %, or from about 72 wt % to about 88 wt %) of substantially amorphous Compound 1 by weight of the solid dispersion and from about 45 wt % to about 5 wt % of polymer (e.g., HPMCAS). For instance, the solid dispersion comprises from about 65 wt % to about 95 wt %, including all of the values and ranges contained therein, (e.g., from about 67 wt % to about 92 wt %, from about 70 wt % to about 90 wt %, or from about 72 wt % to about 88 wt %) of amorphous Compound 1 by weight of the solid dispersion and from about 45 wt % to about 5 wt % of polymer (e.g., HPMCAS).

In alternative embodiments, the solid dispersion comprises from about 45 wt % to about 85 wt % of substantially amorphous or amorphous Compound 1, from about 0.45 wt % to about 0.55 wt % of SLS, and from about 14.45 wt % to about 55.55 wt % of HPMCAS by weight of the solid dispersion. One exemplary solid dispersion contains about 50 wt % of substantially amorphous or amorphous Compound 1, about 49.5 wt % of HPMCAS, and about 0.5 wt % of SLS, by weight of the solid dispersion. Another exemplary solid dispersion contains about 72.4 wt % of substantially amorphous or amorphous Compound 1, about 27.1 wt % of HPMCAS, and about 0.5 wt % of SLS.

Another exemplary solid dispersion contains about 80 wt % of substantially amorphous or amorphous Compound 1, about 19.5 wt % of HPMCAS, and about 0.5 wt % of SLS.

In addition to the solid dispersion of Compound 1, pharmaceutical compositions of the present invention also comprise one or more excipients such as fillers, sweeteners, disintegrants, wetting agents, glidants, lubricants, colorants, flavoring agents or combinations thereof. It is noted that some excipients may serve more than one function, such as some fillers can also be sweeteners and some disintegrants can also be wetting agents (e.g. mannitol is filler and sweetener, SLS is a wetting agent and lubricant).

Fillers suitable for the present invention are compatible with the ingredients of the pharmaceutical composition, i.e., they do not substantially reduce the solubility, the chemical stability, the physical stability, or the biological activity of the pharmaceutical composition. Examples of the filler can include, but are not limited to, mannitol, lactose, sucrose, dextrose, maltodextrin, sorbitol, xylitol, powdered cellulose, polyhydric alcohols, microcrystalline cellulose, silicified microcrystalline cellulose, cellulose acetate, methylcellulose, ethylcellulose, hydroxyethylcellulose, methylhydroxyethylcellulose, talc, starch (i.e. potato starch), pregelatinized starch, dibasic calcium phosphate, calcium sulfate and calcium carbonate. In one embodiment, the pharmaceutical composition comprises at least one filler in an amount of at least about 10 wt % (e.g., at least about 20 wt %, at least about 25 wt %, or at least about 27 wt %) by weight of the composition. For example, the pharmaceutical composition comprises from about 10 wt % to about 90 wt % (e.g., from about 10 wt % to about 60 wt %, from about 20 wt % to about 55 wt %, from about 25 wt % to about 50 wt %, or from about 27 wt % to about 45 wt %) of filler, by weight of the composition. In another example, the pharmaceutical composition comprises at least about 20 wt % (e.g., at least 25 wt % or at least 27 wt %) of mannitol, by weight of the composition. In yet another example, the pharmaceutical composition comprises from about 30 wt % to about 90 wt % (e.g., from about 30 wt % to about 80 wt %, from about 30 wt % to about 60 wt %, from about 35 wt % to about 55 wt % or from about 40 wt % to about 50 wt %) of mannitol, by weight of the composition. In yet another example, the pharmaceutical composition comprises about 45.1% mannitol, by weight of the composition. In another example, the pharmaceutical composition comprises about 80.37% mannitol, by weight of the composition. In another example, the pharmaceutical composition comprises about 82.5% mannitol, by weight of the composition. In another example, the pharmaceutical composition comprises about 82% mannitol, by weight of the composition. In another example, the pharmaceutical composition comprises about 79% mannitol, by weight of the composition. In another example, the pharmaceutical composition comprises about 79.5% mannitol, by weight of the composition. In another example, the pharmaceutical composition comprises about 75% mannitol, by weight of the composition. In another example, the pharmaceutical composition comprises about 59.28% mannitol, by weight of the composition. In yet another example, the pharmaceutical composition comprises about 43.1% mannitol, by weight of the composition. In yet another example, the pharmaceutical composition comprises about 55% mannitol, by weight of the composition. In yet another example, the pharmaceutical composition comprises about 42% (i.e., about 42.0% or about 42.1%) mannitol, by weight of the composition. In yet another example, the pharmaceutical composition comprises about 57% mannitol, by weight of the composition. In yet another example, the pharmaceutical composition comprises about 57.5% mannitol, by weight of the composition. In another example, the pharmaceutical composition comprises about 45.5% mannitol, by weight of the composition. In another example, the pharmaceutical composition comprises about 45.1% mannitol, by weight of the composition. In yet another example, the pharmaceutical composition comprises about 45% mannitol, by weight of the composition. In yet another example, the pharmaceutical composition comprises about 54.5% mannitol, by weight of the composition. In yet another example, the pharmaceutical composition comprises about 54% mannitol, by weight of the composition. In yet another example, the pharmaceutical composition comprises about 42.5% mannitol, by weight of the composition. In yet another example, the pharmaceutical composition comprises about 49.75% mannitol, by weight of the composition. In one embodiment, the pharmaceutical composition comprises at least 10 wt % of mannitol, by weight of the composition. In yet another example, the pharmaceutical composition comprises about 13.5% mannitol, by weight of the composition. In one embodiment, the pharmaceutical composition comprises at least 10 wt % of lactose, by weight of the composition. In yet another example, the pharmaceutical composition comprises about 57% lactose, by weight of the composition. In yet another example, the pharmaceutical composition comprises about 57.5% lactose, by weight of the composition. In another example, the pharmaceutical composition comprises about 45.5% lactose, by weight of the composition. In another example, the pharmaceutical composition comprises about 45.1% lactose, by weight of the composition. In yet another example, the pharmaceutical composition comprises about 45% lactose, by weight of the composition. In yet another example, the pharmaceutical composition comprises about 54.5% lactose, by weight of the composition. In yet another example, the pharmaceutical composition comprises about 54% lactose, by weight of the composition. In yet another example, the pharmaceutical composition comprises about 42.5% lactose, by weight of the composition. In yet another example, the pharmaceutical composition comprises about 49.75% lactose, by weight of the composition. In yet another example, the pharmaceutical composition comprises about 13.5% lactose, by weight of the composition.

In another embodiment, the pharmaceutical composition comprises a plurality of fillers. In one embodiment, the pharmaceutical composition comprises a plurality of fillers, wherein the total amount of filler is at least about 10 wt % (e.g., at least about 20 wt %, at least about 25 wt %, or at least about 27 wt %) by weight of the composition. For example, the pharmaceutical composition comprises from about 10 wt % to about 90 wt % (e.g., from about 20 wt % to about 70 wt %, from about 30 wt % to about 60 wt %, from about 40 wt % to about 55 wt %, from about 40 wt % to about 45 wt %, from about 45 wt % to about 50 wt %, or from about 50 wt % to about 55 wt %; or about 54.5 wt %, about 48.5 wt %, or about 42.5 wt %) of filler, by weight of the composition. In some embodiments, the pharmaceutical composition comprises one to three fillers. In some embodiments, the pharmaceutical composition comprises two fillers (a binary filler). In a further embodiment, the fillers are selected from mannitol and lactose. In one embodiment, the pharmaceutical composition comprises a binary filler, wherein the binary filler comprises mannitol in an amount up to 100 wt % of the binary filler, and lactose in an amount such that the amount of mannitol plus lactose equals 100 wt %. In one embodiment, the pharmaceutical composition comprises a binary filler, wherein the binary filler comprises mannitol and lactose in a ratio of about 3:1 mannitol to lactose. In one embodiment, the pharmaceutical composition comprises a binary filler, wherein the binary filler comprises mannitol and lactose in a ratio of about 1:1 mannitol to lactose. In one embodiment, the pharmaceutical composition comprises a binary filler, wherein the binary filler comprises mannitol and lactose in a ratio of about 1:3 mannitol to lactose. In one embodiment, the pharmaceutical composition comprises a binary filler, wherein the binary filler comprises mannitol in an amount from about 0 wt % to about 70 wt % (for example from about 10 wt % to about 60 wt %, from about 10 wt % to about 15 wt %, from about 20 wt % to about 30 wt %, or from about 40 wt % to about 60 wt %; or about 13.5 wt %, about 21.25 wt %, about 24.25 wt %, about 27.25 wt %, about 41 wt %, about 42.5 wt %, or about 54.5 wt %) of the composition, and lactose in an amount from about 0 wt % to about 70 wt % (for example from about 10 wt % to about 60 wt %, from about 10 wt % to about 15 wt %, from about 20 wt % to about 30 wt %, or from about 40 wt % to about 60 wt %; or about 13.5 wt %, about 21.25 wt %, about 24.25 wt %, about 27.25 wt %, about 41 wt %, about 42.5 wt %, or about 54.5 wt %) of the composition. In a further embodiment, the pharmaceutical composition comprises a binary filler, wherein the binary filler comprises about 13.5 wt % mannitol and about 41 wt % lactose by weight of the composition. In another further embodiment, the pharmaceutical composition comprises a binary filler, wherein the binary filler comprises about 41 wt % mannitol and about 13.5 wt % lactose by weight of the composition. In another further embodiment, the pharmaceutical composition comprises a binary filler, wherein the binary filler comprises about 27.25 wt % mannitol and about 27.25 wt % lactose by weight of the composition. In another further embodiment, the pharmaceutical composition comprises a binary filler, wherein the binary filler comprises about 24.25 wt % mannitol and about 24.25 wt % lactose by weight of the composition. In another further embodiment, the pharmaceutical composition comprises a binary filler, wherein the binary filler comprises about 21.25 wt % mannitol and about 21.25 wt % lactose by weight of the composition.

The pharmaceutical composition also comprises a sweetener to mask and enhance the taste of the composition. In some embodiments, one or more sweeteners include, but are not limited to, monosaccharides, disaccharides and polysaccharides. Examples of suitable sweeteners include both natural and artificial sweeteners. Examples can include, but are not limited to, glucose, sucrose, maltose, mannose, dextrose, fructose, lactose, trehalose, maltitol, lactitol, xylitol, sorbitol, mannitol, tagatose, glycerin, erythritol, isomalt, maltose, sucralose, aspartame, neotame, alitame, neohesperidin dihydrochalcone, cyclamate (i.e. sodium cyclamate), thaumatin, acesulfame potassium, saccharin, and saccharin sodium. The concentration of the sweetener in the present compositions can range from about 0.1 wt % to about 5 wt % (e.g. from about 1 wt % to about 5 wt %, from about 1 wt % to about 3 wt %, from about 1.5 wt % to about 2.5 wt %) of the pharmaceutical composition. In one embodiment, the sweetener is sucralose. In another embodiment, the pharmaceutical composition comprises sucralose in a concentration from about 0.1 wt % to about 5 wt % (e.g. from about 1 wt % to about 5 wt %, from about 1 wt % to about 3 wt %, from about 1.5 wt % to about 2.5 wt %). In a further embodiment, the pharmaceutical composition comprises sucralose in a concentration of about 2 wt %.

Disintegrants suitable for the present invention enhance the dispersal of the pharmaceutical composition and are compatible with the ingredients of the pharmaceutical composition, i.e., they do not substantially reduce the chemical stability, the physical stability, or the biological activity of the pharmaceutical composition. Exemplary disintegrants include: croscarmellose sodium (e.g., AcDiSol), sodium alginate, calcium alginate, alginic acid, starch, pregelatinized starch, sodium starch glycolate, polyvinylpyrrolidone, co polymers of polyvinylpyrrolidone, crospovidone, carboxymethylcellulose calcium, cellulose and its derivatives, carboxymethylcellulose sodium, soy polysaccharide, clays, gums (i.e. guar gum), an ion exchange resin, an effervescent system based on food acids and an alkaline carbonate component, and sodium bicarbonate. In one embodiment, the pharmaceutical composition comprises disintegrant in an amount of about 10 wt % or less (e.g., about 8 wt % or less, about 7 wt % or less, about 6 wt % or less, or about 5 wt % or less) by weight of the composition. For example, the pharmaceutical composition comprises from about 1 wt % to about 10 wt % (e.g., from about 1.5 wt % to about 7.5 wt % or from about 2.5 wt % to about 6 wt %) of disintegrant, by weight of the composition. In another example, the pharmaceutical composition comprises about 10 wt % or less (e.g., 7 wt % or less, 6 wt % or less, or 5 wt % or less) of croscarmellose sodium, by weight of the composition. In some examples, the pharmaceutical composition comprises from about 0.1% to about 10 wt % (e.g., from about 0.5 wt % to about 7.5 wt % or from about 1.5 wt % to about 6 wt %) of disintegrant, by weight of the composition. In still other examples, the pharmaceutical composition comprises from about 0.5% to about 10 wt % (e.g., from about 1.5 wt % to about 7.5 wt %, about 3 wt % to about 6 wt % or from about 2 wt % to about 5 wt %) of disintegrant, by weight of the composition. In yet another example, the pharmaceutical composition comprises from about 0.1 wt % to about 10 wt % (e.g., from about 1.5 wt % to about 7.5 wt %, from about 1 wt % to about 6 wt %, about 3 wt % to about 6 wt % or from about 2 wt % to about 5 wt %) of croscarmellose sodium, by weight of the composition. In yet another example, the pharmaceutical composition comprises about 3 wt % of croscarmellose sodium, by weight of the composition. In another example, the pharmaceutical composition comprises about 4 wt % of croscarmellose sodium, by weight of the composition. In another example, the pharmaceutical composition comprises about 4.5 wt % of croscarmellose sodium, by weight of the composition. In another example, the pharmaceutical composition comprises about 5 wt % of croscarmellose sodium, by weight of the composition. In another example, the pharmaceutical composition comprises about 6 wt % of croscarmellose sodium, by weight of the composition. In another example, the pharmaceutical composition comprises about 7 wt % of croscarmellose sodium, by weight of the composition. In another example, the pharmaceutical composition comprises about 8 wt % of croscarmellose sodium, by weight of the composition.

Wetting agents and/or surfactants suitable for the present invention can enhance the solubility or the wettability of the pharmaceutical composition and are compatible with the ingredients of the pharmaceutical composition, i.e., they do not substantially reduce the chemical stability, the physical stability, or the biological activity of the pharmaceutical composition. In some embodiments, the one or more wetting agents include one or more surfactants. Examples of wetting agents/surfactants may include, but are not limited to the following: sodium lauryl sulfate (also called sodium dodecyl sulfate (SDS)), cetostearyl alcohol, cetomacrogol emulsifying wax, gelatin, casein, docusate sodium, benzalkonium chloride, calcium stearate, polyethylene glycols, phosphates, polyoxyethylene sorbitan fatty acid esters (e.g. Polysorbate 80, Polysorbate 20), gum acacia, cholesterol, tragacanth, polyoxyethylene 20 stearyl ethers, polyoxyethylene alkyl ethers, polyoxyethylene castor oil derivatives, pegylated hydrogenated castor oils, sorbitan esters of fatty acids, Vitamin E or tocopherol derivatives, vitamin E TPGS, tocopheryl esters, lecithin, phospholipids and their derivatives, poloxamers, stearic acid, oleic acid, oleic alcohol, cetyl alcohol, mono and diglycerides, propylene glycol esters of fatty acids, glycerol esters of fatty acids (i.e. glycerol monostearate), ethylene glycol palmitostearate, polyoxylglycerides, propylene glycol monocaprylate, propylene glycol monolaurate, alkyl aryl polyether alcohols (Triton®) and polyglyceryl oleate. In one embodiment, the pharmaceutical composition comprises a wetting agent in an amount of about 10 wt % or less (e.g., about 5 wt % or less, about 2 wt % or less, about 1 wt % or less, about 0.8 wt % or less, or about 0.6 wt % or less) by weight of the composition. For example, the pharmaceutical composition includes from about 10 wt % to about 0.01 wt % (e.g., from about 5 wt % to about 0.05 wt % or from about 2 wt % to about 0.1 wt %) of a wetting agent, by weight of the composition. In another example, the pharmaceutical composition comprises 10 wt % or less (e.g., about 5 wt % or less, about 2 wt % or less, about 1 wt % or less, about 0.8 wt % or less, or about 0.6 wt % or less) of sodium lauryl sulfate, by weight of the composition. In yet another example, the pharmaceutical composition comprises from about 10 wt % to about 0.01 wt % (e.g., from about 3 wt % to about 0.01 wt % or from about 2 wt % to about 0.05 wt %) of sodium lauryl sulfate, by weight of the composition. In still another example, the pharmaceutical composition comprises about 0.5 wt % of sodium lauryl sulfate, by weight of the composition. In another example, the pharmaceutical composition comprises about 0 wt % of sodium lauryl sulfate, by weight of the composition. In still another example, the pharmaceutical composition comprises about 0.175 wt % of sodium lauryl sulfate, by weight of the composition. In still another example, the pharmaceutical composition comprises about 0.205 wt % of sodium lauryl sulfate, by weight of the composition. In still another example, the pharmaceutical composition comprises about 0.235 wt % of sodium lauryl sulfate, by weight of the composition. In still another example, the pharmaceutical composition comprises about 0.675 wt % of sodium lauryl sulfate, by weight of the composition. In still another example, the pharmaceutical composition comprises about 0.705 wt % of sodium lauryl sulfate, by weight of the composition. In still another example, the pharmaceutical composition comprises about 0.735 wt % of sodium lauryl sulfate, by weight of the composition.

Glidants suitable for the present invention enhance the flow properties of the pharmaceutical composition and are compatible with the ingredients of the pharmaceutical composition, i.e., they do not substantially reduce the solubility, the chemical stability, the physical stability, or the biological activity of the pharmaceutical composition. A "glidant" is a substance to promote powder flow by reducing interparticle friction and cohesion. In certain embodiments, the one or more excipients can include one or more glidants. Examples of the glidants may include, but are not limited to, talc, colloidal silica (e.g., Cabosil M-5P), precipitated silica, magnesium oxide, magnesium silicate, leucine and starch. In one embodiment, the pharmaceutical composition comprises a glidant in an amount of 5 wt % or less (e.g., 1.75 wt %, 1.25 wt % or less, or 1.00 wt % or less) by weight of the composition. For example, the pharmaceutical composition comprises from about 5 wt % to about 0.1 wt % (e.g., from about 4 wt % to about 0.02 wt % or from about 3 wt % to about 0.5 wt %) of glidant, by weight of the composition. In another example, the pharmaceutical composition comprises 5 wt % or less (e.g., 1.75 wt %, 1.25 wt % or less, or 1.00 wt % or less) of colloidal silicon dioxide, by weight of the composition. In yet another example, the pharmaceutical composition comprises from about 5 wt % to about 0.1 wt % (e.g., from about 4 wt % to about 0.2 wt % or from about 3 wt % to about 0.5 wt %) of colloidal silicon dioxide, by weight of the composition. In still another example, the pharmaceutical composition comprises about 1 wt % of colloidal silicon dioxide, by weight of the composition.

Lubricants suitable for the present invention improve the compression and ejection of compressed pharmaceutical compositions from a die. Lubricants may further have anti-sticking or anti-tacking properties, and minimize sticking in various operations of the present invention, including operations such as encapsulation, and are compatible with the ingredients of the pharmaceutical composition, i.e., they do not substantially reduce the solubility, or the biological activity of the pharmaceutical composition. Examples of the lubricants may include, but are not limited to, talc, fatty acid, stearic acid, magnesium stearate, calcium stearate, sodium stearate, stearic acid, glyceryl monostearate, sodium lauryl sulfate, sodium stearyl fumarate, hydrogenated oils (i.e. hydrogenated vegetable oil), polyethylene glycol, fatty alcohol, fatty acid ester, glyceryl behenate, mineral oil, vegetable oil, leucine, sodium benzoate, or a combination thereof. In one embodiment, the pharmaceutical composition comprises a lubricant in an amount of 10 wt % or less (e.g., 2.5 wt %, 2.0 wt %, 1.75 wt %, 1.5 wt % or less, 1.25 wt % or less, or 1.00 wt % or less) by weight of the composition. For example, the pharmaceutical composition comprises from about 7 wt % to about 0.10 wt % (e.g., from about 6 wt % to about 0.15 wt % or from about 5 wt % to about 0.30 wt %) of lubricant, by weight of the composition. In another example, the pharmaceutical composition comprises 10 wt % or less (e.g., 2.5 wt % or less, 1.75 wt % or less, 1.5 wt % or less, 1.25 wt % or less, or 1.00 wt % or less) of magnesium stearate, by weight of the composition. In yet another example, the pharmaceutical composition comprises from about 10 wt % to about 0.10 wt % (e.g., from about 7 wt % to about 0.1 wt % or from about 5 wt % to about 0.30 wt %) of magnesium stearate, by weight of the composition. In still another example, the pharmaceutical composition comprises about 1.5 wt % of magnesium stearate, by weight of the composition. In still another example, the pharmaceutical composition comprises about 1.0 wt % of magnesium stearate, by weight of the composition.

Pharmaceutical compositions of the present invention can optionally comprise one or more colorants, flavors, and/or fragrances to enhance the visual appeal, taste, and/or scent of the composition. Suitable colorants, flavors, or fragrances are compatible with the ingredients of the pharmaceutical composition, i.e., they do not substantially reduce the solubility, the chemical stability, the physical stability or the biological activity of the pharmaceutical composition. In one embodiment, the pharmaceutical composition comprises a colorant, a flavor, and/or a fragrance. For example, the pharmaceutical composition comprises less than about 1 wt % (e.g., less than about 0.75 wt % or less than about 0.5 wt %) of each optionally ingredient, i.e., colorant, flavor and/or fragrance, by weight of the composition. In another example, the pharmaceutical composition comprises less than about 1 wt % (e.g., less than about 0.75 wt % or less than about 0.5 wt %) of a colorant. In still another example, the pharmaceutical composition comprises less than about 1 wt % (e.g., less than about 0.75 wt % or less than about 0.5 wt %) of a blue colorant (e.g., FD&C Blue #1 and/or FD&C Blue #2 Aluminum Lake, commercially available from Colorcon, Inc. of West Point, Pa.)

Suitable flavoring agents can include, for example, flavors, which are known to those of skill in the art, such as, for example, natural flavors, artificial flavors, and combinations thereof. Flavoring agents are compatible with the ingredients of the pharmaceutical composition, i.e., they do not substantially reduce the chemical stability, the physical stability, or the biological activity of the pharmaceutical composition. Flavoring agents may be chosen, e.g., from synthetic flavor oils and flavoring aromatics and/or oils, oleoresins, extracts derived from plants, leaves, flowers, fruits, and the like, and combinations thereof. Non-limiting examples of flavor oils include spearmint oil, cinnamon oil, oil of wintergreen (methyl salicylate), peppermint oil, clove oil, bay oil, anise oil, eucalyptus oil, thyme oil, cedar leaf oil, oil of nutmeg, allspice, oil of sage, mace, oil of bitter almonds, and cassia oil. Suitable flavoring agents also include, for example, artificial, natural and synthetic flower derived or fruit flavors such as vanilla, ethyl vanillin, citrus oils (e.g., lemon, orange, tangerine, lime, and grapefruit), and fruit essences (e.g., natural and/or artificial flavor of apple, pear, peach, orange, grape, strawberry, raspberry, cherry, plum, pineapple, and apricot), and the like, and combinations thereof. The flavoring agents may be used in liquid or solid form and, as indicated above, may be used individually or in admixture. Other flavoring agents can include, for example, certain aldehydes and esters, e.g., cinnamyl acetate, cinnamaldehyde, citral diethylacetal, dihydrocarvyl acetate, eugenyl formate, p-methylamisol, and the like, and combinations thereof.

A. Powder Formulations of the Pharmaceutical Composition

In some embodiments, the present invention provides a pharmaceutical composition that can be used to treat a patient who possesses mutant forms of human CFTR. In some embodiments, the pharmaceutical composition can include a powder admixture of the pharmaceutical composition ingredients described above formulated to be contained in a capsule, packet, pouch, sachet or some other container operable to provide a unit dose of the powder pharmaceutical composition to a patient in need thereof.

In some embodiments, the powder pharmaceutical composition or "powder blend" formulation can be formulated to be sprinkled on food or into a liquid for a patient to consume. Such powder pharmaceutical formulations are primarily, although not exclusively, beneficial to patients who cannot ingest an adult sized tablet orally, or that have difficulty in swallowing such adult sized tablets or fragments thereof.

In one embodiment, the powder pharmaceutical composition comprises a solid dispersion and an excipient, for example: one or more fillers, a sweetener, a glidant, a lubricant, and combinations thereof, wherein the solid dispersion comprises from about 30 wt % to about 95 wt % of Compound 1 by weight of the dispersion and a polymer.

In some embodiments, the solid dispersion comprises from about 45 wt % to about 85 wt % including all values and ranges therein (e.g., about 50 wt %, about 72.4 wt %, about 78.8 wt %, or about 80 wt %) of Compound 1 by weight of the dispersion and a polymer.

One exemplary pharmaceutical composition comprises from about 5 wt % to about 70 wt % (e.g., from about 5 wt % to about 65 wt %, from about 5 wt % to about 50 wt %, from about 10 wt % to about 20 wt %, from about 30 wt % to about 40 wt % or from about 40 wt % to about 50 wt %) of a solid dispersion, by weight of the composition, comprising from about 30 wt % to about 90 wt % of substantially amorphous Compound 1, by weight of the dispersion, and from about 70 wt % to about 10 wt % of a polymer, by weight of the dispersion; from about 25 wt % to about 90 wt % of one or more fillers; from about 0.1 wt % to about 5 wt % of a sweetener; from about 5 wt % to about 0.1 wt % of a glidant; and from about 7 wt % to about 0.1 wt % of a lubricant. Or, the powder pharmaceutical composition comprises from about 5 wt % to about 65 wt % (e.g., from about 5 wt % to about 25 wt %, from about 15 wt % to about 40 wt %, or from about 30 wt % to about 50 wt %) of a solid dispersion, by weight of the composition, comprising from about 30 wt % to about 90 wt % of amorphous Compound 1, by weight of the dispersion, and from about 70 wt % to about 20 wt % of a polymer, by weight of the dispersion; from about 10 wt % to about 90 wt % of one or more fillers; from about 0.1 wt % to about 5 wt % of a sweetener; from about 5 wt % to about 0.1 wt % of a glidant; and from about 7 wt % to about 0.1 wt % of a lubricant.

Another exemplary pharmaceutical composition comprises from about 5 wt % to about 60 wt % (e.g., from about 5 wt % to about 55 wt %, from about 15 wt % to about 50 wt %, or from about 30 wt % to about 50 wt %) of a solid dispersion, by weight of the composition, comprising from about 30 wt % to about 90 wt % of substantially amorphous Compound 1, by weight of the dispersion, and from about 70 wt % to about 10 wt % of a polymer, by weight of the dispersion; from about 10 wt % to about 90 wt % of one or more fillers; from about 0.1 wt % to about 5 wt % of a sweetener, from about 7 wt % to about 0.1 wt % of a lubricant; and from about 5 wt % to about 0.1 wt % of a glidant. Or, the pharmaceutical composition comprises from about 5 wt % to about 55 wt % (e.g., from about 5 wt % to about 50 wt %, from about 5 wt % to about 45 wt %, or from about 5 wt % to about 40 wt %) of a solid dispersion, by weight of the composition, comprising from about 30 wt % to about 90 wt % of amorphous Compound 1, by weight of the dispersion, and from about 70 wt % to about 10 wt % of a polymer, by weight of the dispersion; from about 10 wt % to about 90 wt % of one or more fillers; from about 5 wt % to about 0.1 wt % of a sweetener; from about 5 wt % to about 0.1 wt % of a glidant; and from about 7 wt % to about 0.1 wt % of a lubricant.

One powder pharmaceutical composition of the present invention comprises about 46.9 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 49.1 wt % of mannitol by weight of the composition; about 2 wt % of sucralose by weight of the composition; about 1 wt % of colloidal silicon dioxide by weight of the composition; and about 1 wt % of magnesium stearate by weight of the composition. Or, the powder pharmaceutical composition of the present invention comprises about 15 wt % of a solid dispersion by weight of the composition, wherein the dispersion comprises about 80 wt % of amorphous Compound 1 by weight of the dispersion, about 19.5 wt % of HPMCAS by weight of the dispersion, and about 0.5 wt % SLS by weight of the dispersion; about 81 wt % of mannitol by weight of the composition; about 2 wt % of sucralose by weight of the composition; about 1 wt % of colloidal silicon dioxide by weight of the composition; and about 1 wt % of magnesium stearate by weight of the composition. Or, the powder pharmaceutical composition of the present invention comprises about 36.8 wt % of a solid dispersion by weight of the composition, wherein the dispersion comprises about 80 wt % of amorphous Compound 1 by weight of the dispersion, about 19.5 wt % of HPMCAS by weight of the dispersion, and about 0.5 wt % SLS by weight of the dispersion; about 59.2 wt % of mannitol by weight of the composition; about 2 wt % of sucralose by weight of the composition; about 1 wt % of colloidal silicon dioxide by weight of the composition; and about 1 wt % of magnesium stearate by weight of the composition.

Another powder pharmaceutical composition of the present invention comprises about 24.6 wt % (equivalent to 24.6 mg potency in a 200 mg unit dose) of a solid dispersion by weight of the composition, wherein the dispersion comprises about 50 wt % of substantially amorphous or amorphous Compound 1 by weight of the dispersion, about 49.5 wt % of HPMCAS by weight of the dispersion, and about 0.5 wt % SLS by weight of the dispersion; about 71.4 wt % of mannitol by weight of the composition; about 2 wt % of sucralose by weight of the composition; about 1 wt % of colloidal silicon dioxide by weight of the composition; and about 1 wt % of magnesium stearate by weight of the composition. Or, the pharmaceutical composition of the present invention comprises about 34 wt % (equivalent to 49.2 mg potency per 200 mg dose) of a solid dispersion by weight of the composition, wherein the dispersion comprises about 72.4 wt % of substantially amorphous or amorphous Compound 1 by weight of the dispersion, about 27.1 wt % of HPMCAS by weight of the dispersion, and about 0.5 wt % SLS by weight of the dispersion; about 62 wt % of mannitol by weight of the composition; about 2 wt % of sucralose by weight of the composition; about 1 wt % of colloidal silicon dioxide by weight of the composition; and about 1 wt % of magnesium stearate by weight of the composition.

Another powder pharmaceutical composition of the present invention comprises about 61.6 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 34.4 wt % of mannitol by weight of the composition; about 2 wt % of sucralose by weight of the composition; about 1 wt % of colloidal silicon dioxide by weight of the composition; about 1 wt % of magnesium stearate by weight of the composition. Or, the powder pharmaceutical composition of the present invention comprises about 68.7 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 27.3 wt % of mannitol by weight of the composition; about 2 wt % of sucralose by weight of the composition; about 1 wt % of colloidal silicon dioxide by weight of the composition; about 1 wt % of magnesium stearate by weight of the composition. Optionally, the above pharmaceutical compositions can also include about 0.4 wt % of colorant by weight of the composition.

One powder pharmaceutical composition of the present invention comprises about 46.9 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 49.1 wt % of mannitol by weight of the composition; about 2 wt % of sucralose by weight of the composition; about 1 wt % of colloidal silicon dioxide by weight of the composition; and about 1 wt % of magnesium stearate by weight of the composition, wherein the composition comprises about 75 mg of Compound 1. Or, the powder pharmaceutical composition of the present invention comprises about 15 wt % of a solid dispersion by weight of the composition, wherein the dispersion comprises about 80 wt % of amorphous Compound 1 by weight of the dispersion, about 19.5 wt % of HPMCAS by weight of the dispersion, and about 0.5 wt % SLS by weight of the dispersion; about 81 wt % of mannitol by weight of the composition; about 2 wt % of sucralose by weight of the composition; about 1 wt % of colloidal silicon dioxide by weight of the composition; and about 1 wt % of magnesium stearate by weight of the composition, wherein the composition comprises about 50 mg of Compound 1.

Another exemplary pharmaceutical composition comprises from about 30 wt % to about 50 wt % of a solid dispersion, by weight of the composition, comprising from about 30 wt % to about 90 wt % of substantially amorphous Compound 1, by weight of the dispersion, and from about 70 wt % to about 10 wt % of a polymer, by weight of the dispersion; from about 30 wt % to about 60 wt % of two fillers; from about 0.1 wt % to about 5 wt % of a sweetener, from about 7 wt % to about 0.1 wt % of a lubricant; from about 8 wt % to about 0.1 wt % of a disintegrant, and from about 5 wt % to about 0.1 wt % of a glidant. In some embodiments, the two fillers can each be independently present in an amount up to about 60 wt %.

In one aspect, the invention provides a pharmaceutical composition comprising from about 30 wt % to about 50 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; from about 30 wt % to about 60 wt % of a binary filler, wherein the binary filler comprises from about 0 wt % to about 60 wt % of mannitol by weight of the composition and from about 0 wt % to about 60 wt % of lactose by weight of the composition; from about 1.5 wt % to about 2.5 wt % of sucralose by weight of the composition; from about 4 wt % to about 8 wt % of croscarmellose sodium by weight of the composition; from about 0.5 wt % to about 1.5 wt % of colloidal silicon dioxide by weight of the composition; and from about 1 wt % to about 2 wt % of magnesium stearate by weight of the composition.

One powder pharmaceutical composition of the present invention comprises about 35 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 13.5 wt % of mannitol by weight of the composition; about 41 wt % of lactose by weight of the composition; about 2 wt % of sucralose by weight of the composition; about 6 wt % of croscarmellose; about 1 wt % of colloidal silicon dioxide by weight of the composition; and about 1 wt % of magnesium stearate by weight of the composition, wherein the composition comprises about 10 mg of Compound 1.

Another powder pharmaceutical composition of the present invention comprises about 35 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 13.5 wt % of mannitol by weight of the composition; about 41 wt % of lactose by weight of the composition; about 2 wt % of sucralose by weight of the composition; about 6 wt % of croscarmellose; about 1 wt % of colloidal silicon dioxide by weight of the composition; and about 1 wt % of magnesium stearate by weight of the composition, wherein the composition comprises about 12.5 mg of Compound 1.

One powder pharmaceutical composition of the present invention comprises about 35 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 13.5 wt % of mannitol by weight of the composition; about 41 wt % of lactose by weight of the composition; about 2 wt % of sucralose by weight of the composition; about 6 wt % of croscarmellose; about 1 wt % of colloidal silicon dioxide by weight of the composition; and about 1 wt % of magnesium stearate by weight of the composition, wherein the composition comprises about 20 mg of Compound 1.

One powder pharmaceutical composition of the present invention comprises about 35 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 13.5 wt % of mannitol by weight of the composition; about 41 wt % of lactose by weight of the composition; about 2 wt % of sucralose by weight of the composition; about 6 wt % of croscarmellose; about 1 wt % of colloidal silicon dioxide by weight of the composition; and about 1 wt % of magnesium stearate by weight of the composition, wherein the composition comprises about 25 mg of Compound 1.

One powder pharmaceutical composition of the present invention comprises about 35 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 13.5 wt % of mannitol by weight of the composition; about 41 wt % of lactose by weight of the composition; about 2 wt % of sucralose by weight of the composition; about 6 wt % of croscarmellose; about 1 wt % of colloidal silicon dioxide by weight of the composition; and about 1 wt % of magnesium stearate by weight of the composition, wherein the composition comprises about 30 mg of Compound 1.

One powder pharmaceutical composition of the present invention comprises about 35 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 13.5 wt % of mannitol by weight of the composition; about 41 wt % of lactose by weight of the composition; about 2 wt % of sucralose by weight of the composition; about 6 wt % of croscarmellose; about 1 wt % of colloidal silicon dioxide by weight of the composition; and about 1 wt % of magnesium stearate by weight of the composition, wherein the composition comprises about 37.5 mg of Compound 1.

One powder pharmaceutical composition of the present invention comprises about 35 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 13.5 wt % of mannitol by weight of the composition; about 41 wt % of lactose by weight of the composition; about 2 wt % of sucralose by weight of the composition; about 6 wt % of croscarmellose; about 1 wt % of colloidal silicon dioxide by weight of the composition; and about 1 wt % of magnesium stearate by weight of the composition, wherein the composition comprises about 40 mg of Compound 1.

One powder pharmaceutical composition of the present invention comprises about 35 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 13.5 wt % of mannitol by weight of the composition; about 41 wt % of lactose by weight of the composition; about 2 wt % of sucralose by weight of the composition; about 6 wt % of croscarmellose; about 1 wt % of colloidal silicon dioxide by weight of the composition; and about 1 wt % of magnesium stearate by weight of the composition, wherein the composition comprises about 50 mg of Compound 1.

One powder pharmaceutical composition of the present invention comprises about 35 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 13.5 wt % of mannitol by weight of the composition; about 41 wt % of lactose by weight of the composition; about 2 wt % of sucralose by weight of the composition; about 6 wt % of croscarmellose; about 1 wt % of colloidal silicon dioxide by weight of the composition; and about 1 wt % of magnesium stearate by weight of the composition, wherein the composition comprises about 62.5 mg of Compound 1.

One powder pharmaceutical composition of the present invention comprises about 35 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 13.5 wt % of mannitol by weight of the composition; about 41 wt % of lactose by weight of the composition; about 2 wt % of sucralose by weight of the composition; about 6 wt % of croscarmellose; about 1 wt % of colloidal silicon dioxide by weight of the composition; and about 1 wt % of magnesium stearate by weight of the composition, wherein the composition comprises about 75 mg of Compound 1.

One powder pharmaceutical composition of the present invention comprises about 35 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 13.5 wt % of mannitol by weight of the composition; about 41 wt % of lactose by weight of the composition; about 2 wt % of sucralose by weight of the composition; about 6 wt % of croscarmellose; about 1 wt % of colloidal silicon dioxide by weight of the composition; and about 1 wt % of magnesium stearate by weight of the composition, wherein the composition comprises about 100 mg of Compound 1.

One powder pharmaceutical composition of the present invention comprises about 35 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 13.5 wt % of mannitol by weight of the composition; about 41 wt % of lactose by weight of the composition; about 2 wt % of sucralose by weight of the composition; about 6 wt % of croscarmellose; about 1 wt % of colloidal silicon dioxide by weight of the composition; and about 1 wt % of magnesium stearate by weight of the composition, wherein the composition comprises about 125 mg of Compound 1.

One powder pharmaceutical composition of the present invention comprises about 35 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 13.5 wt % of mannitol by weight of the composition; about 41 wt % of lactose by weight of the composition; about 2 wt % of sucralose by weight of the composition; about 6 wt % of croscarmellose; about 1 wt % of colloidal silicon dioxide by weight of the composition; and about 1 wt % of magnesium stearate by weight of the composition, wherein the composition comprises about 150 mg of Compound 1.

One powder pharmaceutical composition of the present invention comprises about 35 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 13.5 wt % of mannitol by weight of the composition; about 41 wt % of lactose by weight of the composition; about 2 wt % of sucralose by weight of the composition; about 6 wt % of croscarmellose; about 1 wt % of colloidal silicon dioxide by weight of the composition; and about 1 wt % of magnesium stearate by weight of the composition, wherein the composition comprises about 175 mg of Compound 1.

One powder pharmaceutical composition of the present invention comprises about 35 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 13.5 wt % of mannitol by weight of the composition; about 41 wt % of lactose by weight of the composition; about 2 wt % of sucralose by weight of the composition; about 6 wt % of croscarmellose; about 1 wt % of colloidal silicon dioxide by weight of the composition; and about 1 wt % of magnesium stearate by weight of the composition, wherein the composition comprises about 200 mg of Compound 1.

One powder pharmaceutical composition of the present invention comprises about 35 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 13.5 wt % of mannitol by weight of the composition; about 41 wt % of lactose by weight of the composition; about 2 wt % of sucralose by weight of the composition; about 6 wt % of croscarmellose; about 1 wt % of colloidal silicon dioxide by weight of the composition; and about 1 wt % of magnesium stearate by weight of the composition, wherein the composition comprises about 225 mg of Compound 1.

One powder pharmaceutical composition of the present invention comprises about 35 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 13.5 wt % of mannitol by weight of the composition; about 41 wt % of lactose by weight of the composition; about 2 wt % of sucralose by weight of the composition; about 6 wt % of croscarmellose; about 1 wt % of colloidal silicon dioxide by weight of the composition; and about 1 wt % of magnesium stearate by weight of the composition, wherein the composition comprises about 250 mg of Compound 1.

B. Compressed Formulations of the Pharmaceutical Composition

Another aspect of the present invention provides solid dose forms and unit dose forms comprising a pharmaceutical composition formulated or compressed into a granule, pellet, particle, mini-tablet, sprinkle and the like. The solid dose forms and unit dose forms comprise compressed powder pharmaceutical compositions as described above with the addition of one or more functional excipients, for example, a disintegrant, glidant, lubricant, filler and/or a wetting agent to facilitate compression of the powder pharmaceutical composition into a compressed pharmaceutical composition, and to facilitate disintegration and dissolution of the compressed powder. The compressed pharmaceutical composition (solid dose forms) such as granules, pellets, particles, mini-tablets and the like can be formulated into unit dose forms such as tablets, capsules, pouches, packets, sachets, bottles and blister packs containing a one or a plurality of such solid dose forms. The number of solid dose forms required for each unit dose form will depend on the concentration of Compound 1 in each solid dose form (e.g., each granule, pellet or mini-tablet), and the required final amount of Compound 1 required by the unit dose form. For purposes of illustration only, if a unit dose form (e.g. a capsule, pouch, packet, sachet, bottle or blister pack containing a mini-tablet or plurality of mini-tablets) requires a final dose of about 75 mg, and each mini-tablet weighs about 7 mg, and each mini-tablet contains about 2.6 mg of Compound 1, then each capsule or packet can contain about 29 mini-tablets. If a unit dose form requires a final dose of about 40 mg, and each mini-tablet weighs about 6.9 mg, then each capsule, pouch, packet, sachet, bottle or blister pack can contain about 21 mini-tablets. If a unit dose form requires a final dose of about 50 mg, and each mini-tablet weighs about 6.9 mg, then each capsule, pouch, packet, sachet, bottle or blister pack can contain about 26 mini-tablets. If a unit dose form requires a final dose of about 75 mg, and each mini-tablet weighs about 7 mg, and each mini-tablet contains about 2 mg of Compound 1, then each capsule, pouch, packet, sachet, bottle or blister pack can contain about 39 mini-tablets. Also, if a unit dose form requires a final dose of about 75 mg, and each mini-tablet weighs about 6.9 mg, then each capsule, pouch, packet, sachet, bottle or blister pack can contain about 39 mini-tablets. If a unit dose form requires a final dose of about 100 mg, and each mini-tablet weighs about 6.9 mg, then each capsule, pouch, packet, sachet, bottle or blister pack can contain about 52 mini-tablets. If a unit dose form requires a final dose of about 75 mg, and each mini-tablet weighs about 7 mg, and each mini-tablet contains about 0.84 mg of Compound 1, then each capsule, pouch, packet, sachet, bottle or blister pack can contain about 90 mini-tablets. If a unit dose form requires a final dose of about 150 mg, and each mini-tablet weighs about 7 mg, and each mini-tablet contains about 2.6 mg of Compound 1, then each capsule, pouch, packet, sachet, bottle or blister pack can contain about 58 mini-tablets. If a unit dose form requires a final dose of about 150 mg, and each mini-tablet weighs about 7 mg, and each mini-tablet contains about 2 mg of Compound 1, then each capsule, pouch, packet, sachet, bottle or blister pack can contain about 75 mini-tablets. If a unit dose form requires a final dose of about 150 mg, and each mini-tablet weighs about 7 mg, and each mini-tablet contains about 0.84 mg of Compound 1, then each capsule, pouch, packet, sachet, bottle or blister pack can contain about 179 mini-tablets. If a unit dose form requires a final dose of about 25 mg, and each mini-tablet weighs about 7 mg, and each mini-tablet contains about 2.6 mg of Compound 1, then each capsule, pouch, packet, sachet, bottle or blister pack can contain about 10 mini-tablets. If a unit dose form requires a final dose of about 25 mg, and each mini-tablet weighs about 7 mg, and each mini-tablet contains about 2 mg of Compound 1, then each capsule, pouch, packet, sachet, bottle or blister pack can contain about 13 mini-tablets. If a unit dose form requires a final dose of about 25 mg, and each mini-tablet weighs about 7 mg, and each mini-tablet contains about 0.84 mg of Compound 1, then each capsule, pouch, packet, sachet, bottle or blister pack can contain about 30 mini-tablets. If a unit dose form requires a final dose of about 50 mg, and each mini-tablet weighs about 7 mg, and each mini-tablet contains about 2.6 mg of Compound 1, then each capsule, pouch, packet, sachet, bottle or blister pack can contain about 19 mini-tablets. If a unit dose form requires a final dose of about 50 mg, and each mini-tablet weighs about 7 mg, and each mini-tablet contains about 2 mg of Compound 1, then each capsule, pouch, packet, sachet, bottle or blister pack can contain about 25 mini-tablets. If a unit dose form requires a final dose of about 50 mg, and each mini-tablet weighs about 7 mg, and each mini-tablet contains about 0.84 mg of Compound 1, then each capsule, pouch, packet, sachet, bottle or blister pack can contain about 60 mini-tablets. If a unit dose form requires a final dose of about 10 mg, and each mini-tablet contains about 10 mg of Compound 1, and each mini-tablet weighs about 26.7 mg or 35.7 mg, then each capsule, pouch, packet, sachet, bottle or blister pack can contain 1 mini-tablet. If a unit dose form requires a final dose of about 20 mg, and each mini-tablet contains about 10 mg of Compound 1, and each mini-tablet weighs about 26.7 mg or 35.7 mg, then each capsule, pouch, packet, sachet, bottle or blister pack can contain about 2 mini-tablets. If a unit dose form requires a final dose of about 30 mg, and each mini-tablet contains about 10 mg of Compound 1, and each mini-tablet weighs about 26.7 mg or 35.7 mg, then each capsule, pouch, packet, sachet, bottle or blister pack can contain about 3 mini-tablets. If a unit dose form requires a final dose of about 40 mg, and each mini-tablet contains about 10 mg of Compound 1, and each mini-tablet weighs about 26.7 mg or 35.7 mg, then each capsule, pouch, packet, sachet, bottle or blister pack can contain about 4 mini-tablets. If a unit dose form requires a final dose of about 50 mg, and each mini-tablet contains about 10 mg of Compound 1, and each mini-tablet weighs about 26.7 mg or 35.7 mg, then each capsule, pouch, packet, sachet, bottle or blister pack can contain about 5 mini-tablets. If a unit dose form requires a final dose of about 70 mg, and each mini-tablet contains about 10 mg of Compound 1, and each mini-tablet weighs about 26.7 mg or 35.7 mg, then each capsule, pouch, packet, sachet, bottle or blister pack can contain about 7 mini-tablets. If a unit dose form requires a final dose of about 80 mg, and each mini-tablet contains about 10 mg of Compound 1, and each mini-tablet weighs about 26.7 mg or 35.7 mg, then each capsule, pouch, packet, sachet, bottle or blister pack can contain about 8 mini-tablets. If a unit dose form requires a final dose of about 100 mg, and each mini-tablet contains about 10 mg of Compound 1, and each mini-tablet weighs about 26.7 mg or 35.7 mg, then each capsule, pouch, packet, sachet, bottle or blister pack can contain about 10 mini-tablets. If a unit dose form requires a final dose of about 150 mg, and each mini-tablet contains about 10 mg of Compound 1, and each mini-tablet weighs about 26.7 mg or 35.7 mg, then each capsule, pouch, packet, sachet, bottle or blister pack can contain about 15 mini-tablets. If a unit dose form requires a final dose of about 12.5 mg, and each mini-tablet contains about 12.5 mg Compound 1, and each mini-tablet weighs about 33.2 mg or 44.6 mg, then each capsule, pouch, packet, sachet, bottle or blister pack can contain about 1 mini-tablet. If a unit dose form requires a final dose of about 25 mg, and each mini-tablet contains about 12.5 mg Compound 1, and each mini-tablet weighs about 33.2 mg or 44.6 mg, then each capsule, pouch, packet, sachet, bottle or blister pack can contain about 2 mini-tablets. If a unit dose form requires a final dose of about 37.5 mg, and each mini-tablet contains about 12.5 mg Compound 1, and each mini-tablet weighs about 33.2 mg or 44.6 mg, then each capsule, pouch, packet, sachet, bottle or blister pack can contain about 3 mini-tablets. If a unit dose form requires a final dose of about 50 mg, and each mini-tablet contains about 12.5 mg Compound 1, and each mini-tablet weighs about 33.2 mg or 44.6 mg, then each capsule, pouch, packet, sachet, bottle or blister pack can contain about 4 mini-tablets. If a unit dose form requires a final dose of about 62.5 mg, and each mini-tablet contains about 12.5 mg Compound 1, and each mini-tablet weighs about 33.2 mg or 44.6 mg, then each capsule, packet, pouch, packet, sachet, bottle or blister pack can contain about 5 mini-tablets. If a unit dose form requires a final dose of about 75 mg, and each mini-tablet contains about 12.5 mg Compound 1, and each mini-tablet weighs about 33.2 mg or 44.6 mg, then each capsule, pouch, packet, sachet, bottle or blister pack can contain about 6 mini-tablets. If a unit dose form requires a final dose of about 87.5 mg, and each mini-tablet contains about 12.5 mg Compound 1, and each mini-tablet weighs about 33.2 mg or 44.6 mg, then each capsule, pouch, packet, sachet, bottle or blister pack can contain about 7 mini-tablets. If a unit dose form requires a final dose of about 100 mg, and each mini-tablet contains about 12.5 mg Compound 1, and each mini-tablet weighs about 33.2 mg or 44.6 mg, then each capsule, pouch, packet, sachet, bottle or blister pack can contain about 8 mini-tablets. If a unit dose form requires a final dose of about 125 mg, and each mini-tablet contains about 12.5 mg Compound 1, and each mini-tablet weighs about 33.2 mg or 44.6 mg, then each capsule, pouch, packet, sachet, bottle or blister pack can contain about 10 mini-tablets. If a unit dose form requires a final dose of about 150 mg, and each mini-tablet contains about 12.5 mg Compound 1, and each mini-tablet weighs about 33.2 mg or 44.6 mg, then each capsule, pouch, packet, sachet, bottle or blister pack can contain about 12 mini-tablets.

If a unit dose form requires a final dose of about 12.5 mg, and each mini-tablet contains about 12.5 mg Compound 1, and each mini-tablet weighs about 44.7 mg, then each capsule, pouch, packet, sachet, bottle or blister pack can contain about 1 mini-tablet. If a unit dose form requires a final dose of about 25 mg, and each mini-tablet contains about 12.5 mg Compound 1, and each mini-tablet weighs about 44.7 mg, then each capsule, pouch, packet, sachet, bottle or blister pack can contain about 2 mini-tablets. If a unit dose form requires a final dose of about 37.5 mg, and each mini-tablet contains about 12.5 mg Compound 1, and each mini-tablet weighs about 44.7 mg, then each capsule, pouch, packet, sachet, bottle or blister pack can contain about 3 mini-tablets. If a unit dose form requires a final dose of about 50 mg, and each mini-tablet contains about 12.5 mg Compound 1, and each mini-tablet weighs about 44.7 mg, then each capsule, pouch, packet, sachet, bottle or blister pack can contain about 4 mini-tablets. If a unit dose form requires a final dose of about 62.5 mg, and each mini-tablet contains about 12.5 mg Compound 1, and each mini-tablet weighs about 44.7 mg, then each capsule, pouch, packet, sachet, bottle or blister pack can contain about 5 mini-tablets. If a unit dose form requires a final dose of about 75 mg, and each mini-tablet contains about 12.5 mg Compound 1, and each mini-tablet weighs about 44.7 mg, then each capsule, pouch, packet, sachet, bottle or blister pack can contain about 6 mini-tablets. If a unit dose form requires a final dose of about 87.5 mg, and each mini-tablet contains about 12.5 mg Compound 1, and each mini-tablet weighs about 44.7 mg, then each capsule, pouch, packet, packet, sachet, bottle or blister pack can contain about 7 mini-tablets. If a unit dose form requires a final dose of about 100 mg, and each mini-tablet contains about 12.5 mg Compound 1, and each mini-tablet weighs about 44.7 mg, then each capsule, pouch, packet, packet, sachet, bottle or blister pack can contain about 8 mini-tablets. If a unit dose form requires a final dose of about 125 mg, and each mini-tablet contains about 12.5 mg Compound 1, and each mini-tablet weighs about 44.7 mg, then each capsule, pouch, sachet, packet, bottle or blister pack can contain about 10 mini-tablets. If a unit dose form requires a final dose of about 150 mg, and each mini-tablet contains about 12.5 mg Compound 1, and each mini-tablet weighs about 44.7 mg, then each capsule, pouch, packet, sachet, bottle or blister pack can contain about 12 mini-tablets.

The final dose is dependent on the amount of Compound 1 in the solid dispersion, the amount of solid dispersion in the mini-tablet, the weight of the mini-tablet, and the quantity of the mini-tablet(s). Although, the examples illustrate 2 mm and 4 mm mini-tablets having weights of 6.9 mg, 7 mg, 35.7 mg, 44.7 mg, one skilled in the art would understand, that for a single formulation composition, any desired dosage can be achieved by adjusting the weight of the mini-tablet and then administering the appropriate number of mini-tablets to deliver the desired dosage. For instance, 100 mini-tablets, in which each mini-tablet weighs 5 mg and includes 35 wt % of the dispersion described as intermediate 1 in the examples, would result in a final dose of 140 mg of Compound 1.

In some embodiments, the compressed formulations are sized from about 1 mm to about 5 mm (e.g. 2 mm or 4 mm) in all dimensions. In some embodiments, the compressed formulations include granules of any shape, including irregular shape, which are sized from about 1 mm to about 5 mm (e.g. 2 mm or 4 mm) in all dimensions. For example, a spherical granule has a diameter ranging from about 1 mm to about 5 mm (e.g. 2 mm or 4 mm). An elliptical granule has a length ranging from about 1 mm to about 5 mm (e.g. 2 mm or 4 mm) and a diameter ranging from about 1 mm to about 5 mm (e.g. 2 mm or 4 mm). A mini-tablet can have a cylindrical shape and have a diameter ranging from about 1 mm to about 5 mm (e.g. 2 mm or 4 mm) and a length or thickness ranging from about 1 mm to about 5 mm (e.g. 2 mm or 4 mm). There are no restrictions on the geometry of the compressed formulation, and is limited only by the geometry of the tooling (i.e., dies and punches) used to compress the powder admixture of the present pharmaceutical composition into the various compressed solid dose forms.

For the purposes of illustration only, the present embodiments will be exemplified using a mini-tablet having a diameter of about 2 mm and a length of about 2 mm. A batch of mini-tablets comprising one pharmaceutical composition are formulated into a capsule, pouch, packet, sachet, bottle or blister pack (a unit dose) the capsule, pouch, packet, sachet, bottle or blister pack containing from about 1 mg to about 250 mg of Compound 1, or from about 10 mg to about 250 mg, or from about 15 mg to about 250 mg of Compound 1. The number of mini-tablets used to make up the capsule, pouch, packet, sachet, bottle or blister pack can vary from 1 to 350 (for example: 1 to 336, 1 to 150, 1 to 100, 1 to 50, 1 to 30) mini-tablets per capsule, pouch, packet, sachet, bottle or blister pack. Each mini-tablet batch exemplified in the Examples below comprises compressed powder pharmaceutical composition, the composition comprising a solid dispersion of Compound 1 in which the solid dispersion comprises a polymer, and one or more fillers, a sweetener, a disintegrant, optionally a wetting agent, a glidant and a lubricant. Different batches of compressed pharmaceutical compositions can comprise the same or different amounts of Compound 1 and/or different amounts of excipients.

In some embodiments, the present invention provides a pharmaceutical composition comprising a mini-tablet or plurality of mini-tablets in a unit dose form, wherein each of the mini-tablets comprises:
 a) a solid dispersion of substantially amorphous or amorphous Compound 1 and a polymer, the polymer comprising HPMCAS;
 b) one or more fillers;
 c) a sweetener;
 d) a disintegrant;
 e) optionally a wetting agent;
 f) a glidant; and
 g) a lubricant,
wherein the unit dose form comprises an amount of substantially amorphous Compound 1 or amorphous Compound 1 ranging from about 1 mg to about 250 mg.

In some embodiments, the present invention provides a pharmaceutical composition comprising a mini-tablet or plurality of mini-tablets in a unit dose form, wherein each of the mini-tablets comprises:
 a) a solid dispersion of substantially amorphous or amorphous Compound 1 and a polymer, the polymer comprising HPMCAS;
 b) one or more fillers;
 c) a sweetener;
 d) a disintegrant;
 e) optionally a wetting agent;
 f) a glidant; and
 g) a lubricant,
wherein the mini-tablet or plurality of mini-tablets comprises about 5 mg of substantially amorphous Compound 1 or amorphous Compound 1.

In some embodiments, the present invention provides a pharmaceutical composition comprising a mini-tablet or plurality of mini-tablets in a unit dose form, wherein each of the mini-tablets comprises:
 a) a solid dispersion of substantially amorphous or amorphous Compound 1 and a polymer, the polymer comprising HPMCAS;
 b) one or more fillers;
 c) a sweetener;
 d) a disintegrant;
 e) optionally a wetting agent;
 f) a glidant; and
 g) a lubricant,
wherein the mini-tablet or plurality of mini-tablets comprises about 10 mg of substantially amorphous Compound 1 or amorphous Compound 1.

In some embodiments, the present invention provides a pharmaceutical composition comprising a mini-tablet or plurality of mini-tablets in a unit dose form, wherein each of the mini-tablets comprises:
 a) a solid dispersion of substantially amorphous or amorphous Compound 1 and a polymer, the polymer comprising HPMCAS;
 b) one or more fillers;
 c) a sweetener;
 d) a disintegrant;
 e) optionally a wetting agent;
 f) a glidant; and
 g) a lubricant, wherein the mini-tablet or plurality of mini-tablets comprises about 12.5 mg of substantially amorphous Compound 1 or amorphous Compound 1.

In some embodiments, the present invention provides a pharmaceutical composition comprising a mini-tablet or plurality of mini-tablets in a unit dose form, wherein each of the mini-tablets comprises:
a) a solid dispersion of substantially amorphous or amorphous Compound 1 and a polymer, the polymer comprising HPMCAS;
b) one or more fillers;
c) a sweetener;
d) a disintegrant;
e) optionally a wetting agent;
f) a glidant; and
g) a lubricant,
wherein the mini-tablet or plurality of mini-tablets comprises about 15 mg of substantially amorphous Compound 1 or amorphous Compound 1.

In some embodiments, the present invention provides a pharmaceutical composition comprising a mini-tablet or plurality of mini-tablets in a unit dose form, wherein each of the mini-tablets comprises:
a) a solid dispersion of substantially amorphous or amorphous Compound 1 and a polymer, the polymer comprising HPMCAS;
b) one or more fillers;
c) a sweetener;
d) a disintegrant;
e) optionally a wetting agent;
f) a glidant; and
g) a lubricant,
wherein the mini-tablet or plurality of mini-tablets comprises about 20 mg of substantially amorphous Compound 1 or amorphous Compound 1.

In some embodiments, the present invention provides a pharmaceutical composition comprising a mini-tablet or plurality of mini-tablets in a unit dose form, wherein each of the mini-tablets comprises:
a) a solid dispersion of substantially amorphous or amorphous Compound 1 and a polymer, the polymer comprising HPMCAS;
b) one or more fillers;
c) a sweetener;
d) a disintegrant;
e) optionally a wetting agent;
f) a glidant; and
g) a lubricant,
wherein the unit dose form comprises about 25 mg of substantially amorphous Compound 1 or amorphous Compound 1.

In some embodiments, the present invention provides a pharmaceutical composition comprising a mini-tablet or plurality of mini-tablets in a unit dose form, wherein each of the mini-tablets comprises:
a) a solid dispersion of substantially amorphous or amorphous Compound 1 and a polymer, the polymer comprising HPMCAS;
b) one or more fillers;
c) a sweetener;
d) a disintegrant;
e) optionally a wetting agent;
f) a glidant; and
g) a lubricant,
wherein the mini-tablet or plurality of mini-tablets comprises about 30 mg of substantially amorphous Compound 1 or amorphous Compound 1.

In some embodiments, the present invention provides a pharmaceutical composition comprising a mini-tablet or plurality of mini-tablets in a unit dose form, wherein each of the mini-tablets comprises:
a) a solid dispersion of substantially amorphous or amorphous Compound 1 and a polymer, the polymer comprising HPMCAS;
b) one or more fillers;
c) a sweetener;
d) a disintegrant;
e) optionally a wetting agent;
f) a glidant; and
g) a lubricant,
wherein the mini-tablet or plurality of mini-tablets comprises about 35 mg of substantially amorphous Compound 1 or amorphous Compound 1.

In some embodiments, the present invention provides a pharmaceutical composition comprising a mini-tablet or plurality of mini-tablets in a unit dose form, wherein each of the mini-tablets comprises:
a) a solid dispersion of substantially amorphous or amorphous Compound 1 and a polymer, the polymer comprising HPMCAS;
b) one or more fillers;
c) a sweetener;
d) a disintegrant;
e) optionally a wetting agent;
f) a glidant; and
g) a lubricant,
wherein the mini-tablet or plurality of mini-tablets comprises about 37.5 mg of substantially amorphous Compound 1 or amorphous Compound 1.

In some embodiments, the present invention provides a pharmaceutical composition comprising a mini-tablet or plurality of mini-tablets in a unit dose form, wherein each of the mini-tablets comprises:
a) a solid dispersion of substantially amorphous or amorphous Compound 1 and a polymer, the polymer comprising HPMCAS;
b) one or more fillers;
c) a sweetener;
d) a disintegrant;
e) optionally a wetting agent;
f) a glidant; and
g) a lubricant,
wherein the mini-tablet or plurality of mini-tablets comprises about 40 mg of substantially amorphous Compound 1 or amorphous Compound 1.

In some embodiments, the present invention provides a pharmaceutical composition comprising a mini-tablet or plurality of mini-tablets in a unit dose form, wherein each of the mini-tablets comprises:
a) a solid dispersion of substantially amorphous or amorphous Compound 1 and a polymer, the polymer comprising HPMCAS;
b) one or more fillers;
c) a sweetener;
d) a disintegrant;
e) optionally a wetting agent;
f) a glidant; and
g) a lubricant,
wherein the mini-tablet or plurality of mini-tablets comprises about 45 mg of substantially amorphous Compound 1 or amorphous Compound 1.

In some embodiments, the present invention provides a pharmaceutical composition comprising a mini-tablet or plurality of mini-tablets in a unit dose form, wherein each of the mini-tablets comprises:

a) a solid dispersion of substantially amorphous or amorphous Compound 1 and a polymer, the polymer comprising HPMCAS;
    b) one or more fillers;
    c) a sweetener;
    d) a disintegrant;
    e) optionally a wetting agent;
    f) a glidant; and
    g) a lubricant, wherein the unit dose form comprises about 50 mg of substantially amorphous Compound 1 or amorphous Compound 1.

In some embodiments, the present invention provides a pharmaceutical composition comprising a mini-tablet or plurality of mini-tablets in a unit dose form, wherein each of the mini-tablets comprises:

a) a solid dispersion of substantially amorphous or amorphous Compound 1 and a polymer, the polymer comprising HPMCAS;
    b) one or more fillers;
    c) a sweetener;
    d) a disintegrant;
    e) optionally a wetting agent;
    f) a glidant; and
    g) a lubricant, wherein the mini-tablet or plurality of mini-tablets comprises about 62.5 mg of substantially amorphous Compound 1 or amorphous Compound 1.

In some embodiments, the present invention provides a pharmaceutical composition comprising a mini-tablet or plurality of mini-tablets in a unit dose form, wherein each of the mini-tablets comprises:

a) a solid dispersion of substantially amorphous or amorphous Compound 1 and a polymer, the polymer comprising HPMCAS;
    b) one or more fillers;
    c) a sweetener;
    d) a disintegrant;
    e) optionally a wetting agent;
    f) a glidant; and
    g) a lubricant, wherein the unit dose form comprises about 75 mg of substantially amorphous Compound 1 or amorphous Compound 1.

In some embodiments, the present invention provides a pharmaceutical composition comprising a mini-tablet or plurality of mini-tablets in a unit dose form, wherein each of the mini-tablets comprises:

a) a solid dispersion of substantially amorphous or amorphous Compound 1 and a polymer, the polymer comprising HPMCAS;
    b) one or more fillers;
    c) a sweetener;
    d) a disintegrant;
    e) optionally a wetting agent;
    f) a glidant; and
    g) a lubricant, wherein the unit dose form comprises about 100 mg of substantially amorphous Compound 1 or amorphous Compound 1.

In some embodiments, the present invention provides a pharmaceutical composition comprising a mini-tablet or plurality of mini-tablets in a unit dose form, wherein each of the mini-tablets comprises:

a) a solid dispersion of substantially amorphous or amorphous Compound 1 and a polymer, the polymer comprising HPMCAS;
    b) one or more fillers;
    c) a sweetener;
    d) a disintegrant;
    e) optionally a wetting agent;
    f) a glidant; and
    g) a lubricant, wherein the mini-tablet or plurality of mini-tablets comprises about 125 mg of substantially amorphous Compound 1 or amorphous Compound 1.

In some embodiments, the present invention provides a pharmaceutical composition comprising a mini-tablet or plurality of mini-tablets in a unit dose form, wherein each of the mini-tablets comprises:

a) a solid dispersion of substantially amorphous or amorphous Compound 1 and a polymer, the polymer comprising HPMCAS;
    b) one or more fillers;
    c) a sweetener;
    d) a disintegrant;
    e) optionally a wetting agent;
    f) a glidant; and
    g) a lubricant, wherein the unit dose form comprises about 150 mg of substantially amorphous Compound 1 or amorphous Compound 1.

In some embodiments, the present invention provides a pharmaceutical composition comprising a mini-tablet or plurality of mini-tablets in a unit dose form, wherein each of the mini-tablets comprises:

a) a solid dispersion of substantially amorphous or amorphous Compound 1 and a polymer, the polymer comprising HPMCAS;
    b) one or more fillers;
    c) a sweetener;
    d) a disintegrant;
    e) optionally a wetting agent;
    f) a glidant; and
    g) a lubricant, wherein the mini-tablet or plurality of mini-tablets comprises about 175 mg of substantially amorphous Compound 1 or amorphous Compound 1.

In some embodiments, the present invention provides a pharmaceutical composition comprising a mini-tablet or plurality of mini-tablets in a unit dose form, wherein each of the mini-tablets comprises:

a) a solid dispersion of substantially amorphous or amorphous Compound 1 and a polymer, the polymer comprising HPMCAS;
    b) one or more fillers;
    c) a sweetener;
    d) a disintegrant;
    e) optionally a wetting agent;
    f) a glidant; and
    g) a lubricant, wherein the mini-tablet or plurality of mini-tablets comprises about 200 mg of substantially amorphous Compound 1 or amorphous Compound 1.

In some embodiments, the present invention provides a pharmaceutical composition comprising a mini-tablet or plurality of mini-tablets in a unit dose form, wherein each of the mini-tablets comprises:

a) a solid dispersion of substantially amorphous or amorphous Compound 1 and a polymer, the polymer comprising HPMCAS;
b) one or more fillers;
c) a sweetener;
d) a disintegrant;
e) optionally a wetting agent;
f) a glidant; and
g) a lubricant, wherein the mini-tablet or plurality of mini-tablets comprises about 225 mg of substantially amorphous Compound 1 or amorphous Compound 1.

In some embodiments, the present invention provides a pharmaceutical composition comprising a mini-tablet or plurality of mini-tablets in a unit dose form, wherein each of the mini-tablets comprises:

a) a solid dispersion of substantially amorphous or amorphous Compound 1 and a polymer, the polymer comprising HPMCAS;
b) one or more fillers;
c) a sweetener;
d) a disintegrant;
e) optionally a wetting agent;
f) a glidant; and
g) a lubricant, wherein the mini-tablet or plurality of mini-tablets comprises about 250 mg of substantially amorphous Compound 1 or amorphous Compound 1.

In a further embodiment, the one or more fillers is a binary filler comprising a mixture of 2 fillers. In another further embodiment, the binary filler is a mixture of mannitol and another filler. In another further embodiment, the binary filler is a mixture of lactose and another filler. In another further embodiment, the binary filler is a mixture of mannitol and lactose.

In another further embodiment, the pharmaceutical composition comprises a binary filler, wherein the binary filler comprises mannitol in an amount up to about 100 wt % of the binary filler, In still another further embodiment, the pharmaceutical composition comprises a binary filler, wherein the binary filler comprises lactose in an amount up to about 100 wt % of the binary filler, In still another further embodiment, the pharmaceutical composition comprises a binary filler, wherein the binary filler comprises mannitol in an amount up to about 100 wt % of the binary filler and lactose in an amount such that the sum of the amount of mannitol and lactose is equal to 100 wt %.

In some embodiments, the pharmaceutical composition comprises a binary filler, wherein the binary filler comprises mannitol and another filler in a ratio of about 3:1 mannitol to other filler, a ratio of about 1:1 mannitol to other filler, or a ratio of about 1:3 mannitol to other filler. In some embodiments, the pharmaceutical composition comprises a binary filler, wherein the binary filler comprises lactose and another filler in a ratio of about 3:1 lactose to other filler, a ratio of about 1:1 lactose to other filler, or a ratio of about 1:3 lactose to other filler. In some embodiments, the pharmaceutical composition comprises a binary filler, wherein the binary filler comprises mannitol and lactose in a ratio of about 3:1 mannitol to lactose, a ratio of about 1:1 mannitol to lactose, or a ratio of about 1:3 mannitol to lactose.

One exemplary compressed pharmaceutical composition comprises from about 5 wt % to about 70 wt % (e.g., from about 5 wt % to about 65 wt %, from about 5 wt % to about 50 wt %, or from about 30 wt % to about 40 wt %) of a solid dispersion, by weight of the composition, comprising from about 30 wt % to about 90 wt % of substantially amorphous Compound 1, by weight of the dispersion, and from about 70 wt % to about 10 wt % of a polymer, by weight of the dispersion; from about 10 wt % to about 90 wt % of one or more fillers; from about 1 wt % to about 10 wt % of a disintegrant; optionally from about 3 wt % to about 0.01 wt % of a wetting agent; from about 0.1 wt % to about 5 wt % of a sweetener; from about 5 wt % to about 0.1 wt % of a glidant; and from about 7 wt % to about 0.1 wt % of a lubricant. Or, the compressed pharmaceutical composition comprises from about 5 wt % to about 65 wt % (e.g., from about 5 wt % to about 25 wt %, from about 15 wt % to about 40 wt %, or from about 30 wt % to about 50 wt %) of a solid dispersion, by weight of the composition, comprising from about 30 wt % to about 90 wt % of amorphous Compound 1, by weight of the dispersion, and from about 70 wt % to about 10 wt % of a polymer, by weight of the dispersion; from about 10 wt % to about 90 wt % of one or more fillers; from about 1 wt % to about 10 wt % of a disintegrant; optionally from about 3 wt % to about 0.01 wt % of a wetting agent; from about 0.1 wt % to about 5 wt % of a sweetener; from about 5 wt % to about 0.1 wt % of a glidant; and from about 7 wt % to about 0.1 wt % of a lubricant.

Another exemplary pharmaceutical composition comprises from about 5 wt % to about 60 wt % (e.g., from about 5 wt % to about 55 wt %, from about 15 wt % to about 50 wt %, or from about 30 wt % to about 50 wt %) of a solid dispersion, by weight of the composition, comprising from about 30 wt % to about 90 wt % of substantially amorphous Compound 1, by weight of the dispersion, and from about 70 wt % to about 10 wt % of a polymer, by weight of the dispersion; from about 10 wt % to about 90 wt % of one or more fillers; from about 1 wt % to about 10 wt % of a disintegrant; from about 0.1 wt % to about 5 wt % of a sweetener, from about 7 wt % to about 0.1 wt % of a lubricant; optionally from about 0.01 wt % to about 3 wt % of a wetting agent; from about 5 wt % to about 0.1 wt % of a glidant. Or, the pharmaceutical composition comprises from about 5 wt % to about 70 wt % (e.g., from about 5 wt % to about 65 wt %, from about 5 wt % to about 50 wt %, or from about 30 wt % to about 50 wt %) of a solid dispersion, by weight of the composition, comprising from about 40 wt % to about 90 wt % of amorphous Compound 1, by weight of the dispersion, and from about 60 wt % to about 10 wt % of a polymer, by weight of the dispersion; from about 10 wt % to about 90 wt % of one or more fillers; from about 1 wt % to about 10 wt % of a disintegrant; from about 5 wt % to about 0.1 wt % of a sweetener; optionally from about 3 wt % to about 0.01 wt % of a wetting agent; from about 5 wt % to about 0.1 wt % of a glidant; and from about 7 wt % to about 0.1 wt % of a lubricant.

One pharmaceutical composition of the present invention comprises about 46.9 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 45.1 wt % of mannitol by weight of the composition; about 2 wt % of sucralose by weight of the composition; about 3 wt % of croscarmellose sodium by weight of the composition; about 0.5 wt % of SLS by weight of the composition; about 1 wt % of colloidal silicon dioxide by weight of the composition; and about 1.5 wt % of magnesium stearate by weight of the composition.

Another compressed pharmaceutical composition of the present invention comprises about 24.6 wt % (equivalent to 24.6 mg potency for 200 mg unit) of a solid dispersion by weight of the composition, wherein the dispersion comprises about 50 wt % of substantially amorphous or amorphous Compound 1 by weight of the dispersion, about 49.5 wt % of HPMCAS by weight of the dispersion, and about 0.5 wt % SLS by weight of the dispersion; about 67.4 wt % of mannitol by weight of the composition; about 2 wt % of sucralose by weight of the composition; about 3 wt % of croscarmellose sodium by weight of the composition; about 0.5 wt % of SLS by weight of the composition; about 1 wt % of colloidal silicon dioxide by weight of the composition; and about 1.5 wt % of magnesium stearate by weight of the composition.

In another embodiment, the compressed pharmaceutical composition of the present invention comprises about 35 wt % of a solid dispersion by weight of the composition, wherein the dispersion comprises about 72.4 wt % of substantially amorphous or amorphous Compound 1 by weight of the dispersion, about 27.1 wt % of HPMCAS by weight of the dispersion, and about 0.5 wt % SLS by weight of the dispersion; about 54 wt % of mannitol by weight of the composition; about 2 wt % of sucralose by weight of the composition; about 6 wt % of croscarmellose sodium by weight of the composition; about 0.5 wt % of SLS by weight of the composition; about 1 wt % of colloidal silicon dioxide by weight of the composition; and about 1.5 wt % of magnesium stearate by weight of the composition.

In some embodiments, a compressed pharmaceutical composition of the present invention comprises about 61.6 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 30.4 wt % of mannitol by weight of the composition; about 2 wt % of sucralose by weight of the composition; about 3 wt % of croscarmellose sodium by weight of the composition; about 0.5 wt % of SLS by weight of the composition; about 1 wt % of colloidal silicon dioxide by weight of the composition; about 1.5 wt % of magnesium stearate by weight of the composition.

In some embodiments, a compressed pharmaceutical composition the present invention comprises about 68.7 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % of SLS by weight of the dispersion; about 23.3 wt % of mannitol by weight of the composition; about 2 wt % of sucralose by weight of the composition; about 3 wt % of croscarmellose sodium by weight of the composition; about 0.5 wt % of SLS by weight of the composition; about 1 wt % of colloidal silicon dioxide by weight of the composition; about 1.5 wt % of magnesium stearate by weight of the composition. Optionally, the above compressed pharmaceutical compositions can also include about 0.4 wt % of colorant by weight of the composition.

In yet a further compressed pharmaceutical composition of the present invention, the pharmaceutical composition comprises about 34 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 58 wt % of mannitol by weight of the composition; about 2 wt % of sucralose by weight of the composition; about 3 wt % of croscarmellose sodium by weight of the composition; about 0.5 wt % of SLS by weight of the composition; about 1 wt % of colloidal silicon dioxide by weight of the composition; and about 1.5 wt % of magnesium stearate by weight of the composition.

In one aspect, the invention provides a pharmaceutical composition comprising from about 30 wt % to about 50 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; from about 30 wt % to about 60 wt % of a binary filler, wherein the binary filler comprises from about 0 wt % to about 60 wt % of mannitol by weight of the composition and from about 0 wt % to about 60 wt % of lactose by weight of the composition; from about 1.5 wt % to about 2.5 wt % of sucralose by weight of the composition; from about 4 wt % to about 8 wt % of croscarmellose sodium by weight of the composition; from about 0.5 wt % to about 1.5 wt % of colloidal silicon dioxide by weight of the composition; and from about 1 wt % to about 2 wt % of magnesium stearate by weight of the composition.

In one embodiment, the pharmaceutical composition comprises about 35 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 13.5 wt % of mannitol by weight of the composition; about 41 wt % of lactose by weight of the composition; about 2 wt % of sucralose by weight of the composition; about 6 wt % of croscarmellose sodium by weight of the composition; about 1 wt % of colloidal silicon dioxide by weight of the composition; and about 1.5 wt % of magnesium stearate by weight of the composition.

In certain embodiments, the compressed pharmaceutical composition comprises 25-40 mini-tablets, the mini-tablets collectively containing 75 mg of Compound 1, which may be further formulated into a unit dose, for example a capsule, pouch, packet, sachet, bottle or blister pack. In other embodiments, a unit dose comprising a capsule, pouch, packet, sachet, bottle or blister pack containing 25-40 mini-tablets can contain about 50 mg, about 40 mg, about 30 mg, about 25 mg, about 20 mg, about 15 mg, about 10 mg or about 5 mg of Compound 1.

In certain embodiments, the compressed pharmaceutical composition comprises 5-30 mini-tablets, the mini-tablets collectively containing 75 mg of Compound 1, which may be further formulated into a unit dose, for example a capsule, pouch, sachet, bottle or blister pack. In other embodiments, a unit dose comprising a capsule, pouch, packet, sachet, bottle or blister pack containing 5-30 mini-tablets can contain about 50 mg, about 40 mg, about 30 mg, about 25 mg, about 20 mg, about 15 mg, about 10 mg or about 5 mg of Compound 1.

In certain embodiments, the compressed pharmaceutical composition comprises 1-30 mini-tablets, the mini-tablets collectively containing 50 mg of Compound 1, which may be further formulated into a unit dose, for example a capsule, pouch, sachet, bottle or blister pack. In other embodiments, a unit dose comprising a capsule, pouch, packet, sachet, bottle or blister pack containing 1-30 mini-tablets can contain about 75 mg, about 50 mg, about 40 mg, about 30 mg, about 25 mg, about 20 mg, about 15 mg, about 10 mg or about 5 mg of Compound 1.

In certain embodiments, the compressed pharmaceutical composition comprises about 1-50 mini-tablets (e.g. from about 27 to about 32) or from about 35 to about 42), the mini-tablets collectively containing 75 mg of Compound 1, which may be further formulated into a unit dose, for example a capsule, pouch, packet, sachet, bottle or blister pack. In other embodiments, a unit dose comprising a capsule, pouch, packet, sachet, bottle or blister pack containing 1-30 mini-tablets (e.g. about 25, about 20, about 19, about 15, about 12, about 10, about 9, about 8, about 7, about 6, about 5, about 4, about 3, about 2 or about 1) can contain about 50 mg, about 40 mg, about 30 mg, about 25 mg, about 20 mg, about 15 mg, about 10 mg or about 5 mg of Compound 1.

In yet a further pharmaceutical composition of the present invention, a mini-tablet compressed pharmaceutical composition has an average tensile strength from about 0.5 MPa. to about 4 MPa and comprises about 46.9 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 45.1 wt % of mannitol by weight of the composition; about 2 wt % of sucralose by weight of the composition; about 3 wt % of croscarmellose sodium by weight of the composition; about 0.5 wt % of SLS by weight of the composition; about 1 wt % of colloidal silicon dioxide by weight of the composition; and about 1.5 wt % of magnesium stearate by weight of the composition. In certain embodiments, the compressed pharmaceutical composition comprising a mini-tablet or plurality of mini-tablets contains 75 mg of Compound 1. In certain embodiments, the compressed pharmaceutical composition formulated into a unit dose has 75 mg of Compound 1.

In still another pharmaceutical composition of the present invention, a mini-tablet compressed pharmaceutical composition having an initial average tensile strength of 3.14 MPa comprises about 49.3 wt % of a solid dispersion by weight of the composition, wherein the dispersion comprises about 50 wt % of substantially amorphous or amorphous Compound 1 by weight of the dispersion, about 49.5 wt % of HPMCAS by weight of the dispersion, and about 0.5 wt % SLS by weight of the dispersion; about 42.7 wt % of mannitol by weight of the composition; about 2% wt % of sucralose by weight of the composition; about 3 wt % of croscarmellose sodium by weight of the composition; about 0.5 wt % of SLS by weight of the composition; about 1 wt % of colloidal silicon dioxide by weight of the composition; and about 1.5 wt % of magnesium stearate by weight of the composition. In certain embodiments, a capsule, pouch, packet, sachet, bottle or blister pack filled with a mini-tablet or plurality of min-tablets contains 50 mg of Compound 1.

In still another compressed pharmaceutical composition of the present invention, a mini-tablet pharmaceutical composition having an initial average tensile strength of 3.1 MPa comprises about 24.6 wt % of a solid dispersion by weight of the composition, wherein the dispersion comprises about 50 wt % of substantially amorphous Compound 1 by weight of the dispersion, about 49.5 wt % of HPMCAS by weight of the dispersion, and about 0.5 wt % SLS by weight of the dispersion; about 67.4 wt % of mannitol by weight of the composition; about 2 wt % of sucralose; about 3 wt % of croscarmellose sodium by weight of the composition; about 0.5 wt % of SLS by weight of the composition; about 1 wt % of colloidal silicon dioxide by weight of the composition; and about 1.5 wt % of magnesium stearate by weight of the composition. In some aspects, a unit dose comprising a capsule or a packet filled with a mini-tablet or plurality of mini-tablets contains 25 mg of Compound 1.

In other aspects, the mini-tablet pharmaceutical composition of the present invention optionally includes a colorant coating. In some embodiments of this aspect, the mini-tablet shaped solid dose form includes a blue OPADRY® II coating. In certain embodiments, a capsule or a packet containing a mini-tablet or plurality of mini-tablets pharmaceutical composition contains 25 mg of Compound 1.

In some embodiments, a capsule or a packet containing 20-40 mini-tablets contains about 75 mg of Compound 1. In some aspects, the mini-tablet pharmaceutical composition can optionally further comprise a colorant coating and/or a wax coating. In some aspects, the pharmaceutical composition comprising 20-60 mini-tablets contained in a capsule or a packet contains 100 mg of Compound 1.

In another compressed pharmaceutical composition of the present invention, a mini-tablet produced in the methods disclosed herein, has an initial average tensile strength between 2.1 and 4.0 MPa and comprises about 61.6 wt % of a solid dispersion by weight of the composition, wherein the dispersion comprises about 80 wt % of substantially amorphous Compound 1 by weight of the dispersion, about 19.5 wt % of HPMCAS by weight of the dispersion, and about 0.5 wt % SLS by weight of the dispersion; about 30.4 wt % of mannitol by weight of the composition; about 2 wt % of sucralose by weight of the composition; about 3 wt % of croscarmellose sodium by weight of the composition; about 0.1 wt % of SLS by weight of the composition; about 1.5 wt % of colloidal silicon dioxide by weight of the composition; and about 1.5 wt % of magnesium stearate by weight of the composition. In some aspects, a capsule or a packet containing a mini-tablet or plurality of mini-tablets contains 100 mg of Compound 1. In some aspects, a unit dose form (e.g. a capsule or a packet) comprises a mini-tablet or plurality of mini-tablets, for example, from about 20 to about 50 mini-tablets. In some embodiments, a capsule or a packet containing 39 mini-tablets contains 150 mg of Compound 1.

In another pharmaceutical composition of the present invention, a pharmaceutical composition comprises about 34.1 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 57.9 wt % of mannitol by weight of the composition; about 2 wt % of sucralose by weight of the composition; about 3 wt % of croscarmellose sodium by weight of the composition; about 0.5 wt % of SLS by weight of the composition; about 1 wt % of colloidal silicon dioxide by weight of the composition; and about 1.5 wt % of magnesium stearate by weight of the composition. In some aspects, the pharmaceutical mini-tablet contains 1.91 mg of Compound 1. In other embodiments, the pharmaceutical composition comprising a mini-tablet contains 1.72 mg of Compound 1.

In one embodiment, the pharmaceutical composition comprises about 35 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 13.5 wt % of mannitol by weight of the composition; about 41 wt % of lactose by weight of the composition; about 2 wt % of sucralose by weight of the composition; about 6 wt % of croscarmellose sodium by weight of the composition; about 1 wt % of colloidal silicon dioxide by weight of the composition; and about 1.5 wt % of magnesium stearate by weight of the composition. In some aspects, the pharmaceutical mini-tablet contains 1.93 mg of Compound 1. In other embodiments, the pharmaceutical composition comprising a mini-tablet contains 1.96 mg of Compound 1. In some aspects, the pharmaceutical mini-tablet contains 10 mg of Compound 1. In other embodiments, the pharmaceutical composition comprising a mini-tablet contains 12.5 mg of Compound 1. In some aspects, the pharmaceutical mini-tablet contains 1.92 mg of Compound 1.

It is also noted that pharmaceutical compositions comprising one or more mini-tablets of the present invention can be processed into a capsule form, or filled into sachets or packets for oral administration or can be reconstituted in an aqueous solvent (e.g., DI water or saline) for oral or IV administration. Preferably the mini-tablet pharmaceutical compositions described herein are formulated and encapsulated in capsules, bottles or sachets. In other embodiments, the pharmaceutical composition comprising a mini-tablet or plurality of mini-tablets can be in pouches, packets, sachets, bottles or blister packs. In one embodiment, the pharmaceutical composition comprising a mini-tablet or plurality of mini-tablets can be in packets.

Another aspect of the present invention provides a pharmaceutical composition consisting of 1-200 mini-tablets, each mini-tablet includes a CF potentiator API (e.g., a solid dispersion of N-[2,4-bis(1,1-dimethylethyl)-5-hydroxyphenyl]-1,4-dihydro-4-oxoquinoline-3-carboxamide) and other excipients (e.g., one or more fillers, a disintegrant, a sweetener, a wetting agent, a glidant, a lubricant, or any combination thereof), each of which is described above and in the Examples below, wherein the mini-tablet or plurality of mini-tablets has a dissolution of at least about 50% (e.g., at least about 60%, at least about 70%, or at least about 80%) in about 30 minutes. In one example, the pharmaceutical composition consists of a capsule or a packet containing about 29 mini-tablets that includes a CF potentiator API (e.g., a solid dispersion of Compound 1) and other excipients (e.g., one or more fillers, a sweetener, a disintegrant, a wetting agent, a glidant; and a lubricant, or any combination thereof), each of which is described above and in the Examples below, wherein in some embodiments, the mini-tablet has a dissolution of from about 50% to about 100% (e.g., from about 55% to about 95%, from about 60% to about 90% or from about 70% to about 80%) in about 30 minutes. In another example, the pharmaceutical composition consists of a capsule or a packet comprising about 29 mini-tablets, each mini-tablets comprising a solid dispersion comprising substantially amorphous or amorphous Compound 1 and HPMCAS; and, one or more fillers, a sweetener, a disintegrant, optionally a wetting agent, a glidant; and a lubricant, wherein the contents of the capsule or packet has a dissolution of at least about 50% (e.g., at least about 60%, at least about 70%, at least about 80%, at least about 90%) in about 30 minutes. In still another example, the pharmaceutical composition consists of a capsule or a packet comprising about 29 mini-tablets, each mini-tablet comprising a solid dispersion comprising substantially amorphous or amorphous Compound 1 and HPMCAS; and, one or more fillers, a sweetener, a disintegrant, optionally a wetting agent, a glidant; and a lubricant, wherein the contents of the capsule or packet has a dissolution of from about 50% to about 100% (e.g., from about 55% to about 95%, from about 60% to about 90% or about 70% to about 80%) in about 30 minutes.

In one embodiment, a capsule or a packet comprises a mini-tablet or plurality of mini-tablets, wherein the mini-tablet or plurality of mini-tablets comprises a solid dispersion comprising at least about 15 mg (e.g., at least about 20 mg, at least about 25 mg, at least about 30 mg, at least about 40 mg, or at least about 50 mg) of substantially amorphous or amorphous Compound 1; HPMCAS polymer and SLS. In another embodiment, a capsule or a packet comprises a mini-tablet or plurality of mini-tablets, wherein the mini-tablet or plurality of mini-tablets comprises a solid dispersion comprising at least about 15 mg (e.g., at least 20 mg, at least 25 mg, at least about 30 mg, at least about 40 mg, at least about 50 mg, at least about 75 mg, at least about 100 mg, or at least 150 mg) of substantially amorphous or amorphous Compound 1; and HPMCAS and SLS.

Dissolution can be measured with a standard USP Type II apparatus containing a dissolution media of 0.5 or 0.7% sodium lauryl sulfate dissolved in 900 mL of 50 mM sodium phosphate buffer at a pH of 6.8 at a temperature of about 37° C. The dissolution of mini-tablets is determined by recording the dissolution of a plurality of mini-tablets containing, in the aggregate, 75 mg (using 0.5% sodium lauryl sulfate) or 150 mg (using 0.7% sodium lauryl sulfate) of Compound 1 in the dissolution media. Individual mini-tablets can exhibit dissolution that is lower, equivalent to or higher than the dissolution of the plurality, with the mean dissolution of each individual mini-tablet being similar to the mean dissolution of the plurality.

Another aspect of the present invention provides a pharmaceutical composition consisting of a mini-tablet that comprises a CF potentiator API (e.g., a solid dispersion of Compound 1) and other excipients (e.g., one or more fillers, a sweetener, a disintegrant, a wetting agent, a glidant; and a lubricant, or any combination thereof), each of which is described above and in the Examples below, wherein the mini-tablet has an average tensile strength ranging from, about 0.5 MPa to about 4 MPa, for example, at least about 0.5 MPa, at least about 1 MPa, or at least about 2 MPa. In one example, the pharmaceutical composition consists of a mini-tablet that comprises a CF potentiator API (e.g., a solid dispersion of Compound 1) and other excipients (e.g., one or more fillers, a sweetener, a disintegrant, a wetting agent, a glidant; and a lubricant, or any combination thereof), each of which is described above and in the Examples below, wherein the mini-tablet has an average tensile strength ranging from, about 0.5 MPa to about 4 MPa, for example, at least about 0.5 MPa, at least about 1 MPa, or at least about 2 MPa.

In yet a further pharmaceutical composition of the present invention, a mini-tablet pharmaceutical composition having an average tensile strength ranging from, about 0.5 MPa to about 4.1 MPa (e.g. from about 0.5 MPa to about 4 MPa, from about 0.5 MPa to about 3 MPa, from about 0.75 MPa to about 3 MPa, from about 1 MPa to about 2 MPa, from about 1 MPa to about 1.5 MPa or from about 2.1 to about 4.05 MPa) and comprises about 46.7 wt % of a solid dispersion by weight of the composition, wherein the dispersion comprises about 78.8 wt % of substantially amorphous or amorphous Compound 1 by weight of the dispersion, about 20.7 wt % of HPMCAS by weight of the dispersion, and about 0.5 wt % SLS by weight of the dispersion; about 45.1 wt % of mannitol by weight of the composition; about 2 wt % of sucralose by weight of the composition; about 3 wt % of croscarmellose sodium by weight of the composition; about 0.5 wt % of SLS by weight of the composition; about 1 wt % of colloidal silicon dioxide by weight of the composition; and about 1.5 wt % of magnesium stearate by weight of the composition. In certain embodiments, the pharmaceutical composition comprising one or more mini-tablets contains 75 mg of Compound 1.

In still another pharmaceutical composition of the present invention, a mini-tablet pharmaceutical composition having an initial average tensile strength ranging from, about 0.5 MPa to about 4.1 MPa (e.g. from about 0.5 MPa to about 4 MPa, from about 0.5 MPa to about 3 MPa, from about 0.75

MPa to about 3 MPa, from about 1 MPa to about 2 MPa, from about 1 MPa to about 1.5 MPa or about 3.14 MPa), and comprises about 49.3 wt % of a solid dispersion by weight of the composition, wherein the dispersion comprises about 50 wt % of substantially amorphous or amorphous Compound 1 by weight of the dispersion, about 49.5 wt % of HPMCAS by weight of the dispersion, and about 0.5 wt % SLS by weight of the dispersion; about 42.7 wt % of mannitol by weight of the composition; about 2% wt % of sucralose by weight of the composition; about 3 wt % of croscarmellose sodium by weight of the composition; about 0.5 wt % of SLS by weight of the composition; about 1 wt % of colloidal silicon dioxide by weight of the composition; and about 1.5 wt % of magnesium stearate by weight of the composition. In certain embodiments, a capsule or a packet filled with a mini-tablet or plurality of min-tablets contains 50 mg of Compound 1.

In still another pharmaceutical composition of the present invention, a mini-tablet pharmaceutical composition having an initial average tensile strength ranging from, about 0.5 MPa to about 4.1 MPa (e.g. from about 0.5 MPa to about 4 MPa, from about 0.5 MPa to about 3 MPa, from about 0.75 MPa to about 3 MPa, from about 1 MPa to about 2 MPa, from about 1 MPa to about 1.5 MPa or about 3.1 MPa), and comprises about 24.6 wt % of a solid dispersion by weight of the composition, wherein the dispersion comprises about 50 wt % of substantially amorphous Compound 1 by weight of the dispersion, about 49.5 wt % of HPMCAS by weight of the dispersion, and about 0.5 wt % SLS by weight of the dispersion; about 67.4 wt % of mannitol by weight of the composition; about 2 wt % of sucralose; about 3 wt % of croscarmellose sodium by weight of the composition; about 0.5 wt % of SLS by weight of the composition; about 1 wt % of colloidal silicon dioxide by weight of the composition; and about 1.5 wt % of magnesium stearate by weight of the composition. In some aspects, a pharmaceutical composition comprising a capsule or a packet filled with a mini-tablet or plurality of mini-tablets contains 25 mg of Compound 1. In certain embodiments, a capsule or a packet containing a mini-tablet or plurality of mini-tablets pharmaceutical composition contains 25 mg of Compound 1.

In another pharmaceutical composition of the present invention, a mini-tablet composition having an initial average tensile strength between 2.1 and 4.0 MPa and comprises about 61.6 wt % of a solid dispersion by weight of the composition, wherein the dispersion comprises about 80 wt % of substantially amorphous Compound 1 by weight of the dispersion, about 19.5 wt % of HPMCAS by weight of the dispersion, and about 0.5 wt % SLS by weight of the dispersion; about 30.4 wt % of mannitol by weight of the composition; about 2 wt % of sucralose by weight of the composition; about 3 wt % of croscarmellose sodium by weight of the composition; about 0.1 wt % of SLS by weight of the composition; about 1.5 wt % of colloidal silicon dioxide by weight of the composition; and about 1.5 wt % of magnesium stearate by weight of the composition. In some aspects, a capsule or a packet containing a mini-tablet or plurality of mini-tablets contains 100 mg of Compound 1. In some aspects, a compressed pharmaceutical composition comprising a mini-tablet or plurality of mini-tablets for example, from about 20 to about 50 mini-tablets, for example 43 mini-tablets, contains 150 mg of Compound 1.

In some embodiments, a capsule or a packet containing 20-40 mini-tablets contains about 75 mg of Compound 1. In some aspects, the pharmaceutical composition comprising 20-40 mini-tablets contained in a capsule or a packet contains 100 mg of Compound 1.

In yet a further pharmaceutical composition of the present invention, a compressed pharmaceutical composition comprises about 34 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 58 wt % of mannitol by weight of the composition; about 2 wt % of sucralose by weight of the composition; about 3 wt % of croscarmellose sodium by weight of the composition; about 0.5 wt % of SLS by weight of the composition; about 1 wt % of colloidal silicon dioxide by weight of the composition; and about 1.5 wt % of magnesium stearate by weight of the composition. In certain embodiments, the pharmaceutical composition comprising a capsule or a packet containing 25-30 (e.g. about 26) mini-tablets contains 50 mg of Compound 1. In other embodiments, the pharmaceutical composition comprising a capsule or a packet containing 20-30 mini-tablets contains 25, 15 or 10 mg of Compound 1.

In another pharmaceutical composition of the present invention, a pharmaceutical composition comprises about 34.1 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 57.9 wt % of mannitol by weight of the composition; about 2 wt % of sucralose by weight of the composition; about 3 wt % of croscarmellose sodium by weight of the composition; about 0.5 wt % of SLS by weight of the composition; about 1 wt % of colloidal silicon dioxide by weight of the composition; and about 1.5 wt % of magnesium stearate by weight of the composition. In some aspects, the compressed mini-tablet contains 1.91 mg of Compound 1. In other embodiments, the mini-tablet contains 1.72 mg of Compound 1.

In one aspect, the invention provides a pharmaceutical composition comprising from about 30 wt % to about 50 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; from about 30 wt % to about 60 wt % of a binary filler, wherein the binary filler comprises from about 0 wt % to about 60 wt % of mannitol by weight of the composition and from about 0 wt % to about 60 wt % of lactose by weight of the composition; from about 1.5 wt % to about 2.5 wt % of sucralose by weight of the composition; from about 4 wt % to about 8 wt % of croscarmellose sodium by weight of the composition; from about 0.5 wt % to about 1.5 wt % of colloidal silicon dioxide by weight of the composition; and from about 1 wt % to about 2 wt % of magnesium stearate by weight of the composition.

In one embodiment, the pharmaceutical composition comprises about 35 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 13.5 wt % of mannitol by weight of the composition; about 41 wt % of lactose by weight of the composition; about 2 wt % of sucralose by weight of the composition; about 6 wt % of croscarmellose sodium by weight of the composition; about 1 wt % of colloidal silicon dioxide by weight of the composition; and about 1.5 wt % of magnesium stearate by weight of the composition.

In a further embodiment of this aspect, the pharmaceutical composition is in the form of a mini-tablet. In another embodiment, the mini-tablet is about 2 mm in size. In another embodiment, the mini-tablet is 4 mm in size. In a further embodiment, a plurality of 2 mm mini-tablets collectively form a dose containing from about 20 mg to about 275 mg of Compound 1, for example, the plurality of 2 mm mini-tablets collectively form a dose containing about 25 mg, about 50 mg, about 75 mg, about 100 mg, about 125 mg, about 150 mg, about 175 mg, about 200 mg, about 225 mg, or about 250 mg. In another further embodiment, a plurality of 4 mm mini-tablets collectively form a dose containing from about 5 mg to about 70 mg of Compound 1, for example, the plurality of 4 mm mini-tablets collectively form a dose containing about 10 mg, 12.5 mg, about 20 mg, 25 mg, about 30 mg, about 37.5 mg, 40 mg, 50 mg, about 62.5 mg, about 75 mg, about 100 mg, about 125 mg, about 150 mg, about 175 mg, about 200 mg, about 225 mg, or about 250 mg.

In one embodiment, the pharmaceutical composition comprises about 35 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 13.5 wt % of mannitol by weight of the composition; about 41 wt % of lactose by weight of the composition; about 2 wt % of sucralose by weight of the composition; about 6 wt % of croscarmellose sodium by weight of the composition; about 1 wt % of colloidal silicon dioxide by weight of the composition; and about 1.5 wt % of magnesium stearate by weight of the composition. In one embodiment, the pharmaceutical composition comprises a plurality of mini-tablets having about 50 mg of Compound 1 per 26 mini-tablets and 75 mg Compound 1 per 39 mini-tablets. In a further embodiment, the mini-tablets are each about 2 mm in diameter and about 2 mm in thickness. In a further embodiment, each mini-tablet weighs about 7 mg. In some embodiments, each mini-tablet weighs about 6.9 mg. In yet a further embodiment, the mini-tablets are cylindrical in shape. In one embodiment, the pharmaceutical composition includes a capsule or a packet containing the plurality of mini-tablets. In one further embodiment, the capsule or packet contains about 26 mini-tablets and about 50 mg of Compound 1. In another further embodiment, the capsule or packet contains about 39 mini-tablets and about 75 mg of Compound 1.

In one embodiment, the pharmaceutical composition comprises about 35 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 13.5 wt % of mannitol by weight of the composition; about 41 wt % of lactose by weight of the composition; about 2 wt % of sucralose by weight of the composition; about 6 wt % of croscarmellose sodium by weight of the composition; about 1 wt % of colloidal silicon dioxide by weight of the composition; and about 1.5 wt % of magnesium stearate by weight of the composition. In one embodiment, the pharmaceutical composition comprises a plurality of mini-tablets having about 40 mg of Compound 1 per 21 mini-tablets and 100 mg Compound 1 per 52 mini-tablets. In a further embodiment, the mini-tablets are each about 2 mm in diameter and about 2 mm in thickness. In a further embodiment, each mini-tablet weighs about 6.9 mg.

In yet a further embodiment, the mini-tablets are cylindrical in shape. In one embodiment, the pharmaceutical composition includes a capsule or a packet containing the plurality of mini-tablets. In one further embodiment, the capsule or packet contains about 21 mini-tablets and about 40 mg of Compound 1. In another further embodiment, the capsule or packet contains about 52 mini-tablets and about 100 mg of Compound 1.

In one embodiment, the pharmaceutical composition comprises about 35 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 13.5 wt % of mannitol by weight of the composition; about 41 wt % of lactose by weight of the composition; about 2 wt % of sucralose by weight of the composition; about 6 wt % of croscarmellose sodium by weight of the composition; about 1 wt % of colloidal silicon dioxide by weight of the composition; and about 1.5 wt % of magnesium stearate by weight of the composition. In one embodiment, the pharmaceutical composition comprises one or more tablets having about 10 mg of Compound 1 per tablet. In a further embodiment, the tablet is about 4 mm in diameter and about 3 mm in thickness. In a further embodiment, the tablet weighs about 35.7 mg. In yet a further embodiment, the mini-tablets are convex cylindrical in shape. In other embodiments, the mini-tablets have any shape, including oval, spherical, cylindrical, elliptical, cubical, square, or rectangular with flat, shallow, standard, deep convex or double deep convex faces or combinations thereof.

In one embodiment, the pharmaceutical composition comprises about 35 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 13.5 wt % of mannitol by weight of the composition; about 41 wt % of lactose by weight of the composition; about 2 wt % of sucralose by weight of the composition; about 6 wt % of croscarmellose sodium by weight of the composition; about 1 wt % of colloidal silicon dioxide by weight of the composition; and about 1.5 wt % of magnesium stearate by weight of the composition. In one embodiment, the pharmaceutical composition comprises one or more tablets having about 12.5 mg of Compound 1 per tablet. In a further embodiment, the tablet is about 4 mm in diameter and about 3.7 mm in thickness. In a further embodiment, the tablet weighs about 44.7 mg. In yet a further embodiment, the mini-tablets are convex cylindrical in shape. In other embodiments, the mini-tablets have any shape, including oval, spherical, cylindrical, elliptical, cubical, square, or rectangular with flat, shallow, standard, deep convex or double deep convex faces or combinations thereof.

In one embodiment, the pharmaceutical composition comprises about 35 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 13.5 wt % of mannitol by weight of the composition; about 41 wt % of lactose by weight of the composition; about 2 wt % of sucralose by weight of the composition; about 6 wt % of croscarmellose sodium by weight of the composition; about 1 wt % of colloidal silicon dioxide by weight of the composition; and about 1.5 wt % of magnesium stearate by weight of the composition. In one embodiment, the pharmaceutical composition comprises a plurality of mini-tablets having about 50 mg of Compound 1 per 26 mini-tablets and 75 mg Compound 1 per 39 mini-tablets. In a further embodiment, the mini-tablets are each about 2 mm in diameter and about 2 mm in thickness. In a further embodiment, each mini-tablet weighs about 7 mg. In yet a further embodiment, the mini-tablets are cylindrical in shape. In one embodiment, the pharmaceutical composition includes a capsule or a packet containing the plurality of mini-tablets. In one further embodiment, the capsule or packet contains about 26 mini-tablets and about 50 mg of Compound 1. In another further embodiment, the capsule or packet contains about 39 mini-tablets and about 75 mg of Compound 1.

It is also noted that unit dose forms comprising compressed pharmaceutical compositions comprising one or more mini-tablets of the present invention can be processed into a tablet form, a capsule form, or filled into sachets, pouches, packets, bottles and the like for oral administration or can be reconstituted in an aqueous solvent (e.g., DI water or saline) for oral or IV administration. Also for oral administration, the unit dose forms can be administered in soft foods, such as apple sauce, plain yogurt, ice cream, baby food. Baby food can include, but is not limited to, carrots or carrot puree. Also for oral administration, the unit dose forms can be administered in liquids, such as milk (including breast milk), baby formula or infant formula. Food may also include strawberry preserves, rice pudding or chocolate pudding. Liquids may also include water. In one embodiment, the unit dose form is sprinkled into soft food and administered. In another embodiment, the unit dose form is sprinkled into soft food, mixed, and administered. In one embodiment, the unit dose form is sprinkled into liquid, such as but not limited to, baby formula, infant formula, milk or breast milk, and administered. In another embodiment, the unit dose form is sprinkled into liquid, such as but not limited to, baby formula, infant formula, milk or breast milk, mixed, and administered. Preferably the mini-tablet compressed pharmaceutical compositions described herein are formulated and encapsulated in capsules, bottles or sachets. In other embodiments, the pharmaceutical composition comprising a mini-tablet or plurality of mini-tablets can be in pouches, packets, sachets, bottles or blister packs. In some instances, for smaller sized mini-tablets or granules, the contents of packets, pouches, capsules, bottles or sachets may be administered directly to the mouth followed by breast milk or formula. Methods of administration of the present invention can optionally also include, for smaller sized mini-tablets or granules, administering the contents of packets, pouches, capsules, bottles or sachets directly to the mouth followed by a liquid or beverage. In some embodiments, any methods of administration of the present invention can optionally include orally administering with fat-containing food such as a standard CF high-calorie, high-fat meal or snack. In one aspect of the present invention, all methods of administration of the present invention can optionally include orally administering currently with, before or after fat-containing food such as a standard CF high-calorie, high-fat meal or snack.

Another aspect of the present invention provides a compressed pharmaceutical composition consisting of 20-50 mini-tablets, each mini-tablet includes a CF potentiator API (e.g., a solid dispersion of N-[2,4-bis(1,1-dimethylethyl)-5-hydroxyphenyl]-1,4-dihydro-4-oxoquinoline-3-carboxamide) and other excipients (e.g., one or more fillers, a disintegrant, a sweetener, a wetting agent, a glidant, a lubricant, or any combination thereof), each of which is described above and in the Examples below, wherein the mini-tablet or plurality of mini-tablets has a dissolution of at least about 50% (e.g., at least about 60%, at least about 70%, or at least about 80%) in about 30 minutes. In one example, the pharmaceutical composition consists of a capsule or a packet containing about 29 mini-tablets that includes a CF potentiator API (e.g., a solid dispersion of Compound 1) and other excipients (e.g., one or more fillers, a sweetener, a disintegrant, a wetting agent, a glidant; and a lubricant, or any combination thereof), each of which is described above and in the Examples below, wherein in some embodiments, the mini-tablet has a dissolution of from about 50% to about 100% (e.g., from about 55% to about 95%, from about 60% to about 90% or from about 70% to about 80%) in about 30 minutes. In another example, the pharmaceutical composition consists of a capsule or a packet comprising about 29 mini-tablets, each mini-tablets comprising a solid dispersion comprising substantially amorphous or amorphous Compound 1 and HPMCAS; and, one or more fillers, a sweetener, a disintegrant, optionally a wetting agent, a glidant; and a lubricant, wherein the contents of the capsule or packet has a dissolution of at least about 50% (e.g., at least about 60%, at least about 70%, at least about 80%, at least about 90%) in about 30 minutes. In still another example, the pharmaceutical composition consists of a capsule or a packet comprising about 29 mini-tablets, each mini-tablet comprising a solid dispersion comprising substantially amorphous or amorphous Compound 1 and HPMCAS; and, one or more fillers, a sweetener, a disintegrant, optionally a wetting agent, a glidant; and a lubricant, wherein the mini-tablets contained in the capsule or packet, collectively, have a dissolution of from about 50% to about 100% (e.g., from about 55% to about 95%, from about 60% to about 90% or about 70% to about 80%) in about 30 minutes.

In one embodiment, a unit-dose form comprising a mini-tablet or plurality of mini-tablets, the mini-tablet or plurality of mini-tablets comprises a solid dispersion comprising at least about 5 mg (e.g., at least about 10 mg, at least about 15 mg, at least about 20 mg, at least about 25 mg, at least about 30 mg, at least about 40 mg, or at least about 50 mg) of substantially amorphous or amorphous Compound 1; HPMCAS and SLS. In another embodiment, a capsule or a packet comprising a mini-tablet or plurality of mini-tablets, the mini-tablet or plurality of mini-tablets comprising a solid dispersion comprising at least about 10 mg (e.g., at least about 15 mg, at least 20 mg, at least 25 mg, at least about 30 mg, at least about 40 mg, at least about 50 mg, at least about 75 mg, at least about 100 mg, or at least 150 mg) of substantially amorphous or amorphous Compound 1; and HPMCAS and SLS.

Dissolution can be measured with a standard USP Type II apparatus containing a dissolution media of 0.5 or 0.7% sodium lauryl sulfate dissolved in 900 mL of 50 mM sodium phosphate buffer at a pH of 6.8 at a temperature of about 37° C. The dissolution of mini-tablets is determined by recording the dissolution of a plurality of mini-tablets containing, in the aggregate, 75 mg (using 0.5% sodium lauryl sulfate) or 150 mg (using 0.7% sodium lauryl sulfate) of Compound 1 in the dissolution media. Individual mini-tablets can exhibit dissolution that is lower, equivalent to or higher than the dissolution of the plurality, with the mean dissolution of each individual mini-tablet being similar to the mean dissolution of the plurality.

Another aspect of the present invention provides a pharmaceutical composition consisting of a mini-tablet that comprises a CF potentiator API (e.g., a solid dispersion of Compound 1) and other excipients (e.g., one or more fillers, a sweetener, a disintegrant, a wetting agent, a glidant; and a lubricant, or any combination thereof), each of which is described above and in the Examples below, wherein the mini-tablet has an average tensile strength ranging from, about 0.5 MPa to about 4 MPa, for example, at least about 0.5 MPa, at least about 1 MPa, or at least about 2 MPa. In one example, the pharmaceutical composition consists of a mini-tablet that comprises a CF potentiator API (e.g., a solid dispersion of Compound 1) and other excipients (e.g., one or more fillers, a sweetener, a disintegrant, a wetting agent, a glidant; and a lubricant, or any combination thereof), each of which is described above and in the Examples below, wherein the mini-tablet has an average tensile strength ranging from, about 0.5 MPa to about 4 MPa, for example, at least about 0.5 MPa, at least about 1 MPa, or at least about 2 MPa.

III. METHOD OF PRODUCING A PHARMACEUTICAL COMPOSITION

Another aspect of the present invention provides a method of producing a pharmaceutical composition comprising providing an admixture of a solid dispersion of substantially amorphous or amorphous N-[2,4-Bis(1,1-dimethylethyl)-5-hydroxyphenyl]-1,4-dihydro-4-oxoquinoline-3-carboxamide, one or more fillers, a sweetener, a disintegrant, optionally a wetting agent, a glidant; and a lubricant, and compressing the admixture into a mini-tablet. In some embodiments, the mini-tablet has a dissolution of at least about 50% in about 30 minutes. In some further embodiments, a mini-tablet or plurality of mini-tablets (e.g., at least 2, at least 4, at least 10, at least 15, at least 20, at least 25) collectively have a dissolution of at least about 50% in about 30 minutes.

Each of the ingredients of this admixture is described above and in the Examples below. Furthermore, the admixture can comprise optional additives such as one or more colorants, one or more flavors, and/or one or more fragrances as described above and in the Examples below. The relative concentrations (e.g., wt %) of each of these ingredients (and any optional additives) in the admixture is also presented above and in the Examples below. The ingredients constituting the admixture can be provided sequentially or in any combination of additions; and, the ingredients or combination of ingredients can be provided in any order. In one embodiment the lubricant or portions of the lubricant is the last component added to the admixture prior to compression.

In another embodiment, the method of producing a pharmaceutical composition comprises providing an admixture of a solid dispersion of substantially amorphous Compound 1, one or more fillers, a sweetener, a disintegrant, optionally a wetting agent, a glidant; and a lubricant; mixing the admixture until the admixture is substantially homogenous, and compressing the admixture into a solid-dose form as described above or in the Examples below. Or, the method of producing a pharmaceutical composition comprises providing an admixture of a solid dispersion of amorphous Compound 1, one or more fillers, a sweetener, a disintegrant, optionally a wetting agent, a glidant; and a lubricant; mixing the admixture until the admixture is substantially homogenous, and compressing the admixture into a mini-tablet as described above or in the Examples below. For example, the admixture is mixed by stirring, blending, shaking, or the like using hand mixing, a mixer, a blender, any combination thereof; or the like. When ingredients or combinations of ingredients are added sequentially, mixing can occur between successive additions, continuously throughout the ingredient addition, after the addition of all of the ingredients or combinations of ingredients, or any combination thereof. In addition, prior to or subsequent to each mixing step, the blended ingredients can be further sieved by passing the ingredients or blend through an appropriately sized mesh screen or delumped using a mill with an appropriate screen size. The admixture is mixed until it has a substantially homogenous composition. The admixture/powder blend can be further filled in an appropriate dosage form or package, i.e. it can be encapsulated or filled into pouches, packets, sachets, bottles, etc. for administration. The powder blend can also be further processed into granules or pellets or mini-tablets and the like. The admixture or part of the admixture (some of the formulation components) can be granulated if necessary, using appropriate granulation methods such as dry granulation (slugging or roller compaction), high shear wet granulation, twin screw granulation, fluid bed granulation, extrusion-spheronization, melt extrusion, spray drying, etc. The granules can be blended with additional ingredients if necessary and compressed into tablets, mini-tablets and the like, or filled in capsules, packets, sachets, etc. The granules, pellets, mini-tablets and the like can also be filled in an appropriate unit dosage form or package for administration, i.e. can be encapsulated or filled in pouches, packets, sachets, bottles, etc., or they can be further processed with additional ingredients if needed and compressed into tablets, troches and the like. It has been found that by adding a portion of lubricant during the blending steps of the solid dispersion, glidant, sweetener and wetting agent and prior to the addition of the filler and disintegrant, resulted in an improvement on solid dispersion loss on surfaces during processing, such as blending, delumping and compression of the pharmaceutical composition in rotary tabletting machines prepared for mini-tablet production. In one embodiment, a method for producing the pharmaceutical composition of the present invention is schematically represented in FIG. 1. In other embodiments, the mini-tablets of the present invention can be made according to the following steps:

a) mixing a solid dispersion of substantially amorphous Compound 1 or amorphous Compound 1 and a polymer, the polymer comprising HPMCAS, PVP/VA or combinations thereof with a glidant, a sweetener and optionally a wetting agent to form a first mixture;

b) screening the first mixture;

c) blending the screened first mixture with 20% of a screened lubricant to form a first blended mixture;

d) blending screened filler and screened disintegrant with the first blended mixture forming a second blended mixture;

e) de-lumping the second blended mixture forming a homogeneous mixture;

f) mixing 80% of the screened lubricant with the homogeneous mixture forming a compression mixture; and g) compressing the compression mixture to form mini-tablets. In other embodiments, the mini-tablets of the present invention can be made according to the following steps:

i) mixing a solid dispersion of substantially amorphous Compound 1 or amorphous Compound 1 and a polymer, the polymer comprising HPMCAS, PVP/VA or combinations thereof with a glidant, and a sweetener to form a first mixture;

ii) screening the first mixture;

iii) blending the screened first mixture;

iv) blending screened filler and screened disintegrant with the first blended mixture forming a second blended mixture;

v) de-lumping the second blended mixture forming a homogeneous mixture;

vi) mixing the screened lubricant with the homogeneous mixture forming a compression mixture; and vii) compressing the compression mixture to form mini-tablets.

In one embodiment, the admixture comprises a solid dispersion of substantially amorphous or amorphous Compound 1, one or more fillers, a sweetener, a disintegrant, optionally a wetting agent, a glidant; and a lubricant, wherein each of these ingredients is provided in a powder form (e.g., provided as particles having a mean diameter, measured by light scattering, of 250 µm or less (e.g., 150 µm or less, 100 µm or less, 50 µm or less, 45 µm or less, 40 µm or less, or 35 µm or less)). For instance, the admixture comprises a solid dispersion of amorphous Compound 1, one or more fillers, a sweetener, a disintegrant, optionally a wetting agent, a glidant; and a lubricant, wherein each of these ingredients is provided in a powder form (e.g., provided as particles having a mean diameter, measured by light scattering, of 250 µm or less (e.g., 150 µm or less, 100 µm or less, 50 µm or less, 45 µm or less, 40 µm or less, or 35 µm or less)).

In another embodiment, the admixture comprises a solid dispersion of substantially amorphous Compound 1, one or more fillers, a sweetener, a disintegrant, optionally a wetting agent, a glidant; and a lubricant, wherein each of these ingredients is substantially free of water. Each of the ingredients comprises less than 6 wt % (e.g., less than 2 wt %, less than 1 wt %, less than 0.75 wt %, less than 0.5 wt %, or less than 0.25 wt %) of water by weight of the ingredient. For instance, the admixture comprises a solid dispersion of amorphous Compound 1, one or more fillers, a sweetener, a disintegrant, optionally a wetting agent, a glidant; and a lubricant, wherein each of these ingredients is substantially free of water.

In another embodiment, compressing the admixture into a mini-tablet is accomplished by filling a form (e.g., a compression die) with the compression admixture and applying pressure to the compression admixture. This can be accomplished using dies and appropriately sized punches on a press or other similar apparatus, such as a rotary tabletting machine. It is also noted that the application of pressure to the compression admixture in the form can be repeated using the same pressure during each compression or using different pressures during the compressions. In another example, the compression admixture can be compressed using sufficient pressure to form a solid dose form, for example, a granule, a pellet, a shaped particle or a mini-tablet, the solid dose form. In some embodiments, a rotary tabletting press commercially available from Kikusui America (Model Virgo), having 19 stations, operable to produce 2 mm cylindrical mini-tablets (7 mg per mini-tablet) can be used for purposed of the present methods. In other embodiments, a rotary tablet press commercially available from IMA KILIAN GMBH & CO., Koln, Germany can be used for the purposes of the present invention. For instance, the compression admixture is compressed using appropriate tooling (dies and punches on a compression machine) to produce 2 mm cylindrical mini-tablet having an average tensile strength of between about 0.5 MPa and about 4 MPa.

IV. ADMINISTRATION OF A PHARMACEUTICAL FORMULATION

In another aspect, the invention also provides a method of treating or lessening the severity of a disease in a patient comprising administering to said patient one of the pharmaceutical compositions as defined herein, and said disease is selected from cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), liver disease, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulinemia, Diabetes mellitus, Laron dwarfism, myeloperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurohypophyseal DI, nephrogenic DI, Charcot-Marie Tooth syndrome, Pelizaeus-Merzbacher disease, neurodegenerative diseases such as Alzheimer's disease, Parkinson's disease, amyotrophic lateral sclerosis, progressive supranuclear palsy, Pick's disease, several polyglutamine neurological disorders such as Huntington's, spinocerebellar ataxia type I, spinal and bulbar muscular atrophy, dentatorubral pallidoluysian atrophy, and myotonic dystrophy, as well as spongiform encephalopathies, such as hereditary Creutzfeldt-Jakob disease (due to prion protein processing defect), Fabry disease, Gerstmann-Strä ussler-Scheinker syndrome, COPD, dry-eye disease, or Sjogren's disease, Osteoporosis, Osteopenia, bone healing and bone growth (including bone repair, bone regeneration, reducing bone resorption and increasing bone deposition), Gorham's Syndrome, chloride channelopathies such as myotonia congenita (Thomson and Becker forms), Bartter's syndrome type III, Dent's disease, epilepsy, hyperekplexia, lysosomal storage disease, Angelman syndrome, and Primary Ciliary Dyskinesia (PCD), a term for inherited disorders of the structure and/or function of cilia, including PCD with situs inversus (also known as Kartagener syndrome), PCD without situs inversus and ciliary aplasia.

Compound 1 (N-[2,4-Bis(1,1-dimethylethyl)-5-hydroxyphenyl]-1,4-dihydro-4-oxoquinoline-3-carboxamide) has been granted a Breakthrough Therapy Designation from the Food and Drug Administration (FDA) for treatment of cystic fibrosis, one of only two such grants at the time of filing of this application. This demonstrates a significant unmet need for the effective treatment of the cause of cystic fibrosis over symptomatic treatments.

In some embodiments, the method includes treating or lessening the severity of cystic fibrosis in a patient, for example, a pediatric patient, the method comprising administering to the patient one of the pharmaceutical compositions as defined herein. While the pharmaceutical compositions of the present invention are not limited for the treatment of pediatric patients, the formulation provided herein are suitable for patients who have difficulty in swallowing their pharmaceutical agents in tablet form or are advised to have their medications mixed with their foods or liquids. Some of these patients typically transfer their pharmaceutical compositions from the unit dose form into a food or liquid medium for ingestion.

In certain embodiments, the patient possesses mutant forms of human CFTR. In other embodiments, the patient possesses one or more of the following mutations ΔF508, R117H, and G551D of human CFTR. In some embodiments, the patient possesses a CFTR gating mutation. In some embodiments, the patient possesses a CFTR gating mutation, including but not limited to, G551D, G178R, G551S, G970R, G1244E, S1255P, G1349D, S549N, S549R, and S1251N. In some embodiments, the patient possesses one or more of the following gating mutations of human CFTR: G551D, G178R, G551S, G970R, G1244E, S1255P, G1349D, S549N, S549R, and S1251N. In one embodiment, the method includes treating or lessening the severity of cystic fibrosis in a patient possessing the ΔF508 mutation of human CFTR comprising administering to said patient one of the pharmaceutical compositions as defined herein. In one embodiment, the method includes treating or lessening the severity of cystic fibrosis in a patient possessing the G551D mutation of human CFTR comprising administering to said patient one of the pharmaceutical compositions as defined herein. In one embodiment, the method includes treating or lessening the severity of cystic fibrosis in a patient possessing the R117H mutation of human CFTR comprising administering to said patient one of the pharmaceutical compositions as defined herein. In one embodiment, the method includes treating or lessening the severity of cystic fibrosis in a patient possessing the ΔF508 mutation of human CFTR in at least one allele comprising administering to said patient one of the compositions as defined herein. In one embodiment, the method includes treating or lessening the severity of cystic fibrosis in a patient possessing the ΔF508 mutation of human CFTR in both alleles comprising administering to said patient one of the compositions as defined herein. In one embodiment, the method includes treating or lessening the severity of cystic fibrosis in a patient possessing the G551D mutation of human CFTR in at least one allele comprising administering to said patient one of the compositions as defined herein. In one embodiment, the method includes treating or lessening the severity of cystic fibrosis in a patient possessing the G551D mutation of human CFTR in both alleles comprising administering to the patient one of the compositions as defined herein. In one embodiment, the method includes treating or lessening the severity of cystic fibrosis in a patient possessing the R117H mutation of human CFTR in at least one allele comprising administering to said patient one of the compositions as defined herein. In one embodiment, the method includes treating or lessening the severity of cystic fibrosis in a patient possessing the R117H mutation of human CFTR in both alleles comprising administering to the patient one of the compositions as defined herein.

In one embodiment, the method includes treating or lessening the severity of cystic fibrosis in a patient possessing a CFTR gating mutation of human comprising administering to said patient one of the pharmaceutical compositions as defined herein. In one embodiment, the method includes treating or lessening the severity of cystic fibrosis in a patient possessing a CFTR gating mutation in at least one allele comprising administering to said patient one of the compositions as defined herein. In one embodiment, the method includes treating or lessening the severity of cystic fibrosis in a patient possessing a CFTR gating mutation in both alleles comprising administering to said patient one of the compositions as defined herein.

In one embodiment, the method includes treating or lessening the severity of cystic fibrosis in a patient possessing the G178R mutation of human CFTR comprising administering to said patient one of the pharmaceutical compositions as defined herein. In another embodiment, the method includes treating or lessening the severity of cystic fibrosis in a patient possessing the G178R mutation of human CFTR in at least one allele comprising administering to said patient one of the compositions as defined herein. In another embodiment, the method includes treating or lessening the severity of cystic fibrosis in a patient possessing the G178R mutation of human CFTR in both alleles comprising administering to said patient one of the compositions as defined herein.

In one embodiment, the method includes treating or lessening the severity of cystic fibrosis in a patient possessing the G551S mutation of human CFTR comprising administering to said patient one of the pharmaceutical compositions as defined herein. In another embodiment, the method includes treating or lessening the severity of cystic fibrosis in a patient possessing the G551S mutation of human CFTR in at least one allele comprising administering to said patient one of the compositions as defined herein. In another embodiment, the method includes treating or lessening the severity of cystic fibrosis in a patient possessing the G551S mutation of human CFTR in both alleles comprising administering to said patient one of the compositions as defined herein.

In one embodiment, the method includes treating or lessening the severity of cystic fibrosis in a patient possessing the G970R mutation of human CFTR comprising administering to said patient one of the pharmaceutical compositions as defined herein. In another embodiment, the method includes treating or lessening the severity of cystic fibrosis in a patient possessing the G970R mutation of human CFTR in at least one allele comprising administering to said patient one of the compositions as defined herein. In another embodiment, the method includes treating or lessening the severity of cystic fibrosis in a patient possessing the G970R mutation of human CFTR in both alleles comprising administering to said patient one of the compositions as defined herein.

In one embodiment, the method includes treating or lessening the severity of cystic fibrosis in a patient possessing the G1244E mutation of human CFTR comprising administering to said patient one of the pharmaceutical compositions as defined herein. In another embodiment, the method includes treating or lessening the severity of cystic fibrosis in a patient possessing the G1244E mutation of human CFTR in at least one allele comprising administering to said patient one of the compositions as defined herein. In another embodiment, the method includes treating or lessening the severity of cystic fibrosis in a patient possessing the G1244E mutation of human CFTR in both alleles comprising administering to said patient one of the compositions as defined herein.

In one embodiment, the method includes treating or lessening the severity of cystic fibrosis in a patient possessing the S1255P mutation of human CFTR comprising administering to said patient one of the pharmaceutical compositions as defined herein. In another embodiment, the method includes treating or lessening the severity of cystic fibrosis in a patient possessing the S1255P mutation of human CFTR in at least one allele comprising administering to said patient one of the compositions as defined herein. In another embodiment, the method includes treating or lessening the severity of cystic fibrosis in a patient possessing the S1255P mutation of human CFTR in both alleles comprising administering to said patient one of the compositions as defined herein.

In one embodiment, the method includes treating or lessening the severity of cystic fibrosis in a patient possessing the G1349D mutation of human CFTR comprising administering to said patient one of the pharmaceutical compositions as defined herein. In another embodiment, the method includes treating or lessening the severity of cystic fibrosis in a patient possessing the G1349D mutation of human CFTR in at least one allele comprising administering to said patient one of the compositions as defined herein. In another embodiment, the method includes treating or lessening the severity of cystic fibrosis in a patient possessing the G1349D mutation of human CFTR in both alleles comprising administering to said patient one of the compositions as defined herein.

In one embodiment, the method includes treating or lessening the severity of cystic fibrosis in a patient possessing the S549N mutation of human CFTR comprising administering to said patient one of the pharmaceutical compositions as defined herein. In another embodiment, the method includes treating or lessening the severity of cystic fibrosis in a patient possessing the S549N mutation of human CFTR in at least one allele comprising administering to said patient one of the compositions as defined herein. In another embodiment, the method includes treating or lessening the severity of cystic fibrosis in a patient possessing the S549N mutation of human CFTR in both alleles comprising administering to said patient one of the compositions as defined herein.

In one embodiment, the method includes treating or lessening the severity of cystic fibrosis in a patient possessing the S549R mutation of human CFTR comprising administering to said patient one of the pharmaceutical compositions as defined herein. In another embodiment, the method includes treating or lessening the severity of cystic fibrosis in a patient possessing the S549R mutation of human CFTR in at least one allele comprising administering to said patient one of the compositions as defined herein. In another embodiment, the method includes treating or lessening the severity of cystic fibrosis in a patient possessing the S549R mutation of human CFTR in both alleles comprising administering to said patient one of the compositions as defined herein.

In one embodiment, the method includes treating or lessening the severity of cystic fibrosis in a patient possessing the S1251N mutation of human CFTR comprising administering to said patient one of the pharmaceutical compositions as defined herein. In another embodiment, the method includes treating or lessening the severity of cystic fibrosis in a patient possessing the S1251N mutation of human CFTR in at least one allele comprising administering to said patient one of the compositions as defined herein. In another embodiment, the method includes treating or lessening the severity of cystic fibrosis in a patient possessing the S1251N mutation of human CFTR in both alleles comprising administering to said patient one of the compositions as defined herein.

In one embodiment, the method includes treating or lessening the severity of cystic fibrosis in a patient possessing CFTR with residual function or a residual function phenotype comprising administering to said patient one of the pharmaceutical compositions as defined herein.

In some embodiments, the methods of administration of the present invention includes orally administering a liquid or beverage including, but not limited to, milk (including breast milk), baby formula or infant formula, or a soft food including, but not limited to, apple sauce, plain yogurt, ice cream, baby food (including carrots and carrot puree). In some embodiments, the methods of administration of the present invention include orally administering a liquid or beverage including, but not limited to, milk (including breast milk), baby formula or infant formula. In some embodiments, the methods of administration of the present invention includes orally administering soft food including, but not limited to, apple sauce, plain yogurt, ice cream, baby food (including carrots and carrot puree). In other embodiments, the methods of administration of the present invention include orally administering a liquid such as water. In one embodiment, the unit dose form is sprinkled into a beverage or liquid, including, but not limited to, baby formula, infant formula, milk or breast milk, and administered. In another embodiment, the unit dose form is sprinkled into a beverage or liquid, including, but not limited to, baby formula, infant formula, milk or breast milk, mixed, and administered. In one embodiment, the unit dose form is sprinkled into a soft food including, but not limited to, apple sauce, plain yogurt, ice cream, baby food (including carrots and carrot puree) and administered. In another embodiment, the unit dose form is sprinkled into a soft food including, but not limited to, apple sauce, plain yogurt, ice cream, baby food (including carrots and carrot puree), mixed, and administered. Methods of administration of the present invention can optionally also include, for smaller sized mini-tablets or granules, administering the contents of packets, pouches, capsules, bottles or sachets directly to the mouth followed by breast milk or formula. Methods of administration of the present invention can optionally also include, for smaller sized mini-tablets or granules, administering the contents of packets, pouches, capsules, bottles or sachets directly to the mouth followed by a liquid or beverage. It is noted that any of the methods of administration of the present invention can optionally include orally administering with fat-containing food such as a standard CF high-calorie, high-fat meal or snack. In some embodiments, any of the methods of administration of the present invention can optionally include orally administering concurrently with, before or after fat-containing food such as a standard CF high-calorie, high-fat meal or snack.

It is also noted that the methods of administration of the present invention include administering the compositions of the present invention to a patient according to age or weight. In some embodiments, the method of administering a pharmaceutical composition includes orally administering to a patient every 12 hours at least one capsule or packet containing a mini-tablet or plurality of mini-tablets, wherein each mini-tablet comprising a pharmaceutical composition as described herein, wherein the patient is younger than six years of age, including, but not limited to, 2 through 5 years of age, younger than 2, zero (i.e., birth) through 2 years of age, 1 through 2 years of age, 9 months through 2 years of age, 6 months through 2 years of age, 3 months through 2 years of age, and 2 months through 2 years of age). In some embodiments, birth means birth after full term gestation. In still other embodiments, the method of administering a pharmaceutical composition includes orally administering to a patient every 12 hours at least one capsule or packet containing a mini-tablet or plurality of mini-tablets, wherein each mini-tablet comprising a pharmaceutical composition as described herein, wherein the patient includes, but not limited to, those weighing greater than or equal to about 14 kilograms. In other embodiments, the method of administering a pharmaceutical composition includes orally administering to a patient every 12 hours at least one capsule or packet containing a mini-tablet or plurality of mini-tablets, wherein each mini-tablet comprising a pharmaceutical composition as described herein, wherein the patient includes, but not limited to, those weighing less than 14 kilograms. In still other embodiments, the method of administering a pharmaceutical composition includes orally administering to a patient every 12 hours at least one capsule or packet containing a mini-tablet or plurality of mini-tablets, wherein each mini-tablet comprising a pharmaceutical composition as described herein, wherein the patient includes those weighing about 7.5 kilograms to less than 14 kilograms. In other embodiments, the method of administering a pharmaceutical composition includes orally administering to a patient every 12 hours at least one capsule or packet containing a mini-tablet or plurality of mini-tablets, wherein each mini-tablet comprising a pharmaceutical composition as described herein, wherein the patient includes to those weighing about 5 kilograms to less than 7.5 kilograms. In other embodiments, the method of administering a pharmaceutical composition includes orally administering to a patient every 12 hours at least one capsule or packet containing a mini-tablet or plurality of mini-tablets, wherein each mini-tablet comprising a pharmaceutical composition as described herein, wherein the patient includes those weighing about 2.5 kilograms to less than 5 kilograms. In other embodiments, the method of administering a pharmaceutical composition includes orally administering to a patient every 12 hours at least one capsule or packet containing a mini-tablet or plurality of mini-tablets, wherein each mini-tablet comprising a pharmaceutical composition as described herein, wherein the patient includes those weighing less than 7.5 kilograms. In other embodiments, the method of administering a pharmaceutical composition includes orally administering to a patient every 12 hours at least one capsule or packet containing a mini-tablet or plurality of mini-tablets, wherein each mini-tablet comprising a pharmaceutical composition as described herein, wherein the patient includes those weighing about 5 kilograms to more than 5 kilograms. In other embodiments, the method of administering a pharmaceutical composition includes orally administering to a patient every 12 hours at least one capsule or packet containing a mini-tablet or plurality of mini-tablets, wherein each mini-tablet comprising a pharmaceutical composition as described herein, wherein the patient includes those weighing less than 5 kilograms. In other embodiments, the method of administering a pharmaceutical composition includes orally administering to a patient every 12 hours at least one capsule or packet containing a mini-tablet or plurality of mini-tablets, wherein each mini-tablet comprising a pharmaceutical composition as described herein, wherein the patient includes those weighing about 2.5 kilograms to more than 2.5 kilograms.

It is also noted that the methods of administration of the present invention include administering the compositions of the present invention to a patient according to age or weight. In some embodiments, the method of administering a pharmaceutical composition includes orally administering to a patient once a day at least one capsule or packet containing a mini-tablet or plurality of mini-tablets, wherein each mini-tablet comprising a pharmaceutical composition as described herein, wherein the patient is younger than six years of age, including, but not limited to, 2 through 5 years of age, younger than 2, zero (i.e., birth) through 2 years of age, 1 through 2 years of age, 9 months through 2 years of age, 6 months through 2 years of age, 3 months through 2 years of age, and 2 months through 2 years of age). In some embodiments, birth means birth after full term gestation. In still other embodiments, the method of administering a pharmaceutical composition includes orally administering to a patient once a day at least one capsule or packet containing a mini-tablet or plurality of mini-tablets, wherein each mini-tablet comprising a pharmaceutical composition as described herein, wherein the patient includes, but not limited to, those weighing greater than or equal to about 14 kilograms. In other embodiments, the method of administering a pharmaceutical composition includes orally administering to a patient once a day at least one capsule or packet containing a mini-tablet or plurality of mini-tablets, wherein each mini-tablet comprising a pharmaceutical composition as described herein, wherein the patient includes, but not limited to, those weighing less than 14 kilograms. In still other embodiments, the method of administering a pharmaceutical composition includes orally administering to a patient once a day at least one capsule or packet containing a mini-tablet or plurality of mini-tablets, wherein each mini-tablet comprising a pharmaceutical composition as described herein, wherein the patient includes those weighing about 7.5 kilograms to less than 14 kilograms. In other embodiments, the method of administering a pharmaceutical composition includes orally administering to a patient once a day at least one capsule or packet containing a mini-tablet or plurality of mini-tablets, wherein each mini-tablet comprising a pharmaceutical composition as described herein, wherein the patient includes to those weighing about 5 kilograms to less than 7.5 kilograms. In other embodiments, the method of administering a pharmaceutical composition includes orally administering to a patient once a day at least one capsule or packet containing a mini-tablet or plurality of mini-tablets, wherein each mini-tablet comprising a pharmaceutical composition as described herein, wherein the patient includes those weighing about 2.5 kilograms to less than 5 kilograms. In other embodiments, the method of administering a pharmaceutical composition includes orally administering to a patient once a day at least one capsule or packet containing a mini-tablet or plurality of mini-tablets, wherein each mini-tablet comprising a pharmaceutical composition as described herein, wherein the patient includes those weighing less than 7.5 kilograms. In other embodiments, the method of administering a pharmaceutical composition includes orally administering to a patient once a day at least one capsule or packet containing a mini-tablet or plurality of mini-tablets, wherein each mini-tablet comprising a pharmaceutical composition as described herein, wherein the patient includes those weighing about 5 kilograms to more than 5 kilograms. In other embodiments, the method of administering a pharmaceutical composition includes orally administering to a patient once a day at least one capsule or packet containing a mini-tablet or plurality of mini-tablets, wherein each mini-tablet comprising a pharmaceutical composition as described herein, wherein the patient includes those weighing less than 5 kilograms. In other embodiments, the method of administering a pharmaceutical composition includes orally administering to a patient once a day at least one capsule or packet containing a mini-tablet or plurality of mini-tablets, wherein each mini-tablet comprising a pharmaceutical composition as described herein, wherein the patient includes those weighing about 2.5 kilograms to more than 2.5 kilograms.

It is also noted that the methods of administration of the present invention include administering the compositions of the present invention to a patient according to age or weight. In some embodiments, the method of administering a pharmaceutical composition includes orally administering to a patient twice a day at least one capsule or packet containing a mini-tablet or plurality of mini-tablets, wherein each mini-tablet comprising a pharmaceutical composition as described herein, wherein the patient is younger than six years of age, including, but not limited to, 2 through 5 years of age, younger than 2, zero (i.e., birth) through 2 years of age, 1 through 2 years of age, 9 months through 2 years of age, 6 months through 2 years of age, 3 months through 2 years of age, and 2 months through 2 years of age). In some embodiments, birth means birth after full term gestation. In still other embodiments, the method of administering a pharmaceutical composition includes orally administering to a patient twice a day at least one capsule or packet containing a mini-tablet or plurality of mini-tablets, wherein each mini-tablet comprising a pharmaceutical composition as described herein, wherein the patient includes, but not limited to, those weighing greater than or equal to about 14 kilograms. In other embodiments, the method of administering a pharmaceutical composition includes orally administering to a patient twice a day at least one capsule or packet containing a mini-tablet or plurality of mini-tablets, wherein each mini-tablet comprising a pharmaceutical composition as described herein, wherein the patient includes, but not limited to, those weighing less than 14 kilograms. In still other embodiments, the method of administering a pharmaceutical composition includes orally administering to a patient twice a day at least one capsule or packet containing a mini-tablet or plurality of mini-tablets, wherein each mini-tablet comprising a pharmaceutical composition as described herein, wherein the patient includes those weighing about 7.5 kilograms to less than 14 kilograms. In other embodiments, the method of administering a pharmaceutical composition includes orally administering to a patient twice a day at least one capsule or packet containing a mini-tablet or plurality of mini-tablets, wherein each mini-tablet comprising a pharmaceutical composition as described herein, wherein the patient includes to those weighing about 5 kilograms to less than 7.5 kilograms. In other embodiments, the method of administering a pharmaceutical composition includes orally administering to a patient twice a day at least one capsule or packet containing a mini-tablet or plurality of mini-tablets, wherein each mini-tablet comprising a pharmaceutical composition as described herein, wherein the patient includes those weighing about 2.5 kilograms to less than 5 kilograms. In other embodiments, the method of administering a pharmaceutical composition includes orally administering to a patient twice a day at least one capsule or packet containing a mini-tablet or plurality of mini-tablets, wherein each mini-tablet comprising a pharmaceutical composition as described herein, wherein the patient includes those weighing less than 7.5 kilograms. In other embodiments, the method of administering a pharmaceutical composition includes orally administering to a patient twice a day at least one capsule or packet containing a mini-tablet or plurality of mini-tablets, wherein each mini-tablet comprising a pharmaceutical composition as described herein, wherein the patient includes those weighing about 5 kilograms to more than 5 kilograms. In other embodiments, the method of administering a pharmaceutical composition includes orally administering to a patient twice a day at least one capsule or packet containing a mini-tablet or plurality of mini-tablets, wherein each mini-tablet comprising a pharmaceutical composition as described herein, wherein the patient includes those weighing less than 5 kilograms. In other embodiments, the method of administering a pharmaceutical composition includes orally administering to a patient twice a day at least one capsule or packet containing a mini-tablet or plurality of mini-tablets, wherein each mini-tablet comprising a pharmaceutical composition as described herein, wherein the patient includes those weighing about 2.5 kilograms to more than 2.5 kilograms.

In some embodiments, the method includes treating or lessening the severity of cystic fibrosis in a patient comprising administering to said patient a pharmaceutical composition comprising a powder composition or a compressed pharmaceutical composition. In one embodiment, a capsule or a packet containing a powder pharmaceutical composition comprising 1 mg to about 250 mg of Compound 1 is administered to the patient.

In some embodiments, the composition can comprise a powder pharmaceutical composition comprising a solid dispersion and an excipient, for example: one or more fillers, a sweetener, a glidant, a lubricant, and combinations thereof, wherein the solid dispersion comprises from about 30 wt % to about 95 wt % of Compound 1 by weight of the dispersion and a polymer.

In some embodiments, the solid dispersion comprises from about 45 wt % to about 85 wt % including all values and ranges therein (e.g., about 50 wt %, about 72.4 wt %, about 78.8 wt %, or about 80 wt %) of Compound 1 by weight of the dispersion and a polymer.

One exemplary pharmaceutical composition comprises from about 5 wt % to about 70 wt % (e.g., from about 5 wt % to about 65 wt %, from about 5 wt % to about 50 wt %, or from about 30 wt % to about 40 wt %) of a solid dispersion, by weight of the composition, comprising from about 30 wt % to about 90 wt % of substantially amorphous Compound 1, by weight of the dispersion, and from about 70 wt % to about 10 wt % of a polymer, by weight of the dispersion; from about 10 wt % to about 90 wt % of one or more fillers; from about 0.1 wt % to about 5 wt % of a sweetener; from about 5 wt % to about 0.1 wt % of a glidant; and from about 7 wt % to about 0.1 wt % of a lubricant. Or, the powder pharmaceutical composition comprises from about 5 wt % to about 65 wt % (e.g., from about 5 wt % to about 25 wt %, from about 15 wt % to about 40 wt %, or from about 30 wt % to about 50 wt %) of a solid dispersion, by weight of the composition, comprising from about 30 wt % to about 90 wt % of amorphous Compound 1, by weight of the dispersion, and from about 70 wt % to about 20 wt % of a polymer, by weight of the dispersion; from about 10 wt % to about 90 wt % of one or more fillers; from about 0.1 wt % to about 5 wt % of a sweetener; from about 5 wt % to about 0.1 wt % of a glidant; and from about 7 wt % to about 0.1 wt % of a lubricant.

Another exemplary pharmaceutical composition comprises from about 5 wt % to about 60 wt % (e.g., from about 5 wt % to about 55 wt %, from about 15 wt % to about 50 wt %, or from about 30 wt % to about 50 wt %) of a solid dispersion, by weight of the composition, comprising from about 30 wt % to about 90 wt % of substantially amorphous Compound 1, by weight of the dispersion, and from about 70 wt % to about 10 wt % of a polymer, by weight of the dispersion; from about 10 wt % to about 90 wt % of one or more fillers; from about 0.1 wt % to about 5 wt % of a sweetener, from about 7 wt % to about 0.1 wt % of a lubricant; and from about 5 wt % to about 0.1 wt % of a glidant. Or, the pharmaceutical composition comprises from about 5 wt % to about 55 wt % (e.g., from about 5 wt % to about 50 wt %, from about 5 wt % to about 45 wt %, or from about 5 wt % to about 40 wt %) of a solid dispersion, by weight of the composition, comprising from about 30 wt % to about 90 wt % of amorphous Compound 1, by weight of the dispersion, and from about 70 wt % to about 10 wt % of a polymer, by weight of the dispersion; from about 10 wt % to about 90 wt % of one or more fillers; from about 5 wt % to about 0.1 wt % of a sweetener; from about 5 wt % to about 0.1 wt % of a glidant; and from about 7 wt % to about 0.1 wt % of a lubricant.

One powder pharmaceutical composition of the present invention comprises about 46.9 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 49.1 wt % of mannitol by weight of the composition; about 2 wt % of sucralose by weight of the composition; about 1 wt % of colloidal silicon dioxide by weight of the composition; and about 1.0 wt % of magnesium stearate by weight of the composition. Or, the powder pharmaceutical composition of the present invention comprises about 15.6 wt % of a solid dispersion by weight of the composition, wherein the dispersion comprises about 80 wt % of amorphous Compound 1 by weight of the dispersion, about 19.5 wt % of HPMCAS by weight of the dispersion, and about 0.5 wt % SLS by weight of the dispersion; about 80.4 wt % of mannitol by weight of the composition; about 2 wt % of sucralose by weight of the composition; about 1 wt % of colloidal silicon dioxide by weight of the composition; and about 1.0 wt % of magnesium stearate by weight of the composition.

Another powder pharmaceutical composition of the present invention comprises about 24.6 wt % of a solid dispersion by weight of the composition, wherein the dispersion comprises about 50 wt % of substantially amorphous or amorphous Compound 1 by weight of the dispersion, about 49.5 wt % of HPMCAS by weight of the dispersion, and about 0.5 wt % SLS by weight of the dispersion; about 71.4 wt % of mannitol by weight of the composition; about 2 wt % of sucralose by weight of the composition; about 1 wt % of colloidal silicon dioxide by weight of the composition; and about 1.0 wt % of magnesium stearate by weight of the composition. Or, the pharmaceutical composition of the present invention comprises about 34 wt % of a solid dispersion by weight of the composition, wherein the dispersion comprises about 72.4 wt % of substantially amorphous or amorphous Compound 1 by weight of the dispersion, about 27.1 wt % of HPMCAS by weight of the dispersion, and about 0.5 wt % SLS by weight of the dispersion; about 62 wt % of mannitol by weight of the composition; about 2 wt % of sucralose by weight of the composition; about 1 wt % of colloidal silicon dioxide by weight of the composition; and about 1.0 wt % of magnesium stearate by weight of the composition.

Another powder pharmaceutical composition of the present invention comprises about 61.6 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 34.4 wt % of mannitol by weight of the composition; about 2 wt % of sucralose by weight of the composition; about 1 wt % of colloidal silicon dioxide by weight of the composition; about 1.0 wt % of magnesium stearate by weight of the composition. Or, the powder pharmaceutical composition of the present invention comprises about 68.7 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 27.3 wt % of mannitol by weight of the composition; about 2 wt % of sucralose by weight of the composition; about 1 wt % of colloidal silicon dioxide by weight of the composition; about 1.0 wt % of magnesium stearate by weight of the composition. Optionally, the above pharmaceutical compositions can also include about 0.4 wt % of colorant by weight of the composition.

In one aspect, the invention provides a pharmaceutical composition comprising from about 30 wt % to about 50 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; from about 30 wt % to about 60 wt % of a binary filler, wherein the binary filler comprises from about 0 wt % to about 60 wt % of mannitol by weight of the composition and from about 0 wt % to about 60 wt % of lactose by weight of the composition; from about 1.5 wt % to about 2.5 wt % of sucralose by weight of the composition; from about 4 wt % to about 8 wt % of croscarmellose sodium by weight of the composition; from about 0.5 wt % to about 1.5 wt % of colloidal silicon dioxide by weight of the composition; and from about 1 wt % to about 2 wt % of magnesium stearate by weight of the composition.

In one embodiment, the pharmaceutical composition comprises about 35 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 13.5 wt % of mannitol by weight of the composition; about 41 wt % of lactose by weight of the composition; about 2 wt % of sucralose by weight of the composition; about 6 wt % of croscarmellose sodium by weight of the composition; about 1 wt % of colloidal silicon dioxide by weight of the composition; and about 1.5 wt % of magnesium stearate by weight of the composition.

In still further embodiments, the pharmaceutical composition comprises 1-200 mini-tablets, (for example, about 1 to 50 or about 25 to 35 mini-tablets). Each mini-tablet of the pharmaceutical composition comprises from about 20 wt % to about 70 wt % of a solid dispersion by weight of the composition, wherein the dispersion comprises from about 30 wt % to about 85 wt % of substantially amorphous or amorphous Compound 1 by weight of the dispersion, from about 70 wt % to about 14 wt % of HPMCAS by weight of the dispersion, and from about 0.45 wt % to about 0.55 wt % SLS by weight of the dispersion; about 22 wt % to about 70 wt % of mannitol by weight of the composition; about 0.1 wt % to about 5 wt % of sucralose by weight of the composition; about 1 wt % to about 10 wt % of croscarmellose sodium by weight of the composition; from about 0.01 wt % to about 3 wt % of SLS by weight of the composition; from about 0.1 wt % to about 3 wt % of colloidal silicon dioxide by weight of the composition; and from about 0.1 wt % to about 7 wt % of magnesium stearate by weight of the composition. In some aspects, the pharmaceutical composition, for example, a mini-tablet or plurality of mini-tablets are filled into a capsule or a packet, wherein the capsule or packet contains 5 mg of Compound 1. In other embodiments, the pharmaceutical composition contains 10 mg of Compound 1. In other embodiments, the pharmaceutical composition contains 12.5 mg of Compound 1. In other embodiments, the pharmaceutical composition contains 15 mg of Compound 1. In other embodiments, the pharmaceutical composition contains 20 mg of Compound 1. In other embodiments, the pharmaceutical composition contains 25 mg of Compound 1. In other embodiments, the pharmaceutical composition contains 30 mg of Compound 1. In other embodiments, the pharmaceutical composition contains 35 mg of Compound 1. In other embodiments, the pharmaceutical composition contains 37.5 mg of Compound 1. In other embodiments, the pharmaceutical composition contains 40 mg of Compound 1. In other embodiments, the pharmaceutical composition contains 45 mg of Compound 1. In other embodiments, the pharmaceutical composition contains 50 mg of Compound 1. In other embodiments, the pharmaceutical composition contains 62.5 mg of Compound 1. In other embodiments, the pharmaceutical composition contains 75 mg of Compound 1. In other embodiments, the pharmaceutical composition contains 100 mg of Compound 1. In other embodiments, the pharmaceutical composition contains 125 mg of Compound 1. In other embodiments, the pharmaceutical composition contains 150 mg of Compound 1. In other embodiments, the pharmaceutical composition contains 175 mg of Compound 1. In other embodiments, the pharmaceutical composition contains 200 mg of Compound 1. In other embodiments, the pharmaceutical composition contains 225 mg of Compound 1. In other embodiments, the pharmaceutical composition contains 250 mg of Compound 1.

In some embodiments, the pharmaceutical composition comprising a mini-tablet or plurality of mini-tablets is encapsulated into capsules, bottles or sachets. In other embodiments, the pharmaceutical composition comprising a mini-tablet or plurality of mini-tablets can be in pouches, packets, sachets, bottles or blister packs.

In some embodiments, the method includes lessening the severity of cystic fibrosis in a patient comprising administering to said patient one of the compositions as defined herein. In certain embodiments, the patient possesses mutant forms of human CFTR. In other embodiments, the patient possesses one or more of the following mutations ΔF508, R117H, and G551D of human CFTR. In one embodiment, the method includes lessening the severity of cystic fibrosis in a patient possessing the ΔF508 mutation of human CFTR comprising administering to said patient one of the compositions as defined herein. In one embodiment, the method includes lessening the severity of cystic fibrosis in a patient possessing the G551D mutation of human CFTR comprising administering to said patient one of the compositions as defined herein. In one embodiment, the method includes lessening the severity of cystic fibrosis in a patient possessing the R117H mutation of human CFTR comprising administering to said patient one of the compositions as defined herein. In one embodiment, the method includes lessening the severity of cystic fibrosis in a patient possessing the ΔF508 mutation of human CFTR in at least one allele comprising administering to said patient one of the compositions as defined herein. In one embodiment, the method includes lessening the severity of cystic fibrosis in a patient possessing the ΔF508 mutation of human CFTR in both alleles comprising administering to said patient one of the compositions as defined herein. In one embodiment, the method includes lessening the severity of cystic fibrosis in a patient possessing the G551D mutation of human CFTR in at least one allele comprising administering to said patient one of the compositions as defined herein. In one embodiment, the method includes lessening the severity of cystic fibrosis in a patient possessing the G551D mutation of human CFTR in both alleles comprising administering to said patient one of the compositions as defined herein. In one embodiment, the method includes lessening the severity of cystic fibrosis in a patient possessing the R117H mutation of human CFTR in at least one allele comprising administering to said patient one of the compositions as defined herein. In one embodiment, the method includes lessening the severity of cystic fibrosis in a patient possessing the R117H mutation of human CFTR in both alleles comprising administering to said patient one of the compositions as defined herein. In another embodiment, the method includes lessening the severity of cystic fibrosis in a patient possessing CFTR with residual function or a residual function phenotype comprising administering to said patient one of the pharmaceutical compositions as defined herein. In one embodiment, the method includes treating or lessening the severity of cystic fibrosis in a patient possessing a CFTR gating mutation of human comprising administering to said patient one of the pharmaceutical compositions as defined herein. In some embodiments, the patient possesses one or more of the following gating mutations of human CFTR: G551D, G178R, G551S, G970R, G1244E, S1255P, G1349D, S549N, S549R, and S1251N. In some embodiments, the patient possesses at least one gating mutations of human CFIR, including, but not limited to, G551D, G178R, G551S, G970R, G1244E, S1255P, G1349D, S549N, S549R, and S1251N. In one embodiment, the method includes treating or lessening the severity of cystic fibrosis in a patient possessing a CFTR gating mutation of human on at least one allele comprising administering to said patient one of the pharmaceutical compositions as defined herein. In one embodiment, the method includes treating or lessening the severity of cystic fibrosis in a patient possessing a CFTR gating mutation of human on both alleles comprising administering to said patient one of the pharmaceutical compositions as defined herein.

In some embodiments, the method includes lessening the severity of cystic fibrosis in a patient comprising administering to said patient a pharmaceutical composition comprising a powder blend, wherein the powder blend composition comprises about 46.9 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 49.1 wt % of mannitol by weight of the composition; about 2 wt % of sucralose by weight of the composition; about 1 wt % of colloidal silicon dioxide by weight of the composition; and about 1.5 wt % of magnesium stearate by weight of the composition.

In some embodiments, the method comprises administering to said patient a pharmaceutical composition comprising from about 30 wt % to about 50 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; from about 30 wt % to about 60 wt % of a binary filler, wherein the binary filler comprises from about 0 wt % to about 60 wt % of mannitol by weight of the composition and from about 0 wt % to about 60 wt % of lactose by weight of the composition; from about 1.5 wt % to about 2.5 wt % of sucralose by weight of the composition; from about 4 wt % to about 8 wt % of croscarmellose sodium by weight of the composition; from about 0.5 wt % to about 1.5 wt % of colloidal silicon dioxide by weight of the composition; and from about 1 wt % to about 2 wt % of magnesium stearate by weight of the composition.

In one embodiment, the pharmaceutical composition comprises about 35 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 13.5 wt % of mannitol by weight of the composition; about 41 wt % of lactose by weight of the composition; about 2 wt % of sucralose by weight of the composition; about 6 wt % of croscarmellose sodium by weight of the composition; about 1 wt % of colloidal silicon dioxide by weight of the composition; and about 1.5 wt % of magnesium stearate by weight of the composition.

In some aspects, the pharmaceutical composition contains 10 mg, of Compound 1. In some aspects, a unit dose comprising the pharmaceutical composition of the present invention, comprises 5 mg of Compound 1. In some aspects, the pharmaceutical composition, for example, a mini-tablet or plurality of mini-tablets are filled into a capsule or a packet, wherein the capsule or packet contains 5 mg of Compound 1. In other embodiments, the pharmaceutical composition contains 10 mg of Compound 1. In other embodiments, the pharmaceutical composition contains 12.5 mg of Compound 1. In other embodiments, the pharmaceutical composition contains 15 mg of Compound 1. In other embodiments, the pharmaceutical composition contains 20 mg of Compound 1. In other embodiments, the pharmaceutical composition contains 25 mg of Compound 1. In other embodiments, the pharmaceutical composition contains 30 mg of Compound 1. In other embodiments, the pharmaceutical composition contains 35 mg of Compound 1. In other embodiments, the pharmaceutical composition contains 37.5 mg of Compound 1. In other embodiments, the pharmaceutical composition contains 40 mg of Compound 1. In other embodiments, the pharmaceutical composition contains 45 mg of Compound 1. In other embodiments, the pharmaceutical composition contains 50 mg of Compound 1. In other embodiments, the pharmaceutical composition contains 62.5 mg of Compound 1. In other embodiments, the pharmaceutical composition contains 75 mg of Compound 1. In other embodiments, the pharmaceutical composition contains 100 mg of Compound 1. In other embodiments, the pharmaceutical composition contains 125 mg of Compound 1. In other embodiments, the pharmaceutical composition contains 150 mg of Compound 1. In other embodiments, the pharmaceutical composition contains 175 mg of Compound 1. In other embodiments, the pharmaceutical composition contains 200 mg of Compound 1. In other embodiments, the pharmaceutical composition contains 225 mg of Compound 1. In other embodiments, the pharmaceutical composition contains 250 mg of Compound 1.

In some further aspects, the pharmaceutical composition comprises a mini-tablet or plurality of mini-tablets. In some embodiments, the method includes lessening the severity of cystic fibrosis in a patient comprising administering to said patient a pharmaceutical composition comprising a mini-tablet or plurality of mini-tablets, ranging from 1 to 40 mini-tablets, for example, about 5, about 10, about 22, about 24, about 26, about 28, about 29, about 30, about 31, about 33, about 35, about 37, or about 39 mini-tablets, wherein each of the mini-tablets in the composition comprises about 46.9 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 45.1 wt % of mannitol by weight of the composition; about 2 wt % of sucralose by weight of the composition; about 3 wt % of croscarmellose sodium by weight of the composition; about 0.5 wt % of SLS by weight of the composition; about 1 wt % of colloidal silicon dioxide by weight of the composition; and about 1.5 wt % of magnesium stearate by weight of the composition.

In some aspects, the pharmaceutical composition contains 5 mg, of Compound 1. In some aspects, the pharmaceutical composition contains 10 mg, of Compound 1. In some aspects, a unit dose comprising the pharmaceutical composition of the present invention, comprises 12.5 mg of Compound 1. In some aspects, a unit dose comprising the pharmaceutical composition of the present invention, comprises 15 mg of Compound 1. In some aspects, the pharmaceutical composition contains 20 mg, of Compound 1. In some aspects, a unit dose comprising the pharmaceutical composition contains 25 mg of Compound 1. In some aspects, the pharmaceutical composition contains 30 mg, of Compound 1. In some aspects, the pharmaceutical composition contains 35 mg, of Compound 1. In some aspects, the pharmaceutical composition contains 37.5 mg, of Compound 1. In some aspects, the pharmaceutical composition contains 40 mg, of Compound 1. In some aspects, the pharmaceutical composition contains 45 mg, of Compound 1. In some aspects, a unit dose comprising the pharmaceutical composition contains 50 mg of Compound 1. In some aspects, the pharmaceutical composition contains 62.5 mg, of Compound 1. In some aspects, a unit dose comprising the pharmaceutical composition contains 75 mg of Compound 1. In other embodiments, a unit dose comprising the pharmaceutical composition contains 100 mg of Compound 1. In some aspects, the pharmaceutical composition contains 125 mg, of Compound 1. In other embodiments, a unit dose comprising the pharmaceutical composition contains 150 mg of substantially amorphous or amorphous Compound 1. In some aspects, the pharmaceutical composition contains 175 mg, of Compound 1. In some aspects, the pharmaceutical composition contains 200 mg, of Compound 1. In some aspects, the pharmaceutical composition contains 225 mg, of Compound 1. In some aspects, the pharmaceutical composition contains 250 mg, of Compound 1.

In some aspects, the invention provides a method of treating or lessening the severity of Osteoporosis in a patient comprising administering to said patient Compound 1 or a pharmaceutically acceptable salt thereof.

In some embodiments, the method of treating or lessening the severity of Osteoporosis in a patient comprises administering to said patient substantially amorphous Compound 1 or a pharmaceutically acceptable salt thereof.

In still other embodiments, the method of treating or lessening the severity of Osteoporosis in a patient comprises administering to said patient amorphous Compound 1 or a pharmaceutically acceptable salt thereof.

In certain embodiments, the method of treating or lessening the severity of Osteoporosis in a patient comprises administering to said patient a pharmaceutical composition comprising a mini-tablet or plurality of mini-tablets as described herein.

In some embodiments, the method includes lessening the severity of Osteoporosis in a patient comprising administering to said patient a pharmaceutical composition comprising a powder blend, wherein the powder blend composition comprises about 46.9 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 49.1 wt % of mannitol by weight of the composition; about 2 wt % of sucralose by weight of the composition; about 1 wt % of colloidal silicon dioxide by weight of the composition; and about 1.0 wt % of magnesium stearate by weight of the composition. In some aspects, the powder blend pharmaceutical composition contains 10 mg, of Compound 1. In some aspects, a unit dose comprising the powder blend pharmaceutical composition of the present invention, comprises 12.5 mg of Compound 1. In some aspects, a unit dose comprising the powder blend pharmaceutical composition of the present invention, comprises 15 mg of Compound 1. In some aspects, a unit dose comprising the powder blend pharmaceutical composition of the present invention, comprises 20 mg of Compound 1. In some aspects, a unit dose comprising the powder blend pharmaceutical composition contains 25 mg of Compound 1. In some aspects, a unit dose comprising the powder blend pharmaceutical composition of the present invention, comprises 30 mg of Compound 1. In some aspects, a unit dose comprising the powder blend pharmaceutical composition of the present invention, comprises 35 mg of Compound 1. In some aspects, a unit dose comprising the powder blend pharmaceutical composition of the present invention, comprises 40 mg of Compound 1. In some aspects, a unit dose comprising the powder blend pharmaceutical composition of the present invention, comprises 45 mg of Compound 1. In some aspects, a unit dose comprising the powder blend pharmaceutical composition contains 50 mg of Compound 1. In some aspects, a unit dose comprising the powder blend pharmaceutical composition contains 75 mg of Compound 1. In other embodiments, a unit dose comprising the powder blend pharmaceutical composition contains 100 mg of Compound 1. In other embodiments, a unit dose comprising the powder blend pharmaceutical composition contains 150 mg of substantially amorphous or amorphous Compound 1.

In specific embodiments, the method of treating or lessening the severity of Osteoporosis in a patient comprises administering to said patient a pharmaceutical composition comprising a mini-tablet or plurality of mini-tablets, wherein the composition comprises from about 20 wt % to about 70 wt % of a solid dispersion by weight of the composition, wherein the dispersion comprises from about 30 wt % to about 85 wt % of substantially amorphous or amorphous Compound 1 by weight of the dispersion, from about 70 wt % to about 14 wt % of HPMCAS by weight of the dispersion, and from about 0.45 wt % to about 0.55 wt % SLS by weight of the dispersion; about 22 wt % to about 70 wt % of mannitol by weight of the composition; about 0.1 wt % to about 5 wt % of sucralose by weight of the composition; about 1 wt % to about 8 wt % of croscarmellose sodium by weight of the composition; from about 0.01 wt % to about 3 wt % of SLS by weight of the composition; from about 0.1 wt % to about 3 wt % of colloidal silicon dioxide by weight of the composition; and from about 0.1 wt % to about 7 wt % of magnesium stearate by weight of the composition. In some aspects, the pharmaceutical composition, for example, a mini-tablet or plurality of mini-tablets are formulated into a capsule or a packet, wherein the capsule or packet contains 5 mg of Compound 1. In some aspects, the pharmaceutical composition, for example, a mini-tablet or plurality of mini-tablets are formulated into a capsule or a packet, wherein the capsule or packet contains 10 mg of Compound 1. In some aspects, the pharmaceutical composition, for example, a mini-tablet or plurality of mini-tablets are formulated into a capsule or a packet, wherein the capsule or packet contains 12.5 mg of Compound 1. In some aspects, the pharmaceutical composition, for example, a mini-tablet or plurality of mini-tablets are formulated into a capsule or a packet, wherein the capsule or packet contains 15 mg of Compound 1. In other embodiments, a unit dose comprising the pharmaceutical composition contains 20 mg of Compound 1. In other embodiments, a unit dose comprising the pharmaceutical composition contains 25 mg of Compound 1. In other embodiments, a unit dose comprising the pharmaceutical composition contains 30 mg of Compound 1. In other embodiments, a unit dose comprising the pharmaceutical composition contains 35 mg of Compound 1. In other embodiments, a unit dose comprising the pharmaceutical composition contains 40 mg of Compound 1. In other embodiments, a unit dose comprising the pharmaceutical composition contains 45 mg of Compound 1. In other embodiments, a unit dose comprising the pharmaceutical composition contains 50 mg of Compound 1. In other embodiments, a unit dose comprising the pharmaceutical composition contains 75 mg of Compound 1. In other embodiments, a unit dose comprising the pharmaceutical composition contains 100 mg of Compound 1. In other embodiments, a unit dose comprising the pharmaceutical composition contains 150 mg of Compound 1.

In other embodiments, the method of treating or lessening the severity of Osteoporosis in a patient comprises administering to a patient a pharmaceutical composition comprising from about 30 wt % to about 50 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; from about 30 wt % to about 60 wt % of a binary filler, wherein the binary filler comprises from about 0 wt % to about 60 wt % of mannitol by weight of the composition and from about 0 wt % to about 60 wt % of lactose by weight of the composition; from about 1.5 wt % to about 2.5 wt % of sucralose by weight of the composition; from about 4 wt % to about 8 wt % of croscarmellose sodium by weight of the composition; from about 0.5 wt % to about 1.5 wt % of colloidal silicon dioxide by weight of the composition; and from about 1 wt % to about 2 wt % of magnesium stearate by weight of the composition.

In one embodiment, the pharmaceutical composition comprises about 35 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 13.5 wt % of mannitol by weight of the composition; about 41 wt % of lactose by weight of the composition; about 2 wt % of sucralose by weight of the composition; about 6 wt % of croscarmellose sodium by weight of the composition; about 1 wt % of colloidal silicon dioxide by weight of the composition; and about 1.5 wt % of magnesium stearate by weight of the composition.

In some aspects, the pharmaceutical composition contains 10 mg, of Compound 1. In some aspects, a unit dose comprising the pharmaceutical composition of the present invention, comprises 5 mg of Compound 1. In some aspects, the pharmaceutical composition, for example, a mini-tablet or plurality of mini-tablets are filled into a capsule or a packet, wherein the capsule or packet contains 5 mg of Compound 1. In other embodiments, the pharmaceutical composition contains 10 mg of Compound 1. In other embodiments, the pharmaceutical composition contains 12.5 mg of Compound 1. In other embodiments, the pharmaceutical composition contains 15 mg of Compound 1. In other embodiments, the pharmaceutical composition contains 20 mg of Compound 1. In other embodiments, the pharmaceutical composition contains 25 mg of Compound 1. In other embodiments, the pharmaceutical composition contains 30 mg of Compound 1. In other embodiments, the pharmaceutical composition contains 35 mg of Compound 1. In other embodiments, the pharmaceutical composition contains 37.5 mg of Compound 1. In other embodiments, the pharmaceutical composition contains 40 mg of Compound 1. In other embodiments, the pharmaceutical composition contains 45 mg of Compound 1. In other embodiments, the pharmaceutical composition contains 50 mg of Compound 1. In other embodiments, the pharmaceutical composition contains 62.5 mg of Compound 1. In other embodiments, the pharmaceutical composition contains 75 mg of Compound 1. In other embodiments, the pharmaceutical composition contains 100 mg of Compound 1. In other embodiments, the pharmaceutical composition contains 125 mg of Compound 1. In other embodiments, the pharmaceutical composition contains 150 mg of Compound 1. In other embodiments, the pharmaceutical composition contains 175 mg of Compound 1. In other embodiments, the pharmaceutical composition contains 200 mg of Compound 1. In other embodiments, the pharmaceutical composition contains 225 mg of Compound 1. In other embodiments, the pharmaceutical composition contains 250 mg of Compound 1.

In some aspects, the invention provides a method of treating or lessening the severity of Osteopenia in a patient comprising administering to said patient Compound 1 or a pharmaceutically acceptable salt thereof.

In some embodiments, the method of treating or lessening the severity of Osteopenia in a patient comprises administering to said patient substantially amorphous Compound 1 or a pharmaceutically acceptable salt thereof.

In still other embodiments, the method of treating or lessening the severity of Osteopenia in a patient comprises administering to said patient amorphous Compound 1.

In certain embodiments, the method of treating or lessening the severity of Osteopenia in a patient comprises administering to said patient a pharmaceutical composition as described herein.

In specific embodiments, the method includes lessening the severity of Osteopenia in a patient comprising administering to said patient a pharmaceutical composition comprising a powder blend, wherein the powder blend composition comprises about 46.9 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 49.1 wt % of mannitol by weight of the composition; about 2 wt % of sucralose by weight of the composition; about 1 wt % of colloidal silicon dioxide by weight of the composition; and about 1.0 wt % of magnesium stearate by weight of the composition. In some aspects, the powder blend pharmaceutical composition contains 5 mg, of Compound 1. In some aspects, the powder blend pharmaceutical composition contains 10 mg, of Compound 1. In some aspects, the powder blend pharmaceutical composition contains 12.5 mg, of Compound 1. In some aspects, a unit dose comprising the powder blend pharmaceutical composition of the present invention, comprises 15 mg of Compound 1. In some aspects, a unit dose comprising the powder blend pharmaceutical composition of the present invention, comprises 20 mg of Compound 1. In some aspects, a unit dose comprising the powder blend pharmaceutical composition contains 25 mg of Compound 1. In some aspects, a unit dose comprising the powder blend pharmaceutical composition of the present invention, comprises 30 mg of Compound 1. In some aspects, a unit dose comprising the powder blend pharmaceutical composition of the present invention, comprises 35 mg of Compound 1. In some aspects, a unit dose comprising the powder blend pharmaceutical composition of the present invention, comprises 40 mg of Compound 1. In some aspects, a unit dose comprising the powder blend pharmaceutical composition of the present invention, comprises 45 mg of Compound 1. In some aspects, a unit dose comprising the powder blend pharmaceutical composition contains 50 mg of Compound 1. In some aspects, a unit dose comprising the powder blend pharmaceutical composition contains 75 mg of Compound 1. In other embodiments, a unit dose comprising the powder blend pharmaceutical composition contains 100 mg of Compound 1. In other embodiments, a unit dose comprising the powder blend pharmaceutical composition contains 150 mg of substantially amorphous or amorphous Compound 1.

In specific embodiments, the method of treating or lessening the severity of Osteopenia in a patient comprises administering to said patient a pharmaceutical composition comprising a mini-tablet or plurality of mini-tablets, wherein the composition comprises from about 20 wt % to about 70 wt % of a solid dispersion by weight of the composition, wherein the dispersion comprises from about 30 wt % to about 85 wt % of substantially amorphous or amorphous Compound 1 by weight of the dispersion, from about 70 wt % to about 14 wt % of HPMCAS by weight of the dispersion, and from about 0.45 wt % to about 0.55 wt % SLS by weight of the dispersion; about 22 wt % to about 70 wt % of mannitol by weight of the composition; about 0.1 wt % to about 5 wt % of sucralose by weight of the composition; about 1 wt % to about 8 wt % of croscarmellose sodium by weight of the composition; from about 0.01 wt % to about 3 wt % of SLS by weight of the composition; from about 0.1 wt % to about 3 wt % of colloidal silicon dioxide by weight of the composition; and from about 0.1 wt % to about 7 wt % of magnesium stearate by weight of the composition. In some aspects, the pharmaceutical composition, for example, a mini-tablet or plurality of mini-tablets are formulated into a capsule or a packet, wherein the capsule or packet contains 5 mg of Compound 1. In other embodiments, the pharmaceutical composition contains 10 mg of Compound 1. In other embodiments, the pharmaceutical composition contains 12.5 mg of Compound 1. In other embodiments, the pharmaceutical composition contains 15 mg of Compound 1. In other embodiments, the pharmaceutical composition contains 20 mg of Compound 1. In other embodiments, the pharmaceutical composition contains 25 mg of Compound 1. In other embodiments, the pharmaceutical composition contains 30 mg of Compound 1. In other embodiments, the pharmaceutical composition contains 35 mg of Compound 1. In other embodiments, the pharmaceutical composition contains 40 mg of Compound 1. In other embodiments, the pharmaceutical composition contains 45 mg of Compound 1. In other embodiments, the pharmaceutical composition contains 50 mg of Compound 1. In other embodiments, the pharmaceutical composition contains 75 mg of Compound 1. In other embodiments, the pharmaceutical composition contains 100 mg of Compound 1. In other embodiments, the pharmaceutical composition contains 150 mg of Compound 1. In some further aspects, the pharmaceutical composition comprises one or more mini-tablets.

In specific embodiments, the method of treating or lessening the severity of Osteopenia in a patient comprises administering to said patient a pharmaceutical composition comprising from about 30 wt % to about 50 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; from about 30 wt % to about 60 wt % of a binary filler, wherein the binary filler comprises from about 0 wt % to about 60 wt % of mannitol by weight of the composition and from about 0 wt % to about 60 wt % of lactose by weight of the composition; from about 1.5 wt % to about 2.5 wt % of sucralose by weight of the composition; from about 4 wt % to about 8 wt % of croscarmellose sodium by weight of the composition; from about 0.5 wt % to about 1.5 wt % of colloidal silicon dioxide by weight of the composition; and from about 1 wt % to about 2 wt % of magnesium stearate by weight of the composition.

In one embodiment, the pharmaceutical composition comprises about 35 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 13.5 wt % of mannitol by weight of the composition; about 41 wt % of lactose by weight of the composition; about 2 wt % of sucralose by weight of the composition; about 6 wt % of croscarmellose sodium by weight of the composition; about 1 wt % of colloidal silicon dioxide by weight of the composition; and about 1.5 wt % of magnesium stearate by weight of the composition.

In some aspects, the pharmaceutical composition contains 10 mg, of Compound 1. In some aspects, a unit dose comprising the pharmaceutical composition of the present invention, comprises 5 mg of Compound 1. In some aspects, the pharmaceutical composition, for example, a mini-tablet or plurality of mini-tablets are filled into a capsule or a packet, wherein the capsule or packet contains 5 mg of Compound 1. In other embodiments, the pharmaceutical composition contains 10 mg of Compound 1. In other embodiments, the pharmaceutical composition contains 12.5 mg of Compound 1. In other embodiments, the pharmaceutical composition contains 15 mg of Compound 1. In other embodiments, the pharmaceutical composition contains 20 mg of Compound 1. In other embodiments, the pharmaceutical composition contains 25 mg of Compound 1. In other embodiments, the pharmaceutical composition contains 30 mg of Compound 1. In other embodiments, the pharmaceutical composition contains 35 mg of Compound 1. In other embodiments, the pharmaceutical composition contains 37.5 mg of Compound 1. In other embodiments, the pharmaceutical composition contains 40 mg of Compound 1. In other embodiments, the pharmaceutical composition contains 45 mg of Compound 1. In other embodiments, the pharmaceutical composition contains 50 mg of Compound 1. In other embodiments, the pharmaceutical composition contains 62.5 mg of Compound 1. In other embodiments, the pharmaceutical composition contains 75 mg of Compound 1. In other embodiments, the pharmaceutical composition contains 100 mg of Compound 1. In other embodiments, the pharmaceutical composition contains 125 mg of Compound 1. In other embodiments, the pharmaceutical composition contains 150 mg of Compound 1. In other embodiments, the pharmaceutical composition contains 175 mg of Compound 1. In other embodiments, the pharmaceutical composition contains 200 mg of Compound 1. In other embodiments, the pharmaceutical composition contains 225 mg of Compound 1. In other embodiments, the pharmaceutical composition contains 250 mg of Compound 1.

In some aspects, the invention provides a method of bone healing and/or bone repair in a patient comprising administering to said patient Compound 1 or a pharmaceutically acceptable salt thereof.

In some embodiments, the method of bone healing and/or bone repair in a patient comprises administering to said patient substantially amorphous Compound 1 or a pharmaceutically acceptable salt thereof.

In still other embodiments, the method of bone healing and/or bone repair in a patient comprises administering to said patient amorphous Compound 1 or a pharmaceutically acceptable salt thereof.

In certain embodiments, the method of bone healing and/or bone repair in a patient comprises administering to said patient a pharmaceutical composition as described herein.

In some embodiments, the method of bone healing and/or bone repair in a patient comprises administering to said patient a pharmaceutical composition comprising a powder blend, wherein the powder blend composition comprises about 46.9 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 49.1 wt % of mannitol by weight of the composition; about 2 wt % of sucralose by weight of the composition; about 1 wt % of colloidal silicon dioxide by weight of the composition; and about 1.0 wt % of magnesium stearate by weight of the composition. In some aspects, the powder blend pharmaceutical composition contains 5 mg, of Compound 1. In some aspects, the powder blend pharmaceutical composition contains 10 mg, of Compound 1. In some aspects, a unit dose comprising the powder blend pharmaceutical composition of the present invention, comprises 12.5 mg of Compound 1. In some aspects, a unit dose comprising the powder blend pharmaceutical composition of the present invention, comprises 15 mg of Compound 1. In some aspects, a unit dose comprising the powder blend pharmaceutical composition of the present invention, comprises 20 mg of Compound 1. In some aspects, a unit dose comprising the powder blend pharmaceutical composition contains 25 mg of Compound 1. In some aspects, a unit dose comprising the powder blend pharmaceutical composition of the present invention, comprises 30 mg of Compound 1. In some aspects, a unit dose comprising the powder blend pharmaceutical composition of the present invention comprises 35 mg of Compound 1. In some aspects, a unit dose comprising the powder blend pharmaceutical composition of the present invention, comprises 40 mg of Compound 1. In some aspects, a unit dose comprising the powder blend pharmaceutical composition of the present invention comprises 45 mg of Compound 1. In some aspects, a unit dose comprising the powder blend pharmaceutical composition contains 50 mg of Compound 1. In some aspects, a unit dose comprising the powder blend pharmaceutical composition contains 75 mg of Compound 1. In other embodiments, a unit dose comprising the powder blend pharmaceutical composition contains 100 mg of Compound 1. In other embodiments, a unit dose comprising the powder blend pharmaceutical composition contains 150 mg of substantially amorphous or amorphous Compound 1.

In specific embodiments, the method of bone healing and/or bone repair in a patient comprises administering to said patient a pharmaceutical composition comprising a mini-tablet or plurality of mini-tablets, wherein the composition comprises from about 20 wt % to about 70 wt % of a solid dispersion by weight of the composition, wherein the dispersion comprises from about 30 wt % to about 85 wt % of substantially amorphous or amorphous Compound 1 by weight of the dispersion, from about 70 wt % to about 14 wt % of HPMCAS by weight of the dispersion, and from about 0.45 wt % to about 0.55 wt % SLS by weight of the dispersion; about 22 wt % to about 70 wt % of mannitol by weight of the composition; about 0.1 wt % to about 5 wt % of sucralose by weight of the composition; about 1 wt % to about 8 wt % of croscarmellose sodium by weight of the composition; from about 0.01 wt % to about 3 wt % of SLS by weight of the composition; from about 0.1 wt % to about 3 wt % of colloidal silicon dioxide by weight of the composition; and from about 0.1 wt % to about 7 wt % of magnesium stearate by weight of the composition. In some aspects, the pharmaceutical composition, for example, a mini-tablet or plurality of mini-tablets are formulated into a capsule or a packet, wherein the capsule or packet contains 5 mg of Compound 1. In other embodiments, the pharmaceutical composition contains 10 mg of Compound 1. In other embodiments, the pharmaceutical composition contains 12.5 mg of Compound 1. In other embodiments, the pharmaceutical composition contains 15 mg of Compound 1. In other embodiments, the pharmaceutical composition contains 20 mg of Compound 1. In other embodiments, the pharmaceutical composition contains 25 mg of Compound 1. In other embodiments, the pharmaceutical composition contains 30 mg of Compound 1. In other embodiments, the pharmaceutical composition contains 35 mg of Compound 1. In other embodiments, the pharmaceutical composition contains 40 mg of Compound 1. In other embodiments, the pharmaceutical composition contains 45 mg of Compound 1. In other embodiments, the pharmaceutical composition contains 50 mg of Compound 1. In other embodiments, the pharmaceutical composition contains 75 mg of Compound 1. In other embodiments, the pharmaceutical composition contains 100 mg of Compound 1. In other embodiments, the pharmaceutical composition contains 150 mg of Compound 1.

In specific embodiments, the method of bone healing and/or bone repair in a patient comprises administering to said patient a pharmaceutical composition comprising from about 30 wt % to about 50 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; from about 30 wt % to about 60 wt % of a binary filler, wherein the binary filler comprises from about 0 wt % to about 60 wt % of mannitol by weight of the composition and from about 0 wt % to about 60 wt % of lactose by weight of the composition; from about 1.5 wt % to about 2.5 wt % of sucralose by weight of the composition; from about 4 wt % to about 8 wt % of croscarmellose sodium by weight of the composition; from about 0.5 wt % to about 1.5 wt % of colloidal silicon dioxide by weight of the composition; and from about 1 wt % to about 2 wt % of magnesium stearate by weight of the composition.

In one embodiment, the pharmaceutical composition comprises about 35 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 13.5 wt % of mannitol by weight of the composition; about 41 wt % of lactose by weight of the composition; about 2 wt % of sucralose by weight of the composition; about 6 wt % of croscarmellose sodium by weight of the composition; about 1 wt % of colloidal silicon dioxide by weight of the composition; and about 1.5 wt % of magnesium stearate by weight of the composition.

In some aspects, the pharmaceutical composition contains 10 mg, of Compound 1. In some aspects, a unit dose comprising the pharmaceutical composition of the present invention, comprises 5 mg of Compound 1. In some aspects, the pharmaceutical composition, for example, a mini-tablet or plurality of mini-tablets are filled into a capsule or packet, wherein the capsule or packet contains 5 mg of Compound 1. In other embodiments, the pharmaceutical composition contains 10 mg of Compound 1. In other embodiments, the pharmaceutical composition contains 12.5 mg of Compound 1. In other embodiments, the pharmaceutical composition contains 15 mg of Compound 1. In other embodiments, the pharmaceutical composition contains 20 mg of Compound 1. In other embodiments, the pharmaceutical composition contains 25 mg of Compound 1. In other embodiments, the pharmaceutical composition contains 30 mg of Compound 1. In other embodiments, the pharmaceutical composition contains 35 mg of Compound 1. In other embodiments, the pharmaceutical composition contains 37.5 mg of Compound 1. In other embodiments, the pharmaceutical composition contains 40 mg of Compound 1. In other embodiments, the pharmaceutical composition contains 45 mg of Compound 1. In other embodiments, the pharmaceutical composition contains 50 mg of Compound 1. In other embodiments, the pharmaceutical composition contains 62.5 mg of Compound 1. In other embodiments, the pharmaceutical composition contains 75 mg of Compound 1. In other embodiments, the pharmaceutical composition contains 100 mg of Compound 1. In other embodiments, the pharmaceutical composition contains 125 mg of Compound 1. In other embodiments, the pharmaceutical composition contains 150 mg of Compound 1. In other embodiments, the pharmaceutical composition contains 175 mg of Compound 1. In other embodiments, the pharmaceutical composition contains 200 mg of Compound 1. In other embodiments, the pharmaceutical composition contains 225 mg of Compound 1. In other embodiments, the pharmaceutical composition contains 250 mg of Compound 1.

In some aspects, the invention provides a method of reducing bone resorption in a patient comprising administering to said patient Compound 1 or a pharmaceutically acceptable salt thereof.

In some embodiments, the method of reducing bone resorption in a patient comprises administering to said patient substantially amorphous Compound 1 or a pharmaceutically acceptable salt thereof.

In still other embodiments, the method of reducing bone resorption in a patient comprises administering to said patient amorphous Compound 1 or a pharmaceutically acceptable salt thereof.

In certain embodiments, the method of reducing bone resorption in a patient comprises administering to said patient a pharmaceutical composition as described herein.

In some embodiments, the method of reducing bone resorption in a patient comprises administering to said patient a pharmaceutical composition comprising a powder blend, wherein the powder blend composition comprises about 46.9 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 49.1 wt % of mannitol by weight of the composition; about 2 wt % of sucralose by weight of the composition; about 1 wt % of colloidal silicon dioxide by weight of the composition; and about 1.0 wt % of magnesium stearate by weight of the composition. In some aspects, the powder blend pharmaceutical composition contains 5 mg, of Compound 1. In some aspects, the powder blend pharmaceutical composition contains 10 mg, of Compound 1. In some aspects, a unit dose comprising the powder blend pharmaceutical composition of the present invention, comprises 12.5 mg of Compound 1. In some aspects, a unit dose comprising the powder blend pharmaceutical composition of the present invention, comprises 15 mg of Compound 1. In some aspects, a unit dose comprising the powder blend pharmaceutical composition of the present invention, comprises 20 mg of Compound 1. In some aspects, a unit dose comprising the powder blend pharmaceutical composition contains 25 mg of Compound 1. In some aspects, a unit dose comprising the powder blend pharmaceutical composition of the present invention, comprises 30 mg of Compound 1. In some aspects, a unit dose comprising the powder blend pharmaceutical composition of the present invention comprises 35 mg of Compound 1. In some aspects, a unit dose comprising the powder blend pharmaceutical composition of the present invention, comprises 40 mg of Compound 1. In some aspects, a unit dose comprising the powder blend pharmaceutical composition of the present invention comprises 45 mg of Compound 1. In some aspects, a unit dose comprising the powder blend pharmaceutical composition contains 50 mg of Compound 1. In some aspects, a unit dose comprising the powder blend pharmaceutical composition contains 75 mg of Compound 1. In other embodiments, a unit dose comprising the powder blend pharmaceutical composition contains 100 mg of Compound 1. In other embodiments, a unit dose comprising the powder blend pharmaceutical composition contains 150 mg of substantially amorphous or amorphous Compound 1.

In specific embodiments, the method of reducing bone resorption in a patient comprises administering to said patient a pharmaceutical composition comprising a mini-tablet or plurality of mini-tablets, wherein the composition comprises from about 20 wt % to about 70 wt % of a solid dispersion by weight of the composition, wherein the dispersion comprises from about 30 wt % to about 85 wt % of substantially amorphous or amorphous Compound 1 by weight of the dispersion, from about 70 wt % to about 14 wt % of HPMCAS by weight of the dispersion, and from about 0.45 wt % to about 0.55 wt % SLS by weight of the dispersion; about 22 wt % to about 70 wt % of mannitol by weight of the composition; about 0.1 wt % to about 5 wt % of sucralose by weight of the composition; about 1 wt % to about 8 wt % of croscarmellose sodium by weight of the composition; from about 0.01 wt % to about 3 wt % of SLS by weight of the composition; from about 0.1 wt % to about 3 wt % of colloidal silicon dioxide by weight of the composition; and from about 0.1 wt % to about 7 wt % of magnesium stearate by weight of the composition. In some aspects, the pharmaceutical composition, for example, a mini-tablet or plurality of mini-tablets are formulated into a capsule or a packet, wherein the capsule or packet contains 5 mg of Compound 1. In other embodiments, the pharmaceutical composition contains 10 mg of Compound 1. In other embodiments, the pharmaceutical composition contains 12.5 mg of Compound 1. In other embodiments, the pharmaceutical composition contains 15 mg of Compound 1. In other embodiments, the pharmaceutical composition contains 25 mg of Compound 1. In other embodiments, the pharmaceutical composition contains 30 mg of Compound 1. In other embodiments, the pharmaceutical composition contains 35 mg of Compound 1. In other embodiments, the pharmaceutical composition contains 40 mg of Compound 1. In other embodiments, the pharmaceutical composition contains 45 mg of Compound 1. In other embodiments, the pharmaceutical composition contains 50 mg of Compound 1. In other embodiments, the pharmaceutical composition contains 75 mg of Compound 1. In other embodiments, the pharmaceutical composition contains 100 mg of Compound 1. In other embodiments, the pharmaceutical composition contains 150 mg of Compound 1.

In certain embodiments, the method of reducing bone resorption in a patient comprises administering to said patient a pharmaceutical composition comprising from about 30 wt % to about 50 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; from about 30 wt % to about 60 wt % of a binary filler, wherein the binary filler comprises from about 0 wt % to about 60 wt % of mannitol by weight of the composition and from about 0 wt % to about 60 wt % of lactose by weight of the composition; from about 1.5 wt % to about 2.5 wt % of sucralose by weight of the composition; from about 4 wt % to about 8 wt % of croscarmellose sodium by weight of the composition; from about 0.5 wt % to about 1.5 wt % of colloidal silicon dioxide by weight of the composition; and from about 1 wt % to about 2 wt % of magnesium stearate by weight of the composition.

In one embodiment, the pharmaceutical composition comprises about 35 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 13.5 wt % of mannitol by weight of the composition; about 41 wt % of lactose by weight of the composition; about 2 wt % of sucralose by weight of the composition; about 6 wt % of croscarmellose sodium by weight of the composition; about 1 wt % of colloidal silicon dioxide by weight of the composition; and about 1.5 wt % of magnesium stearate by weight of the composition.

In some aspects, the pharmaceutical composition contains 10 mg, of Compound 1. In some aspects, a unit dose comprising the pharmaceutical composition of the present invention, comprises 5 mg of Compound 1. In some aspects, the pharmaceutical composition, for example, a mini-tablet or plurality of mini-tablets are filled into a capsule or a packet, wherein the capsule or packet contains 5 mg of Compound 1. In other embodiments, the pharmaceutical composition contains 10 mg of Compound 1. In other embodiments, the pharmaceutical composition contains 12.5 mg of Compound 1. In other embodiments, the pharmaceutical composition contains 15 mg of Compound 1. In other embodiments, the pharmaceutical composition contains 20 mg of Compound 1. In other embodiments, the pharmaceutical composition contains 25 mg of Compound 1. In other embodiments, the pharmaceutical composition contains 30 mg of Compound 1. In other embodiments, the pharmaceutical composition contains 35 mg of Compound 1. In other embodiments, the pharmaceutical composition contains 37.5 mg of Compound 1. In other embodiments, the pharmaceutical composition contains 40 mg of Compound 1. In other embodiments, the pharmaceutical composition contains 45 mg of Compound 1. In other embodiments, the pharmaceutical composition contains 50 mg of Compound 1. In other embodiments, the pharmaceutical composition contains 62.5 mg of Compound 1. In other embodiments, the pharmaceutical composition contains 75 mg of Compound 1. In other embodiments, the pharmaceutical composition contains 100 mg of Compound 1. In other embodiments, the pharmaceutical composition contains 125 mg of Compound 1. In other embodiments, the pharmaceutical composition contains 150 mg of Compound 1. In other embodiments, the pharmaceutical composition contains 175 mg of Compound 1. In other embodiments, the pharmaceutical composition contains 200 mg of Compound 1. In other embodiments, the pharmaceutical composition contains 225 mg of Compound 1. In other embodiments, the pharmaceutical composition contains 250 mg of Compound 1.

In some aspects, the invention provides a method of increasing bone deposition in a patient comprising administering to said patient Compound 1 or a pharmaceutically acceptable salt thereof.

In some embodiments, the method of increasing bone deposition in a patient comprises administering to said patient substantially amorphous Compound 1 or a pharmaceutically acceptable salt thereof.

In still other embodiments, the method of increasing bone deposition in a patient comprises administering to said patient amorphous Compound 1 or a pharmaceutically acceptable salt thereof.

In certain embodiments, the method of increasing bone deposition in a patient comprises administering to said patient a pharmaceutical composition as described herein.

In some embodiments, the method of increasing bone deposition in a patient comprises administering to said patient a pharmaceutical composition comprising a powder blend, wherein the powder blend composition comprises about 46.9 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 49.1 wt % of mannitol by weight of the composition; about 2 wt % of sucralose by weight of the composition; about 1 wt % of colloidal silicon dioxide by weight of the composition; and about 1.0 wt % of magnesium stearate by weight of the composition. In some aspects, the powder blend pharmaceutical composition contains 5 mg, of Compound 1. In some aspects, the powder blend pharmaceutical composition contains 10 mg, of Compound 1. In some aspects, a unit dose comprising the powder blend pharmaceutical composition of the present invention, comprises 12.5 mg of Compound 1. In some aspects, a unit dose comprising the powder blend pharmaceutical composition of the present invention, comprises 15 mg of Compound 1. In some aspects, the powder blend pharmaceutical composition contains 20 mg, of Compound 1. In some aspects, a unit dose comprising the powder blend pharmaceutical composition contains 25 mg of Compound 1. In some aspects, the powder blend pharmaceutical composition contains 30 mg, of Compound 1. In some aspects, the powder blend pharmaceutical composition contains 35 mg, of Compound 1. In some aspects, the powder blend pharmaceutical composition contains 40 mg, of Compound 1. In some aspects, the powder blend pharmaceutical composition contains 45 mg, of Compound 1. In some aspects, a unit dose comprising the powder blend pharmaceutical composition contains 50 mg of Compound 1. In some aspects, a unit dose comprising the powder blend pharmaceutical composition contains 75 mg of Compound 1. In other embodiments, a unit dose comprising the powder blend pharmaceutical composition contains 100 mg of Compound 1. In other embodiments, a unit dose comprising the powder blend pharmaceutical composition contains 150 mg of substantially amorphous or amorphous Compound 1.

In specific embodiments, the method of increasing bone deposition in a patient comprises administering to said patient a pharmaceutical composition comprising a mini-tablet or plurality of mini-tablets, wherein the composition comprises from about 20 wt % to about 70 wt % of a solid dispersion by weight of the composition, wherein the dispersion comprises from about 30 wt % to about 85 wt % of substantially amorphous or amorphous Compound 1 by weight of the dispersion, from about 70 wt % to about 14 wt % of HPMCAS by weight of the dispersion, and from about 0.45 wt % to about 0.55 wt % SLS by weight of the dispersion; about 22 wt % to about 70 wt % of mannitol by weight of the composition; about 0.1 wt % to about 5 wt % of sucralose by weight of the composition; about 1 wt % to about 8 wt % of croscarmellose sodium by weight of the composition; from about 0.01 wt % to about 3 wt % of SLS by weight of the composition; from about 0.1 wt % to about 3 wt % of colloidal silicon dioxide by weight of the composition; and from about 0.1 wt % to about 7 wt % of magnesium stearate by weight of the composition. In some aspects, the pharmaceutical composition, for example, a mini-tablet or plurality of mini-tablets are formulated into a capsule or a packet, wherein the capsule or packet contains 5 mg of Compound 1. In other embodiments, the pharmaceutical composition contains 10 mg of Compound 1. In other embodiments, the pharmaceutical composition contains 12.5 mg of Compound 1. In other embodiments, the pharmaceutical composition contains 15 mg of Compound 1. In other embodiments, the pharmaceutical composition contains 25 mg of Compound 1. In other embodiments, the pharmaceutical composition contains 30 mg of Compound 1. In other embodiments, the pharmaceutical composition contains 35 mg of Compound 1. In other embodiments, the pharmaceutical composition contains 40 mg of Compound 1. In other embodiments, the pharmaceutical composition contains 45 mg of Compound 1. In other embodiments, the pharmaceutical composition contains 50 mg of Compound 1. In other embodiments, the pharmaceutical composition contains 75 mg of Compound 1. In other embodiments, the pharmaceutical composition contains 100 mg of Compound 1. In other embodiments, the pharmaceutical composition contains 150 mg of Compound 1.

In certain embodiments, the method of increasing bone deposition in a patient comprises administering to said patient a pharmaceutical composition comprising from about 30 wt % to about 50 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; from about 30 wt % to about 60 wt % of a binary filler, wherein the binary filler comprises from about 0 wt % to about 60 wt % of mannitol by weight of the composition and from about 0 wt % to about 60 wt % of lactose by weight of the composition; from about 1.5 wt % to about 2.5 wt % of sucralose by weight of the composition; from about 4 wt % to about 8 wt % of croscarmellose sodium by weight of the composition; from about 0.5 wt % to about 1.5 wt % of colloidal silicon dioxide by weight of the composition; and from about 1 wt % to about 2 wt % of magnesium stearate by weight of the composition.

In one embodiment, the pharmaceutical composition comprises about 35 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 13.5 wt % of mannitol by weight of the composition; about 41 wt % of lactose by weight of the composition; about 2 wt % of sucralose by weight of the composition; about 6 wt % of croscarmellose sodium by weight of the composition; about 1 wt % of colloidal silicon dioxide by weight of the composition; and about 1.5 wt % of magnesium stearate by weight of the composition.

In some aspects, the pharmaceutical composition contains 10 mg, of Compound 1. In some aspects, a unit dose comprising the pharmaceutical composition of the present invention, comprises 5 mg of Compound 1. In some aspects, the pharmaceutical composition, for example, a mini-tablet or plurality of mini-tablets are filled into a capsule or a packet, wherein the capsule or packet contains 5 mg of Compound 1. In other embodiments, the pharmaceutical composition contains 10 mg of Compound 1. In other embodiments, the pharmaceutical composition contains 12.5 mg of Compound 1. In other embodiments, the pharmaceutical composition contains 15 mg of Compound 1. In other embodiments, the pharmaceutical composition contains 20 mg of Compound 1. In other embodiments, the pharmaceutical composition contains 25 mg of Compound 1. In other embodiments, the pharmaceutical composition contains 30 mg of Compound 1. In other embodiments, the pharmaceutical composition contains 35 mg of Compound 1. In other embodiments, the pharmaceutical composition contains 37.5 mg of Compound 1. In other embodiments, the pharmaceutical composition contains 40 mg of Compound 1. In other embodiments, the pharmaceutical composition contains 45 mg of Compound 1. In other embodiments, the pharmaceutical composition contains 50 mg of Compound 1. In other embodiments, the pharmaceutical composition contains 62.5 mg of Compound 1. In other embodiments, the pharmaceutical composition contains 75 mg of Compound 1. In other embodiments, the pharmaceutical composition contains 100 mg of Compound 1. In other embodiments, the pharmaceutical composition contains 125 mg of Compound 1. In other embodiments, the pharmaceutical composition contains 150 mg of Compound 1. In other embodiments, the pharmaceutical composition contains 175 mg of Compound 1. In other embodiments, the pharmaceutical composition contains 200 mg of Compound 1. In other embodiments, the pharmaceutical composition contains 225 mg of Compound 1. In other embodiments, the pharmaceutical composition contains 250 mg of Compound 1.

In some aspects, the invention provides a method of treating or lessening the severity of COPD in a patient comprising administering to said patient Compound 1 or a pharmaceutically acceptable salt thereof. In some embodiments, the method of treating or lessening the severity of COPD in a patient comprises administering to said patient substantially amorphous Compound 1 or a pharmaceutically acceptable salt thereof.

In still other embodiments, the method of treating or lessening the severity of COPD in a patient comprises administering to said patient amorphous Compound 1 or a pharmaceutically acceptable salt thereof.

In certain embodiments, the method of treating or lessening the severity of COPD in a patient comprises administering to said patient a pharmaceutical composition as described herein.

In some embodiments, the method of treating or lessening the severity of COPD in a patient comprises administering to said patient a pharmaceutical composition comprising a powder blend, wherein the powder blend composition comprises about 46.9 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 49.1 wt % of mannitol by weight of the composition; about 2 wt % of sucralose by weight of the composition; about 1 wt % of colloidal silicon dioxide by weight of the composition; and about 1.0 wt % of magnesium stearate by weight of the composition. In some aspects, the powder blend pharmaceutical composition contains 5 mg, of Compound 1. In some aspects, the powder blend pharmaceutical composition contains 10 mg, of Compound 1. In some aspects, a unit dose comprising the powder blend pharmaceutical composition of the present invention, comprises 12.5 mg of Compound 1. In some aspects, a unit dose comprising the powder blend pharmaceutical composition of the present invention, comprises 15 mg of Compound 1. In some aspects, the powder blend pharmaceutical composition contains 20 mg, of Compound 1. In some aspects, a unit dose comprising the powder blend pharmaceutical composition contains 25 mg of Compound 1. In some aspects, the powder blend pharmaceutical composition contains 30 mg, of Compound 1. In some aspects, the powder blend pharmaceutical composition contains 40 mg, of Compound 1. In some aspects, a unit dose comprising the powder blend pharmaceutical composition contains 50 mg of Compound 1. In some aspects, a unit dose comprising the powder blend pharmaceutical composition contains 75 mg of Compound 1. In other embodiments, a unit dose comprising the powder blend pharmaceutical composition contains 100 mg of Compound 1. In other embodiments, a unit dose comprising the powder blend pharmaceutical composition contains 150 mg of substantially amorphous or amorphous Compound 1.

In specific embodiments, the method of treating or lessening the severity of COPD in a patient comprises administering to said patient a pharmaceutical composition comprising a mini-tablet or plurality of mini-tablets, wherein the composition comprises from about 20 wt % to about 70 wt % of a solid dispersion by weight of the composition, wherein the dispersion comprises from about 30 wt % to about 85 wt % of substantially amorphous or amorphous Compound 1 by weight of the dispersion, from about 70 wt % to about 14 wt % of HPMCAS by weight of the dispersion, and from about 0.45 wt % to about 0.55 wt % SLS by weight of the dispersion; about 22 wt % to about 70 wt % of mannitol by weight of the composition; about 0.1 wt % to about 5 wt % of sucralose by weight of the composition; about 1 wt % to about 8 wt % of croscarmellose sodium by weight of the composition; from about 0.01 wt % to about 3 wt % of SLS by weight of the composition; from about 0.1 wt % to about 3 wt % of colloidal silicon dioxide by weight of the composition; and from about 0.1 wt % to about 7 wt % of magnesium stearate by weight of the composition. In some aspects, the pharmaceutical composition, for example, a mini-tablet or plurality of mini-tablets are formulated into a capsule or a packet, wherein the capsule or packet contains 5 mg of Compound 1. In other embodiments, the pharmaceutical composition contains 10 mg of Compound 1. In other embodiments, the pharmaceutical composition contains 12.5 mg of Compound 1. In other embodiments, the pharmaceutical composition contains 15 mg of Compound 1. In other embodiments, the pharmaceutical composition contains 20 mg of Compound 1. In other embodiments, the pharmaceutical composition contains 25 mg of Compound 1. In other embodiments, the pharmaceutical composition contains 30 mg of Compound 1. In other embodiments, the pharmaceutical composition contains 35 mg of Compound 1. In other embodiments, the pharmaceutical composition contains 40 mg of Compound 1. In other embodiments, the pharmaceutical composition contains 45 mg of Compound 1. In other embodiments, the pharmaceutical composition contains 50 mg of Compound 1. In other embodiments, the pharmaceutical composition contains 75 mg of Compound 1. In other embodiments, the pharmaceutical composition contains 100 mg of Compound 1. In other embodiments, the pharmaceutical composition contains 150 mg of Compound 1.

In certain embodiments, the method of treating or lessening the severity of COPD in a patient comprises administering to said patient a pharmaceutical composition comprising from about 30 wt % to about 50 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; from about 30 wt % to about 60 wt % of a binary filler, wherein the binary filler comprises from about 0 wt % to about 60 wt % of mannitol by weight of the composition and from about 0 wt % to about 60 wt % of lactose by weight of the composition; from about 1.5 wt % to about 2.5 wt % of sucralose by weight of the composition; from about 4 wt % to about 8 wt % of croscarmellose sodium by weight of the composition; from about 0.5 wt % to about 1.5 wt % of colloidal silicon dioxide by weight of the composition; and from about 1 wt % to about 2 wt % of magnesium stearate by weight of the composition.

In one embodiment, the pharmaceutical composition comprises about 35 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 13.5 wt % of mannitol by weight of the composition; about 41 wt % of lactose by weight of the composition; about 2 wt % of sucralose by weight of the composition; about 6 wt % of croscarmellose sodium by weight of the composition; about 1 wt % of colloidal silicon dioxide by weight of the composition; and about 1.5 wt % of magnesium stearate by weight of the composition.

In some aspects, the pharmaceutical composition contains 10 mg, of Compound 1. In some aspects, a unit dose comprising the pharmaceutical composition of the present invention, comprises 5 mg of Compound 1. In some aspects, the pharmaceutical composition, for example, a mini-tablet or plurality of mini-tablets are filled into a capsule or a packet, wherein the capsule or packet contains 5 mg of Compound 1. In other embodiments, the pharmaceutical composition contains 10 mg of Compound 1. In other embodiments, the pharmaceutical composition contains 12.5 mg of Compound 1. In other embodiments, the pharmaceutical composition contains 15 mg of Compound 1. In other embodiments, the pharmaceutical composition contains 20 mg of Compound 1. In other embodiments, the pharmaceutical composition contains 25 mg of Compound 1. In other embodiments, the pharmaceutical composition contains 30 mg of Compound 1. In other embodiments, the pharmaceutical composition contains 35 mg of Compound 1. In other embodiments, the pharmaceutical composition contains 37.5 mg of Compound 1. In other embodiments, the pharmaceutical composition contains 40 mg of Compound 1. In other embodiments, the pharmaceutical composition contains 45 mg of Compound 1. In other embodiments, the pharmaceutical composition contains 50 mg of Compound 1. In other embodiments, the pharmaceutical composition contains 62.5 mg of Compound 1. In other embodiments, the pharmaceutical composition contains 75 mg of Compound 1. In other embodiments, the pharmaceutical composition contains 100 mg of Compound 1. In other embodiments, the pharmaceutical composition contains 125 mg of Compound 1. In other embodiments, the pharmaceutical composition contains 150 mg of Compound 1. In other embodiments, the pharmaceutical composition contains 175 mg of Compound 1. In other embodiments, the pharmaceutical composition contains 200 mg of Compound 1. In other embodiments, the pharmaceutical composition contains 225 mg of Compound 1. In other embodiments, the pharmaceutical composition contains 250 mg of Compound 1.

In some aspects, the invention provides a method of treating or lessening the severity of smoke induced COPD in a patient comprising administering to said patient Compound 1 or a pharmaceutically acceptable salt thereof.

In some embodiments, the method of treating or lessening the severity of smoke induced COPD in a patient comprises administering to said patient substantially amorphous Compound 1 or a pharmaceutically acceptable salt thereof.

In still other embodiments, the method of treating or lessening the severity of smoke induced COPD in a patient comprises administering to said patient amorphous Compound 1 or a pharmaceutically acceptable salt thereof.

In certain embodiments, the method of treating or lessening the severity of smoke induced COPD in a patient comprises administering to said patient a pharmaceutical composition as described herein.

In some embodiments, the method of treating or lessening the severity of smoke induced COPD in a patient comprises administering to said patient a pharmaceutical composition comprising a powder blend, wherein the powder blend composition comprises about 46.9 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 49.1 wt % of mannitol by weight of the composition; about 2 wt % of sucralose by weight of the composition; about 1 wt % of colloidal silicon dioxide by weight of the composition; and about 1.0 wt % of magnesium stearate by weight of the composition. In some aspects, the powder blend pharmaceutical composition contains 5 mg, of Compound 1. In some aspects, the powder blend pharmaceutical composition contains 10 mg, of Compound 1. In some aspects, a unit dose comprising the powder blend pharmaceutical composition of the present invention, comprises 12.5 mg of Compound 1. In some aspects, a unit dose comprising the powder blend pharmaceutical composition of the present invention, comprises 15 mg of Compound 1. In some aspects, the powder blend pharmaceutical composition contains 20 mg, of Compound 1. In some aspects, a unit dose comprising the powder blend pharmaceutical composition contains 25 mg of Compound 1. In some aspects, the powder blend pharmaceutical composition contains 30 mg, of Compound 1. In some aspects, the powder blend pharmaceutical composition contains 35 mg, of Compound 1. In some aspects, the powder blend pharmaceutical composition contains 40 mg, of Compound 1. In some aspects, the powder blend pharmaceutical composition contains 45 mg, of Compound 1. In some aspects, a unit dose comprising the powder blend pharmaceutical composition contains 50 mg of Compound 1. In some aspects, a unit dose comprising the powder blend pharmaceutical composition contains 75 mg of Compound 1. In other embodiments, a unit dose comprising the powder blend pharmaceutical composition contains 100 mg of Compound 1. In other embodiments, a unit dose comprising the powder blend pharmaceutical composition contains 150 mg of substantially amorphous or amorphous Compound 1.

In specific embodiments, the method of treating or lessening the severity of smoke induced COPD in a patient comprises administering to said patient a pharmaceutical composition comprising a mini-tablet or plurality of mini-tablets, wherein the composition comprises from about 20 wt % to about 70 wt % of a solid dispersion by weight of the composition, wherein the dispersion comprises from about 30 wt % to about 85 wt % of substantially amorphous or amorphous Compound 1 by weight of the dispersion, from about 70 wt % to about 14 wt % of HPMCAS by weight of the dispersion, and from about 0.45 wt % to about 0.55 wt % SLS by weight of the dispersion; about 22 wt % to about 70 wt % of mannitol by weight of the composition; about 0.1 wt % to about 5 wt % of sucralose by weight of the composition; about 1 wt % to about 8 wt % of croscarmellose sodium by weight of the composition; from about 0.01 wt % to about 3 wt % of SLS by weight of the composition; from about 0.1 wt % to about 3 wt % of colloidal silicon dioxide by weight of the composition; and from about 0.1 wt % to about 7 wt % of magnesium stearate by weight of the composition. In some aspects, the pharmaceutical composition, for example, a mini-tablet or plurality of mini-tablets are formulated into a capsule or a packet, wherein the capsule or packet contains 5 mg of Compound 1. In other embodiments, the pharmaceutical composition contains 10 mg of Compound 1. In other embodiments, the pharmaceutical composition contains 15 mg of Compound 1. In other embodiments, the pharmaceutical composition contains 12.5 mg of Compound 1. In other embodiments, the pharmaceutical composition contains 25 mg of Compound 1. In other embodiments, the pharmaceutical composition contains 30 mg of Compound 1. In other embodiments, the pharmaceutical composition contains 35 mg of Compound 1. In other embodiments, the pharmaceutical composition contains 40 mg of Compound 1. In other embodiments, the pharmaceutical composition contains 45 mg of Compound 1. In other embodiments, the pharmaceutical composition contains 50 mg of Compound 1. In other embodiments, the pharmaceutical composition contains 75 mg of Compound 1. In other embodiments, the pharmaceutical composition contains 100 mg of Compound 1. In other embodiments, the pharmaceutical composition contains 150 mg of Compound 1.

In certain embodiments, the method of treating or lessening the severity of smoke induced COPD in a patient comprises administering to said patient a pharmaceutical composition comprising from about 30 wt % to about 50 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; from about 30 wt % to about 60 wt % of a binary filler, wherein the binary filler comprises from about 0 wt % to about 60 wt % of mannitol by weight of the composition and from about 0 wt % to about 60 wt % of lactose by weight of the composition; from about 1.5 wt % to about 2.5 wt % of sucralose by weight of the composition; from about 4 wt % to about 8 wt % of croscarmellose sodium by weight of the composition; from about 0.5 wt % to about 1.5 wt % of colloidal silicon dioxide by weight of the composition; and from about 1 wt % to about 2 wt % of magnesium stearate by weight of the composition.

In one embodiment, the pharmaceutical composition comprises about 35 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 13.5 wt % of mannitol by weight of the composition; about 41 wt % of lactose by weight of the composition; about 2 wt % of sucralose by weight of the composition; about 6 wt % of croscarmellose sodium by weight of the composition; about 1 wt % of colloidal silicon dioxide by weight of the composition; and about 1.5 wt % of magnesium stearate by weight of the composition.

In some aspects, the pharmaceutical composition contains 10 mg, of Compound 1. In some aspects, a unit dose comprising the pharmaceutical composition of the present invention, comprises 5 mg of Compound 1. In some aspects, the pharmaceutical composition, for example, a mini-tablet or plurality of mini-tablets are filled into a capsule or a packet, wherein the capsule or packet contains 5 mg of Compound 1. In other embodiments, the pharmaceutical composition contains 10 mg of Compound 1. In other embodiments, the pharmaceutical composition contains 12.5 mg of Compound 1. In other embodiments, the pharmaceutical composition contains 15 mg of Compound 1. In other embodiments, the pharmaceutical composition contains 20 mg of Compound 1. In other embodiments, the pharmaceutical composition contains 25 mg of Compound 1. In other embodiments, the pharmaceutical composition contains 30 mg of Compound 1. In other embodiments, the pharmaceutical composition contains 35 mg of Compound 1. In other embodiments, the pharmaceutical composition contains 37.5 mg of Compound 1. In other embodiments, the pharmaceutical composition contains 40 mg of Compound 1. In other embodiments, the pharmaceutical composition contains 45 mg of Compound 1. In other embodiments, the pharmaceutical composition contains 50 mg of Compound 1. In other embodiments, the pharmaceutical composition contains 62.5 mg of Compound 1. In other embodiments, the pharmaceutical composition contains 75 mg of Compound 1. In other embodiments, the pharmaceutical composition contains 100 mg of Compound 1. In other embodiments, the pharmaceutical composition contains 125 mg of Compound 1. In other embodiments, the pharmaceutical composition contains 150 mg of Compound 1. In other embodiments, the pharmaceutical composition contains 175 mg of Compound 1. In other embodiments, the pharmaceutical composition contains 200 mg of Compound 1. In other embodiments, the pharmaceutical composition contains 225 mg of Compound 1. In other embodiments, the pharmaceutical composition contains 250 mg of Compound 1.

In some aspects, the invention provides a method of treating or lessening the severity of chronic bronchitis in a patient comprising administering to said patient Compound 1 or a pharmaceutically acceptable salt thereof.

In some embodiments, the method of treating or lessening the severity of chronic bronchitis in a patient comprises administering to said patient substantially amorphous Compound 1 or a pharmaceutically acceptable salt thereof.

In still other embodiments, the method of treating or lessening the severity of chronic bronchitis in a patient comprises administering to said patient amorphous Compound 1 or a pharmaceutically acceptable salt thereof.

In certain embodiments, the method of treating or lessening the severity of chronic bronchitis in a patient comprises administering to said patient a pharmaceutical composition as described herein.

In some embodiments, the method of treating or lessening the severity of chronic bronchitis in a patient comprises administering to said patient a pharmaceutical composition comprising a powder blend, wherein the powder blend composition comprises about 46.9 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 49.1 wt % of mannitol by weight of the composition; about 2 wt % of sucralose by weight of the composition; about 1 wt % of colloidal silicon dioxide by weight of the composition; and about 1.0 wt % of magnesium stearate by weight of the composition. In some aspects, the powder blend pharmaceutical composition contains 5 mg, of Compound 1. In some aspects, a unit dose comprising the powder blend pharmaceutical composition of the present invention, comprises 10 mg of Compound 1. In some aspects, a unit dose comprising the powder blend pharmaceutical composition of the present invention, comprises 12.5 mg of Compound 1. In some aspects, a unit dose comprising the powder blend pharmaceutical composition of the present invention, comprises 15 mg of Compound 1. In some aspects, a unit dose comprising the powder blend pharmaceutical composition of the present invention, comprises 20 mg of Compound 1. In some aspects, a unit dose comprising the powder blend pharmaceutical composition contains 25 mg of Compound 1. In some aspects, a unit dose comprising the powder blend pharmaceutical composition of the present invention, comprises 30 mg of Compound 1. In some aspects, a unit dose comprising the powder blend pharmaceutical composition of the present invention comprises 35 mg of Compound 1. In some aspects, a unit dose comprising the powder blend pharmaceutical composition of the present invention, comprises 40 mg of Compound 1. In some aspects, a unit dose comprising the powder blend pharmaceutical composition of the present invention comprises 45 mg of Compound 1. In some aspects, a unit dose comprising the powder blend pharmaceutical composition contains 50 mg of Compound 1. In some aspects, a unit dose comprising the powder blend pharmaceutical composition contains 75 mg of Compound 1. In other embodiments, a unit dose comprising the powder blend pharmaceutical composition contains 100 mg of Compound 1. In other embodiments, a unit dose comprising the powder blend pharmaceutical composition contains 150 mg of substantially amorphous or amorphous Compound 1.

In specific embodiments, the method of treating or lessening the severity of chronic bronchitis in a patient comprises administering to said patient a pharmaceutical composition comprising a mini-tablet or plurality of mini-tablets, wherein the composition comprises from about 20 wt % to about 70 wt % of a solid dispersion by weight of the composition, wherein the dispersion comprises from about 30 wt % to about 85 wt % of substantially amorphous or amorphous Compound 1 by weight of the dispersion, from about 70 wt % to about 14 wt % of HPMCAS by weight of the dispersion, and from about 0.45 wt % to about 0.55 wt % SLS by weight of the dispersion; about 22 wt % to about 70 wt % of mannitol by weight of the composition; about 0.1 wt % to about 5 wt % of sucralose by weight of the composition; about 1 wt % to about 8 wt % of croscarmellose sodium by weight of the composition; from about 0.01 wt % to about 3 wt % of SLS by weight of the composition; from about 0.1 wt % to about 3 wt % of colloidal silicon dioxide by weight of the composition; and from about 0.1 wt % to about 7 wt % of magnesium stearate by weight of the composition. In some aspects, the pharmaceutical composition, for example, a mini-tablet or plurality of mini-tablets are formulated into a capsule or a packet, wherein the capsule or packet contains 5 mg of Compound 1. In other embodiments, the pharmaceutical composition contains 10 mg of Compound 1. In other embodiments, the pharmaceutical composition contains 12.5 mg of Compound 1. In other embodiments, the pharmaceutical composition contains 15 mg of Compound 1. In other embodiments, the pharmaceutical composition contains 20 mg of Compound 1. In other embodiments, the pharmaceutical composition contains 25 mg of Compound 1. In other embodiments, the pharmaceutical composition contains 30 mg of Compound 1. In other embodiments, the pharmaceutical composition contains 35 mg of Compound 1. In other embodiments, the pharmaceutical composition contains 40 mg of Compound 1. In other embodiments, the pharmaceutical composition contains 45 mg of Compound 1. In other embodiments, the pharmaceutical composition contains 50 mg of Compound 1. In other embodiments, the pharmaceutical composition contains 75 mg of Compound 1. In other embodiments, the pharmaceutical composition contains 100 mg of Compound 1. In other embodiments, the pharmaceutical composition contains 150 mg of Compound 1.

In certain embodiments, the method of treating or lessening the severity of chronic bronchitis in a patient comprises administering to said patient a pharmaceutical composition comprising from about 30 wt % to about 50 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; from about 30 wt % to about 60 wt % of a binary filler, wherein the binary filler comprises from about 0 wt % to about 60 wt % of mannitol by weight of the composition and from about 0 wt % to about 60 wt % of lactose by weight of the composition; from about 1.5 wt % to about 2.5 wt % of sucralose by weight of the composition; from about 4 wt % to about 8 wt % of croscarmellose sodium by weight of the composition; from about 0.5 wt % to about 1.5 wt % of colloidal silicon dioxide by weight of the composition; and from about 1 wt % to about 2 wt % of magnesium stearate by weight of the composition.

In one embodiment, the pharmaceutical composition comprises about 35 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion; about 13.5 wt % of mannitol by weight of the composition; about 41 wt % of lactose by weight of the composition; about 2 wt % of sucralose by weight of the composition; about 6 wt % of croscarmellose sodium by weight of the composition; about 1 wt % of colloidal silicon dioxide by weight of the composition; and about 1.5 wt % of magnesium stearate by weight of the composition.

In some aspects, the pharmaceutical composition contains 10 mg, of Compound 1. In some aspects, a unit dose comprising the pharmaceutical composition of the present invention, comprises 5 mg of Compound 1. In some aspects, the pharmaceutical composition, for example, a mini-tablet or plurality of mini-tablets are filled into a capsule or a packet, wherein the capsule or packet contains 5 mg of Compound 1. In other embodiments, the pharmaceutical composition contains 10 mg of Compound 1. In other embodiments, the pharmaceutical composition contains 12.5 mg of Compound 1. In other embodiments, the pharmaceutical composition contains 15 mg of Compound 1. In other embodiments, the pharmaceutical composition contains 20 mg of Compound 1. In other embodiments, the pharmaceutical composition contains 25 mg of Compound 1. In other embodiments, the pharmaceutical composition contains 30 mg of Compound 1. In other embodiments, the pharmaceutical composition contains 35 mg of Compound 1. In other embodiments, the pharmaceutical composition contains 37.5 mg of Compound 1. In other embodiments, the pharmaceutical composition contains 40 mg of Compound 1. In other embodiments, the pharmaceutical composition contains 45 mg of Compound 1. In other embodiments, the pharmaceutical composition contains 50 mg of Compound 1. In other embodiments, the pharmaceutical composition contains 62.5 mg of Compound 1. In other embodiments, the pharmaceutical composition contains 75 mg of Compound 1. In other embodiments, the pharmaceutical composition contains 100 mg of Compound 1. In other embodiments, the pharmaceutical composition contains 125 mg of Compound 1. In other embodiments, the pharmaceutical composition contains 150 mg of Compound 1. In other embodiments, the pharmaceutical composition contains 175 mg of Compound 1. In other embodiments, the pharmaceutical composition contains 200 mg of Compound 1. In other embodiments, the pharmaceutical composition contains 225 mg of Compound 1. In other embodiments, the pharmaceutical composition contains 250 mg of Compound 1.

Another aspect of the present invention provides a method of administering a pharmaceutical composition by orally administering to a patient at least once per day the composition comprising one or more mini-tablets, wherein the composition comprises up to about 1 mg of substantially amorphous or amorphous Compound 1.

Another aspect of the present invention provides a method of administering a pharmaceutical composition by orally administering to a patient at least once per day the composition comprising a mini-tablet or plurality of mini-tablets, wherein the composition comprises up to about 5 mg of substantially amorphous or amorphous Compound 1.

Another aspect of the present invention provides a method of administering a pharmaceutical composition by orally administering to a patient at least once per day the composition comprising a mini-tablet or plurality of mini-tablets, wherein the composition comprises up to about 10 mg of substantially amorphous or amorphous Compound 1.

Another aspect of the present invention provides a method of administering a pharmaceutical composition by orally administering to a patient at least once per day the composition comprising a mini-tablet or plurality of mini-tablets, wherein the composition comprises up to about 12.5 mg of substantially amorphous or amorphous Compound 1.

Another aspect of the present invention provides a method of administering a pharmaceutical composition by orally administering to a patient at least once per day the composition comprising a mini-tablet or plurality of mini-tablets, wherein the composition comprises up to about 15 mg of substantially amorphous or amorphous Compound 1.

Another aspect of the present invention provides a method of administering a pharmaceutical composition by orally administering to a patient at least once per day the composition comprising a mini-tablet or plurality of mini-tablets, wherein the composition comprises up to about 20 mg of substantially amorphous or amorphous Compound 1.

Another aspect of the present invention provides a method of administering a pharmaceutical composition by orally administering to a patient at least once per day the composition comprising a mini-tablet or plurality of mini-tablets, wherein the composition comprises up to about 25 mg of substantially amorphous or amorphous Compound 1.

Another aspect of the present invention provides a method of administering a pharmaceutical composition by orally administering to a patient at least once per day the composition comprising a mini-tablet or plurality of mini-tablets, wherein the composition comprises up to about 30 mg of substantially amorphous or, amorphous Compound 1.

Another aspect of the present invention provides a method of administering a pharmaceutical composition by orally administering to a patient at least once per day the composition comprising a mini-tablet or plurality of mini-tablets, wherein the composition comprises up to about 35 mg of substantially amorphous or amorphous Compound 1.

Another aspect of the present invention provides a method of administering a pharmaceutical composition by orally administering to a patient at least once per day the composition comprising a mini-tablet or plurality of mini-tablets, wherein the composition comprises up to about 37.5 mg of substantially amorphous or amorphous Compound 1.

Another aspect of the present invention provides a method of administering a pharmaceutical composition by orally administering to a patient at least once per day the composition comprising a mini-tablet or plurality of mini-tablets, wherein the composition comprises up to about 40 mg of substantially amorphous or amorphous Compound 1.

Another aspect of the present invention provides a method of administering a pharmaceutical composition by orally administering to a patient at least once per day the composition comprising a mini-tablet or plurality of mini-tablets, wherein the composition comprises up to about 45 mg of substantially amorphous or amorphous Compound 1.

Another aspect of the present invention provides a method of administering a pharmaceutical composition by orally administering to a patient at least once per day the composition comprising a mini-tablet or plurality of mini-tablets, wherein the composition comprises up to about 50 mg of substantially amorphous or amorphous Compound 1.

Another aspect of the present invention provides a method of administering a pharmaceutical composition by orally administering to a patient at least once per day the composition comprising a mini-tablet or plurality of mini-tablets, wherein the composition comprises up to about 62.5 mg of substantially amorphous or amorphous Compound 1.

Another aspect of the present invention provides a method of administering a pharmaceutical composition by orally administering to a patient at least once per day the composition comprising a mini-tablet or plurality of mini-tablets, wherein the composition comprises up to about 75 mg of substantially amorphous or amorphous Compound 1.

Another aspect of the present invention provides a method of administering a pharmaceutical composition by orally administering to a patient at least once per day the composition comprising a mini-tablet or plurality of mini-tablets, wherein the composition comprises up to about 100 mg of substantially amorphous or amorphous Compound 1.

Another aspect of the present invention provides a method of administering a pharmaceutical composition by orally administering to a patient at least once per day the composition comprising a mini-tablet or plurality of mini-tablets, wherein the composition comprises up to about 125 mg of substantially amorphous or amorphous Compound 1.

Another aspect of the present invention provides a method of administering a pharmaceutical composition by orally administering to a patient at least once per day the composition comprising a mini-tablet or plurality of mini-tablets, wherein the composition comprises up to about 150 mg of substantially amorphous or amorphous Compound 1.

Another aspect of the present invention provides a method of administering a pharmaceutical composition by orally administering to a patient at least once per day the composition comprising a mini-tablet or plurality of mini-tablets, wherein the composition comprises up to about 175 mg of substantially amorphous or amorphous Compound 1.

Another aspect of the present invention provides a method of administering a pharmaceutical composition by orally administering to a patient at least once per day the composition comprising a mini-tablet or plurality of mini-tablets, wherein the composition comprises up to about 200 mg of substantially amorphous or amorphous Compound 1.

Another aspect of the present invention provides a method of administering a pharmaceutical composition by orally administering to a patient at least once per day the composition comprising a mini-tablet or plurality of mini-tablets, wherein the composition comprises up to about 225 mg of substantially amorphous or amorphous Compound 1.

Another aspect of the present invention provides a method of administering a pharmaceutical composition by orally administering to a patient at least once per day the composition comprising a mini-tablet or plurality of mini-tablets, wherein the composition comprises up to about 250 mg of substantially amorphous or amorphous Compound 1.

Another aspect of the present invention provides a method of administering a pharmaceutical composition by orally administering to a patient twice per day the composition comprising one or more mini-tablets, wherein the composition comprises up to about 1 mg of substantially amorphous or amorphous Compound 1.

Another aspect of the present invention provides a method of administering a pharmaceutical composition by orally administering to a patient twice per day the composition comprising a mini-tablet or plurality of mini-tablets, wherein the composition comprises up to about 5 mg of substantially amorphous or amorphous Compound 1.

Another aspect of the present invention provides a method of administering a pharmaceutical composition by orally administering to a patient twice per day the composition comprising a mini-tablet or plurality of mini-tablets, wherein the composition comprises up to about 10 mg of substantially amorphous or amorphous Compound 1.

Another aspect of the present invention provides a method of administering a pharmaceutical composition by orally administering to a patient twice per day the composition comprising a mini-tablet or plurality of mini-tablets, wherein the composition comprises up to about 12.5 mg of substantially amorphous or amorphous Compound 1.

Another aspect of the present invention provides a method of administering a pharmaceutical composition by orally administering to a patient twice per day the composition comprising a mini-tablet or plurality of mini-tablets, wherein the composition comprises up to about 15 mg of substantially amorphous or amorphous Compound 1.

Another aspect of the present invention provides a method of administering a pharmaceutical composition by orally administering to a patient twice per day the composition comprising a mini-tablet or plurality of mini-tablets, wherein the composition comprises up to about 20 mg of substantially amorphous or amorphous Compound 1.

Another aspect of the present invention provides a method of administering a pharmaceutical composition by orally administering to a patient twice per day the composition comprising a mini-tablet or plurality of mini-tablets, wherein the composition comprises up to about 25 mg of substantially amorphous or amorphous Compound 1.

Another aspect of the present invention provides a method of administering a pharmaceutical composition by orally administering to a patient twice per day the composition comprising a mini-tablet or plurality of mini-tablets, wherein the composition comprises up to about 30 mg of substantially amorphous or amorphous Compound 1.

Another aspect of the present invention provides a method of administering a pharmaceutical composition by orally administering to a patient twice per day the composition comprising a mini-tablet or plurality of mini-tablets, wherein the composition comprises up to about 35 mg of substantially amorphous or amorphous Compound 1.

Another aspect of the present invention provides a method of administering a pharmaceutical composition by orally administering to a patient twice per day the composition comprising a mini-tablet or plurality of mini-tablets, wherein the composition comprises up to about 37.5 mg of substantially amorphous or amorphous Compound 1.

Another aspect of the present invention provides a method of administering a pharmaceutical composition by orally administering to a patient twice per day the composition comprising a mini-tablet or plurality of mini-tablets, wherein the composition comprises up to about 40 mg of substantially amorphous or amorphous Compound 1.

Another aspect of the present invention provides a method of administering a pharmaceutical composition by orally administering to a patient twice per day the composition comprising a mini-tablet or plurality of mini-tablets, wherein the composition comprises up to about 45 mg of substantially amorphous or amorphous Compound 1.

Another aspect of the present invention provides a method of administering a pharmaceutical composition by orally administering to a patient twice per day the composition comprising a mini-tablet or plurality of mini-tablets, wherein the composition comprises up to about 50 mg of substantially amorphous or amorphous Compound 1.

Another aspect of the present invention provides a method of administering a pharmaceutical composition by orally administering to a patient twice per day the composition comprising a mini-tablet or plurality of mini-tablets, wherein the composition comprises up to about 62.5 mg of substantially amorphous or amorphous Compound 1.

Another aspect of the present invention provides a method of administering a pharmaceutical composition by orally administering to a patient twice per day the composition comprising a mini-tablet or plurality of mini-tablets, wherein the composition comprises up to about 75 mg of substantially amorphous or amorphous Compound 1.

Another aspect of the present invention provides a method of administering a pharmaceutical composition by orally administering to a patient twice per day the composition comprising a mini-tablet or plurality of mini-tablets, wherein the composition comprises up to about 100 mg of substantially amorphous or amorphous Compound 1.

Another aspect of the present invention provides a method of administering a pharmaceutical composition by orally administering to a patient twice per day the composition comprising a mini-tablet or plurality of mini-tablets, wherein the composition comprises up to about 125 mg of substantially amorphous or amorphous Compound 1.

Another aspect of the present invention provides a method of administering a pharmaceutical composition by orally administering to a patient twice per day the composition comprising a mini-tablet or plurality of mini-tablets, wherein the composition comprises up to about 150 mg of substantially amorphous or amorphous Compound 1.

Another aspect of the present invention provides a method of administering a pharmaceutical composition by orally administering to a patient twice per day the composition comprising a mini-tablet or plurality of mini-tablets, wherein the composition comprises up to about 175 mg of substantially amorphous or amorphous Compound 1.

Another aspect of the present invention provides a method of administering a pharmaceutical composition by orally administering to a patient twice per day the composition comprising a mini-tablet or plurality of mini-tablets, wherein the composition comprises up to about 200 mg of substantially amorphous or amorphous Compound 1.

Another aspect of the present invention provides a method of administering a pharmaceutical composition by orally administering to a patient twice per day the composition comprising a mini-tablet or plurality of mini-tablets, wherein the composition comprises up to about 225 mg of substantially amorphous or amorphous Compound 1.

Another aspect of the present invention provides a method of administering a pharmaceutical composition by orally administering to a patient twice per day the composition comprising a mini-tablet or plurality of mini-tablets, wherein the composition comprises up to about 250 mg of substantially amorphous or amorphous Compound 1.

Another aspect of the present invention provides a method of administering a pharmaceutical composition by orally administering to a patient once every 12 hours. The composition comprising a mini-tablet or plurality of mini-tablets, wherein the composition comprises up to about 1 mg of substantially amorphous or amorphous Compound 1.

Another aspect of the present invention provides a method of administering a pharmaceutical composition by orally administering to a patient once every 12 hours. The composition comprising a mini-tablet or plurality of mini-tablets, wherein the composition comprises up to about 5 mg of substantially amorphous or amorphous Compound 1.

Another aspect of the present invention provides a method of administering a pharmaceutical composition by orally administering to a patient once every 12 hours. The composition comprising a mini-tablet or plurality of mini-tablets, wherein the composition comprises up to about 10 mg of substantially amorphous or amorphous Compound 1.

Another aspect of the present invention provides a method of administering a pharmaceutical composition by orally administering to a patient once every 12 hours. The composition comprising a mini-tablet or plurality of mini-tablets, wherein the composition comprises up to about 12.5 mg of substantially amorphous or amorphous Compound 1.

Another aspect of the present invention provides a method of administering a pharmaceutical composition by orally administering to a patient once every 12 hours. The composition comprising a mini-tablet or plurality of mini-tablets, wherein the composition comprises up to about 15 mg of substantially amorphous or amorphous Compound 1.

Another aspect of the present invention provides a method of administering a pharmaceutical composition by orally administering to a patient once every 12 hours. The composition comprising a mini-tablet or plurality of mini-tablets, wherein the composition comprises up to about 20 mg of substantially amorphous or amorphous Compound 1.

Another aspect of the present invention provides a method of administering a pharmaceutical composition by orally administering to a patient once every 12 hours. The composition comprising a mini-tablet or plurality of mini-tablets, wherein the composition comprises up to about 25 mg of substantially amorphous or amorphous Compound 1.

Another aspect of the present invention provides a method of administering a pharmaceutical composition by orally administering to a patient once every 12 hours. The composition comprising a mini-tablet or plurality of mini-tablets, wherein the composition comprises up to about 30 mg of substantially amorphous or amorphous Compound 1.

Another aspect of the present invention provides a method of administering a pharmaceutical composition by orally administering to a patient once every 12 hours. The composition comprising a mini-tablet or plurality of mini-tablets, wherein the composition comprises up to about 35 mg of substantially amorphous or amorphous Compound 1.

Another aspect of the present invention provides a method of administering a pharmaceutical composition by orally administering to a patient once every 12 hours. The composition comprising a mini-tablet or plurality of mini-tablets, wherein the composition comprises up to about 37.5 mg of substantially amorphous or amorphous Compound 1.

Another aspect of the present invention provides a method of administering a pharmaceutical composition by orally administering to a patient once every 12 hours. The composition comprising a mini-tablet or plurality of mini-tablets, wherein the composition comprises up to about 40 mg of substantially amorphous or amorphous Compound 1.

Another aspect of the present invention provides a method of administering a pharmaceutical composition by orally administering to a patient once every 12 hours. The composition comprising a mini-tablet or plurality of mini-tablets, wherein the composition comprises up to about 45 mg of substantially amorphous or amorphous Compound 1.

Another aspect of the present invention provides a method of administering a pharmaceutical composition by orally administering to a patient once every 12 hours. The composition comprising a mini-tablet or plurality of mini-tablets, wherein the composition comprises up to about 50 mg of substantially amorphous or amorphous Compound 1.

Another aspect of the present invention provides a method of administering a pharmaceutical composition by orally administering to a patient once every 12 hours. The composition comprising a mini-tablet or plurality of mini-tablets, wherein the composition comprises up to about 62.5 mg of substantially amorphous or amorphous Compound 1.

Another aspect of the present invention provides a method of administering a pharmaceutical composition by orally administering to a patient once every 12 hours. The composition comprising a mini-tablet or plurality of mini-tablets, wherein the composition comprises up to about 75 mg of substantially amorphous or amorphous Compound 1.

Another aspect of the present invention provides a method of administering a pharmaceutical composition by orally administering to a patient once every 12 hours. The composition comprising a mini-tablet or plurality of mini-tablets, wherein the composition comprises up to about 100 mg of substantially amorphous or amorphous Compound 1.

Another aspect of the present invention provides a method of administering a pharmaceutical composition by orally administering to a patient once every 12 hours. The composition comprising a mini-tablet or plurality of mini-tablets, wherein the composition comprises up to about 125 mg of substantially amorphous or amorphous Compound 1.

Another aspect of the present invention provides a method of administering a pharmaceutical composition by orally administering to a patient once every 12 hours. The composition comprising a mini-tablet or plurality of mini-tablets, wherein the composition comprises up to about 150 mg of substantially amorphous or amorphous Compound 1.

Another aspect of the present invention provides a method of administering a pharmaceutical composition by orally administering to a patient once every 12 hours. The composition comprising a mini-tablet or plurality of mini-tablets, wherein the composition comprises up to about 175 mg of substantially amorphous or amorphous Compound 1.

Another aspect of the present invention provides a method of administering a pharmaceutical composition by orally administering to a patient once every 12 hours. The composition comprising a mini-tablet or plurality of mini-tablets, wherein the composition comprises up to about 200 mg of substantially amorphous or amorphous Compound 1.

Another aspect of the present invention provides a method of administering a pharmaceutical composition by orally administering to a patient once every 12 hours. The composition comprising a mini-tablet or plurality of mini-tablets, wherein the composition comprises up to about 225 mg of substantially amorphous or amorphous Compound 1.

Another aspect of the present invention provides a method of administering a pharmaceutical composition by orally administering to a patient once every 12 hours. The composition comprising a mini-tablet or plurality of mini-tablets, wherein the composition comprises up to about 250 mg of substantially amorphous or amorphous Compound 1.

In still other aspects of the present invention, a pharmaceutical composition as described herein is orally administered to a patient once every 24 hours.

Another aspect of the present invention provides a method of administering a pharmaceutical composition by orally administering to a patient once per day the composition comprising a mini-tablet or plurality of mini-tablets, wherein the composition comprises at least about 10 mg of substantially amorphous or amorphous Compound 1.

Another aspect of the present invention provides a method of administering a pharmaceutical composition by orally administering to a patient once per day the composition comprising a mini-tablet or plurality of mini-tablets, wherein the composition comprises at least about 12.5 mg of substantially amorphous or amorphous Compound 1.

Another aspect of the present invention provides a method of administering a pharmaceutical composition by orally administering to a patient once per day the composition comprising a mini-tablet or plurality of mini-tablets, wherein the composition comprises at least about 15 mg of substantially amorphous or amorphous Compound 1.

Another aspect of the present invention provides a method of administering a pharmaceutical composition by orally administering to a patient once per day the composition comprising a mini-tablet or plurality of mini-tablets, wherein the composition comprises at least about 20 mg of substantially amorphous or amorphous Compound 1.

Another aspect of the present invention provides a method of administering a pharmaceutical composition by orally administering to a patient once per day the composition comprising a mini-tablet or plurality of mini-tablets, wherein the composition comprises at least about 25 mg of substantially amorphous or amorphous Compound 1.

Another aspect of the present invention provides a method of administering a pharmaceutical composition by orally administering to a patient once per day the composition comprising a mini-tablet or plurality of mini-tablets, wherein the composition comprises at least about 30 mg of substantially amorphous or amorphous Compound 1.

Another aspect of the present invention provides a method of administering a pharmaceutical composition by orally administering to a patient once per day the composition comprising a mini-tablet or plurality of mini-tablets, wherein the composition comprises at least about 35 mg of substantially amorphous or amorphous Compound 1.

Another aspect of the present invention provides a method of administering a pharmaceutical composition by orally administering to a patient once per day the composition comprising a mini-tablet or plurality of mini-tablets, wherein the composition comprises at least about 37.5 mg of substantially amorphous or amorphous Compound 1.

Another aspect of the present invention provides a method of administering a pharmaceutical composition by orally administering to a patient once per day the composition comprising a mini-tablet or plurality of mini-tablets, wherein the composition comprises at least about 40 mg of substantially amorphous or amorphous Compound 1.

Another aspect of the present invention provides a method of administering a pharmaceutical composition by orally administering to a patient once per day the composition comprising a mini-tablet or plurality of mini-tablets, wherein the composition comprises at least about 45 mg of substantially amorphous or amorphous Compound 1.

Another aspect of the present invention provides a method of administering a pharmaceutical composition by orally administering to a patient once per day the composition comprising a mini-tablet or plurality of mini-tablets, wherein the composition comprises at least about 50 mg of substantially amorphous or amorphous Compound 1.

Another aspect of the present invention provides a method of administering a pharmaceutical composition by orally administering to a patient once per day the composition comprising a mini-tablet or plurality of mini-tablets, wherein the composition comprises at least about 62.5 mg of substantially amorphous or amorphous Compound 1.

Another aspect of the present invention provides a method of administering a pharmaceutical composition by orally administering to a patient once per day the composition comprising a mini-tablet or plurality of mini-tablets, wherein the composition comprises at least about 75 mg of substantially amorphous or amorphous Compound 1.

Another aspect of the present invention provides a method of administering a pharmaceutical composition by orally administering to a patient once per day the composition comprising a mini-tablet or plurality of mini-tablets, wherein the composition comprises at least about 100 mg of substantially amorphous or amorphous Compound 1.

Another aspect of the present invention provides a method of administering a pharmaceutical composition by orally administering to a patient once per day the composition comprising a mini-tablet or plurality of mini-tablets, wherein the composition comprises at least about 125 mg of substantially amorphous or amorphous Compound 1.

Another aspect of the present invention provides a method of administering a pharmaceutical composition by orally administering to a patient once per day the composition comprising a mini-tablet or plurality of mini-tablets, wherein the composition comprises at least about 150 mg of substantially amorphous or amorphous Compound 1.

Another aspect of the present invention provides a method of administering a pharmaceutical composition by orally administering to a patient once per day the composition comprising a mini-tablet or plurality of mini-tablets, wherein the composition comprises at least about 175 mg of substantially amorphous or amorphous Compound 1.

Another aspect of the present invention provides a method of administering a pharmaceutical composition by orally administering to a patient once per day the composition comprising a mini-tablet or plurality of mini-tablets, wherein the composition comprises at least about 200 mg of substantially amorphous or amorphous Compound 1.

Another aspect of the present invention provides a method of administering a pharmaceutical composition by orally administering to a patient once per day the composition comprising a mini-tablet or plurality of mini-tablets, wherein the composition comprises at least about 225 mg of substantially amorphous or amorphous Compound 1.

Another aspect of the present invention provides a method of administering a pharmaceutical composition by orally administering to a patient once per day the composition comprising a mini-tablet or plurality of mini-tablets, wherein the composition comprises at least about 250 mg of substantially amorphous or amorphous Compound 1.

Another aspect of the present invention provides a method of administering a pharmaceutical composition comprising orally administering to a patient at least once per day at least one capsule or packet containing a mini-tablet or plurality of mini-tablets (in one example, ranging from about 2 to 20; from about 2 to 6; from about 5 to 15; from about 20 to 50, from about 25 to about 35, or from about 27 to about 32 mini-tablets, for example, 6, 10, 29 or 48 mini-tablets per capsule or packet, and in a specific example, 29 mini-tablets per capsule or packet; in another example, ranging from about 1 to about 20; in another example, 1 mini-tablet per capsule or packet or 2, 3, 4, 5, 7, 8, 10, 15 or 20 tablets per capsule, packet, or plurality of capsules or packets) and wherein each mini-tablet comprises a pharmaceutical composition containing a solid dispersion of substantially amorphous Compound 1, one or more fillers, a sweetener, a disintegrant, optionally a wetting agent, a glidant, and a lubricant, each of which is described above and in the Examples below, wherein the solid dispersion comprises up to about 5 mg (e.g., about 0.25 mg, about 0.5 mg, about 0.75 mg, about 1 mg, about 1.25 mg, about 1.5 mg, about 1.75 mg, about 2 mg, about 2.25 mg, about 2.5 mg, about 2.75 mg, about 3 mg, about 3.25 mg, about 3.5 mg, about 3.75 mg, about 4 mg, about 4.25 mg, about 4.5 mg or about 4.75 mg) of substantially amorphous or amorphous Compound 1.

Another aspect of the present invention provides a method of administering a pharmaceutical composition comprising orally administering to a patient at least once per day at least one capsule or packet containing a mini-tablet or plurality of mini-tablets (in one example, ranging from about 2 to 20; from about 2 to 6; from about 5 to 15; from about 20 to 50, from about 25 to about 35, or from about 27 to about 32 mini-tablets, for example, 6, 10, 29 or 48 mini-tablets per capsule or packet, and in a specific example, 29 mini-tablets per capsule or packet; in another example, ranging from about 1 to about 20; in another example, 1 mini-tablet per capsule or packet or 2, 3, 4, 5, 7, 8, 10, 15 or 20 mini-tablets per capsule, packet or plurality of capsules or packets) and wherein each mini-tablet comprises a pharmaceutical composition containing a solid dispersion of substantially amorphous Compound 1, one or more fillers, a sweetener, a disintegrant, a glidant, and a lubricant, each of which is described above and in the Examples below, wherein the solid dispersion comprises up to about 5 mg (e.g., about 0.25 mg, about 0.5 mg, about 0.75 mg, about 1 mg, about 1.25 mg, about 1.5 mg, about 1.75 mg, about 2 mg, about 2.25 mg, about 2.5 mg, about 2.75 mg, about 3 mg, about 3.25 mg, about 3.5 mg, about 3.75 mg, about 4 mg, about 4.25 mg, about 4.5 mg or about 4.75 mg) of substantially amorphous or amorphous Compound 1.

Another aspect of the present invention provides a method of administering a pharmaceutical composition comprising orally administering to a patient at least once per day a mini-tablet or plurality of mini-tablets (for example, ranging from about 20 to 40, from about 25 to about 35, or from about 27 to about 32 mini-tablets per capsule or packet, such as 21, 26, 39, and 52 mini-tablets) and wherein each mini-tablet comprises a pharmaceutical composition containing a solid dispersion of substantially amorphous Compound 1, one or more fillers, a sweetener, a disintegrant, optionally a wetting agent, a glidant, and a lubricant, each of which is described above and in the Examples below, and wherein the mini-tablet or plurality of mini-tablets, collectively, comprises up to about 250 mg (e.g., about 5 mg, about 10 mg, about 12.5 mg, about 15 mg, about 20 mg, about 25 mg, about 30 mg, about 35 mg, about 37.5 mg, about 40 mg, about 45 mg, about 50 mg, about 55 mg, about 60 mg, about 62.5 mg, about 65 mg, about 70 mg, about 75 mg, about 80 mg, about 85 mg, about 87.5 mg, about 90 mg, about 95 mg, about 100 mg about 110 mg, about 112.5 mg, about 120 mg, about 125 mg, about 130 mg, about 137.5 mg, about 140 mg, about 150 mg, about 160 mg, about 162.5 mg, about 170 mg, about 175 mg, about 187.5 mg, about 200 mg, about 212.5 mg, about 225 mg, about 237.5 mg or about 250 mg) of substantially amorphous or amorphous Compound 1.

Another aspect of the present invention provides a method of administering a pharmaceutical composition comprising orally administering to a patient at least once per day a mini-tablet or plurality of mini-tablets (for example, ranging from about 1 to about 140, from about 20 to about 100, from about 20 to about 80, from about 20 to about 60, from about 20 to about 40, from about 25 to about 35, or from about 27 to about 32 mini-tablets per capsule or packet) and wherein each mini-tablet comprises a pharmaceutical composition containing a solid dispersion of substantially amorphous Compound 1, one or more fillers, a sweetener, a disintegrant, a glidant, and a lubricant, each of which is described above and in the Examples below, and wherein the mini-tablet or plurality of mini-tablets comprises up to about 250 mg (e.g., about 5 mg, about 10 mg, 12.5 mg, about 15 mg, about 20 mg, about 25 mg, about 30 mg, about 35 mg, about 37.5 mg, about 40 mg, about 45 mg, about 50 mg, about 55 mg, about 60 mg, about 62.5 mg, about 65 mg, about 70 mg, about 75 mg, about 80 mg, about 85 mg, about 87.5 mg, about 90 mg, about 95 mg, about 100 mg about 110 mg, about 112.5 mg, about 120 mg, about 125 mg, about 130 mg, about 137.5 mg, about 140 mg, about 150 mg, about 160 mg, about 162.5 mg, about 170 mg, about 175 mg, about 187.5 mg, about 200 mg, about 212.5 mg, about 225 mg, about 237.5 mg or about 250 mg) of substantially amorphous or amorphous Compound 1.

Another aspect of the present invention provides a method of administering a pharmaceutical composition by orally administering to a pediatric patient every 12 hours wherein the composition comprising 50 mg of substantially amorphous or amorphous Compound 1; wherein the composition can be in a form of tablet, mini-tablet, granules, pellets, troches and other dosage forms. In one embodiment, the pediatric patient is two through five years of age. In another embodiment, the pediatric patient weighs less than 14 kilograms.

Another aspect of the present invention provides a method of administering a pharmaceutical composition by orally administering to a pediatric patient every 12 hours wherein the composition comprising 50 mg of substantially amorphous or amorphous Compound 1; wherein the composition can be in a form of tablet, mini-tablet, granules, pellets, troches and other dosage forms; wherein the pediatric patient is two through five years of age and weighs less than 14 kilograms.

Another aspect of the present invention provides a method of administering a pharmaceutical composition by orally administering to a pediatric patient every 12 hours wherein the composition comprising 75 mg of substantially amorphous or amorphous Compound 1; wherein the composition can be in a form of tablet, mini-tablet, granules, pellets, troches and other dosage forms. In one embodiment, the pediatric patient is two through five years of age. In another embodiment, the pediatric patient weighs 14 kilograms or more than 14 kilograms.

Another aspect of the present invention provides a method of administering a pharmaceutical composition by orally administering to a pediatric patient every 12 hours wherein the composition comprising 75 mg of substantially amorphous or amorphous Compound 1; wherein the composition can be in a form of tablet, mini-tablet, granules, pellets, troches and other dosage forms; wherein the pediatric patient is two through five years of age and weighs 14 kilograms or more than 14 kilograms.

Another aspect of the present invention provides a method of administering a pharmaceutical composition by orally administering to a pediatric patient every 12 hours wherein the composition comprising 50 mg of substantially amorphous or amorphous Compound 1; wherein the composition can be in a form of tablet, mini-tablet, granules, pellets, troches and other dosage forms. In one embodiment, the pediatric patient is less than 2 years of age. In another embodiment, the pediatric patient weighs from about 7.5 kilograms to less than 14 kilograms.

Another aspect of the present invention provides a method of administering a pharmaceutical composition by orally administering to a pediatric patient every 12 hours wherein the composition comprising 50 mg of substantially amorphous or amorphous Compound 1; wherein the composition can be in a form of tablet, mini-tablet, granules, pellets, troches and other dosage forms; wherein the pediatric patient is less than two years of age and weighs from about 7.5 kilograms to less than 14 kilograms.

Another aspect of the present invention provides a method of administering a pharmaceutical composition by orally administering to a pediatric patient every 12 hours wherein the composition comprising 35 mg of substantially amorphous or amorphous Compound 1; wherein the composition can be in a form of tablet, mini-tablet, granules, pellets, troches and other dosage forms. In one embodiment, the pediatric patient is less than 2 years of age. In another embodiment, the pediatric patient weighs from about 5 kilograms to less than 7.5 kilograms.

Another aspect of the present invention provides a method of administering a pharmaceutical composition by orally administering to a pediatric patient every 12 hours wherein the composition comprising 35 mg of substantially amorphous or amorphous Compound 1; wherein the composition can be in a form of tablet, mini-tablet, granules, pellets, troches and other dosage forms; wherein the pediatric patient is less than two years of age and weighs from about 5 kilograms to less than 7.5 kilograms.

Another aspect of the present invention provides a method of administering a pharmaceutical composition by orally administering to a pediatric patient every 12 hours wherein the composition comprising 35 mg of substantially amorphous or amorphous Compound 1; wherein the composition can be in a form of tablet, mini-tablet, granules, pellets, troches and other dosage forms. In one embodiment, the pediatric patient is less than 2 years of age. In another embodiment, the pediatric patient weighs less than 7.5 kilograms.

Another aspect of the present invention provides a method of administering a pharmaceutical composition by orally administering to a pediatric patient every 12 hours wherein the composition comprising 35 mg of substantially amorphous or amorphous Compound 1; wherein the composition can be in a form of tablet, mini-tablet, granules, pellets, troches and other dosage forms; wherein the pediatric patient is less than two years of age and weighs less than 7.5 kilograms.

Another aspect of the present invention provides a method of administering a pharmaceutical composition by orally administering to a pediatric patient every 12 hours wherein the composition comprising 35 mg of substantially amorphous or amorphous Compound 1; wherein the composition can be in a form of tablet, mini-tablet, granules, pellets, troches and other dosage forms. In one embodiment, the pediatric patient is less than 2 years of age. In another embodiment, the pediatric patient weighs 5 kilograms or more than 5 kilograms.

Another aspect of the present invention provides a method of administering a pharmaceutical composition by orally administering to a pediatric patient every 12 hours wherein the composition comprising 35 mg of substantially amorphous or amorphous Compound 1; wherein the composition can be in a form of tablet, mini-tablet, granules, pellets, troches and other dosage forms; wherein the pediatric patient is less than two years of age and weighs 5 kilograms or more than 5 kilograms.

Another aspect of the present invention provides a method of administering a pharmaceutical composition by orally administering to a pediatric patient every 12 hours wherein the composition comprising 25 mg of substantially amorphous or amorphous Compound 1; wherein the composition can be in a form of tablet, mini-tablet, granules, pellets, troches and other dosage forms. In one embodiment, the pediatric patient is less than 2 years of age. In another embodiment, the pediatric patient weighs from about 2.5 kilograms to less than 5 kilograms.

Another aspect of the present invention provides a method of administering a pharmaceutical composition by orally administering to a pediatric patient every 12 hours wherein the composition comprising 25 mg of substantially amorphous or amorphous Compound 1; wherein the composition can be in a form of tablet, mini-tablet, granules, pellets, troches and other dosage forms; wherein the pediatric patient is less than two years of age and weighs from about 2.5 kilograms to less than 5 kilograms.

Another aspect of the present invention provides a method of administering a pharmaceutical composition by orally administering to a pediatric patient every 12 hours wherein the composition comprising 25 mg of substantially amorphous or amorphous Compound 1; wherein the composition can be in a form of tablet, mini-tablet, granules, pellets, troches and other dosage forms. In one embodiment, the pediatric patient is less than 2 years of age. In another embodiment, the pediatric patient weighs less than 5 kilograms.

Another aspect of the present invention provides a method of administering a pharmaceutical composition by orally administering to a pediatric patient every 12 hours wherein the composition comprising 25 mg of substantially amorphous or amorphous Compound 1; wherein the composition can be in a form of tablet, mini-tablet, granules, pellets, troches and other dosage forms; wherein the pediatric patient is less than two years of age and weighs less than 5 kilograms.

Another aspect of the present invention provides a method of administering a pharmaceutical composition by orally administering to a pediatric patient every 12 hours wherein the composition comprising 25 mg of substantially amorphous or amorphous Compound 1; wherein the composition can be in a form of tablet, mini-tablet, granules, pellets, troches and other dosage forms. In one embodiment, the pediatric patient is less than 2 years of age. In another embodiment, the pediatric patient weighs 2.5 kilograms or more than 2.5 kilograms.

Another aspect of the present invention provides a method of administering a pharmaceutical composition by orally administering to a pediatric patient every 12 hours wherein the composition comprising 25 mg of substantially amorphous or amorphous Compound 1; wherein the composition can be in a form of tablet, mini-tablet, granules, pellets, troches and other dosage forms; wherein the pediatric patient is less than two years of age and weighs 2.5 kilograms or more than 2.5 kilograms.

Another aspect of the present invention provides a method of administering a pharmaceutical composition by orally administering to a pediatric patient every 12 hours wherein the composition comprising 50 mg of substantially amorphous or amorphous Compound 1; wherein the composition can be in a form of tablet, mini-tablet, granules, pellets, troches and other dosage forms; wherein the pediatric patient is two through five years of age and has a CFTR gating mutation in at least one allele. Another aspect of the present invention provides a method of administering a pharmaceutical composition by orally administering to a pediatric patient every 12 hours wherein the composition comprising 50 mg of substantially amorphous or amorphous Compound 1; wherein the composition can be in a form of tablet, mini-tablet, granules, pellets, troches and other dosage forms; wherein the pediatric patient is less than two years of age and has a CFTR gating mutation in at least one allele.

Another aspect of the present invention provides a method of administering a pharmaceutical composition by orally administering to a pediatric patient every 12 hours wherein the composition comprising 75 mg of substantially amorphous or amorphous Compound 1; wherein the composition can be in a form of tablet, mini-tablet, granules, pellets, troches and other dosage forms; wherein the pediatric patient is two through five years of age and has a CFTR gating mutation in at least one allele. Another aspect of the present invention provides a method of administering a pharmaceutical composition by orally administering to a pediatric patient every 12 hours wherein the composition comprising 75 mg of substantially amorphous or amorphous Compound 1; wherein the composition can be in a form of tablet, mini-tablet, granules, pellets, troches and other dosage forms; wherein the pediatric patient is less than two years of age and has a CFTR gating mutation in at least one allele.

Another aspect of the present invention provides a method of administering a pharmaceutical composition by orally administering to a pediatric patient every 12 hours wherein the composition comprising 75 mg of substantially amorphous or amorphous Compound 1; wherein the composition can be in a form of tablet, mini-tablet, granules, pellets, troches and other dosage forms; wherein the pediatric patient weighs 14 kilograms or more and has a CFTR gating mutation in at least one allele. Another aspect of the present invention provides a method of administering a pharmaceutical composition by orally administering to a pediatric patient every 12 hours wherein the composition comprising 50 mg of substantially amorphous or amorphous Compound 1; wherein the composition can be in a form of tablet, mini-tablet, granules, pellets, troches and other dosage forms; wherein the pediatric patient weighs less than 14 kilograms and has a CFTR gating mutation in at least one allele. Another aspect of the present invention provides a method of administering a pharmaceutical composition by orally administering to a pediatric patient every 12 hours wherein the composition comprising 50 mg of substantially amorphous or amorphous Compound 1; wherein the composition can be in a form of tablet, mini-tablet, granules, pellets, troches and other dosage forms; wherein the pediatric patient weighs from about 7.5 kilograms to less than 14 kilograms and has a CFTR gating mutation in at least one allele. Another aspect of the present invention provides a method of administering a pharmaceutical composition by orally administering to a pediatric patient every 12 hours wherein the composition comprising 35 mg of substantially amorphous or amorphous Compound 1; wherein the composition can be in a form of tablet, mini-tablet, granules, pellets, troches and other dosage forms; wherein the pediatric patient weighs from about 5 kilograms to less than 7.5 kilograms and has a CFTR gating mutation in at least one allele. Another aspect of the present invention provides a method of administering a pharmaceutical composition by orally administering to a pediatric patient every 12 hours wherein the composition comprising 25 mg of substantially amorphous or amorphous Compound 1; wherein the composition can be in a form of tablet, mini-tablet, granules, pellets, troches and other dosage forms; wherein the pediatric patient weighs from about 2.5 kilograms to less than 5 kilograms and has a CFTR gating mutation in at least one allele.

In some embodiments, the present invention provides a method of administering a pharmaceutical composition comprising orally administering to a patient a unit dose form comprising a mini-tablet or plurality of mini-tablets, wherein each of the mini-tablets comprises:
  a) a solid dispersion of substantially amorphous or amorphous Compound 1 and a polymer, the polymer comprising HPMCAS;
  b) one or more fillers;
  c) a sweetener;
  d) a disintegrant;
  e) optionally a wetting agent;
  f) a glidant; and
  g) a lubricant,
wherein the unit dose form comprises an amount of substantially amorphous Compound 1 or amorphous Compound 1 ranging from about 1 mg to about 250 mg.

In some embodiments, the present invention provides a method of administering a pharmaceutical composition comprising orally administering to a patient a unit dose form comprising a mini-tablet or plurality of mini-tablets, wherein each of the mini-tablets comprises:
  a) a solid dispersion of substantially amorphous or amorphous Compound 1 and a polymer, the polymer comprising HPMCAS;
  b) one or more fillers;
  c) a sweetener;
  d) a disintegrant;
  e) optionally a wetting agent;
  f) a glidant; and
  g) a lubricant,
wherein the unit dose form comprises about 15 mg of substantially amorphous Compound 1 or amorphous Compound 1.

In some embodiments, the present invention provides a method of administering a pharmaceutical composition comprising orally administering to a patient a unit dose form comprising a mini-tablet or plurality of mini-tablets, wherein each of the mini-tablets comprises:
  a) a solid dispersion of substantially amorphous or amorphous Compound 1 and a polymer, the polymer comprising HPMCAS;
  b) one or more fillers;
  c) a sweetener;
  d) a disintegrant;
  e) optionally a wetting agent;
  f) a glidant; and
  g) a lubricant,
wherein the unit dose form comprises about 5 mg of substantially amorphous Compound 1 or amorphous Compound 1.

In some embodiments, the present invention provides a method of administering a pharmaceutical composition comprising orally administering to a patient a unit dose form comprising a mini-tablet or plurality of mini-tablets, wherein each of the mini-tablets comprises:
  a) a solid dispersion of substantially amorphous or amorphous Compound 1 and a polymer, the polymer comprising HPMCAS;
  b) one or more fillers;
  c) a sweetener;
  d) a disintegrant;
  e) optionally a wetting agent;
  f) a glidant; and
  g) a lubricant,
wherein the unit dose form comprises about 10 mg of substantially amorphous Compound 1 or amorphous Compound 1.

In some embodiments, the present invention provides a method of administering a pharmaceutical composition comprising orally administering to a patient a unit dose form comprising a mini-tablet or plurality of mini-tablets, wherein each of the mini-tablets comprises:
  a) a solid dispersion of substantially amorphous or amorphous Compound 1 and a polymer, the polymer comprising HPMCAS;
  b) one or more fillers;
  c) a sweetener;
  d) a disintegrant;
  e) optionally a wetting agent;
  f) a glidant; and
  g) a lubricant,
wherein the unit dose form comprises about 12.5 mg of substantially amorphous Compound 1 or amorphous Compound 1.

In some embodiments, the present invention provides a method of administering a pharmaceutical composition comprising orally administering to a patient a unit dose form comprising a mini-tablet or plurality of mini-tablets, wherein each of the mini-tablets comprises:

a) a solid dispersion of substantially amorphous or amorphous Compound 1 and a polymer, the polymer comprising HPMCAS;
b) one or more fillers;
c) a sweetener;
d) a disintegrant;
e) optionally a wetting agent;
f) a glidant; and
g) a lubricant, wherein the unit dose form comprises about 20 mg of substantially amorphous Compound 1 or amorphous Compound 1.

In some embodiments, the present invention provides a method of administering a pharmaceutical composition comprising orally administering to a patient a unit dose form comprising a mini-tablet or plurality of mini-tablets, wherein each of the mini-tablets comprises:

a) a solid dispersion of substantially amorphous or amorphous Compound 1 and a polymer, the polymer comprising HPMCAS;
b) one or more fillers;
c) a sweetener;
d) a disintegrant;
e) optionally a wetting agent;
f) a glidant; and
g) a lubricant, wherein the unit dose form comprises about 25 mg of substantially amorphous Compound 1 or amorphous Compound 1.

In some embodiments, the present invention provides a method of administering a pharmaceutical composition comprising orally administering to a patient a unit dose form comprising a mini-tablet or plurality of mini-tablets, wherein each of the mini-tablets comprises:

a) a solid dispersion of substantially amorphous or amorphous Compound 1 and a polymer, the polymer comprising HPMCAS;
b) one or more fillers;
c) a sweetener;
d) a disintegrant;
e) optionally a wetting agent;
f) a glidant; and
g) a lubricant, wherein the unit dose form comprises about 30 mg of substantially amorphous Compound 1 or amorphous Compound 1.

In some embodiments, the present invention provides a method of administering a pharmaceutical composition comprising orally administering to a patient a unit dose form comprising a mini-tablet or plurality of mini-tablets, wherein each of the mini-tablets comprises:

a) a solid dispersion of substantially amorphous or amorphous Compound 1 and a polymer, the polymer comprising HPMCAS;
b) one or more fillers;
c) a sweetener;
d) a disintegrant;
e) optionally a wetting agent;
f) a glidant; and
g) a lubricant, wherein the unit dose form comprises about 35 mg of substantially amorphous Compound 1 or amorphous Compound 1.

In some embodiments, the present invention provides a method of administering a pharmaceutical composition comprising orally administering to a patient a unit dose form comprising a mini-tablet or plurality of mini-tablets, wherein each of the mini-tablets comprises:

a) a solid dispersion of substantially amorphous or amorphous Compound 1 and a polymer, the polymer comprising HPMCAS;
b) one or more fillers;
c) a sweetener;
d) a disintegrant;
e) optionally a wetting agent;
f) a glidant; and
g) a lubricant, wherein the unit dose form comprises about 37.5 mg of substantially amorphous Compound 1 or amorphous Compound 1.

In some embodiments, the present invention provides a method of administering a pharmaceutical composition comprising orally administering to a patient a unit dose form comprising a mini-tablet or plurality of mini-tablets, wherein each of the mini-tablets comprises:

a) a solid dispersion of substantially amorphous or amorphous Compound 1 and a polymer, the polymer comprising HPMCAS;
b) one or more fillers;
c) a sweetener;
d) a disintegrant;
e) optionally a wetting agent;
f) a glidant; and
g) a lubricant, wherein the unit dose form comprises about 40 mg of substantially amorphous Compound 1 or amorphous Compound 1.

In some embodiments, the present invention provides a method of administering a pharmaceutical composition comprising orally administering to a patient a unit dose form comprising a mini-tablet or plurality of mini-tablets, wherein each of the mini-tablets comprises:

a) a solid dispersion of substantially amorphous or amorphous Compound 1 and a polymer, the polymer comprising HPMCAS;
b) one or more fillers;
c) a sweetener;
d) a disintegrant;
e) optionally a wetting agent;
f) a glidant; and
g) a lubricant, wherein the unit dose form comprises about 45 mg of substantially amorphous Compound 1 or amorphous Compound 1.

In some embodiments, the present invention provides a method of administering a pharmaceutical composition comprising orally administering to a patient a unit dose form comprising a mini-tablet or plurality of mini-tablets, wherein each of the mini-tablets comprises:

a) a solid dispersion of substantially amorphous or amorphous Compound 1 and a polymer, the polymer comprising HPMCAS;
b) one or more fillers;
c) a sweetener;
d) a disintegrant;
e) optionally a wetting agent;
f) a glidant; and
g) a lubricant, wherein the unit dose form comprises about 50 mg of substantially amorphous Compound 1 or amorphous Compound 1.

In some embodiments, the present invention provides a method of administering a pharmaceutical composition comprising orally administering to a patient a unit dose form comprising a mini-tablet or plurality of mini-tablets, wherein each of the mini-tablets comprises:
 a) a solid dispersion of substantially amorphous or amorphous Compound 1 and a polymer, the polymer comprising HPMCAS;
 b) one or more fillers;
 c) a sweetener;
 d) a disintegrant;
 e) optionally a wetting agent;
 f) a glidant; and
 g) a lubricant,
wherein the unit dose form comprises about 62.5 mg of substantially amorphous Compound 1 or amorphous Compound 1.

In some embodiments, the present invention provides a method of administering a pharmaceutical composition comprising orally administering to a patient a unit dose form comprising a mini-tablet or plurality of mini-tablets, wherein each of the mini-tablets comprises:
 a) a solid dispersion of substantially amorphous or amorphous Compound 1 and a polymer, the polymer comprising HPMCAS;
 b) one or more fillers;
 c) a sweetener;
 d) a disintegrant;
 e) optionally a wetting agent;
 f) a glidant; and
 g) a lubricant,
wherein the unit dose form comprises about 75 mg of substantially amorphous Compound 1 or amorphous Compound 1.

In some embodiments, the present invention provides a method of administering a pharmaceutical composition comprising orally administering to a patient a unit dose form comprising a mini-tablet or plurality of mini-tablets, wherein each of the mini-tablets comprises:
 a) a solid dispersion of substantially amorphous or amorphous Compound 1 and a polymer, the polymer comprising HPMCAS;
 b) one or more fillers;
 c) a sweetener;
 d) a disintegrant;
 e) optionally a wetting agent;
 f) a glidant; and
 g) a lubricant,
wherein the unit dose form comprises about 100 mg of substantially amorphous Compound 1 or amorphous Compound 1.

In some embodiments, the present invention provides a method of administering a pharmaceutical composition comprising orally administering to a patient a unit dose form comprising a mini-tablet or plurality of mini-tablets, wherein each of the mini-tablets comprises:
 a) a solid dispersion of substantially amorphous or amorphous Compound 1 and a polymer, the polymer comprising HPMCAS;
 b) one or more fillers;
 c) a sweetener;
 d) a disintegrant;
 e) optionally a wetting agent;
 f) a glidant; and
 g) a lubricant,
wherein the unit dose form comprises about 125 mg of substantially amorphous Compound 1 or amorphous Compound 1.

In some embodiments, the present invention provides a method of administering a pharmaceutical composition comprising orally administering to a patient a unit dose form comprising a mini-tablet or plurality of mini-tablets, wherein each of the mini-tablets comprises:
 a) a solid dispersion of substantially amorphous or amorphous Compound 1 and a polymer, the polymer comprising HPMCAS;
 b) one or more fillers;
 c) a sweetener;
 d) a disintegrant;
 e) optionally a wetting agent;
 f) a glidant; and
 g) a lubricant,
wherein the unit dose form comprises about 150 mg of substantially amorphous Compound 1 or amorphous Compound 1.

In some embodiments, the present invention provides a method of administering a pharmaceutical composition comprising orally administering to a patient a unit dose form comprising a mini-tablet or plurality of mini-tablets, wherein each of the mini-tablets comprises:
 a) a solid dispersion of substantially amorphous or amorphous Compound 1 and a polymer, the polymer comprising HPMCAS;
 b) one or more fillers;
 c) a sweetener;
 d) a disintegrant;
 e) optionally a wetting agent;
 f) a glidant; and
 g) a lubricant,
wherein the unit dose form comprises about 175 mg of substantially amorphous Compound 1 or amorphous Compound 1.

In some embodiments, the present invention provides a method of administering a pharmaceutical composition comprising orally administering to a patient a unit dose form comprising a mini-tablet or plurality of mini-tablets, wherein each of the mini-tablets comprises:
 a) a solid dispersion of substantially amorphous or amorphous Compound 1 and a polymer, the polymer comprising HPMCAS;
 b) one or more fillers;
 c) a sweetener;
 d) a disintegrant;
 e) optionally a wetting agent;
 a glidant; and
 g) a lubricant,
wherein the unit dose form comprises about 200 mg of substantially amorphous Compound 1 or amorphous Compound 1.

In some embodiments, the present invention provides a method of administering a pharmaceutical composition comprising orally administering to a patient a unit dose form comprising a mini-tablet or plurality of mini-tablets, wherein each of the mini-tablets comprises:
 a) a solid dispersion of substantially amorphous or amorphous Compound 1 and a polymer, the polymer comprising HPMCAS;
 b) one or more fillers;
 c) a sweetener;
 d) a disintegrant;
 e) optionally a wetting agent;

f) a glidant; and
g) a lubricant,
wherein the unit dose form comprises about 225 mg of substantially amorphous Compound 1 or amorphous Compound 1.

In some embodiments, the present invention provides a method of administering a pharmaceutical composition comprising orally administering to a patient a unit dose form comprising a mini-tablet or plurality of mini-tablets, wherein each of the mini-tablets comprises:
a) a solid dispersion of substantially amorphous or amorphous Compound 1 and a polymer, the polymer comprising HPMCAS;
b) one or more fillers;
c) a sweetener;
d) a disintegrant;
e) optionally a wetting agent;
f) a glidant; and
g) a lubricant,
wherein the unit dose form comprises about 250 mg of substantially amorphous Compound 1 or amorphous Compound 1.

In a further embodiment, the one or more fillers is a binary filler comprising a mixture of 2 fillers. In another further embodiment, the binary filler is a mixture of mannitol and another filler. In another further embodiment, the binary filler is a mixture of lactose and another filler. In another further embodiment, the binary filler is a mixture of mannitol and lactose.

In another further embodiment, the pharmaceutical composition comprises a binary filler, wherein the binary filler comprises mannitol in an amount up to about 100 wt % of the binary filler, In still another further embodiment, the pharmaceutical composition comprises a binary filler, wherein the binary filler comprises lactose in an amount up to about 100 wt % of the binary filler, In still another further embodiment, the pharmaceutical composition comprises a binary filler, wherein the binary filler comprises mannitol in an amount up to about 100 wt % of the binary filler and lactose in an amount such that the sum of the amount of mannitol and lactose is equal to 100 wt %.

In some embodiments, the pharmaceutical composition comprises a binary filler, wherein the binary filler comprises mannitol and another filler in a ratio of about 3:1 mannitol to other filler, a ratio of about 1:1 mannitol to other filler, or a ratio of about 1:3 mannitol to other filler. In some embodiments, the pharmaceutical composition comprises a binary filler, wherein the binary filler comprises lactose and another filler in a ratio of about 3:1 lactose to other filler, a ratio of about 1:1 lactose to other filler, or a ratio of about 1:3 lactose to other filler. In some embodiments, the pharmaceutical composition comprises a binary filler, wherein the binary filler comprises mannitol and lactose in a ratio of about 3:1 mannitol to lactose, a ratio of about 1:1 mannitol to lactose, or a ratio of about 1:3 mannitol to lactose.

In some embodiments, the present invention provides for a method of orally administering the pharmaceutical composition described herein once a day. In other embodiments, the present invention provides for a method of orally administering the pharmaceutical composition described herein twice a day.

Another aspect of the present invention provides a method of administering a pharmaceutical composition by orally administering to a patient at least once per day a mini-tablet or plurality of mini-tablets, the mini-tablets comprising a solid dispersion of substantially amorphous or amorphous Compound 1, one or more fillers, a sweetener, a disintegrant, optionally a wetting agent, a glidant; and a lubricant, in which the capsule or packet comprises at least about 15 mg of substantially amorphous or amorphous Compound 1. In some embodiments, the composition is orally administered to the patient once per day. In another method, the administration comprises orally administering to a patient twice per day a mini-tablet or plurality of mini-tablets, the mini-tablets comprising a mini-tablets of substantially amorphous or amorphous Compound 1, one or more fillers, a sweetener, a disintegrant, optionally a wetting agent, a glidant; and a lubricant, in which the capsule or packet contains at least about 5 mg of substantially amorphous or amorphous Compound 1. In another method, the administration comprises orally administering to a patient twice per day a mini-tablet or plurality of mini-tablets, the mini-tablets comprising a mini-tablets of substantially amorphous or amorphous Compound 1, one or more fillers, a sweetener, a disintegrant, optionally a wetting agent, a glidant; and a lubricant, in which the capsule or packet contains at least about 10 mg of substantially amorphous or amorphous Compound 1. In another method, the administration comprises orally administering to a patient twice per day a mini-tablet or plurality of mini-tablets, the mini-tablets comprising a mini-tablets of substantially amorphous or amorphous Compound 1, one or more fillers, a sweetener, a disintegrant, optionally a wetting agent, a glidant; and a lubricant, in which the capsule or packet contains at least about 15 mg of substantially amorphous or amorphous Compound 1. In another method, the administration comprises orally administering to a patient twice per day a mini-tablet or plurality of mini-tablets, the mini-tablets comprising a mini-tablets of substantially amorphous or amorphous Compound 1, one or more fillers, a sweetener, a disintegrant, optionally a wetting agent, a glidant; and a lubricant, in which the capsule or packet contains at least about 12.5 mg of substantially amorphous or amorphous Compound 1. In another method, the administration comprises orally administering to a patient once per day a mini-tablet or plurality of mini-tablets, the mini-tablets comprising a mini-tablets of substantially amorphous or amorphous Compound 1, one or more fillers, a sweetener, a disintegrant, optionally a wetting agent, a glidant; and a lubricant, in which the capsule or packet contains at least about 25 mg of substantially amorphous or amorphous Compound 1. In another method, the administration comprises orally administering to a patient twice per day a mini-tablet or plurality of mini-tablets, the mini-tablets comprising a mini-tablets of substantially amorphous or amorphous Compound 1, one or more fillers, a sweetener, a disintegrant, optionally a wetting agent, a glidant; and a lubricant, in which the capsule or packet contains at least about 30 mg of substantially amorphous or amorphous Compound 1. In another method, the administration comprises orally administering to a patient twice per day a mini-tablet or plurality of mini-tablets, the mini-tablets comprising a mini-tablets of substantially amorphous or amorphous Compound 1, one or more fillers, a sweetener, a disintegrant, optionally a wetting agent, a glidant; and a lubricant, in which the capsule or packet contains at least about 37.5 mg of substantially amorphous or amorphous Compound 1. In another method, the administration comprises orally administering to a patient twice per day a mini-tablet or plurality of mini-tablets, the mini-tablets comprising a mini-tablets of substantially amorphous or amorphous Compound 1, one or more fillers, a sweetener, a disintegrant, optionally a wetting agent, a glidant; and a lubricant, in which the capsule or packet contains at least about 40 mg of substantially amorphous or amorphous Compound 1. In another method, the administration comprises orally administering to a patient twice per day a mini-tablet or plurality of mini-tablets, the mini-tablets comprising a mini-tablets of substantially amorphous or amorphous Compound 1, one or more fillers, a sweetener, a disintegrant, optionally a wetting agent, a glidant; and a lubricant, in which the capsule or packet contains at least about 50 mg of substantially amorphous or amorphous Compound 1. In another method, the administration comprises orally administering to a patient twice per day a mini-tablet or plurality of mini-tablets, the mini-tablets comprising a mini-tablets of substantially amorphous or amorphous Compound 1, one or more fillers, a sweetener, a disintegrant, optionally a wetting agent, a glidant; and a lubricant, in which the capsule or packet contains at least about 62.5 mg of substantially amorphous or amorphous Compound 1. In another method, the administration comprises orally administering to a patient twice per day a mini-tablet or plurality of mini-tablets, the mini-tablets comprising a mini-tablets of substantially amorphous or amorphous Compound 1, one or more fillers, a sweetener, a disintegrant, optionally a wetting agent, a glidant; and a lubricant, in which the capsule or packet contains at least about 75 mg of substantially amorphous or amorphous Compound 1. In another method, the administration comprises orally administering to a patient twice per day a mini-tablet or plurality of mini-tablets, the mini-tablets comprising a mini-tablets of substantially amorphous or amorphous Compound 1, one or more fillers, a sweetener, a disintegrant, optionally a wetting agent, a glidant; and a lubricant, in which the capsule or packet contains at least about 100 mg of substantially amorphous or amorphous Compound 1. In another method, the administration comprises orally administering to a patient twice per day a mini-tablet or plurality of mini-tablets, the mini-tablets comprising a mini-tablets of substantially amorphous or amorphous Compound 1, one or more fillers, a sweetener, a disintegrant, optionally a wetting agent, a glidant; and a lubricant, in which the capsule or packet contains at least about 125 mg of substantially amorphous or amorphous Compound 1. In another method, the administration comprises orally administering to a patient twice per day a mini-tablet or plurality of mini-tablets, the mini-tablets comprising a mini-tablets of substantially amorphous or amorphous Compound 1, one or more fillers, a sweetener, a disintegrant, optionally a wetting agent, a glidant; and a lubricant, in which the capsule or packet contains at least about 150 mg of substantially amorphous or amorphous Compound 1. In another method, the administration comprises orally administering to a patient twice per day a mini-tablet or plurality of mini-tablets, the mini-tablets comprising a mini-tablets of substantially amorphous or amorphous Compound 1, one or more fillers, a sweetener, a disintegrant, optionally a wetting agent, a glidant; and a lubricant, in which the capsule or packet contains at least about 175 mg of substantially amorphous or amorphous Compound 1. In another method, the administration comprises orally administering to a patient twice per day a mini-tablet or plurality of mini-tablets, the mini-tablets comprising a mini-tablets of substantially amorphous or amorphous Compound 1, one or more fillers, a sweetener, a disintegrant, optionally a wetting agent, a glidant; and a lubricant, in which the capsule or packet contains at least about 200 mg of substantially amorphous or amorphous Compound 1. In another method, the administration comprises orally administering to a patient twice per day a mini-tablet or plurality of mini-tablets, the mini-tablets comprising a mini-tablets of substantially amorphous or amorphous Compound 1, one or more fillers, a sweetener, a disintegrant, optionally a wetting agent, a glidant; and a lubricant, in which the capsule or packet contains at least about 225 mg of substantially amorphous or amorphous Compound 1. In another method, the administration comprises orally administering to a patient twice per day a mini-tablet or plurality of mini-tablets, the mini-tablets comprising a mini-tablets of substantially amorphous or amorphous Compound 1, one or more fillers, a sweetener, a disintegrant, optionally a wetting agent, a glidant; and a lubricant, in which the capsule or packet contains at least about 250 mg of substantially amorphous or amorphous Compound 1.

In another method, the administration includes orally administering to a patient once per day a mini-tablet or plurality of mini-tablets, the mini-tablets comprising a solid dispersion of substantially amorphous or amorphous Compound 1, one or more fillers, a sweetener, a disintegrant, optionally a wetting agent, a glidant; and a lubricant, in which the capsule or packet contains at least about 50 mg of substantially amorphous or amorphous Compound 1. In another method, the administration includes orally administering to a patient twice per day a mini-tablet or plurality of mini-tablets, the mini-tablets comprising a solid dispersion of substantially amorphous or amorphous Compound 1, one or more fillers, a sweetener, a disintegrant, optionally a wetting agent, a glidant; and a lubricant, in which the capsule or packet contains at least about 50 mg of substantially amorphous or amorphous Compound 1. Some pharmaceutical compositions useful in this method comprise a mini-tablet or plurality of mini-tablets comprising a solid dispersion containing at least about 75 mg of substantially amorphous or amorphous Compound 1. In another method, the administration includes orally administering to a patient once per day a mini-tablet or plurality of mini-tablets, the mini-tablets comprising a solid dispersion of substantially amorphous or amorphous Compound 1, one or more fillers, a sweetener, a disintegrant, a glidant, and a lubricant, in which the capsule or packet contains at least about 75 mg of substantially amorphous or amorphous Compound 1. In another method, the administration includes orally administering to a patient twice per day a mini-tablet or plurality of mini-tablets, the mini-tablets comprising a solid dispersion of substantially amorphous or amorphous Compound 1, one or more fillers, a sweetener, a disintegrant, a glidant, and a lubricant, in which the capsule or packet contains at least about 75 mg of substantially amorphous or amorphous Compound 1.

Another aspect of the present invention provides a method of administering a pharmaceutical composition by orally administering to a patient at least once per day a solid dispersion of substantially amorphous or amorphous Compound 1, one or more fillers, a sweetener, a disintegrant, a glidant, and a lubricant, in which the solid dispersion comprises at least about 10 mg of substantially amorphous or amorphous Compound 1. In some embodiments, the solid dispersion is orally administered to the patient once per day. In another method, the administration comprises orally administering to a patient twice per day the solid dispersion, wherein the solid dispersion comprises a solid dispersion of substantially amorphous or amorphous Compound 1, one or more fillers, a sweetener, a disintegrant, a glidant, and a lubricant, in which the solid dispersion comprises at least about 10 mg of substantially amorphous or amorphous Compound 1.

Another aspect of the present invention provides a method of administering a pharmaceutical composition by orally administering to a patient at least once per day a solid dispersion of substantially amorphous or amorphous Compound 1, one or more fillers, a sweetener, a disintegrant, a glidant, and a lubricant, in which the solid dispersion comprises at least about 12.5 mg of substantially amorphous or amorphous Compound 1. In some embodiments, the solid dispersion is orally administered to the patient once per day. In another method, the administration comprises orally administering to a patient twice per day the solid dispersion, wherein the solid dispersion comprises a solid dispersion of substantially amorphous or amorphous Compound 1, one or more fillers, a sweetener, a disintegrant, a glidant, and a lubricant, in which the solid dispersion comprises at least about 12.5 mg of substantially amorphous or amorphous Compound 1.

Another aspect of the present invention provides a method of administering a pharmaceutical composition by orally administering to a patient at least once per day a solid dispersion of substantially amorphous or amorphous Compound 1, one or more fillers, a sweetener, a disintegrant, a glidant, and a lubricant, in which the solid dispersion comprises at least about 15 mg of substantially amorphous or amorphous Compound 1. In some embodiments, the solid dispersion is orally administered to the patient once per day. In another method, the administration comprises orally administering to a patient twice per day the solid dispersion, wherein the solid dispersion comprises a solid dispersion of substantially amorphous or amorphous Compound 1, one or more fillers, a sweetener, a disintegrant, a glidant, and a lubricant, in which the solid dispersion comprises at least about 15 mg of substantially amorphous or amorphous Compound 1.

Another aspect of the present invention provides a method of administering a pharmaceutical composition by orally administering to a patient at least once per day a solid dispersion of substantially amorphous or amorphous Compound 1, one or more fillers, a sweetener, a disintegrant, a glidant, and a lubricant, in which the solid dispersion comprises at least about 20 mg of substantially amorphous or amorphous Compound 1. In some embodiments, the solid dispersion is orally administered to the patient once per day. In another method, the administration comprises orally administering to a patient twice per day the solid dispersion, wherein the solid dispersion comprises a solid dispersion of substantially amorphous or amorphous Compound 1, one or more fillers, a sweetener, a disintegrant, a glidant, and a lubricant, in which the solid dispersion comprises at least about 20 mg of substantially amorphous or amorphous Compound 1.

Another aspect of the present invention provides a method of administering a pharmaceutical composition by orally administering to a patient at least once per day a solid dispersion of substantially amorphous or amorphous Compound 1, one or more fillers, a sweetener, a disintegrant, a glidant, and a lubricant, in which the solid dispersion comprises at least about 25 mg of substantially amorphous or amorphous Compound 1. In some embodiments, the solid dispersion is orally administered to the patient once per day. In another method, the administration comprises orally administering to a patient twice per day the solid dispersion, wherein the solid dispersion comprises a solid dispersion of substantially amorphous or amorphous Compound 1, one or more fillers, a sweetener, a disintegrant, a glidant, and a lubricant, in which the solid dispersion comprises at least about 25 mg of substantially amorphous or amorphous Compound 1.

Another aspect of the present invention provides a method of administering a pharmaceutical composition by orally administering to a patient at least once per day a solid dispersion of substantially amorphous or amorphous Compound 1, one or more fillers, a sweetener, a disintegrant, a glidant, and a lubricant, in which the solid dispersion comprises at least about 30 mg of substantially amorphous or amorphous Compound 1. In some embodiments, the solid dispersion is orally administered to the patient once per day. In another method, the administration comprises orally administering to a patient twice per day the solid dispersion, wherein the solid dispersion comprises a solid dispersion of substantially amorphous or amorphous Compound 1, one or more fillers, a sweetener, a disintegrant, a glidant, and a lubricant, in which the solid dispersion comprises at least about 30 mg of substantially amorphous or amorphous Compound 1.

Another aspect of the present invention provides a method of administering a pharmaceutical composition by orally administering to a patient at least once per day a solid dispersion of substantially amorphous or amorphous Compound 1, one or more fillers, a sweetener, a disintegrant, a glidant, and a lubricant, in which the solid dispersion comprises at least about 35 mg of substantially amorphous or amorphous Compound 1. In some embodiments, the solid dispersion is orally administered to the patient once per day. In another method, the administration comprises orally administering to a patient twice per day the solid dispersion, wherein the solid dispersion comprises a solid dispersion of substantially amorphous or amorphous Compound 1, one or more fillers, a sweetener, a disintegrant, a glidant, and a lubricant, in which the solid dispersion comprises at least about 35 mg of substantially amorphous or amorphous Compound 1.

Another aspect of the present invention provides a method of administering a pharmaceutical composition by orally administering to a patient at least once per day a solid dispersion of substantially amorphous or amorphous Compound 1, one or more fillers, a sweetener, a disintegrant, a glidant, and a lubricant, in which the solid dispersion comprises at least about 37.5 mg of substantially amorphous or amorphous Compound 1. In some embodiments, the solid dispersion is orally administered to the patient once per day. In another method, the administration comprises orally administering to a patient twice per day the solid dispersion, wherein the solid dispersion comprises a solid dispersion of substantially amorphous or amorphous Compound 1, one or more fillers, a sweetener, a disintegrant, a glidant, and a lubricant, in which the solid dispersion comprises at least about 37.5 mg of substantially amorphous or amorphous Compound 1.

Another aspect of the present invention provides a method of administering a pharmaceutical composition by orally administering to a patient at least once per day a solid dispersion of substantially amorphous or amorphous Compound 1, one or more fillers, a sweetener, a disintegrant, a glidant, and a lubricant, in which the solid dispersion comprises at least about 40 mg of substantially amorphous or amorphous Compound 1. In some embodiments, the solid dispersion is orally administered to the patient once per day. In another method, the administration comprises orally administering to a patient twice per day the solid dispersion, wherein the solid dispersion comprises a solid dispersion of substantially amorphous or amorphous Compound 1, one or more fillers, a sweetener, a disintegrant, a glidant, and a lubricant, in which the solid dispersion comprises at least about 40 mg of substantially amorphous or amorphous Compound 1.

Another aspect of the present invention provides a method of administering a pharmaceutical composition by orally administering to a patient at least once per day a solid dispersion of substantially amorphous or amorphous Compound 1, one or more fillers, a sweetener, a disintegrant, a glidant, and a lubricant, in which the solid dispersion comprises at least about 45 mg of substantially amorphous or amorphous Compound 1. In some embodiments, the solid dispersion is orally administered to the patient once per day. In another method, the administration comprises orally administering to a patient twice per day the solid dispersion, wherein the solid dispersion comprises a solid dispersion of substantially amorphous or amorphous Compound 1, one or more fillers, a sweetener, a disintegrant, a glidant, and a lubricant, in which the solid dispersion comprises at least about 45 mg of substantially amorphous or amorphous Compound 1.

Another aspect of the present invention provides a method of administering a pharmaceutical composition by orally administering to a patient at least once per day a solid dispersion of substantially amorphous or amorphous Compound 1, one or more fillers, a sweetener, a disintegrant, a glidant, and a lubricant, in which the solid dispersion comprises at least about 50 mg of substantially amorphous or amorphous Compound 1. In some embodiments, the solid dispersion is orally administered to the patient once per day. In another method, the administration comprises orally administering to a patient twice per day the solid dispersion, wherein the solid dispersion comprises a solid dispersion of substantially amorphous or amorphous Compound 1, one or more fillers, a sweetener, a disintegrant, a glidant, and a lubricant, in which the solid dispersion comprises at least about 50 mg of substantially amorphous or amorphous Compound 1.

Another aspect of the present invention provides a method of administering a pharmaceutical composition by orally administering to a patient at least once per day a solid dispersion of substantially amorphous or amorphous Compound 1, one or more fillers, a sweetener, a disintegrant, a glidant, and a lubricant, in which the solid dispersion comprises at least about 62.5 mg of substantially amorphous or amorphous Compound 1. In some embodiments, the solid dispersion is orally administered to the patient once per day. In another method, the administration comprises orally administering to a patient twice per day the solid dispersion, wherein the solid dispersion comprises a solid dispersion of substantially amorphous or amorphous Compound 1, one or more fillers, a sweetener, a disintegrant, a glidant, and a lubricant, in which the solid dispersion comprises at least about 62.5 mg of substantially amorphous or amorphous Compound 1.

Another aspect of the present invention provides a method of administering a pharmaceutical composition by orally administering to a patient at least once per day a solid dispersion of substantially amorphous or amorphous Compound 1, one or more fillers, a sweetener, a disintegrant, a glidant, and a lubricant, in which the solid dispersion comprises at least about 75 mg of substantially amorphous or amorphous Compound 1. In some embodiments, the solid dispersion is orally administered to the patient once per day. In another method, the administration comprises orally administering to a patient twice per day the solid dispersion, wherein the solid dispersion comprises a solid dispersion of substantially amorphous or amorphous Compound 1, one or more fillers, a sweetener, a disintegrant, a glidant, and a lubricant, in which the solid dispersion comprises at least about 75 mg of substantially amorphous or amorphous Compound 1.

Another aspect of the present invention provides a method of administering a pharmaceutical composition by orally administering to a patient at least once per day a solid dispersion of substantially amorphous or amorphous Compound 1, one or more fillers, a sweetener, a disintegrant, a glidant, and a lubricant, in which the solid dispersion comprises at least about 100 mg of substantially amorphous or amorphous Compound 1. In some embodiments, the solid dispersion is orally administered to the patient once per day. In another method, the administration comprises orally administering to a patient twice per day the solid dispersion, wherein the solid dispersion comprises a solid dispersion of substantially amorphous or amorphous Compound 1, one or more fillers, a sweetener, a disintegrant, a glidant, and a lubricant, in which the solid dispersion comprises at least about 100 mg of substantially amorphous or amorphous Compound 1.

Another aspect of the present invention provides a method of administering a pharmaceutical composition by orally administering to a patient at least once per day a solid dispersion of substantially amorphous or amorphous Compound 1, one or more fillers, a sweetener, a disintegrant, a glidant, and a lubricant, in which the solid dispersion comprises at least about 125 mg of substantially amorphous or amorphous Compound 1. In some embodiments, the solid dispersion is orally administered to the patient once per day. In another method, the administration comprises orally administering to a patient twice per day the solid dispersion, wherein the solid dispersion comprises a solid dispersion of substantially amorphous or amorphous Compound 1, one or more fillers, a sweetener, a disintegrant, a glidant, and a lubricant, in which the solid dispersion comprises at least about 125 mg of substantially amorphous or amorphous Compound 1.

Another aspect of the present invention provides a method of administering a pharmaceutical composition by orally administering to a patient at least once per day a solid dispersion of substantially amorphous or amorphous Compound 1, one or more fillers, a sweetener, a disintegrant, a glidant, and a lubricant, in which the solid dispersion comprises at least about 150 mg of substantially amorphous or amorphous Compound 1. In some embodiments, the solid dispersion is orally administered to the patient once per day. In another method, the administration comprises orally administering to a patient twice per day the solid dispersion, wherein the solid dispersion comprises a solid dispersion of substantially amorphous or amorphous Compound 1, one or more fillers, a sweetener, a disintegrant, a glidant, and a lubricant, in which the solid dispersion comprises at least about 150 mg of substantially amorphous or amorphous Compound 1.

Another aspect of the present invention provides a method of administering a pharmaceutical composition by orally administering to a patient at least once per day a solid dispersion of substantially amorphous or amorphous Compound 1, one or more fillers, a sweetener, a disintegrant, a glidant, and a lubricant, in which the solid dispersion comprises at least about 175 mg of substantially amorphous or amorphous Compound 1. In some embodiments, the solid dispersion is orally administered to the patient once per day. In another method, the administration comprises orally administering to a patient twice per day the solid dispersion, wherein the solid dispersion comprises a solid dispersion of substantially amorphous or amorphous Compound 1, one or more fillers, a sweetener, a disintegrant, a glidant, and a lubricant, in which the solid dispersion comprises at least about 175 mg of substantially amorphous or amorphous Compound 1.

Another aspect of the present invention provides a method of administering a pharmaceutical composition by orally administering to a patient at least once per day a solid dispersion of substantially amorphous or amorphous Compound 1, one or more fillers, a sweetener, a disintegrant, a glidant, and a lubricant, in which the solid dispersion comprises at least about 200 mg of substantially amorphous or amorphous Compound 1. In some embodiments, the solid dispersion is orally administered to the patient once per day. In another method, the administration comprises orally administering to a patient twice per day the solid dispersion, wherein the solid dispersion comprises a solid dispersion of substantially amorphous or amorphous Compound 1, one or more fillers, a sweetener, a disintegrant, a glidant, and a lubricant, in which the solid dispersion comprises at least about 200 mg of substantially amorphous or amorphous Compound 1.

Another aspect of the present invention provides a method of administering a pharmaceutical composition by orally administering to a patient at least once per day a solid dispersion of substantially amorphous or amorphous Compound 1, one or more fillers, a sweetener, a disintegrant, a glidant, and a lubricant, in which the solid dispersion comprises at least about 225 mg of substantially amorphous or amorphous Compound 1. In some embodiments, the solid dispersion is orally administered to the patient once per day. In another method, the administration comprises orally administering to a patient twice per day the solid dispersion, wherein the solid dispersion comprises a solid dispersion of substantially amorphous or amorphous Compound 1, one or more fillers, a sweetener, a disintegrant, a glidant, and a lubricant, in which the solid dispersion comprises at least about 225 mg of substantially amorphous or amorphous Compound 1.

Another aspect of the present invention provides a method of administering a pharmaceutical composition by orally administering to a patient at least once per day a solid dispersion of substantially amorphous or amorphous Compound 1, one or more fillers, a sweetener, a disintegrant, a glidant, and a lubricant, in which the solid dispersion comprises at least about 250 mg of substantially amorphous or amorphous Compound 1. In some embodiments, the solid dispersion is orally administered to the patient once per day. In another method, the administration comprises orally administering to a patient twice per day the solid dispersion, wherein the solid dispersion comprises a solid dispersion of substantially amorphous or amorphous Compound 1, one or more fillers, a sweetener, a disintegrant, a glidant, and a lubricant, in which the solid dispersion comprises at least about 250 mg of substantially amorphous or amorphous Compound 1.

In one embodiment, the method of administering a pharmaceutical composition including orally administering to a patient at least once per day at least one capsule or the contents of a pouch or a packet containing a mini-tablet or plurality of mini-tablets, each mini-tablet includes a pharmaceutical composition comprising a solid dispersion of amorphous Compound 1, one or more fillers, a sweetener, a disintegrant, optionally a wetting agent, a glidant; and a lubricant, each of which is described above and in the Examples below, wherein the capsule, pouch, or packet containing the mini-tablet or plurality of mini-tablets comprises at least 5 mg (e.g., at least 10 mg, at least 12.5 mg, at least 15 mg, at least 20 mg, at least 25 mg, at least 30 mg, at least 35 mg, at least 37.5 mg, at least 40 mg, at least 45 mg, at least 50 mg, at least 55 mg, at least 60 mg, at least 62.5 mg, at least 65 mg, at least 70, at least 75 mg, at least 100 mg, at least 125 mg, at least 150 mg, at least 175 mg, at least 200 mg, at least 225 mg, or at least 250 mg) of substantially amorphous or amorphous Compound 1.

In one embodiment, the method of administering a pharmaceutical composition includes orally administering to a patient at least once per day at least one capsule or the contents of a pouch or a packet containing mini-tablet or plurality of mini-tablets, each mini-tablet including a pharmaceutical composition containing a solid dispersion of substantially amorphous or amorphous Compound 1, one or more fillers, a sweetener, a disintegrant, optionally a wetting agent, a glidant; and a lubricant, wherein the capsule, pouch, or packet containing the mini-tablet or plurality of mini-tablets comprises from about 10 mg to about 300 mg (e.g., from about 15 mg to about 280 mg, or from about 25 mg to about 260 mg, or from about 30 mg to about 200 mg, or from about 10 mg to about 150 mg, or from about 10 mg to about 100 mg, or from about 15 mg to about 75 mg) of substantially amorphous or amorphous Compound 1. Or, the method of administering a pharmaceutical composition includes orally administering to a patient at least once per day at least one capsule or the contents of a pouch or a packet containing a mini-tablet or plurality of mini-tablets each mini-tablet comprising a pharmaceutical composition containing a solid dispersion of amorphous Compound 1, one or more fillers, a sweetener, a disintegrant, optionally a wetting agent, a glidant; and a lubricant, wherein the capsule, pouch, or packet comprises from about 10 mg to about 300 mg (e.g., from about 15 mg to about 280 mg or from about 25 mg to about 260 mg, or from about 30 mg to about 200 mg, or from about 10 mg to about 150 mg, or from about 10 mg to about 100 mg, or from about 15 mg to about 75 mg) of amorphous Compound 1.

In another embodiment, the method of administering a pharmaceutical composition includes orally administering to a patient once per day at least one at least one capsule or the contents of a pouch or a packet containing a mini-tablet or plurality of mini-tablets wherein each mini-tablet comprises a pharmaceutical composition containing a solid dispersion of Compound 1, one or more fillers, a sweetener, a disintegrant, optionally a wetting agent, a glidant; and a lubricant, each of which is described above and in the Examples below, wherein the capsule, pouch, or packet containing the mini-tablet or plurality of mini-tablets comprises at least 5 mg (e.g., at least 10 mg, at least 15 mg, at least 20 mg, at least 25 mg, at least 30 mg, at least 37.5 mg, at least 35 mg, at least 40 mg, at least 45 mg, at least 50 mg, at least 55 mg, at least 60 mg, at least 62.5 mg, at least 65 mg, at least 70 mg, at least 75 mg, at least 100 mg, at least 125 mg, at least about 150 mg, at least 175 mg, at least 200 mg, at least 225 mg, or at least about 250 mg) of substantially amorphous Compound 1 or amorphous Compound 1. For example, the method of administering a pharmaceutical composition includes orally administering to a patient once per day at least one capsule or the contents of a pouch or a packet containing a pharmaceutical composition comprising a mini-tablet or plurality of mini-tablets, each mini-tablet containing a solid dispersion of Compound 1, one or more fillers, a sweetener, a disintegrant, optionally a wetting agent, a glidant; and a lubricant, wherein the capsule, pouch, or packet containing the mini-tablet or plurality of mini-tablets comprises at least 75 mg (e.g., at least 100 mg, at least 125 mg, at least 140 mg, at least 150 mg, at least 175 mg, at least 200 mg, at least 225 mg, or at least 250 mg) of substantially amorphous Compound 1 or amorphous Compound 1. In another example, the method of administering a pharmaceutical composition includes orally administering to a patient once per day a mini-tablet or plurality of capsules or packets (e.g., two capsules, three capsules, four or five capsules), wherein each capsule or packet contains a mini-tablet or plurality of mini-tablets, each mini-tablet comprises a pharmaceutical composition comprising a solid dispersion of substantially amorphous Compound 1 or amorphous Compound 1, one or more fillers, a sweetener, a disintegrant, optionally a wetting agent, a glidant; and a lubricant, wherein the capsule or packet containing the mini-tablet or plurality of mini-tablets comprises at least 5 mg (e.g., at least 10 mg, at least 15 mg, at least 20 mg, at least 25 mg, at least 30 mg, at least 37.5 mg, at least 35 mg, at least 40 mg, at least 45 mg, at least 50 mg, at least 55 mg, at least 60 mg, at least 62.5 mg, at least 65 mg, at least 70 mg, at least 75 mg, at least 100 mg, at least 125 mg, at least about 150 mg, at least 175 mg, at least 200 mg, at least 225 mg, or at least about 250 mg) of substantially amorphous Compound 1 or amorphous Compound 1.

In another embodiment, the method of administering a pharmaceutical composition includes orally administering to a patient twice per day at least one capsule or the contents of a pouch or packet comprising a mini-tablet or plurality of mini-tablets, wherein each mini-tablet comprises a pharmaceutical composition containing a solid dispersion of Compound 1, one or more fillers, a sweetener, a disintegrant, optionally a wetting agent, a glidant; and a lubricant, each of which is described above and in the Examples below, and wherein the capsule, pouch or packet containing the mini-tablet or plurality of mini-tablets comprises at least 5 mg (e.g., at least 10 mg, at least 15 mg, at least 20 mg, at least 25 mg, at least 30 mg, at least 37.5 mg, at least 35 mg, at least 40 mg, at least 45 mg, at least 50 mg, at least 55 mg, at least 60 mg, at least 62.5 mg, at least 65 mg, at least 70 mg, at least 75 mg, at least 100 mg, at least 125 mg, at least about 150 mg, at least 175 mg, at least 200 mg, at least 225 mg, or at least about 250 mg) of substantially amorphous Compound 1 or amorphous Compound 1. For example, the method of administering a pharmaceutical composition includes orally administering to a patient twice per day one capsule or the contents of a pouch or a packet comprising mini-tablet or plurality of mini-tablets, each mini-tablet comprising a pharmaceutical composition containing a solid dispersion of Compound 1, one or more fillers, a sweetener, a disintegrant, a glidant, and a lubricant, wherein the capsule, pouch or a packet comprises at least 75 mg (e.g., at least 100 mg, at least 125 mg, at least 140 mg, at least 150 mg, at least 175 mg, at least 200 mg, at least 225 mg, or at least 250 mg) of substantially amorphous Compound 1 or amorphous Compound 1. In another example, the method of administering a pharmaceutical composition includes orally administering to a patient twice per day a mini-tablet or plurality of capsules (e.g., two capsules, three capsules, four or five capsules) or the contents of a pouch or a packet, wherein each capsule, packet or pouch contains a mini-tablet or plurality of mini-tablets, each mini-tablet comprises a pharmaceutical composition comprising a solid dispersion of substantially amorphous Compound 1 or amorphous Compound 1, one or more fillers, a sweetener, a disintegrant, optionally a wetting agent, a glidant; and a lubricant, and wherein the capsule, packet, or pouch comprises at least 5 mg (e.g., at least 10 mg, at least 15 mg, at least 20 mg, at least 25 mg, at least 30 mg, at least 37.5 mg, at least 35 mg, at least 40 mg, at least 45 mg, at least 50 mg, at least 55 mg, at least 60 mg, at least 62.5 mg, at least 65 mg, at least 70 mg, at least 75 mg, at least 100 mg, at least 125 mg, at least about 150 mg, at least 175 mg, at least 200 mg, at least 225 mg, or at least about 250 mg) of substantially amorphous Compound 1 or amorphous Compound 1.

It is noted that the methods of administration of the present invention can optionally include orally administering a beverage (milk (including breast milk), baby formula or infant formula, or the like), soft food (including apple sauce, plain yogurt, ice cream, baby food (including carrots and carrot puree) or the like), and/or additional pharmaceutical compositions including additional APIs. In some embodiments, a liquid may also include water. When the method of administration includes orally administering a beverage (water, milk (including breast milk), baby formula or infant formula, or the like), soft food or food (including a standard high fat high calorie CF meal or snack), and/or additional pharmaceutical compositions including additional APIs, the oral administration of the beverage, food, and/or additional API can occur concurrently with the oral administration of the mini-tablet or plurality of mini-tablets, prior to the oral administration of the mini-tablet or plurality of mini-tablets, and/or after the administration of the mini-tablet or plurality of mini-tablets. In one embodiment, the unit dose form is sprinkled into soft food including, but not limited to, apple sauce, plain yogurt, ice cream, baby food (including carrots and carrot puree) and administered. In another embodiment, the unit dose form is sprinkled into soft food including, but not limited to, apple sauce, plain yogurt, ice cream, baby food (including carrots and carrot puree), mixed, and administered. In one embodiment, the unit dose form is sprinkled into a liquid including, but not limited to, baby formula, infant formula, milk or breast milk, mixed, and administered. In another embodiment, the unit dose form is sprinkled into a liquid including, but not limited to, baby formula, infant formula, milk or breast milk, and administered. Methods of administration of the present invention can optionally also include, for smaller sized mini-tablets or granules, administering the contents of packets, pouches, capsules, bottles or sachets directly to the mouth followed by breast milk or formula. Methods of administration of the present invention can optionally also include, for smaller sized mini-tablets or granules, administering the contents of packets, pouches, capsules, bottles or sachets directly to the mouth followed by a liquid or beverage. It is also noted that all methods of administration of the present invention can optionally include orally administering concurrently with, before or after fat-containing food such as a standard CF high-calorie, high-fat meal or snack. In some embodiments, all methods of administration of the present invention can optionally include orally administering with fat-containing food such as a standard CF high-calorie, high-fat meal or snack. In one example, the method of administering a pharmaceutical composition includes orally administering to a patient at least once per day at least one capsule or one packet comprising a mini-tablet or plurality of mini-tablets, each mini-tablet containing a solid dispersion of substantially amorphous Compound 1 or amorphous Compound 1, one or more fillers, a sweetener, a disintegrant, optionally a wetting agent, a glidant; and a lubricant, and a second API. In another example, the method of administering a pharmaceutical composition includes orally administering to a patient at least once per day at least one capsule or the contents of a packet or a pouch comprising a mini-tablet or plurality of mini-tablets, each mini-tablet comprising a solid dispersion of substantially amorphous Compound 1 or amorphous Compound 1, one or more fillers, a sweetener, a disintegrant, optionally a wetting agent, a glidant; and a lubricant, wherein the capsule, packet or pouch comprises at least 5 mg (e.g., at least 10 mg, at least 15 mg, at least 20 mg, at least 25 mg, at least 30 mg, at least 37.5 mg, at least 35 mg, at least 40 mg, at least 45 mg, at least 50 mg, at least 55 mg, at least 60 mg, at least 62.5 mg, at least 65 mg, at least 70 mg, at least 75 mg, at least 100 mg, at least 125 mg, at least about 150 mg, at least 175 mg, at least 200 mg, at least 225 mg, or at least about 250 mg) of substantially amorphous Compound 1 or amorphous Compound 1, and orally administering to a patient at least once per day a second pharmaceutical composition comprising a second API. In still other examples, the method of administering a pharmaceutical composition includes orally administering to a patient every 12 hours at least one capsule or packet containing a mini-tablet or plurality of mini-tablets, each mini-tablet comprising a pharmaceutical composition as described herein, in which the mini-tablet or plurality of mini-tablets are mixed with a food or beverage for consumption by a patient having difficulty swallowing an adult sized tablet, for example, a pediatric patient, including, but not limited to those younger than six years of age, to those who are 2 through 5 years of age, to those younger than 2, to those who are zero (i.e., birth) through 2 years of age, to those who are 1 through 2 years of age, to those who are 9 months through 2 years of age, to those who are 6 months through 2 years of age, to those who are 3 months through 2 years of age, and to those who are 2 months through 2 years of age. In some embodiments, birth means birth after full term gestation. In still other examples, the method of administering a pharmaceutical composition includes orally administering to a patient every 12 hours at least one capsule or packet containing a mini-tablet or plurality of mini-tablets, each mini-tablet comprising a pharmaceutical composition as described herein, in which the mini-tablet or plurality of mini-tablets are mixed with a food or beverage for consumption by a patient having difficulty swallowing an adult sized tablet, for example, a pediatric patient, including, but not limited to those greater than or equal to about 14 kilograms, to those less than 14 kilograms, to those about 7.5 kilograms to less than 14 kilograms, to those about 5 kilograms to less than 7.5 kilograms, and to those about 2.5 kilograms to less than 5 kilograms.

It is also noted that the methods of administration of the present invention can optionally include orally administering a pharmaceutical composition as described herein in the absence of food or beverage. In the present method, the oral administration is performed directly after, or shortly after (e.g. within 30 minutes) the patient eats or drinks. In another embodiment, the oral administration is performed at least 1 hour (e.g. at least 2 hours, at least 3 hours, at least 4 hours, at least 5 hours, at least 8 hours, at least 12 hours or at least 24 hours) after eating or drinking. For instance, in one example, the method of administering a pharmaceutical composition includes orally administering to a patient at least once per day at least one capsule or the contents of a packet or a pouch comprising a mini-tablet or plurality of mini-tablets, each mini-tablet containing a solid dispersion of substantially amorphous Compound 1 or amorphous Compound 1, one or more fillers, a sweetener, a disintegrant, optionally a wetting agent, a glidant; and a lubricant, and a second API. In another example, the method of administering a pharmaceutical composition includes orally administering to a patient at least once per day at least one capsule of the contents of a packet or a pouch comprising a mini-tablet or plurality of mini-tablets, each mini-tablet comprising a solid dispersion of substantially amorphous Compound 1 or amorphous Compound 1, one or more fillers, a sweetener, a disintegrant, optionally a wetting agent, a glidant; and a lubricant, wherein the capsule, packet or pouch comprises at least 5 mg (e.g., at least 10 mg, at least 15 mg, at least 20 mg, at least 25 mg, at least 30 mg, at least 37.5 mg, at least 35 mg, at least 40 mg, at least 45 mg, at least 50 mg, at least 55 mg, at least 60 mg, at least 62.5 mg, at least 65 mg, at least 70 mg, at least 75 mg, at least 100 mg, at least 125 mg, at least about 150 mg, at least 175 mg, at least 200 mg, at least 225 mg, or at least about 250 mg) of substantially amorphous Compound 1 or amorphous Compound 1, and orally administering to a patient at least once per day a second pharmaceutical composition comprising a second API. In still other examples, the method of administering a pharmaceutical composition includes orally administering to a patient every 12 hours at least one capsule or packet containing a mini-tablet or plurality of mini-tablets, each mini-tablet comprising a pharmaceutical composition as described herein, in which the mini-tablet or plurality of mini-tablets are administered to a patient having difficulty swallowing an adult sized tablet, for example, a pediatric patient, including, but not limited to those to those younger than six years of age, to those who are 2 through 5 years of age, to those younger than 2, to those who are zero (i.e., birth) through 2 years of age, to those who are 1 through 2 years of age, to those who are 9 months through 2 years of age, to those who are 6 months through 2 years of age, to those who are 3 months through 2 years of age, and to those who are 2 months through 2 years of age. In some embodiments, birth means birth after full term gestation. In still other examples, the method of administering a pharmaceutical composition includes orally administering to a patient every 12 hours at least one capsule or packet containing a mini-tablet or plurality of mini-tablets, each mini-tablet comprising a pharmaceutical composition as described herein, in which the mini-tablet or plurality of mini-tablets are mixed with a food or beverage for consumption by a patient having difficulty swallowing an adult sized tablet, for example, a pediatric patient, including, but not limited to those greater than or equal to about 14 kilograms, to those less than 14 kilograms, to those about 7.5 kilograms to less than 14 kilograms, to those about 5 kilograms to less than 7.5 kilograms, and to those about 2.5 kilograms to less than 5 kilograms. It will also be appreciated that the compound and pharmaceutically acceptable compositions of the present invention can be employed in combination therapies, that is, the compound and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated."

In one embodiment, the additional agent is selected from a mucolytic agent, bronchodilator, an anti-biotic, an anti-infective agent, an anti-inflammatory agent, a CFTR modulator other than Compound 1 of the present invention, or a nutritional agent.

In certain embodiments wherein cystic fibrosis is treated, prevented and/or managed, a compound or composition provided herein can be combined with, for example, 552-02, 5-methyltetrahydrofolate and vitamin B12, Ad5-CB-CFTR, Adeno-associated virus-CFTR vector, albuterol, alendronate, alpha tocopherol plus ascorbic acid, amiloride HCl, aquADEK™. ataluren (PTC124), AZD1236, AZD9668, azithromycin, bevacizumab, biaxin (clarithromycin), BIIL 283 BS (amelubent), buprofen, calcium carbonate, ceftazidime, cholecalciferol, choline supplementation, CPX, cystic fibrosis transmembrane conductance regulator, DHA-rich supplement, digitoxin, cocosahexaenoic acid (DHA), doxycycline, ECGC, ecombinant human IGF-1, educed glutathione sodium salt, ergocalciferol (vitamin D2), fluorometholone, gadobutrol (GADOVIST®, BAY86-4875), gentamicin, ghrelin, glargine, glutamine, growth hormone, GS-9411, H5.001CBCFTR, human recombinant growth hormone, hydroxychloroquine, hyperbaric oxygen, hypertonic saline, IH636 grape seed proanthocyanidin extract, insulin, interferon gamma-1b, IoGen (molecular iodine), iosartan potassium, isotonic saline, itraconazole, IV gallium nitrate (GANITE®) infusion, ketorolac acetate, lansoprazole, L-arginine, linezolid, lubiprostone, meropenem, miglustat, MP-376 (levofloxacin solution for inhalation), normal saline IV, Nutropin AQ, omega-3 triglycerides, pGM169/GL67A, pGT-1 gene lipid complex, pioglitazone, PTC124, QAU145, salmeterol, SB656933, SB656933, simvastatin, sitagliptin, sodium 4-phenylbutyrate, standardized turmeric root extract, tgAAVCF, TNF blocker, TOBI, tobramycin, tocotrienol, unconjugated Isoflavones 100, vitamin: choline bitartrate (2-hydroxyethyl)trimethylammonium salt 1:1, zinc acetate, or combinations thereof.

In one embodiment, the invention features a kit comprising a tablet of the present invention, and a separate therapeutic agent or pharmaceutical composition thereof. In one embodiment, the additional therapeutic agent is a CFTR corrector. In another embodiment, the therapeutic agent is (3-(6-(1-(2,2-difluorobenzo[d][1,3]dioxol-5-yl)cyclopropanecarboxamido)-3-methylpyridin-2-yl)benzoic acid or (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide. In another embodiment, the therapeutic agent is (3-(6-(1-(2,2-difluorobenzo[d][1,3]dioxol-5-yl)cyclopropanecarboxamido)-3-methylpyridin-2-yl)benzoic acid. In another embodiment, the therapeutic agent is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide In another embodiment, the tablet and the therapeutic agent are in separate containers. In another embodiment, the separate containers are bottles. In another embodiment, the separate containers are vials. In another embodiment, the separate containers are blister packs.

In one embodiment, the additional agent is an antibiotic. Exemplary antibiotics useful herein include tobramycin, including tobramycin inhaled powder (TIP), azithromycin, aztreonam, including the aerosolized form of aztreonam, amikacin, including liposomal formulations thereof, ciprofloxacin, including formulations thereof suitable for administration by inhalation, levofloxacin, including aerosolized formulations thereof, and combinations of two antibiotics, e.g., fosfomycin and tobramycin.

In another embodiment, the additional agent is a mucolyte. Exemplary mucolytes useful herein includes Pulmozyme®.

In another embodiment, the additional agent is a bronchodilator. Exemplary bronchodilators include albuterol, metaproterenol sulfate, pirbuterol acetate, salmeterol, or terbutaline sulfate.

In another embodiment, the additional agent is effective in restoring lung airway surface liquid. Such agents improve the movement of salt in and out of cells, allowing mucus in the lung airway to be more hydrated and, therefore, cleared more easily. Exemplary such agents include hypertonic saline, denufosol tetrasodium ([[(3S,5R)-5-(4-amino-2-oxopyrimidin-1-yl)-3-hydroxyoxolan-2-yl]methoxy-hydroxyphosphoryl][[[(2R,3S,4R,5R)-5-(2,4-dioxopyrimidin-1-yl)-3,4-dihydroxyoxolan-2-yl]methoxy-hydroxyphosphoryl]oxy-hydroxyphosphoryl]hydrogen phosphate), or bronchitol (inhaled formulation of mannitol).

In another embodiment, the additional agent is an anti-inflammatory agent, i.e., an agent that can reduce the inflammation in the lungs. Exemplary such agents useful herein include ibuprofen, docosahexaenoic acid (DHA), sildenafil, inhaled glutathione, pioglitazone, hydroxychloroquine, or simavastatin.

In another embodiment, the additional agent is a CFTR modulator other than compound 1, i.e., an agent that has the effect of modulating CFTR activity. Exemplary such agents include ataluren ("PTC1248"; 3-[5-(2-fluorophenyl)-1,2,4-oxadiazol-3-yl]benzoic acid), sinapultide, lancovutide, depelestat (a human recombinant neutrophil elastase inhibitor), cobiprostone (7-{(2R,4aR,5R,7aR)-2-[(3S)-1,1-difluoro-3-methylpentyl]-2-hydroxy-6-oxooctahydrocyclopenta[b]pyran-5-yl}heptanoic acid), or (3-(6-(1-(2,2-difluorobenzo[d][1,3]dioxol-5-yl)cyclopropanecarboxamido)-3-methylpyridin-2-yl)benzoic acid. In another embodiment, the additional agent is (3-(6-(1-(2,2-difluorobenzo[d][1,3]dioxol-5-yl)cyclopropanecarboxamido)-3-methylpyridin-2-yl)benzoic acid.

In another embodiment, the additional agent is a nutritional agent. Exemplary such agents include pancrelipase (pancreating enzyme replacement), including Pancrease®, Pancreacarb®, Ultrase®, or Creon®, Liprotamase® (formerly Trizytek®), Aquadeks®, or glutathione inhalation. In one embodiment, the additional nutritional agent is pancrelipase.

V. EXAMPLES

In order that the invention described herein may be more fully understood, the following examples are set forth. It should be understood that these examples are for illustrative purposes only and are not to be construed as limiting this invention in any manner.

A. Manufacture of Capsules

Example 1

Manufacturing Intermediate 1 Containing Substantially Amorphous or Amorphous Compound 1

The synthesis of N-[2,4-Bis(1,1-dimethylethyl)-5-hydroxyphenyl]-1,4-dihydro-4-oxoquinoline-3-carboxamide is described in United States patent application publication numbers US 2006/0074075 (now U.S. Pat. No. 7,495,103), US 2011/0064811, US 2010/0267768, and US 2011/0230519, the contents of which are hereby incorporated by reference in their entirety. A solvent system of MEK and DI water, formulated according to the ratio 90 wt % MEK/10 wt % DI water, was heated to a temperature of 20-30° C. in a reactor, equipped with a magnetic stirrer and thermal circuit. Into this solvent system, hypromellose acetate succinate polymer (HPMCAS) (HG grade), SLS, and N-[2,4-Bis(1,1-dimethylethyl)-5-hydroxyphenyl]-1,4-dihydro-4-oxoquinoline-3-carboxamide were added according to the ratio 19.5 wt % hypromellose acetate succinate/0.5 wt % SLS/80 wt % N-[2,4-Bis(1,1-dimethylethyl)-5-hydroxyphenyl]-1,4-dihydro-4-oxoquinoline-3-carboxamide. The resulting mixture contained 10.5 wt % solids. The actual amounts of ingredients and solvents used to generate this mixture are recited in Table 1a, below:

TABLE 1a

Solid Spray Dispersion Ingredients for Intermediate 1.

| | Units | Batch |
|---|---|---|
| N-[2,4-Bis(1,1-dimethylethyl)-5-hydroxyphenyl]-1,4-dihydro-4-oxoquinoline-3-carboxamide | Kg | 70.0 |
| HPMCAS | Kg | 17.1 |
| SLS | Kg | 0.438 |
| Total Solids | Kg | 87.5 |
| MEK | Kg | 671 |
| Water | Kg | 74.6 |
| Total Solvents | Kg | 746 |
| Total Spray Solution Weight | Kg | 833 |

The mixture temperature was adjusted to a range of 20-45° C. and mixed until it was substantially homogenous and all components were substantially dissolved.

A spray drier, Niro PSD4 Commercial Spray Dryer, fitted with pressure nozzle (Spray Systems Maximum Passage series SK-MFP having orifice/core size 54/21) equipped with anti-bearding cap, was used under normal spray drying mode, following the dry spray process parameters recited in Table 1b, below.

TABLE 1b

Dry spray process parameters used to generate Intermediate 1.

| Parameter | Value |
|---|---|
| Feed Pressure | 20 bar |
| Feed Flow Rate | 92-100 Kg/hr |
| Inlet Temperature | 93-99° C. |
| Outlet Temperature | 53-57° C. |
| Vacuum Dryer Temperature | 80° C. for 2 hours then 110° C. (+/−5° C.) |
| Vacuum Drying Time | 20-24 hours |

A high efficiency cyclone separated the wet product from the spray gas and solvent vapors. The wet product contained 8.5-9.7% MEK and 0.56-0.83% water and had a mean particle size of 17-19 μm and a bulk density of 0.27-0.33 g/cc. The wet product was transferred to a 4000 L stainless steel double cone vacuum dryer for drying to reduce residual solvents to a level of less than about 5000 ppm and to generate dry Intermediate 1. The dry Intermediate 1 contained <0.03% MEK and 0.3% water.

Although Intermediate 1 was described above as being formed, in part, by admixing the solid spray dispersion ingredients with application of heat to form a homogeneous mixture, the solid spray dispersion ingredients can also be mixed without application of heat to form a mixture of the solid spray dispersion ingredients.

Example 2

Manufacturing a Powder Blend Containing About 75 mg of Substantially Amorphous or Amorphous Compound 1 Encapsulated in Exemplary Capsule 1

A batch of powder blend is formulated for encapsulation to have approximately 75 mg of Compound 1 per capsule using the amounts of ingredients recited in Table 2.

TABLE 2

Ingredients for Exemplary Capsule 1 Containing a Powder Blend.

| Formulation | Percent Dose % Wt./Wt. | Dose (mg) | Batch (g) |
|---|---|---|---|
| Intermediate 1 | 46.9% | 95.2 | 952 |
| Mannitol | 49.1% | 99.7 | 997 |
| Sucralose | 2.0% | 4.1 | 41 |
| Colloidal silicon dioxide | 1.0% | 2.0 | 20 |
| Magnesium stearate | 1.0% | 2.0 | 30 |
| Total | 100% | 203 | 2030 |

Intermediate 1, mannitol (Pearlitol® 100 SD commercially available from Roquette America Inc. of Keokuk Iowa), sucralose (Splenda® commercially available from Tate and Lyle of Decatur, Ill.), colloidal silicon dioxide (Cabot Cab-O-Sil® M-5P Fumed Silicon Dioxide, commercially available from Cabot Corporation of Alpharetta, Ga.) and magnesium stearate (Fisher Scientific or as Hyqual®, commercially available from Mallinckrodt Chemicals) are sieved through a 20 and 60 mesh screen to remove lumps.

Intermediate 1, colloidal silicon dioxide, and sucralose are blended together for 25 minutes and sieved through a 20 mesh screen to remove any lumps. Magnesium stearate is sieved through a 60 mesh screen to remove lumps. The Intermediate 1 mixture is added to 20% of the total amount of magnesium stearate and combined in an 8 quart V blender and blended for 25 minutes at 20-24 rpm thereby forming a first blended mixture. Mannitol is sieved through a 20 mesh screen to remove lumps. The mannitol is then added to the first blended mixture and blended for an additional 25 minutes at 20-24 rpm forming a second blended mixture. The second blended mixture is further delumped through a 024R screen using a Comil and then the remaining 80% of the total magnesium stearate is added to the screened second blended mixture forming a powder blend. One unit dose equivalent of the powder blend (203 mg total) containing about 75 mg of substantially amorphous or amorphous Compound 1 is then encapsulated using IN-CAP® automatic tabletop capsule filling machine using hard-gelatin or HPMC capsules.

Example 3

Manufacturing a Powder Blend Containing About 75 mg of Substantially Amorphous or Amorphous Compound 1 Encapsulated in Exemplary Capsule 2

A batch of powder blend was formulated for encapsulation to have approximately 75 mg of Compound 1 per capsule using the amounts of ingredients recited in Table 3.

TABLE 3

Ingredients for Exemplary Capsule 2 Containing a Powder Blend.

| Formulation | Percent Dose % Wt./Wt. | Dose (mg) | Batch (g) |
|---|---|---|---|
| Intermediate 1 | 46.9% | 93.8 | 469.07 |
| Mannitol | 49.1% | 98.2 | 491.17 |
| Sucralose | 2.0% | 4.0 | 20.01 |
| Colloidal silicon dioxide | 1.0% | 2.0 | 10.02 |
| Magnesium stearate | 1.0% | 2.0 | 10.03 |
| Total | 100% | 200 | 1000.3 |

Intermediate 1 and Sucralose (commercially available from Tate and Lyle of Decatur, Ill.) were co-screened through 20 mesh (850 micrometer) screen. Mannitol (Pearlitol® 100 SD commercially available from Roquette America Inc. of Keokuk Iowa) and colloidal silicon dioxide (Cabot Cab-O-Sil® M-5P Fumed Silicon Dioxide, commercially available from Cabot Corporation of Alpharetta, Ga.) were co-screened through 20 mesh (850 micrometer) screen. Magnesium stearate (commercially available from Fisher Scientific, Pittsburgh, Pa.) was sieved through a 60 mesh (250 micrometer) screen to remove lumps.

Intermediate 1 and sucralose (co-screened) and Mannitol and colloidal silicon dioxide (co-screened) were blended together for 6.5 minutes at 20-27 rpm in a 4 quart V-blender. Magnesium stearate (pre-screened) was added to this blend in the 4 quart V-blender and blended for 4 minutes at 20-27 rpm. One unit dose equivalent of the powder blend (200 mg total containing about 75 mg of substantially amorphous or amorphous Compound 1) was then encapsulated using IN-CAP® automatic tabletop capsule filling machine using hard gelatin or HPMC capsules.

Example 4

Manufacturing a Powder Blend Containing About 75 mg of Substantially Amorphous or Amorphous Compound 1 Encapsulated in Exemplary Capsule 3

A batch of powder blend was formulated for encapsulation to have approximately 75 mg of Compound 1 per capsule using the amounts of ingredients recited in Table 4.

TABLE 4

Ingredients for Exemplary Capsule 3 Containing a Powder Blend.

| Formulation | Percent Dose % Wt./Wt. | Dose (mg) | Batch (g) |
| --- | --- | --- | --- |
| Intermediate 1 | 46.875% | 93.75 | 234.4 |
| Mannitol | 49.375% | 98.75 | 246.8 |
| Sucralose | 2.0% | 4.0 | 10 |
| Colloidal silicon dioxide | 0.875% | 1.75 | 4.4 |
| Magnesium stearate | 0.875% | 1.75 | 4.4 |
| Total | 100% | 200 | 500 |

Intermediate 1 and Sucralose (commercially available from Tate and Lyle of Decatur, Ill.) were co-screened through 30 mesh (600 micrometer) screen. Mannitol (Pearlitol® 100 SD commercially available from Roquette America Inc. of Keokuk Iowa) and colloidal silicon dioxide (Cabot Cab-O-Sil® M-5P Fumed Silicon Dioxide, commercially available from Cabot Corporation of Alpharetta, Ga.) were co-screened through 30 mesh (600 micrometer) screen. Magnesium stearate (commercially available from Fisher Scientific, Pittsburgh, Pa.) was sieved through a 60 mesh (250 micrometer) screen to remove lumps.

Intermediate 1 and sucralose (co-screened) and Mannitol and colloidal silicon dioxide (co-screened) were blended together for 7 minutes at 20-27 rpm in a 2 quart V-blender. This blend was delumped through a 024R screen (610 micrometers) at 5,000 rpm using a Quadro Comil U5. Magnesium stearate (pre-screened) is added to the blend in the 2 quart V-blender and blended for 5.5 minutes at 20-27 rpm. One unit dose equivalent of the powder blend (200 mg total containing about 75 mg of substantially amorphous or amorphous Compound 1) was then encapsulated using IN-CAP® automatic tabletop capsule filling machine using HPMC capsules.

Example 5

Manufacturing a Powder Blend Containing about 15 mg of Substantially Amorphous or Amorphous Compound 1 Encapsulated in Exemplary Capsule 4

A batch of powder blend was formulated for encapsulation to have approximately 15 mg of Compound 1 per capsule using the amounts of ingredients recited in Table 5.

TABLE 5

Ingredients for exemplary capsule 4 containing a powder blend

| Formulation | Percent Dose % Wt./Wt. | Dose (mg) | Batch (g) |
| --- | --- | --- | --- |
| Intermediate 1 | 15.63 | 18.8 | 94.05 |
| Mannitol | 80.37 | 96.4 | 483.16 |
| Sucralose | 2 | 2.4 | 12.17 |
| Colloidal Silicon dioxide | 1 | 1.2 | 6.35 |
| Magnesium Stearate | 1 | 1.2 | 6.14 |
| Total | 100 | 120 | 601.87 |

Intermediate 1 and Sucralose (commercially available from Tate and Lyle of Decatur, Ill.) were co-screened through 20 mesh (850 micrometer) screen. Mannitol (Pearlitol® 100 SD commercially available from Roquette America Inc. of Keokuk Iowa) and colloidal silicon dioxide (Cabot Cab-O-Sil® M-5P Fumed Silicon Dioxide, commercially available from Cabot Corporation of Alpharetta, Ga.) were co-screened through 20 mesh (850 micrometer) screen. Magnesium stearate (commercially available from Fisher Scientific, Pittsburgh, Pa.) was sieved through a 60 mesh (250 micrometer) screen to remove lumps.

Intermediate 1 and sucralose (co-screened) and Mannitol and colloidal silicon dioxide (co-screened) were blended together for 6 minutes at 20-27 rpm in a 4 quart V-blender. Magnesium stearate (pre-screened) was added to this blend in the 4 quart V-blender and blended for 4 minutes at 20-27 rpm. One unit dose equivalent of the powder blend (120 mg total containing about 15 mg of substantially amorphous or amorphous Compound 1) was then encapsulated using IN-CAP® automatic tabletop capsule filling machine using hard gelatin or HPMC capsules.

Example 6

Manufacturing a Powder Blend Containing about 50 mg of Substantially Amorphous or Amorphous Compound 1 Encapsulated in Exemplary Capsule 5

A batch of powder blend was formulated for encapsulation to have approximately 50 mg of Compound 1 per capsule using the amounts of ingredients recited in Table 6.

TABLE 6

Ingredients for exemplary capsule 5 containing a powder blend

| Formulation | Percent Dose % Wt./Wt. | Dose (mg) | Batch (g) |
| --- | --- | --- | --- |
| Intermediate 1 | 36.76 | 62.7 | 367.6 |
| Mannitol | 59.28 | 100.8 | 592.8 |
| Sucralose | 1.96 | 3.3 | 19.6 |
| Colloidal Silicon dioxide | 1 | 1.7 | 10 |
| Magnesium Stearate | 1 | 1.7 | 10 |
| Total | 100 | 170 | 1000 |

Intermediate 1 and Sucralose (commercially available from Tate and Lyle of Decatur, Ill.) were co-screened through 20 mesh (850 micrometer) screen. Mannitol (Pearlitol® 100 SD commercially available from Roquette America Inc. of Keokuk Iowa) and colloidal silicon dioxide (Cabot Cab-O-Sil® M-5P Fumed Silicon Dioxide, commercially available from Cabot Corporation of Alpharetta, Ga.) were co-screened through 30 mesh (600 micrometer) screen. Magnesium stearate (commercially available from Fisher Scientific, Pittsburgh, Pa.) was sieved through a 60 mesh (250 micrometer) screen to remove lumps.

Intermediate 1 and sucralose (co-screened) and Mannitol and colloidal silicon dioxide (co-screened) were blended together for 6 minutes at 20-27 rpm in a 4 quart V-blender. This blend was delumped through a 018R screen at 5000 rpm using a Quadro Comil U5. Magnesium Stearate (pre-screened) was added to the blend in the 4 Q V-blender and blended for 4 minutes at 20-27 rpm. One unit dose equivalent of the powder blend (170 mg total containing about 50 mg of substantially amorphous or amorphous compound 1) was then encapsulated using IN-CAP automatic tabletop capsule filling machine using hard gelatin or HPMC capsules.

B. Manufacture of Mini-Tablets and Capsules Containing Mini-Tablets

Example 7

Exemplary Mini-Tablet 1 Formulated in Exemplary Capsule 6 (Capsule Formulated to have about 75 mg of Compound 1)

A batch of cylindrical, 2 mm diameter, 2 mm length mini-tablets (each mini-tablet weighing about 7.0 mg each) is formulated to have approximately 75 mg of Compound 1 per about 29 mini-tablets using the amounts of ingredients recited in Table 7, below.

TABLE 7

Ingredients for Exemplary Mini-Tablets For Capsule 6.

| Formulation | Percent Dose % Wt./Wt. | Dose (mg) | Batch (g) |
| --- | --- | --- | --- |
| Intermediate 1 | 46.9% | 95.2 | 952 |
| Mannitol | 45.1% | 91.6 | 916 |
| Sucralose | 2.0% | 4.1 | 41 |
| Croscarmellose sodium | 3.0% | 6.1 | 61 |
| SLS | 0.5% | 1.0 | 10 |
| Colloidal silicon dioxide | 1.0% | 2.0 | 20 |
| Magnesium stearate | 1.5% | 3.0 | 30 |
| Total | 100% | 203 | 2030 |

Intermediate 1, mannitol (Pearlitol® 100 SD commercially available from Roquette America Inc. of Keokuk Iowa), sucralose (Splenda® commercially available from Lyle and Tate of Decatur, Ill.), croscarmellose sodium (FMC Ac-Di-Sol®, commercially available from FMC BioPolymer Corporation of Philadelphia, Pa.), sodium lauryl sulfate (SLS) available from Fischer Scientific, and colloidal silicon dioxide (Cabot Cab-O-Sil® M-5P Fumed Silicon Dioxide, commercially available from Cabot Corporation of Alpharetta, Ga.) and magnesium stearate (Hyqual®, commercially available from Mallinckrodt Chemicals) are sieved through a 30 and 60 mesh screen to remove lumps.

Intermediate 1, colloidal silicon dioxide, sucralose and SLS are blended together for 25 minutes and sieved through a 20 mesh screen to remove any lumps. Magnesium stearate is sieved through a 60 mesh screen to remove lumps. The Intermediate 1 mixture is added to 20% of the total amount of magnesium stearate and combined a 8 quart V blender and blended for 25 minutes at 20-24 rpm thereby forming a first blended mixture. Mannitol and croscarmellose sodium are added together and sieved through a 20 mesh screen to remove lumps. The mannitol and croscarmellose sodium mixture is then added to the first blended mixture and blended for an additional 25 minutes at 20-24 rpm forming a second blended mixture. The second blended mixture is further delumped using a Comil through a 30 mesh screen and then the remaining 80% of the total magnesium stearate is added to the screened second blended mixture forming a compression mixture. Once the compression mixture has been finally completed the compression mixture is transferred to a Kikusui B-Tooling, 19 station rotary tablet press (half tooled) for compression (Kikusui USA, Lakewood, N.J.). Pressing the mixture into mini-tablets generated 2 mm diameter cylindrical mini-tablets having a length of 2 mm, each mini-tablet having approximately 2.63 mg of N-[2,4-Bis(1,1-dimethylethyl)-5-hydroxyphenyl]-1,4-dihydro-4-oxoquinoline-3-carboxamide and having an initial tensile strength of between about 0.5 MPa and about 4 MPa. About 29 mini-tablets (203 mg total) are then encapsulated using IN-CAP® automatic tabletop capsule filling machine using hard-gelatin or HPMC capsules.

Example 8

Exemplary Mini-Tablet 1 Formulated in Exemplary Capsule 7 (Capsule Formulated to have about 75 mg of Compound 1)

A batch of shallow convex cylindrical, 2 mm diameter, 2 mm length mini-tablets (each mini-tablet weighing about 7.0 mg) was formulated to have approximately 75 mg of Compound 1 per about 29 mini-tablets using the amounts of ingredients recited in Table 8, below.

TABLE 8

Ingredients for Exemplary Mini-Tablets For Capsule 7.

| Formulation | Percent Dose % Wt./Wt. | Dose (mg) | Batch (g) |
| --- | --- | --- | --- |
| Intermediate 1 | 46.9% | 95.2 | 469 |
| Mannitol | 45.1% | 91.6 | 451 |
| Sucralose | 2.0% | 4.1 | 20 |
| Croscarmellose sodium | 3.0% | 6.1 | 30 |
| SLS | 0.5% | 1.0 | 5 |
| Colloidal silicon dioxide | 1.0% | 2.0 | 10 |
| Magnesium stearate | 1.5% | 3.0 | 15 |
| Total | 100% | 203 | 1000 |

Intermediate 1, sucralose (commercially available from Tate and Lyle of Decatur, Ill.), sodium lauryl sulfate (SLS, of Fisher Scientific), and colloidal silicon dioxide (Cabot Cab-O-Sil® M-5P Fumed Silicon Dioxide, commercially available from Cabot Corporation of Alpharetta, Ga.) were co-screened through 30 mesh (600 micrometer) screen. Mannitol (Pearlitol® 100 SD commercially available from Roquette America Inc. of Keokuk Iowa), and croscarmellose sodium (FMC Ac-Di-Sol®, commercially available from FMC BioPolymer Corporation of Philadelphia, Pa.), were co-screened through 30 mesh (600 micrometer) screen. Magnesium stearate (Hyqual®, commercially available from Mallinckrodt Chemicals) was sieved through a 60 mesh (250 micrometer) screen.

The co-screened Intermediate 1, colloidal silicon dioxide, sucralose, and SLS, and 20 wt % of screened magnesium stearate were blended together for 15 minutes at 20-27 rpm in a 4 quart V-blender. The co-screened mannitol and croscarmellose sodium were added to this blend and blended for 7 minutes at 20-27 rpm. The second blended mixture was delumped through a 610 micrometer screen using a Comil. The remaining 80% of the total magnesium stearate was added to the blend in a 4 quart V-blender and blended for 5 minutes at 20-27 rpm forming a compression mixture. Once the compression mixture was finally completed, the compression mixture was transferred to a Kikusui B-tooling rotary tablet press. The powder blend was compressed into mini-tablets using all 19 stations of Kikusui tablet press (Kikusui USA, Lakewood, N.J.). Mini-tablets were compressed into 2 mm diameter shallow convex cylindrical shape at approximately 2 mm thickness, weighing approximately 7 mg, each mini-tablet having approximately 2.6 mg of N-[2,4-Bis(1,1-dimethylethyl)-5-hydroxyphenyl]-1,4-dihydro-4-oxoquinoline-3-carboxamide, and having average tensile strength of approximately 3.1 MPa. About 29 mini-tablets (203 mg total)

Example 9

Exemplary Mini-Tablet 1 Formulated in Exemplary Capsule 8 (Capsule Formulated to have about 75 mg of Compound 1)

A batch of shallow convex cylindrical, 2 mm diameter, 2 mm length mini-tablets (each mini-tablet weighing about 7.0 mg) was formulated to have approximately 75 mg of Compound 1 per about 29 mini-tablets using the amounts of ingredients recited in Table 9, below.

TABLE 9

Ingredients for Exemplary Mini-Tablets For Capsule 8.

| Formulation | Percent Dose % Wt./Wt. | Dose (mg) | Batch (g) |
|---|---|---|---|
| Intermediate 1 | 46.9% | 95.2 | 469 |
| Mannitol | 45.1% | 91.6 | 451 |
| Sucralose | 2.0% | 4.1 | 20 |
| Croscarmellose sodium | 3.0% | 6.1 | 30 |
| SLS | 0.5% | 1.0 | 5 |
| Colloidal silicon dioxide | 1.0% | 2.0 | 10 |
| Magnesium stearate | 1.5% | 3.0 | 15 |
| Total | 100% | 203 | 1000 |

Intermediate 1, sucralose (commercially available from Tate and Lyle of Decatur, Ill.), sodium lauryl sulfate (SLS, of Fisher Scientific), and colloidal silicon dioxide (Cabot Cab-O-Sil® M-5P Fumed Silicon Dioxide, commercially available from Cabot Corporation of Alpharetta, Ga.) were co-screened through 30 mesh (600 micrometer) screen. Mannitol (Pearlitol® 100 SD commercially available from Roquette America Inc. of Keokuk Iowa), and croscarmellose sodium (FMC Ac-Di-Sol®, commercially available from FMC BioPolymer Corporation of Philadelphia, Pa.), were co-screened through 30 mesh (600 micrometer) screen. Magnesium stearate (Hyqual®, commercially available from Mallinckrodt Chemicals) was sieved through a 60 mesh (250 micrometer) screen.

The co-screened Intermediate 1, colloidal silicon dioxide, sucralose, and SLS, and 20 wt % of screened Mg stearate were blended together for 15 minutes at 20-27 rpm in a 4 quart V-blender. The co-screened mannitol and croscarmellose sodium were added to this blend and blended for 7 minutes at 20-27 rpm. This blend was delumped through 024R screen (610 micrometers) at 2700 rpm using a Quadro Comil 197. The remaining 80% of the total magnesium stearate was added to the blend (delumped using a comil) in a 4 quart V-blender and blended for 5 minutes at 20-27 rpm forming a compression mixture. Once the compression mixture was finally completed, the compression mixture was transferred to a Kikusui B-tooling rotary tablet press. The powder blend was compressed into mini-tablets using all 19 stations of Kikusui tablet press (Kikusui USA, Lakewood, N.J.). Mini-tablets were compressed into 2 mm diameter shallow convex cylindrical shape at approximately 2 mm thickness, weighing approximately 7 mg, each mini-tablet having approximately 2.6 mg of N-[2,4-Bis(1,1-dimethylethyl)-5-hydroxyphenyl]-1,4-dihydro-4-oxoquinoline-3-carboxamide, and having average tensile strength of approximately 2.5 MPa. About 29 mini-tablets (203 mg total) were then encapsulated using IN-CAP® automatic tabletop capsule filling machine using HPMC capsules.

Example 10

Exemplary Mini-Tablet 2 Containing Approximately 10 mg of Substantially Amorphous or Amorphous Compound 1

A batch of standard convex cylindrical 4 mm diameter, approximately 2.5-3 mm thickness tablets was formulated to have approximately 10 mg of Compound 1 per tablet using the amounts of ingredients recited in Table 10.

TABLE 10

Ingredients for exemplary Mini-tablet 2

| Formulation | Percent Dose % Wt./Wt. | Dose (mg) | Batch (g) |
|---|---|---|---|
| Intermediate 1 | 46.9 | 12.5 | 468.8 |
| Mannitol | 43.1 | 11.5 | 431.3 |
| Sucralose | 2 | 0.53 | 20.1 |
| Crosscarmellose sodium | 5 | 1.33 | 5 |
| SLS | 0.5 | 0.13 | 50 |
| Colloidal Silicon dioxide | 1 | 0.27 | 10 |
| Magnesium Stearate | 1.5 | 0.4 | 14.8 |
| Total | 100 | 26.66 | 1000 |

Intermediate 1, sucralose (commercially available from Tate and Lyle of Decatur, Ill.), sodium lauryl sulfate (SLS, of Fisher Scientific), and colloidal silicon dioxide (Cabot Cab-O-Sil® M-5P Fumed Silicon Dioxide, commercially available from Cabot Corporation of Alpharetta, Ga.) were co-screened through 30 mesh (600 micrometer) screen. Mannitol (Pearlitol® 100 SD commercially available from Roquette America Inc. of Keokuk Iowa), and croscarmellose sodium (FMC Ac-Di-Sol®, commercially available from FMC BioPolymer Corporation of Philadelphia, Pa.), were co-screened through 30 mesh (600 micrometer) screen. Magnesium stearate (commercially available from Fisher Scientific, Pittsburgh, Pa.) was sieved through a 60 mesh (250 micrometer) screen.

The co-screened Intermediate 1, colloidal silicon dioxide, sucralose, and SLS, and 20 wt % of screened magnesium stearate were blended together for 15 minutes at 20-27 rpm in a 4 quart V-blender. The co-screened mannitol and croscarmellose sodium were added to this blend and blended for 7 minutes at 20-27 rpm. The second blended mixture was delumped using a Comil through a 610 micrometer screen. The remaining 80% of the total magnesium stearate was added to the blend in a 4 quart V-blender and blended for 5 minutes at 20-27 rpm forming a compression mixture. The compression mixture was transferred to a Piccola 8-Station tablet press. 4 mm diameter round convex tablets were compressed using 4 mm diameter round standard cup tooling. Each tablet weighed approximately 26.7 mg and had a thickness of ~2.5 to 3 mm. Each tablet contained approximately 10 mg of Compound 1.

Example 11

Exemplary Mini-Tablet 3 Containing Approximately 10 mg of Substantially Amorphous or Amorphous Compound 1

A batch of standard convex cylindrical 4 mm diameter, approximately 2.5-3.5 mm thickness tablets was formulated to have approximately 10 mg of Compound 1 per tablet using the amounts of ingredients recited in Table 11.

TABLE 11

Ingredients for exemplary Mini-tablet 3.

| Formulation | Percent Dose % Wt./Wt. | Dose (mg) | Batch (g) |
|---|---|---|---|
| Intermediate 1 | 35 | 12.5 | 350.1 |
| Mannitol | 55 | 19.6 | 550 |
| Sucralose | 2 | 0.71 | 20 |
| Crosscarmellose sodium | 5 | 1.79 | 5 |
| SLS | 0.5 | 0.18 | 50 |
| Colloidal Silicon dioxide | 1 | 0.36 | 10 |
| Magnesium Stearate | 1.5 | 0.54 | 14.7 |
| Total | 100 | 35.7 | 1000 |

Intermediate 1, sucralose (commercially available from Tate and Lyle of Decatur, Ill.), sodium lauryl sulfate (SLS, of Fisher Scientific), and colloidal silicon dioxide (Cabot Cab-O-Sil® M-5P Fumed Silicon Dioxide, commercially available from Cabot Corporation of Alpharetta, Ga.) were co-screened through 30 mesh (600 micrometer) screen. Mannitol (Pearlitol® 100 SD commercially available from Roquette America Inc. of Keokuk Iowa), and croscarmellose sodium (FMC Ac-Di-Sol®, commercially available from FMC BioPolymer Corporation of Philadelphia, Pa.), were co-screened through 30 mesh (600 micrometer) screen. Magnesium stearate (commercially available from Fisher Scientific, Pittsburgh, Pa.) was sieved through a 60 mesh (250 micrometer) screen.

The co-screened Intermediate 1, colloidal silicon dioxide, sucralose, and SLS, and 20 wt % of screened magnesium stearate were blended together for 15 minutes at 20-27 rpm in a 4 quart V-blender. The co-screened mannitol and croscarmellose sodium were added to this blend and blended for 7 minutes at 20-27 rpm. The second blended mixture was delumped using a Comil through a 610 micrometer screen. The remaining 80% of the total magnesium stearate was added to the blend in a 4 quart V-blender and blended for 5 minutes at 20-27 rpm forming a compression mixture. The compression mixture was transferred to a Piccola 8-Station tablet press. 4 mm diameter round convex tablets were compressed using 4 mm diameter round standard cup tooling. Each tablet weighed approximately 35.7 mg and had a thickness of 2.5-3.5 mm. Each tablet contained approximately 10 mg of Compound 1.

Example 12

Exemplary Mini-Tablet 4 Formulated in Exemplary Capsule 9 (Capsule Formulated to have about 75 mg of Compound 1)

A batch of cylindrical, 2 mm diameter, approximately 2 mm thickness mini-tablets (each mini-tablet weighing approximately 7 mg) was formulated to have approximately 75 mg of Compound 1 per about 38 mini-tablets using the amounts of ingredients recited in Table 12.

TABLE 12

Ingredients for exemplary Mini-tablet 4

| Formulation | Percent Dose % Wt./Wt. | Dose (mg) | Batch (g) |
|---|---|---|---|
| Intermediate 1 | 35 | 93.8 | 210 |
| Mannitol | 55 | 147.4 | 330 |
| Sucralose | 2 | 5.36 | 12 |

TABLE 12-continued

Ingredients for exemplary Mini-tablet 4

| Formulation | Percent Dose % Wt./Wt. | Dose (mg) | Batch (g) |
|---|---|---|---|
| Crosscarmellose sodium | 5 | 13.4 | 30 |
| SLS | 0.5 | 1.34 | 3 |
| Colloidal Silicon dioxide | 1 | 2.68 | 6 |
| Magnesium Stearate | 1.5 | 4.02 | 8.8 |
| Total | 100 | 268 | 599.8 |

Intermediate 1, sucralose (commercially available from Tate and Lyle of Decatur, Ill.), sodium lauryl sulfate (SLS, of Fisher Scientific), and colloidal silicon dioxide (Cabot Cab-O-Sil® M-5P Fumed Silicon Dioxide, commercially available from Cabot Corporation of Alpharetta, Ga.) were co-screened through 30 mesh (600 micrometer) screen. Mannitol (Pearlitol® 100 SD commercially available from Roquette America Inc. of Keokuk Iowa), and croscarmellose sodium (FMC Ac-Di-Sol®, commercially available from FMC BioPolymer Corporation of Philadelphia, Pa.), were co-screened through 30 mesh (600 micrometer) screen. Magnesium stearate (commercially available from Fisher Scientific, Pittsburgh, Pa.) was sieved through a 60 mesh (250 micrometer) screen.

The co-screened Intermediate 1, colloidal silicon dioxide, sucralose, and SLS, and 20 wt % of screened magnesium stearate were blended together for 15 minutes at 20-27 rpm in a 2 quart V-blender. The co-screened mannitol and croscarmellose sodium were added to this blend and blended for 7 minutes at 20-27 rpm. The second blended mixture was delumped through a 610 micrometer screen using a Comil. The remaining 80% of the total magnesium stearate was added to the blend in a 2 quart V-blender and blended for 5 minutes at 20-27 rpm forming a compression mixture. The compression mixture was transferred to a Piccola 8-Station tablet press. 2 mm diameter round convex tablets were compressed using 2 mm diameter round shallow cup tooling. Each tablet weighs approximately 7 mg and has a thickness of ~2 mm. Each tablet contains approximately 1.97 mg of Compound 1.

Example 13

Exemplary Mini-Tablet 5 Made by Dry Granulation Method, Formulated in Exemplary Capsule 10 (Capsule Formulated to have about 75 mg of Compound 1)

A batch of cylindrical, 2 mm diameter, approximately 2 mm thickness mini-tablets (each mini-tablet weighing approximately 7 mg) was formulated to have approximately 75 mg of Compound 1 per about 29 mini-tablets using the amounts of ingredients recited in Table 13.

TABLE 13

Ingredients for exemplary Mini-tablet 5

| Formulation | Percent Dose % Wt./Wt. | Dose (mg) | Batch (g) |
|---|---|---|---|
| Intermediate 1 | 46.9 | 93.8 | 74.6 |
| Mannitol (Pearlitol 25C) | 42.1 | 84.2 | 66.9 |
| Sucralose | 2 | 4 | 3.18 |
| Crosscarmellose sodium | 6 | 12 | 9.5 |
| SLS | 0.5 | 1 | 0.8 |

TABLE 13-continued

Ingredients for exemplary Mini-tablet 5

| Formulation | Percent Dose % Wt./Wt. | Dose (mg) | Batch (g) |
|---|---|---|---|
| Colloidal Silicon dioxide | 1 | 2 | 1.6 |
| Magnesium Stearate | 1.5 | 3 | 2.4 |
| Total | 100 | 200 | 159 |

Intermediate 1 and Cabosil were sieved through 20 mesh screen and then mixed manually in a small container, and then co-screened through 40 mesh screen. The mixture was blended in Turbula blender for 10 minutes at 32 rpm. The mixture was passed through a Comil 193, at 2000 rpm using a 032R screen. Mannitol (Pearlitol 25C) and SLS and Sucralose and AcDiSol were screened through 20 mesh screen. This blend and the Intermediate 1 and Cabosil mixture were blended for 10 minutes at 32 rpm in Turbula blender. The blend was passed through a 193, at 2000 rpm, using a 032R screen. The material was then blended for 15 minutes in Turbula blender at 32 rpm. Magnesium Stearate was screened through 40 mesh screen and half was manually blended with 3 times of its volume of the blend. This mixture was blended for 4 minutes in a Turbula blender with the rest of the blend at 32 rpm. The powder blend is then compressed into ~0.5 inch flat round slugs having a tensile strength of ~0.25 MPa using an F-Press. The slugs were gently milled manually using a pestle mortar and passed through a 30 mesh screen. The remaining half of the screened magnesium Stearate was manually blended with 3 times of its volume of the blend. This mixture was blended for 4 min with the rest of the blend in Turbula blender at 32 rpm to provide the compression blend. The compression blend was then compressed into 2 mm diameter convex 2 mm mini-tablets on a Key Press using 2 mm diameter round shallow cup tooling. Each mini-tablet weight was ~7 mg and contained ~2.63 mg of Compound 1.

Example 14

Exemplary Mini-Tablet 6 Formulated in Exemplary Capsule 11 (Capsule Formulated to have about 50 mg and about 75 mg of Compound 1)

A batch of cylindrical, ~2 mm diameter, ~2 mm thickness mini-tablets (each mini-tablet weighing about 6.9 mg) was formulated to have approximately 50 mg of Compound 1 per 26 mini-tablets and approximately 75 mg of Compound 1 per 39 mini-tablets using the amounts of ingredients recited in Table 14, below.

TABLE 14

Ingredients for mini-tablets for capsule 11 at 50 mg and 75 mg potency

| Tablet Formulation | Percent Dose % Wt./Wt. | Dose (mg) 50 mg potency | Dose (mg) 75 mg potency | Batch (g) |
|---|---|---|---|---|
| Intermediate 1 | 35 | 62.5 | 93.8 | 1753.4 |
| Mannitol | 13.5 | 24.1 | 36.2 | 675.2 |
| Lactose | 41 | 73.2 | 109.8 | 2050.2 |
| Sucralose | 2.0 | 3.6 | 5.4 | 100.06 |
| Croscarmellose sodium | 6.0 | 10.7 | 16.1 | 300.1 |
| Colloidal silicon dioxide | 1.0 | 1.8 | 2.7 | 50.0 |
| Magnesium stearate | 1.5 | 2.7 | 4.0 | 74.19 |
| Total | 100 | 178.6 | 268 | 5003.15 |

Intermediate 1, sucralose (commercially available from Tate and Lyle of Decatur, Ill.), and colloidal silicon dioxide (Cabot Cab-O-Sil® M-5P Fumed Silicon Dioxide, commercially available from Cabot Corporation of Alpharetta, Ga.) were co-screened through 30 mesh (600 micrometer) screen. Mannitol (Pearlitol® 100 SD commercially available from Roquette America Inc. of Keokuk Iowa), Lactose (spray dried lactose monohydrate Fast Flo 316 commercially available from Foremost Bara-boo, WI) and croscarmellose sodium (Ac-Di-Sol®, commercially available from FMC BioPolymer Corporation of Philadelphia, Pa.), were co-screened through 30 mesh (600 micrometer) screen. Magnesium stearate (commercially available from Fisher Scientific) was sieved through a 60 mesh (250 micrometer) screen.

The co-screened Intermediate 1, colloidal silicon dioxide, sucralose, and 20 wt % of screened Mg stearate were blended together for 15 minutes at 35 rpm in a 20 liter stainless steel Bohle bin blender. The co-screened mannitol and lactose and croscarmellose sodium were added to this blend and blended for 7 minutes at 35 rpm. This blend was comiled through 024R screen (610 micrometer) at 5000 rpm using Quadro Comil 197. The remaining 80% of the total magnesium stearate was added to the comiled blend in the 20 liter stainless steel Bohle bin blender and blended for 5 minutes at 35 rpm forming a compression blend. The compression blend was transferred to a Korsch XM12 B-tooling rotary tablet press tooled with 9 sets of multi-tip tooling (8 tips per punch). The blend was compressed into ~2 mm diameter cylindrical shape mini-tablets at approximately 1.94 mm thickness, weighing approximately 6.9 mg, each mini-tablet having approximately 1.92 mg of N-[2,4-Bis(1,1-dimethylethyl)-5-hydroxyphenyl]-1,4-dihydro-4-oxoquinoline-3-carboxamide, and having average tensile strength of approximately 1 MPa. 26 mini-tablets (~178.6 mg total, 50 mg potency) were then encapsulated using IN-CAP® automatic tabletop capsule filling machine using Vcaps Plus HPMC capsules. 75 mg potency capsules were made by filling Vcaps Plus HPMC capsules with 39 mini-tablets.

Example 15

Exemplary Mini-Tablet 7 Formulated in Exemplary Capsule 12 (Capsule Formulated to have about 40 mg and about 100 mg of Compound 1)

A batch of cylindrical, ~2 mm diameter, ~2 mm thickness mini-tablets (each mini-tablet weighing about 6.9 mg) was formulated to have approximately 40 mg of Compound 1 per 21 mini-tablets and approximately 100 mg of Compound 1 per 52 mini-tablets using the amounts of ingredients recited in Table 15, below.

TABLE 15

Ingredients for mini-tablets for Capsule 12 at 40 mg and 100 mg potency.

| Tablet Formulation | Percent Dose % Wt./Wt. | Dose (mg) 40 mg potency | Dose (mg) 100 mg potency | Batch (g) |
|---|---|---|---|---|
| Intermediate 1 | 35 | 50 | 125 | 1046.1 |
| Mannitol | 13.5 | 19.3 | 48.2 | 402.4 |
| Lactose | 41 | 58.6 | 146.4 | 1229.0 |
| Sucralose | 2.0 | 2.9 | 7.1 | 57.0 |
| Croscarmellose sodium | 6.0 | 8.6 | 21.4 | 178.7 |
| Colloidal silicon dioxide | 1.0 | 1.4 | 3.6 | 28.1 |
| Magnesium stearate | 1.5 | 2.1 | 5.4 | 45.03 |
| Total | 100 | 142.9 | 357.1 | 2986.33 |

Intermediate 1, sucralose (commercially available from Tate and Lyle of Decatur, Ill.), and colloidal silicon dioxide (Cabot Cab-O-Sil® M-5P Fumed Silicon Dioxide, commercially available from Cabot Corporation of Alpharetta, Ga.) were co-screened through 30 mesh (600 micrometer) screen. Mannitol (Pearlitol® 100 SD commercially available from Roquette America Inc. of Keokuk Iowa), lactose (spray dried lactose monohydrate Fast Flo 316 commercially available from Foremost Bara-boo, WI) and croscarmellose sodium (Ac-Di-Sol®, commercially available from FMC BioPolymer Corporation of Philadelphia, Pa.), were co-screened through 30 mesh (600 micrometer) screen. Magnesium stearate (Hyqual®, commercially available from Mallinckrodt Chemicals) was sieved through a 60 mesh (250 micrometer) screen.

The co-screened Intermediate 1, colloidal silicon dioxide, sucralose, and 20 wt % of screened Mg stearate were blended together for 41 minutes at 12 rpm in an 8 quart stainless steel V-blender. The co-screened mannitol and lactose and croscarmellose sodium were added to this blend and blended for 15 minutes at 12 rpm. This blend was comiled through 024R screen (610 micrometer) at 5000 rpm using Quadro Comil 197. The remaining 80% of the total magnesium stearate was added to the comiled blend and blended for 10 minutes at 12 rpm in the 8 quart stainless steel V-blender forming a compression blend. The compression blend was transferred to a Korsch XM12 B-tooling rotary tablet press tooled with 9 sets of multi-tip tooling (8 tips per punch). The blend was compressed into ~2 mm diameter cylindrical shape mini-tablets at approximately 1.97 mm thickness, weighing approximately 6.9 mg, each mini-tablet having approximately 1.92 mg of N-[2,4-Bis(1,1-dimethylethyl)-5-hydroxyphenyl]-1,4-dihydro-4-oxoquinoline-3-carboxamide, and having average tensile strength of approximately 1 MPa. 21 mini-tablets (~142.9 mg total, 40 mg potency) were then encapsulated using IN-CAP® automatic tabletop capsule filling machine using Vcaps Plus HPMC capsules. 100 mg potency capsules were made by filling Vcaps Plus HPMC capsules with 52 mini-tablets.

Example 16

Exemplary tablet 8 at 10 mg potency

A batch of standard convex cylindrical, ~4 mm diameter, ~3 mm thickness tablets (each tablet weighing about 35.7 mg) was formulated to have approximately 10 mg of Compound 1 per tablet using the amounts of ingredients recited in Table 16, below.

TABLE 16

Ingredients for Exemplary tablet 8 at 10 mg potency

| Tablet Formulation | Percent Dose % Wt./Wt. | Dose (mg) 10 mg potency | Batch (g) |
|---|---|---|---|
| Intermediate 1 | 35 | 12.50 | 1046.1 |
| Mannitol | 13.5 | 4.82 | 402.4 |
| Lactose | 41 | 14.64 | 1229.0 |
| Sucralose | 2.0 | 0.71 | 57.0 |
| Croscarmellose sodium | 6.0 | 2.14 | 178.7 |
| Colloidal silicon dioxide | 1.0 | 0.36 | 28.1 |
| Magnesium stearate | 1.5 | 0.54 | 45.03 |
| Total | 100 | 35.7 | 2986.33 |

Intermediate 1, sucralose (commercially available from Tate and Lyle of Decatur, Ill.), and colloidal silicon dioxide (Cabot Cab-O-Sil® M-5P Fumed Silicon Dioxide, commercially available from Cabot Corporation of Alpharetta, Ga.) were co-screened through 30 mesh (600 micrometer) screen. Mannitol (Pearlitol® 100 SD commercially available from Roquette America Inc. of Keokuk Iowa), lactose (spray dried lactose monohydrate Fast Flo 316 commercially available from Foremost Bara-boo, WI) and croscarmellose sodium (Ac-Di-Sol®, commercially available from FMC BioPolymer Corporation of Philadelphia, Pa.), were co-screened through 30 mesh (600 micrometer) screen. Magnesium stearate (Hyqual®, commercially available from Mallinckrodt Chemicals) was sieved through a 60 mesh (250 micrometer) screen.

The co-screened Intermediate 1, colloidal silicon dioxide, sucralose, and 20 wt % of screened Mg stearate were blended together for 41 minutes at 12 rpm in an 8 quart stainless steel V-blender. The co-screened mannitol and lactose and croscarmellose sodium were added to this blend and blended for 15 minutes at 12 rpm. This blend was comiled through 024R screen (610 micrometer) at 5000 rpm using Quadro Comil 197. The remaining 80% of the total magnesium stearate was added to the comiled blend and blended for 10 minutes at 12 rpm in the 8 quart stainless steel V-blender forming a compression blend. The compression blend was transferred to an 8 station Piccola D-tooling rotary tablet press tooled with 4 sets of tooling. The powder blend was compressed into ~4 mm diameter standard convex tablets at approximately 3 mm thickness, weighing approximately 35.7 mg, each tablet having approximately 10 mg of N-[2,4-Bis(1,1-dimethylethyl)-5-hydroxyphenyl]-1,4-dihydro-4-oxoquinoline-3-carboxamide, and having average tensile strength of approximately 1 MPa.

Example 17

Exemplary Tablet 9 at 12.5 mg Potency

A batch of standard convex cylindrical, ~4 mm diameter, ~3.7 mm thickness tablets (each tablet weighing about 44.7 mg) was formulated to have approximately 12.5 mg of Compound 1 per tablet using the amounts of ingredients recited in Table 17, below.

TABLE 17

Ingredients for Exemplary tablet at 12.5 mg potency

| Tablet Formulation | Percent Dose % Wt./Wt. | Dose (mg) 12.5 mg potency | Batch (g) |
|---|---|---|---|
| Intermediate 1 | 35 | 15.65 | 1046.1 |
| Mannitol | 13.5 | 6.03 | 402.4 |

TABLE 17-continued

Ingredients for Exemplary tablet at 12.5 mg potency

| Tablet Formulation | Percent Dose % Wt./Wt. | Dose (mg) 12.5 mg potency | Batch (g) |
|---|---|---|---|
| Lactose | 41 | 18.33 | 1229.0 |
| Sucralose | 2.0 | 0.89 | 57.0 |
| Croscarmellose sodium | 6.0 | 2.68 | 178.7 |
| Colloidal silicon dioxide | 1.0 | 0.45 | 28.1 |
| Magnesium stearate | 1.5 | 0.67 | 45.03 |
| Total | 100 | 44.7 | 2986.33 |

Intermediate 1, sucralose (commercially available from Tate and Lyle of Decatur, Ill.), and colloidal silicon dioxide (Cabot Cab-O-Sil® M-5P Fumed Silicon Dioxide, commercially available from Cabot Corporation of Alpharetta, Ga.) were co-screened through 30 mesh (600 micrometer) screen. Mannitol (Pearlitol® 100 SD commercially available from Roquette America Inc. of Keokuk Iowa), lactose (spray dried lactose monohydrate Fast Flo 316 commercially available from Foremost Bara-boo, WI) and croscarmellose sodium (Ac-Di-Sol®, commercially available from FMC BioPolymer Corporation of Philadelphia, Pa.), were co-screened through 30 mesh (600 micrometer) screen. Magnesium stearate (Hyqual®, commercially available from Mallinckrodt Chemicals) was sieved through a 60 mesh (250 micrometer) screen.

The co-screened Intermediate 1, colloidal silicon dioxide, sucralose, and 20 wt % of screened Mg stearate were blended together for 41 minutes at 12 rpm in an 8 quart stainless steel V-blender. The co-screened mannitol and lactose and croscarmellose sodium were added to this blend and blended for 15 minutes at 12 rpm. This blend was comiled through 024R screen (610 micrometer) at 5000 rpm using Quadro Comil 197. The remaining 80% of the total magnesium stearate was added to the comiled blend and blended for 10 minutes at 12 rpm in the 8 quart stainless steel V-blender forming a compression blend. The compression blend was transferred to an 8 station Piccola D-tooling rotary tablet press tooled with 4 sets of tooling. The powder blend was compressed into ~4 mm diameter standard convex tablets at approximately 3.7 mm thickness, weighing approximately 44.7 mg, each tablet having approximately 12.5 mg of N-[2,4-Bis(1,1-dimethylethyl)-5-hydroxyphenyl]-1,4-dihydro-4-oxoquinoline-3-carboxamide, and having average tensile strength of approximately 1 MPa.

Example 18

Exemplary Mini-Tablets 10

A batch of cylindrical, ~2 mm diameter, ~2 mm thickness mini-tablets (each mini-tablet weighing about 7 mg) was formulated to have approximately 50 mg of Compound 1 per 26 mini-tablets and approximately 75 mg of Compound 1 per 39 mini-tablets using the amounts of ingredients recited in Table 18, below.

TABLE 18

Ingredients for mini-tablets at 50 mg and 75 mg potency

| Tablet Formulation | Percent Dose % Wt./Wt. | Dose (mg) 50 mg potency | Dose (mg) 75 mg potency | Batch (g) |
|---|---|---|---|---|
| Intermediate 1 | 35 | 62.5 | 93.8 | 525.07 |
| Mannitol | 13.5 | 24.1 | 36.2 | 202.54 |
| Lactose | 41 | 73.2 | 109.8 | 614.99 |
| Sucralose | 2.0 | 3.6 | 5.4 | 30.10 |
| Croscarmellose sodium | 6.0 | 10.7 | 16.1 | 90.06 |
| Colloidal silicon dioxide | 1.0 | 1.8 | 2.7 | 15.00 |
| Magnesium stearate | 1.5 | 2.7 | 4.0 | 22.54 |
| Total | 100 | 178.6 | 268 | 1500.3 |

Intermediate 1, sucralose (commercially available from Tate and Lyle of Decatur, Ill.), and colloidal silicon dioxide (Cabot Cab-O-Sil® M-5P Fumed Silicon Dioxide, commercially available from Cabot Corporation of Alpharetta, Ga.) were co-screened through 30 mesh (600 micrometer) screen. Mannitol (Pearlitol® 100 SD commercially available from Roquette America Inc. of Keokuk Iowa), lactose (spray dried lactose monohydrate Fast Flo 316 commercially available from Foremost Bara-boo, WI) and croscarmellose sodium (Ac-Di-Sol®, commercially available from FMC BioPolymer Corporation of Philadelphia, Pa.), were co-screened through 30 mesh (600 micrometer) screen. Magnesium stearate (commercially available from Fisher Scientific) was sieved through a 60 mesh (250 micrometer) screen.

The co-screened Intermediate 1, colloidal silicon dioxide and sucralose, were blended together for 15 minutes at 35 rpm in a 5 liter stainless steel Bohle bin blender. The co-screened mannitol and lactose and croscarmellose sodium were added to this blend and blended for 7 minutes at 35 rpm. This blend was comiled through 024R screen (610 micrometer) at 5000 rpm using a Quadro Comil 197. 50% of the total magnesium stearate was added to the comiled blend and blended for 5 minutes at 35 rpm in the 5 liter stainless steel Bohle bin blender forming a blend for dry granulation.

Dry granulation of the above blend was carried out on an Alexanderwerk WP-120 roller compactor with a constant roll speed of 3.0 rpm, a roll gap setting of 2.5 mm, and roll pressures of 30 and 40 bar. Ribbons were milled through the Alexanderwerk Rotary Fine Granulator (100 rpm) or the Comil (3000 rpm) using ~500 micron screen size.

Four batches of milled granules were lubricated with the remaining magnesium stearate. Mg stearate was added at 0.75 wt % and blended in a glass container for 5 minutes at 32 rpm using Turbula blender.

The lubricated granules were transferred to an 8 station Piccola D-tooling rotary tablet press tooled with 1 set of multi-tip tooling (10 tips per punch), and were compressed into mini-tablets of ~2 mm diameter cylindrical shape at approximately 1.95 mm thickness, weighing approximately 7 mg, each mini-tablet having approximately 1.92 mg of N-[2,4-Bis(1,1-dimethylethyl)-5-hydroxyphenyl]-1,4-dihydro-4-oxoquinoline-3-carboxamide, and having average tensile strength of approximately 1-1.5 MPa.

Example 19

Exemplary Mini-Tablets 11

A batch of shallow convex cylindrical, 2 mm diameter, 2 mm length mini-tablets (each mini-tablet weighing about 7.0 mg) was formulated using the amounts of ingredients recited in Table 19, below.

TABLE 19

Ingredients for Exemplary Mini-Tablets

| Tablet Formulation | Percent Dose % Wt./Wt. | Batch (kg) |
|---|---|---|
| Intermediate 1 | 35.0% | 8.750 |
| Mannitol | 13.5% | 3.375 |
| Lactose | 41 | 10.25 |
| Sucralose | 2.0% | 0.50 |
| Croscarmellose sodium | 6.0% | 0.25 |
| Colloidal silicon dioxide | 1.0% | 1.50 |
| Magnesium stearate | 1.5% | 0.375 |
| Total | 100% | 25.000 |

Intermediate 1, sucralose (commercially available from Tate and Lyle of Decatur, Ill.), and colloidal silicon dioxide (Cabot Cab-O-Sil® M-5P Fumed Silicon Dioxide, commercially available from Cabot Corporation of Alpharetta, Ga.) were co-screened through 30 mesh (600 micrometer) screen. Mannitol (Pearlitol® 100 SD commercially available from Roquette America Inc. of Keokuk Iowa), and croscarmellose sodium (FMC Ac-Di-Sol®, commercially available from FMC BioPolymer Corporation of Philadelphia, Pa.), and Lactose (Fast Flo Lactose 316 available from Foremost of Baraboo, Wis.) were co-screened through 30 mesh (600 micrometer) screen. Magnesium stearate (Hyqual®, commercially available from Mallinckrodt Chemicals) was sieved through a 60 mesh (250 micrometer) screen.

The co-screened Intermediate 1, colloidal silicon dioxide, and sucralose, were blended together for 40 minutes at 12 rpm in a 3 cu ft bin blender. The co-screened mannitol, lactose, and croscarmellose sodium were added to this blend and blended for 15 minutes at 12 rpm. The second blended mixture was co-milled through a 610 micrometer screen. The screened magnesium stearate was added to the comiled blend in a 3 cu ft bin blender and blended for 10 minutes at 12 rpm forming a compression mixture. Once the compression mixture was finally completed, the compression mixture was transferred to a Kilian TX32 B-tooling rotary tablet press. The powder blend was compressed into mini-tablets using Kilian tablet press (IMA KILIAN GMBH & CO. KG, Koln, Germany). Mini-tablets were compressed 2 mm diameter shallow convex cylindrical shape at approximately 2 mm thickness, weighing approximately 7 mg, each mini-tablet having approximately 1.92 mg of N-[2,4-Bis(1,1-dimethylethyl)-5-hydroxyphenyl]-1,4-dihydro-4-oxoquinoline-3-carboxamide, and having average tensile strength of approximately 1 MPa.

Example 20

Exemplary Mini-Tablets 12

A batch of shallow convex cylindrical, 2 mm diameter, 2 mm length mini-tablets (each mini-tablet weighing about 7.0 mg) were formulated according to Example 19 above. Doses of 25 mg, 50 mg, 75 mg and 100 mg are made by varying the number of mini-tablets of the batch in Example 19 above used (see Table 20) in a capsule, a packet, or a pouch.

TABLE 20

Ingredients for Exemplary Mini-Tablets

| Tablet Formulation | Percent Dose % Wt./Wt. | Amount per 25 mg dose (mg) | Amount per 50 mg dose (mg) | Amount per 75 mg dose (mg) | Amount per 100 mg dose (mg) |
|---|---|---|---|---|---|
| Intermediate 1 | 35.0% | 31.25 | 62.5 | 93.8 | 125 |
| Mannitol | 13.5% | 12.05 | 24.1 | 36.2 | 48.2 |
| Lactose | 41 | 36.6 | 73.2 | 109.9 | 146.4 |
| Sucralose | 2.0% | 1.8 | 3.6 | 5.4 | 7.2 |
| Croscarmellose sodium | 6.0% | 5.35 | 10.7 | 16.0 | 21.4 |
| Colloidal silicon dioxide | 1.0% | 0.9 | 1.8 | 2.7 | 3.6 |
| Magnesium stearate | 1.5% | 1.35 | 2.7 | 4.0 | 5.4 |
| Number of Mini-tablets | Not applicable | 13 | 26 | 39 | 52 |
| Total | 100% | 89.3 | 178.6 | 268 | 357.2 |

One of ordinary skill in the art would recognize that other doses can also be made by varying the number of mini-tablets from Example 19 above used in a capsule, a packet, or a pouch.

As one of ordinary skill in the art would appreciate, the above recitation of percentages and/or weights of each of the ingredients may also include deviations commonly expected in the formulation arts. For example, each quantity of excipient, Compound 1, weight of the powdered blend, and weight of each mini-tablet may vary by as much as 0.01%, or about 0.1%, or about 0.5% or about 1.0% or about 1.5%, or about 2% or about as much as 5% or at least as much as the standard deviation of each measurement tolerated by the measurement devices employed therein. For example, a 7 mg mini-tablet may weigh from about 0.01 to about 5% above or below the estimated 7 mg. Similarly, the amount of Compound 1 in each of the formulated doses may vary from about 0.01 to about 5% above or below the estimated amounts disclosed in the compositions and methods described herein. In another example, the weight of each mini-tablet may vary by as much as 0.01%, or about 0.1%, or about 0.5%, or about 1.0%, or about 1.5%, or about 2%, or about 5%, or about 7.5%, or about as much as 15% or at least twice as much as the standard deviation of each measurement tolerated by the measurement devices employed therein. For example, a 7 mg mini-tablet may weigh from about 0.01 to about 15% above or below the estimated 7 mg.

C. Administration of Pharmaceutical Formulations

Example 21

Exemplary Administration A

Human pediatric patients are orally administered a pharmaceutical formulation according to Table 21:

TABLE 21

Exemplary administration A of pharmaceutical formulations of the present invention to pediatric patients.

| Frequency of dosing (per day) | Description | Conditions |
|---|---|---|
| One administration | 1 × 75 mg dose of Compound 1 of any Example 7-9 or 13 | Administered mini-tablets (about 29) in 5 mL of baby formula or 5 mL apple sauce. |

TABLE 21-continued

Exemplary administration A of pharmaceutical formulations of the present invention to pediatric patients.

| Frequency of dosing (per day) | Description | Conditions |
|---|---|---|
| One administration | 1 × 75 mg dose of Compound 1 of Example 12 | Administered mini-tablets (about 38) in 5 mL of baby formula or 5 mL apple sauce. |
| One administration | 1 × 75 mg dose of Compound 1 of Example 3 | Administered powder blend (about 200 mg) in 5 mL of baby formula or 5 mL apple sauce. |
| One administration | 2 × 75 mg doses of Compound 1 of Example 3 | Administered powder blend (about 400 mg) in 5-10 mL of baby formula or 5-10 mL of apple sauce |
| One administration | 2 × 75 mg doses of Compound 1 of any Example 7-9 or 13 | Administered mini-tablets (about 58) in 10 mL of baby formula or 10 mL apple sauce. |
| One administration | 2 × 75 mg dose of Compound 1 of Example 12 | Administered mini-tablets (about 76) in 10 mL of baby formula or 10 mL apple sauce. |
| One administration | 1 × 10 mg of Compound 1 in 1 mini-tablet of Examples 10 or 11 | Administered mini-tablet in 5 mL of baby formula or 5 mL of apple sauce |
| One administration | 2 × 10 mg of Compound 1 in 2 mini-tablets of Examples 10 or 11 | Administered mini-tablet in 5 mL of baby formula or 5 mL of apple sauce |
| One administration | 1 × 50 mg of Compound 1 of Example 14 or 18 | Administered mini-tablets (about 26) in 5-10 mL of baby formula or 5-10 mL apple sauce. |
| One administration | 2 × 50 mg of Compound 1 of Example 14 or 18 | Administered mini-tablets (about 52) in 5-10 mL of baby formula or 5-10 mL apple sauce. |
| One administration | 1 × 75 mg of Compound 1 of Example 14 or 18 | Administered mini-tablets (about 39) in 5-10 mL of baby formula or 5-10 mL apple sauce. |
| One administration | 2 × 75 mg of Compound 1 of Example 14 or 18 | Administered mini-tablets (about 78) in 5-10 mL of baby formula or 5-10 mL apple sauce. |
| One administration | 1 × 40 mg of Compound 1 of Example 15 | Administered mini-tablets (about 21) in 5-10 mL of baby formula or 5-10 mL apple sauce. |
| One administration | 2 × 40 mg of Compound 1 of Example 15 | Administered mini-tablets (about 42) in 5-10 mL of baby formula or 5-10 mL apple sauce. |
| One administration | 1 × 100 mg of Compound 1 of Example 15 | Administered mini-tablets (about 52) in 5-10 mL of baby formula or 5-10 mL apple sauce. |
| One administration | 2 × 100 mg of Compound 1 of Example 15 | Administered mini-tablets (about 104) in 5-10 mL of baby formula or 5-10 mL apple sauce. |
| One administration | 1, 2, 3, or 4 × 10 mg of Compound 1 of Example 16 | Administered tablet(s) in 5-10 mL of baby formula or 5-10 mL of apple sauce |
| One administration | 1, 2, 3, 4, or 5 × 12.5 mg of Compound 1 of Example 17 | Administered tablet(s) in 5-10 mL of baby formula or 5-10 mL of apple sauce |

The pharmaceutical formulations are administered to subjects in the morning who had previously eaten, and the pharmaceutical formulation is given at approximately the same time (within a 1-hour window) on each dosing occasion. Prior to administration, the contents of an appropriate container (e.g., capsule, sachet, blister pack, pouch, packet, bottle, or the like) including Compound 1 are added to the baby formula or infant formula or apple sauce, mixed, and allowed to disintegrate for about 3 minutes before administration. The formulations are orally administered with fat-containing food such as a standard CF high-calorie, high-fat meal or snack. For children able to eat foods, examples of a standard CF high-calorie, high-fat meal or snack may include eggs, butter, peanut butter, cheese pizza and the like. For younger children unable to eat foods, examples would be formula and breast milk. For children able to eat soft foods, examples of a standard CF high-calorie, high-fat meal or snack include would include ice cream and yogurt.

Example 22

Exemplary Administration B

Human pediatric patients are orally administered a pharmaceutical formulation according to Table 22:

TABLE 22

Exemplary administration B of pharmaceutical formulations of the present invention.

| Frequency of dosing (per day) | Description | Conditions |
|---|---|---|
| 12 hour intervals | 1 × 75 mg dose of Compound 1 of any Example 7-9 or 13 | Administered mini-tablets (about 29) in 5 mL of baby formula or 5 mL apple sauce. |
| 12 hour intervals | 1 × 75 mg dose of Compound 1 of Example 12 | Administered mini-tablets (about 38) in 5 mL of baby formula or 5 mL apple sauce. |
| 12 hour intervals | 1 × 75 mg dose of Compound 1 of Example 3 | Administered powder blend (about 200 mg) in 5 mL of baby formula or 5 mL apple sauce. |
| 12 hour intervals | 2 × 75 mg doses of Compound 1 of Example 3 | Administered powder blend (about 400 mg) in 5-10 mL of baby formula or 5-10 mL of apple sauce |
| 12 hour intervals | 2 × 75 mg doses of Compound 1 of any Example 7-9 or 13 | Administered mini-tablets (about 58) in 10 mL of baby formula or 10 mL apple sauce. |
| 12 hour intervals | 2 × 75 mg dose of Compound 1 of Example 12 | Administered mini-tablets (about 76) in 10 mL of baby formula or 10 mL apple sauce. |
| 12 hour intervals | 1 × 10 mg of Compound 1 in 1 mini-tablet of Examples 10 or 11 | Administered mini-tablet in 5 mL of baby formula or 5 mL of apple sauce |
| 12 hour intervals | 2 × 10 mg of Compound 1 in 2 mini-tablets of Examples 10 or 11 | Administered mini-tablet in 5 mL of baby formula or 5 mL of apple sauce |
| 12 hour intervals | 1 × 50 mg of Compound 1 of Example 14 or 18 | Administered mini-tablets (about 26) in 10 mL of baby formula or 10 mL apple sauce. |
| 12 hour intervals | 2 × 50 mg of Compound 1 of Example 14 or 18 | Administered mini-tablets (about 52) in 5-10 mL of baby formula or 5-10 mL apple sauce. |
| 12 hour intervals | 1 × 75 mg of Compound 1 of Example 14 or 18 | Administered mini-tablets (about 39) in 5-10 mL of baby formula or 5-10 mL apple sauce. |
| 12 hour intervals | 2 × 75 mg of Compound 1 of Example 14 or 18 | Administered mini-tablets (about 78) in 5-10 mL of baby formula or 5-10 mL apple sauce. |
| 12 hour intervals | 1 × 40 mg of Compound 1 of Example 15 | Administered mini-tablets (about 21) in 5-10 mL of baby formula or 5-10 mL apple sauce. |

TABLE 22-continued

Exemplary administration B of pharmaceutical formulations of the present invention.

| Frequency of dosing (per day) | Description | Conditions |
|---|---|---|
| 12 hour intervals | 2 × 40 mg of Compound 1 of Example 15 | Administered mini-tablets (about 42) in 5-10 mL of baby formula or 5-10 mL apple sauce. |
| 12 hour intervals | 1 × 100 mg of Compound 1 of Example 15 | Administered mini-tablets (about 52) in 5-10 mL of baby formula or 5-10 mL apple sauce. |
| 12 hour intervals | 2 × 100 mg of Compound 1 of Example 15 | Administered mini-tablets (about 104) in 5-10 mL of baby formula or 5-10 mL apple sauce. |
| 12 hour intervals | 1, 2, 3, or 4 × 10 mg of Compound 1 of Example 16 | Administered tablet(s) in 5-10 mL of baby formula or 5-10 mL of apple sauce |
| 12 hour intervals | 1, 2, 3, 4, or 5 × 12.5 mg of Compound 1 of Example 17 | Administered tablet(s) in 5-10 mL of baby formula or 5-10 mL of apple sauce |

The pharmaceutical formulations are administered to pediatric patients approximately every 12 hours, wherein each administration is given to the patient after ingestion of food. In other embodiments, the pharmaceutical formulations containing 75 of Compound 1 are administered to adult patients every 12 hours. Prior to administration, the contents of an appropriate container (e.g., capsule, sachet, blister pack, pouch, packet, bottle, or the like) including Compound 1 are added to the baby formula or infant formula or apple sauce, mixed, and allowed to disintegrate for about 3 minutes before administration. The formulations are orally administered with fat-containing food such as a standard CF high-calorie, high-fat meal or snack. For children able to eat foods, examples of a standard CF high-calorie, high-fat meal or snack may include eggs, butter, peanut butter, cheese pizza and the like. For younger children unable to eat foods, examples would be formula and breast milk. For children able to eat soft foods, examples of a standard CF high-calorie, high-fat meal or snack include would include ice cream and yogurt.

VI. EMBODIMENTS/CLAUSES

Embodiment 1

A pharmaceutical composition comprising a solid dispersion of amorphous or substantially amorphous Compound 1, one or more fillers, a sweetener, a disintegrant, a glidant and a lubricant, and optionally a wetting agent.

Embodiment 2

The pharmaceutical composition embodiment 1, wherein the pharmaceutical composition comprises from about 30 to about 50 percent of a solid dispersion, by weight of the composition.

Embodiment 3

The pharmaceutical composition embodiment 2, wherein the pharmaceutical composition comprises about 35 percent of a solid dispersion, by weight of the composition.

Embodiment 4

The pharmaceutical composition of embodiment 1, wherein the one or more fillers comprise: mannitol, lactose, sucrose, dextrose, maltodextrin, sorbitol, xylitol, powdered cellulose, polyhydric alcohols, microcrystalline cellulose, silicified microcrystalline cellulose, cellulose acetate, methylcellulose, ethylcellulose, hydroxyethylcellulose, methylhydroxyethylcellulose, talc, starch, pregelatinized starch, dibasic calcium phosphate, calcium sulfate, calcium carbonate or combinations thereof.

Embodiment 5

The pharmaceutical composition of embodiment 4, wherein the one or more fillers are selected from the group consisting of mannitol, lactose, sucrose, dextrose, and maltodextrin.

Embodiment 6

The pharmaceutical composition of embodiment 5, wherein the one or more fillers collectively are present in an amount from about 30 to about 60 percent by weight of the composition.

Embodiment 7

The pharmaceutical composition of any of embodiments 1-6, wherein the one or more fillers comprises mannitol.

Embodiment 8

The pharmaceutical composition of embodiment 7, wherein the mannitol is present in an amount from about 0 wt % to about 60 wt %.

Embodiment 9

The pharmaceutical composition of embodiment 7, wherein the one or more fillers further comprises lactose.

Embodiment 10

The pharmaceutical composition of embodiment 9, wherein the lactose is present in an amount from about 0 wt % to about 60 wt %.

Embodiment 11

The pharmaceutical composition of embodiment 10, wherein the mannitol is present in an amount from about 0 wt % to about 60 wt %.

Embodiment 12

The pharmaceutical composition of any of embodiments 1-6, wherein the one or more fillers comprise: lactose.

Embodiment 13

The pharmaceutical composition of embodiment 12, wherein the lactose is present in an amount from about 0 wt % to about 60 wt %.

Embodiment 14

The pharmaceutical composition of embodiment 9, wherein the filler comprises mannitol and mannitol and lactose in a ratio of about 3:1 mannitol to lactose.

Embodiment 15

The pharmaceutical composition of embodiment 9, wherein the filler comprises mannitol and mannitol and lactose in a ratio of about 1:1 mannitol to lactose.

Embodiment 16

The pharmaceutical composition of embodiment 9, wherein the filler comprises mannitol and mannitol and lactose in a ratio of about 1:3 mannitol to lactose.

Embodiment 17

The pharmaceutical composition of embodiment 16, wherein mannitol is present in an amount of about 13.5 percent by weight of the composition.

Embodiment 18

The pharmaceutical composition of embodiments 16 or 17, wherein lactose is present in an amount of about 41 percent by weight of the composition.

Embodiment 19

The pharmaceutical composition of embodiment 1, wherein the sweetener comprises:
glucose, sucrose, maltose, mannose, dextrose, fructose, lactose, trehalose, maltitol, lactitol, xylitol, sorbitol, mannitol, tagatose, glycerin, erythritol, isomalt, maltose, sucralose, aspartame, neotame, alitame, neohesperidin dihydrochalcone, cyclamate, thaumatin, acesulfame potassium, saccharin, saccharin sodium or combinations thereof.

Embodiment 20

The pharmaceutical composition of embodiment 19, wherein the sweetener comprises sucralose which is present in an amount from about 0.1 to about 5 percent by weight of the composition.

Embodiment 21

The pharmaceutical composition of embodiment 1, wherein the disintegrant comprises: croscarmellose sodium, sodium alginate, calcium alginate, alginic acid, starch, pregelatinized starch, sodium starch glycolate, polyvinylpyrrolidone, copolymers of polyvinylpyrrolidone, crospovidone, carboxymethylcellulose calcium, cellulose and its derivatives, carboxymethylcellulose sodium, soy polysaccharide, clays, gums, an ion exchange resin, an effervescent system based on food acids and an alkaline carbonate component, sodium bicarbonate or combinations thereof.

Embodiment 22

The pharmaceutical composition of embodiment 21, wherein the disintegrant comprises croscarmellose sodium which is present in an amount from about 4 to about 8 percent by weight of the composition.

Embodiment 23

The pharmaceutical composition of embodiment 1, wherein the wetting agent comprises: sodium lauryl sulfate, cetostearyl alcohol, cetomacrogol emulsifying wax, gelatin, casein, docusate sodium, benzalkonium chloride, calcium stearate, polyethylene glycols, phosphates, polyoxyethylene sorbitan fatty acid esters, gum acacia, cholesterol, tragacanth, polyoxyethylene 20 stearyl ethers, polyoxyethylene alkyl ethers, polyoxyethylene castor oil derivatives, pegylated hydrogenated castor oils, sorbitan esters of fatty acids, Vitamin E or tocopherol derivatives, vitamin E TPGS, tocopheryl esters, lecithin, phospholipids and their derivatives, poloxamers, stearic acid, oleic acid, oleic alcohol, cetyl alcohol, mono and diglycerides, propylene glycol esters of fatty acids, glycerol esters of fatty acids, ethylene glycol palmitostearate, polyoxylglycerides, propylene glycol monocaprylate, propylene glycol monolaurate, alkyl aryl polyether alcohols and polyglyceryl oleate or combinations thereof.

Embodiment 24

The pharmaceutical composition of embodiment 23, wherein the wetting agent comprises sodium lauryl sulfate which is present in an amount of about 2 or less percent by weight of the composition.

Embodiment 25

The pharmaceutical composition of embodiment 1, wherein the glidant comprises: talc, colloidal silica, precipitated silica, magnesium oxide, magnesium silicate, leucine and starch.

Embodiment 26

The pharmaceutical composition of embodiment 25, wherein the glidant comprises colloidal silica which is present in an amount from about 0.1 to about 5 percent by weight of the composition.

Embodiment 27

The pharmaceutical composition of embodiment 1, wherein the lubricant comprises: talc, fatty acid, stearic acid, magnesium stearate, calcium stearate, sodium stearate, stearic acid, glyceryl monostearate, sodium lauryl sulfate, sodium stearyl fumarate, hydrogenated oils, polyethylene glycol, fatty alcohol, fatty acid ester, glyceryl behenate, mineral oil, vegetable oil, leucine, sodium benzoate, or a combination thereof.

Embodiment 28

The pharmaceutical composition of embodiment 27, wherein the lubricant comprises magnesium stearate which is present in an amount from about 0.1 to about 7 percent by weight of the composition.

Embodiment 29

The pharmaceutical composition of embodiment 1, wherein the solid dispersion comprises about 80 percent of amorphous Compound 1 by weight of the solid dispersion, and about 19.5 percent of HPMCAS by weight of the solid dispersion, and about 0.5 percent SLS by weight of the dispersion.

Embodiment 30

A pharmaceutical composition comprising:
a solid dispersion of amorphous or substantially amorphous Compound 1 in an amount of about 30 to about 50 percent by weight of the pharmaceutical composition;
sucralose in an amount of between about 1.5 wt % to about 2.5 wt % percent by weight of the pharmaceutical composition;
croscarmellose sodium in an amount from about 4 to about 8 percent of by weight of the pharmaceutical composition;
colloidal silicon dioxide in an amount from about 0.5 wt % to about 1.5 wt % percent by weight of the pharmaceutical composition;
magnesium stearate in an amount from about 0.5 wt % to about 1.5 wt % percent by weight of the pharmaceutical composition; and
one or more fillers, collectively, in an amount of about 30 to about 60 percent of by weight of the pharmaceutical composition.

Embodiment 31

The pharmaceutical composition of embodiment 30, wherein the one or more fillers comprises mannitol.

Embodiment 32

The pharmaceutical composition of embodiments 30 or 31, wherein the one or more fillers comprise lactose.

Embodiment 33

The pharmaceutical composition of embodiment 32, wherein the filler comprises mannitol and lactose in a ratio of about 3:1 mannitol to lactose.

Embodiment 34

The pharmaceutical composition of embodiment 32, wherein the filler comprises mannitol and lactose in a ratio of about 1:1 mannitol to lactose.

Embodiment 35

The pharmaceutical composition of embodiment 32, wherein the filler comprises mannitol and lactose in a ratio of about 1:3 mannitol to lactose.

Embodiment 36

The pharmaceutical composition of embodiment 30, wherein the one or more fillers comprises mannitol in an amount of about 13.5 percent by weight of the composition.

Embodiment 37

The pharmaceutical composition of embodiment 36, wherein the one or more fillers comprises lactose.

Embodiment 38

The pharmaceutical composition of embodiment 37, wherein lactose is present in an amount of about 41 percent by weight of the composition.

Embodiment 39

The pharmaceutical composition of any of embodiments 30-38, wherein the croscarmellose sodium is present in an amount of about 6 percent of by weight of the pharmaceutical composition.

Embodiment 40

The pharmaceutical composition of any of embodiments 30-39, wherein the solid dispersion is present in an amount of about 35 percent by weight of the pharmaceutical composition.

Embodiment 41

A pharmaceutical composition comprising:
about 35 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion;
about 13.5 wt % of mannitol by weight of the composition;
about 41 wt % of lactose by weight of the composition;
about 2 wt % of sucralose by weight of the composition;
about 6 wt % of croscarmellose sodium by weight of the composition;
about 1 wt % of colloidal silicon dioxide by weight of the composition; and
about 1.5 wt % of magnesium stearate by weight of the composition.

Embodiment 42

The pharmaceutical composition of any of embodiments 30-41, wherein the pharmaceutical composition is a unit dose form comprising one or a plurality of granules, pellets, particles or mini-tablets, and wherein the unit dose form comprises from about 1 mg to about 250 mg of substantially amorphous or amorphous Compound 1.

Embodiment 42.5

The pharmaceutical composition of embodiment 42, wherein the unit dose form comprises about 5 mg of substantially amorphous or amorphous Compound 1.

Embodiment 43

The pharmaceutical composition of embodiment 42, wherein the unit dose form comprises about 10 mg of substantially amorphous or amorphous Compound 1.

Embodiment 44

The pharmaceutical composition of embodiment 42, wherein the unit dose form comprises about 12.5 mg of substantially amorphous or amorphous Compound 1.

Embodiment 45

The pharmaceutical composition of embodiment 42, wherein the unit dose form comprises about 15 mg of substantially amorphous or amorphous Compound 1.

Embodiment 46

The pharmaceutical composition of embodiment 42, wherein the unit dose form comprises about 20 mg of substantially amorphous or amorphous Compound 1.

Embodiment 47

The pharmaceutical composition of embodiment 42, wherein the unit dose form comprises about 25 mg of substantially amorphous or amorphous Compound 1.

Embodiment 48

The pharmaceutical composition of embodiment 42, wherein the unit dose form comprises about 30 mg of substantially amorphous or amorphous Compound 1.

Embodiment 48.5

The pharmaceutical composition of embodiment 42, wherein the unit dose form comprises about 35 mg of substantially amorphous or amorphous Compound 1.

Embodiment 49

The pharmaceutical composition of embodiment 42, wherein the unit dose form comprises about 40 mg of substantially amorphous or amorphous Compound 1.

Embodiment 49.5

The pharmaceutical composition of embodiment 42, wherein the unit dose form comprises about 45 mg of substantially amorphous or amorphous Compound 1.

Embodiment 50

The pharmaceutical composition of embodiment 42, wherein the unit dose form comprises from about 50 mg of substantially amorphous or amorphous Compound 1.

Embodiment 51

The pharmaceutical composition of embodiment 42, wherein the unit dose form comprises about 62.5 mg of substantially amorphous or amorphous Compound 1.

Embodiment 52

The pharmaceutical composition of embodiment 42, wherein the unit dose form comprises from about 75 mg of substantially amorphous or amorphous Compound 1.

Embodiment 53

The pharmaceutical composition of embodiment 42, wherein the unit dose form comprises about 100 mg of substantially amorphous or amorphous Compound 1.

Embodiment 54

The pharmaceutical composition of embodiment 42, wherein the unit dose form comprises about 125 mg of substantially amorphous or amorphous Compound 1.

Embodiment 55

The pharmaceutical composition of embodiment 42, wherein the unit dose form comprises about 150 mg of substantially amorphous or amorphous Compound 1.

Embodiment 56

The pharmaceutical composition of embodiment 42, wherein the unit dose form comprises about 175 mg of substantially amorphous or amorphous Compound 1.

Embodiment 57

The pharmaceutical composition of embodiment 42, wherein the unit dose form comprises about 200 mg of substantially amorphous or amorphous Compound 1.

Embodiment 58

The pharmaceutical composition of embodiment 42, wherein the unit dose form comprises about 225 mg of substantially amorphous or amorphous Compound 1.

Embodiment 59

The pharmaceutical composition of embodiment 42, wherein the unit dose form comprises about 250 mg of substantially amorphous or amorphous Compound 1.

Embodiment 60

The pharmaceutical composition of embodiment 42, wherein the unit dose form comprises from about 25 to about 40 mini-tablets.

Embodiment 61

The pharmaceutical composition of embodiment 42, wherein the solid dispersion is present in an amount of about 35 percent by weight of the pharmaceutical composition and the unit dose form comprises from about 26 mini-tablets.

Embodiment 62

The pharmaceutical composition of embodiment 61, wherein the unit dose form comprises about 50 mg of substantially amorphous or amorphous Compound 1.

Embodiment 63

The pharmaceutical composition of embodiment 42, wherein the solid dispersion is present in an amount of about 35 percent by weight of the pharmaceutical composition and the unit dose form comprises from about 21 mini-tablets.

Embodiment 64

The pharmaceutical composition of embodiment 63, wherein the unit dose form comprises from about 40 mg of substantially amorphous or amorphous Compound 1.

Embodiment 65

The pharmaceutical composition of embodiment 42, wherein the solid dispersion is present in an amount of about 35 percent by weight of the pharmaceutical composition and the unit dose form comprises from about 39 mini-tablets.

Embodiment 66

The pharmaceutical composition of embodiment 65, wherein the unit dose form comprises from about 75 mg of substantially amorphous or amorphous Compound 1.

Embodiment 67

The pharmaceutical composition of embodiment 42, wherein the solid dispersion is present in an amount of about 35 percent by weight of the pharmaceutical composition and the unit dose form comprises from about 52 mini-tablets.

Embodiment 68

The pharmaceutical composition of embodiment 67, wherein the unit dose form comprises from about 100 mg of substantially amorphous or amorphous Compound 1.

Embodiment 69

The pharmaceutical composition of any of embodiments 60-68, wherein the mini-tablet has a shape that is cylinder-like, oval-like, cone-like, sphere-like, ellipsis-like, polygon-like or combinations thereof, wherein the mini-tablet has as its longest dimension or diameter a length of about 2 mm.

Embodiment 70

The pharmaceutical composition of embodiment 42, wherein the pharmaceutical composition is a unit dose form comprising a granule, pellet, particle or mini-tablet, and wherein the unit dose form comprises from about 10 mg of substantially amorphous or amorphous Compound 1.

Embodiment 71

The pharmaceutical composition of embodiment 42, wherein the pharmaceutical composition is a unit dose form comprising a granule, pellet, particle or mini-tablet, and wherein the unit dose form comprises from about 12.5 mg of substantially amorphous or amorphous Compound 1.

Embodiment 72

The pharmaceutical composition of embodiment 70 or embodiment 71, wherein the solid dispersion is present in an amount of about 35 percent by weight of the pharmaceutical composition and the unit dose form is a mini-tablet having a shape that is cylinder-like, oval-like, cone-like, sphere-like, ellipsis-like, polygon-like or combinations thereof, wherein the mini-tablet has as its longest dimension or diameter a length of about 4 mm.

Embodiment 73

A method of treating or lessening the severity of CFTR mediated disease in a pediatric patient comprising administering to the pediatric patient a pharmaceutical composition of any of embodiments 1-72 and 78-80.

Embodiment 74

The method of embodiment 73, wherein the CFTR mediated disease is selected from cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), liver disease, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulinemia, Diabetes mellitus, Laron dwarfism, myeloperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurohypophyseal DI, nephrogenic DI, Charcot-Marie Tooth syndrome, Pelizaeus-Merzbacher disease, neurodegenerative diseases such as Alzheimer's disease, Parkinson's disease, amyotrophic lateral sclerosis, progressive supranuclear palsy, Pick's disease, several polyglutamine neurological disorders such as Huntington's, spinocerebellar ataxia type I, spinal and bulbar muscular atrophy, dentatorubral pallidoluysian atrophy, and myotonic dystrophy, as well as spongiform encephalopathies, such as hereditary Creutzfeldt-Jakob disease (due to prion protein processing defect), Fabry disease, Gerstmann-Strä ussler-Scheinker syndrome, COPD, dry-eye disease, Sjogren's disease, Osteoporosis, Osteopenia, Gorham's Syndrome, chloride channelopathies such as myotonia congenita (Thomson and Becker forms), Bartter's syndrome type III, Dent's disease, epilepsy, hyperekplexia, lysosomal storage disease, Angelman syndrome, and Primary Ciliary Dyskinesia (PCD), a term for inherited disorders of the structure and/or function of cilia, including PCD with situs inversus (also known as Kartagener syndrome), PCD without situs inversus and ciliary aplasia.

Embodiment 75

The method of embodiment 74, wherein the CFTR mediated disease is cystic fibrosis, COPD, emphysema, dry-eye disease or osteoporosis.

Embodiment 76

The method of embodiment 75, wherein the CFTR mediated disease is cystic fibrosis.

Embodiment 77

The method of embodiment 76, wherein the patient possesses one or more of the following mutations of human CFTR: ΔF508, R117H, and G551D.

Embodiment 78

A pharmaceutical composition comprising:
a solid dispersion of amorphous or substantially amorphous Compound 1 in an amount of about 30 to about 50 percent by weight of the pharmaceutical composition;
sucralose in an amount of between about 1.5 wt % to about 2.5 wt % percent by weight of the pharmaceutical composition;
croscarmellose sodium in an amount from about 4 to about 8 percent of by weight of the pharmaceutical composition;
colloidal silicon dioxide in an amount from about 0.5 wt % to about 1.5 wt % percent by weight of the pharmaceutical composition;

magnesium stearate in an amount from about 0.5 wt % to about 5 wt % percent by weight of the pharmaceutical composition; and one or more fillers, collectively, in an amount of about 30 to about 60 percent of by weight of the pharmaceutical composition.

Embodiment 79

A pharmaceutical composition comprising:
a solid dispersion of amorphous or substantially amorphous Compound 1 in an amount of about 30 to about 50 percent by weight of the pharmaceutical composition;
sucralose in an amount of between about 1.5 wt % to about 2.5 wt % percent by weight of the pharmaceutical composition;
croscarmellose sodium in an amount from about 4 to about 8 percent of by weight of the pharmaceutical composition;
colloidal silicon dioxide in an amount from about 0.5 wt % to about 1.5 wt % percent by weight of the pharmaceutical composition;
magnesium stearate in an amount from about 0.5 wt % to about 5 wt % percent by weight of the pharmaceutical composition; and
lactose in an amount of about 30 to about 60 percent of by weight of the pharmaceutical composition.

Embodiment 80

A pharmaceutical composition comprising:
about 35 wt % of a solid dispersion by weight of the composition, wherein the dispersion comprises about 80 wt % of substantially amorphous or amorphous Compound 1 by weight of the dispersion, about 19.5 wt % of HPMCAS by weight of the dispersion, and about 0.5 wt % SLS by weight of the dispersion;
about 54.5 wt % of lactose by weight of the composition;
about 2 wt % of sucralose by weight of the composition;
about 6 wt % of croscarmellose sodium by weight of the composition;
about 1 wt % of colloidal silicon dioxide by weight of the composition; and
about 1.5 wt % of magnesium stearate by weight of the composition.

Embodiment 81

The method according to embodiment 76, wherein the patient possesses a CFTR gating mutation.

Embodiment 82

The method according to embodiment 81, wherein the gating mutation is selected from G551D, G178R, G551S, G970R, G1244E, S1255P, G1349D, S549N, S549R, and S1251N.

Embodiment 83

The method according to embodiment 81, wherein the CFTR gating mutation is in at least one allele.

Embodiment 84

The method according to embodiment 81, wherein the CFTR gating mutation is in both alleles.

Embodiment 85

The method according to embodiments 73-77 and 81-84, wherein the patient is 2 through 5 years of age.

Embodiment 86

The method according to embodiments 73-77 and 81-84, wherein the patient is 0 through 2 years of age.

Embodiment 87

The method according to embodiments 73-77 and 81-84, wherein the patient weighs 14 kilograms or more than 14 kilograms.

Embodiment 88

The method according to embodiments 73-77 and 81-84, wherein the patient weighs less than 14 kilograms.

Embodiment 89

The method according to embodiment 76, wherein the patient has a residual function phenotype.

Embodiment 90

The method according to embodiment 76, wherein the patient has CFTR residual function.

Embodiment 91

The method according to embodiment 76, wherein the patient has a R117H CFTR mutation.

What is claimed is:
1. A pharmaceutical composition consisting of:
about 35 wt % of a solid dispersion by weight of the composition, wherein the dispersion comprises about 80 wt % of substantially amorphous or amorphous N-[2,4-Bis(1,1-dimethylethyl)-5-hydroxyphenyl]-1,4-dihydro-4-oxoquinoline-3-carboxamide by weight of the dispersion, about 19.5 wt % of HPMCAS by weight of the dispersion, and about 0.5 wt % SLS by weight of the dispersion;
about 13.5 wt % of mannitol by weight of the composition;
about 41 wt % of lactose by weight of the composition;
about 2 wt % of sucralose by weight of the composition;
about 6 wt % of croscarmellose sodium by weight of the composition;
about 1 wt % of colloidal silicon dioxide by weight of the composition; and
about 1.5 wt % of magnesium stearate by weight of the composition.

2. The pharmaceutical composition of claim 1, wherein the pharmaceutical composition is a unit dose form comprising one or a plurality of granules, pellets, particles or mini-tablets, and wherein the unit dose form comprises from about 1 mg to about 100 mg of substantially amorphous or amorphous N-[2,4-Bis(1,1-dimethylethyl)-5-hydroxyphenyl]-1,4-dihydro-4-oxoquinoline-3-carboxamide.

3. The pharmaceutical composition of claim 2, wherein the unit dose form comprises about 50 mg of substantially amorphous or amorphous N-[2,4-Bis(1,1-dimethylethyl)-5-hydroxyphenyl]-1,4-dihydro-4-oxoquinoline-3-carboxamide.

4. The pharmaceutical composition of claim 2, wherein the unit dose form comprises about 75 mg of substantially amorphous or amorphous N-[2,4-Bis(1,1-dimethylethyl)-5-hydroxyphenyl]-1,4-dihydro-4-oxoquinoline-3-carboxamide.

5. The pharmaceutical composition of claim 2, wherein the unit dose form comprises from about 25 to about 40 mini-tablets.

6. The pharmaceutical composition of claim 2, wherein the solid dispersion is present in an amount of about 35 percent by weight of the pharmaceutical composition and the unit dose form comprises from about 26 mini-tablets.

7. The pharmaceutical composition of claim 6, wherein the unit dose form comprises about 50 mg of substantially amorphous or amorphous N-[2,4-Bis(1,1-dimethylethyl)-5-hydroxyphenyl]-1,4-dihydro-4-oxoquinoline-3-carboxamide.

8. The pharmaceutical composition of claim 2, wherein the solid dispersion is present in an amount of about 35 percent by weight of the pharmaceutical composition and the unit dose form comprises about 39 mini-tablets.

9. The pharmaceutical composition of claim 8, wherein the unit dose form comprises about 75 mg of substantially amorphous or amorphous N-[2,4-Bis(1,1-dimethylethyl)-5-hydroxyphenyl]-1,4-dihydro-4-oxoquinoline-3-carboxamide.

10. The pharmaceutical composition of claim 5, wherein the mini-tablet has a shape that is cylinder-like, oval-like, cone-like, sphere-like, ellipsis-like, polygon-like or combinations thereof, wherein the mini-tablet has as its longest dimension or diameter a length of about 2 mm.

* * * * *